United States Patent
Knowlton

(10) Patent No.: US 11,612,410 B2
(45) Date of Patent: Mar. 28, 2023

(54) PIXEL ARRAY MEDICAL SYSTEMS, DEVICES AND METHODS

(71) Applicant: Edward Knowlton, Henderson, NV (US)

(72) Inventor: Edward Knowlton, Henderson, NV (US)

(73) Assignee: SRGI Holdings, LLC, Henderson, NV (US)

( * ) Notice: Subject to any disclaimer, the term of this patent is extended or adjusted under 35 U.S.C. 154(b) by 534 days.

(21) Appl. No.: 15/890,046

(22) Filed: Feb. 6, 2018

(65) Prior Publication Data

US 2018/0344343 A1    Dec. 6, 2018

Related U.S. Application Data

(63) Continuation-in-part of application No. 15/821,258, filed on Nov. 22, 2017, and a continuation-in-part of
(Continued)

(51) Int. Cl.
*A61B 17/3211*   (2006.01)
*A61F 2/10*   (2006.01)
(Continued)

(52) U.S. Cl.
CPC ........ *A61B 17/3211* (2013.01); *A61B 17/322* (2013.01); *A61B 17/3205* (2013.01);
(Continued)

(58) Field of Classification Search
CPC ............ A61B 17/32053; A61B 17/322; A61B 2017/3225; A61B 2017/320064;
(Continued)

(56) References Cited

U.S. PATENT DOCUMENTS 1,610,089 A    12/1926    Steven et al.
3,613,242 A    10/1971    Hill et al.
(Continued)

FOREIGN PATENT DOCUMENTS

CN    101530636 B    2/2012
KR    200303833 Y1    8/2003
(Continued)

OTHER PUBLICATIONS

Branski, Ludwik K., et al.; "A Porcine Model of Full-Thickness Burn, Excision, and Skin Autographing"; Science Direct, www.sciencedirect.com, 2008 Elsevier Ltd and ISBI, Mar. 2008, 9 pages.
(Continued)

*Primary Examiner* — Anh T Dang
(74) *Attorney, Agent, or Firm* — Adams and Reese LLP; Richard L. Gregory

(57) ABSTRACT

Systems, instruments, and methods for minimally invasive procedures including one or more of fractional resection, fractional lipectomy, fractional skin grafting, and/or fractional scar revision are described. Embodiments include instrumentation comprising a scalpet assembly coupled to a carrier, and the scalpet assembly includes a scalpet array. The scalpet array includes one or more scalpets configured for fractional resection, fractional lipectomy, fractional skin grafting, and/or fractional scar revision. The system includes a vacuum component coupled to the scalpet assembly and configured to evacuate tissue from the a site. The carrier is configured to control application of a rotational force and/or a vacuum force to the scalpet assembly.

32 Claims, 145 Drawing Sheets

Related U.S. Application Data application No. 15/821,325, filed on Nov. 22, 2017, now Pat. No. 10,335,191, and a continuation-in-part of application No. 15/812,952, filed on Nov. 14, 2017, now Pat. No. 10,773,064, which is a continuation-in-part of application No. 15/431,247, filed on Feb. 13, 2017, now Pat. No. 10,368,904, and a continuation-in-part of application No. 15/431,230, filed on Feb. 13, 2017, now Pat. No. 11,109,887, which is a continuation-in-part of application No. 15/017,007, filed on Feb. 5, 2016, now abandoned, and a continuation-in-part of application No. 15/016,954, filed on Feb. 5, 2016, now Pat. No. 10,517,635, and a continuation-in-part of application No. 14/840,284, filed on Aug. 31, 2015, now Pat. No. 10,485,575, and a continuation-in-part of application No. 14/840,290, filed on Aug. 31, 2015, now Pat. No. 10,321,948, and a continuation-in-part of application No. 14/840,307, filed on Aug. 31, 2015, now Pat. No. 10,314,640, and a continuation-in-part of application No. 14/840,267, filed on Aug. 31, 2015, now Pat. No. 10,342,574, and a continuation-in-part of application No. 14/840,274, filed on Aug. 31, 2015, now Pat. No. 10,485,606, and a continuation-in-part of application No. 14/556,648, filed on Dec. 1, 2014, now Pat. No. 9,987,473, and a continuation-in-part of application No. 14/505,183, filed on Oct. 2, 2014, now Pat. No. 10,080,581, and a continuation-in-part of application No. 14/505,090, filed on Oct. 2, 2014, now Pat. No. 10,076,354, and a continuation-in-part of application No. 14/099,380, filed on Dec. 6, 2013, now Pat. No. 10,219,827, which is a continuation-in-part of application No. 12/972,013, filed on Dec. 17, 2010, now Pat. No. 8,900,181.

(60) Provisional application No. 62/504,844, filed on May 11, 2017, provisional application No. 62/456,775, filed on Feb. 9, 2017.

(51) Int. Cl.

| | | |
|---|---|---|
| *A61B 17/322* | (2006.01) | |
| *A61B 90/00* | (2016.01) | |
| *A61B 17/3205* | (2006.01) | |
| *A61B 17/3209* | (2006.01) | |
| *A61B 17/3207* | (2006.01) | |
| *A61B 18/14* | (2006.01) | |
| *A61B 17/00* | (2006.01) | |
| *A61B 17/32* | (2006.01) | |
| *A61B 17/42* | (2006.01) | |
| *A61B 18/00* | (2006.01) | |
| *A61M 37/00* | (2006.01) | |
| *A61B 18/20* | (2006.01) | |
| *A61N 7/00* | (2006.01) | |
| *A61B 17/20* | (2006.01) | |
| *A61B 17/34* | (2006.01) | |
| *A61B 17/30* | (2006.01) | |

(52) U.S. Cl.
CPC .. *A61B 17/32053* (2013.01); *A61B 17/32093* (2013.01); *A61B 17/320758* (2013.01); *A61B 18/14* (2013.01); *A61B 90/02* (2016.02); *A61B 90/03* (2016.02); *A61B 90/39* (2016.02); *A61B 17/205* (2013.01); *A61B 17/320068* (2013.01); *A61B 17/42* (2013.01); *A61B 18/1402* (2013.01); *A61B 18/20* (2013.01); *A61B 2017/00398* (2013.01); *A61B 2017/00747* (2013.01); *A61B 2017/00752* (2013.01); *A61B 2017/00761* (2013.01); *A61B 2017/00769* (2013.01); *A61B 2017/00792* (2013.01); *A61B 2017/00796* (2013.01); *A61B 2017/306* (2013.01); *A61B 2017/32007* (2017.08); *A61B 2017/3225* (2013.01); *A61B 2017/320044* (2013.01); *A61B 2017/320052* (2013.01); *A61B 2017/3409* (2013.01); *A61B 2018/0047* (2013.01); *A61B 2018/00291* (2013.01); *A61B 2018/00452* (2013.01); *A61B 2018/00464* (2013.01); *A61B 2018/00476* (2013.01); *A61B 2018/00601* (2013.01); *A61B 2090/033* (2016.02); *A61B 2090/034* (2016.02); *A61B 2090/395* (2016.02); *A61B 2090/3908* (2016.02); *A61B 2090/3933* (2016.02); *A61B 2217/005* (2013.01); *A61B 2218/007* (2013.01); *A61F 2/105* (2013.01); *A61M 37/0015* (2013.01); *A61M 2037/0023* (2013.01); *A61M 2037/0061* (2013.01); *A61M 2202/08* (2013.01); *A61M 2210/04* (2013.01); *A61N 7/00* (2013.01); *A61N 2007/0034* (2013.01)

(58) Field of Classification Search
CPC ...... A61B 2017/00792; A61M 35/003; A61M 2037/0023
See application file for complete search history.

(56) References Cited

U.S. PATENT DOCUMENTS

| | | | |
|---|---|---|---|
| 3,820,543 | A | 6/1974 | Vanjushin et al. |
| 3,867,942 | A | 2/1975 | Bellantoni et al. |
| 4,018,228 | A | 4/1977 | Goosen |
| 4,098,278 | A | 7/1978 | Schwartz |
| 4,122,855 | A * | 10/1978 | Tezel ................... A61B 17/322 |
| | | | 606/131 |
| 4,160,453 | A | 7/1979 | Miller |
| 4,362,157 | A * | 12/1982 | Keeth ................... A61M 5/427 |
| | | | 604/116 |
| 4,476,864 | A | 10/1984 | Tezel |
| 4,542,742 | A | 9/1985 | Winkelman et al. |
| 4,582,640 | A | 4/1986 | Smestad et al. |
| 4,803,075 | A | 2/1989 | Wallace et al. |
| 4,944,737 | A | 7/1990 | Bloom |
| 5,123,907 | A | 6/1992 | Romaine |
| 5,141,513 | A | 8/1992 | Fortune et al. |
| 5,209,755 | A | 5/1993 | Abrahan et al. |
| 5,415,182 | A | 5/1995 | Chin et al. |
| 5,417,683 | A | 5/1995 | Shiao |
| 5,570,700 | A | 11/1996 | Vogeler |
| 5,578,054 | A | 11/1996 | Arnold |
| 5,591,444 | A | 1/1997 | Boss, Jr. |
| 5,643,308 | A | 7/1997 | Markman |
| 5,665,372 | A | 9/1997 | Boss, Jr. |
| 5,693,064 | A * | 12/1997 | Arnold ....................... A61F 2/10 |
| | | | 606/187 |
| 5,827,297 | A | 10/1998 | Boudjema |
| 5,858,019 | A | 1/1999 | Ashraf |
| 5,871,495 | A | 2/1999 | Mueller |
| 5,879,326 | A | 3/1999 | Godshall et al. |
| 5,895,403 | A | 4/1999 | Collinsworth |
| 5,922,000 | A * | 7/1999 | Chodorow ......... A61B 17/3468 |
| | | | 600/567 |
| 5,928,162 | A | 7/1999 | Giurtino et al. |
| 5,964,729 | A | 10/1999 | Choi et al. |
| 5,970,709 | A | 10/1999 | Tohji |
| 5,989,278 | A | 11/1999 | Mueller |
| 6,027,512 | A * | 2/2000 | Bridges ................ A61B 17/322 |
| | | | 606/131 |
| 6,059,807 | A | 5/2000 | Boudjema |
| 6,126,615 | A | 10/2000 | Allen et al. |
| 6,432,710 | B1 | 8/2002 | Boss, Jr. et al. |

(56) References Cited

U.S. PATENT DOCUMENTS

| | | |
|---|---|---|
| 6,471,712 B2 | 10/2002 | Burres |
| 6,497,875 B1 | 12/2002 | Sorrell et al. |
| 6,572,625 B1 | 6/2003 | Rassman |
| 6,585,746 B2 | 7/2003 | Gildenberg |
| 6,589,202 B1 | 7/2003 | Powell |
| 6,626,865 B1 | 9/2003 | Prisell |
| 6,669,685 B1 | 12/2003 | Rizoiu et al. |
| 6,997,923 B2 | 2/2006 | Anderson et al. |
| 7,204,828 B2 | 4/2007 | Rosiello |
| 7,261,721 B2 | 8/2007 | Feller |
| 7,316,822 B2 | 1/2008 | Binette et al. |
| 7,331,953 B2 | 2/2008 | Manstein et al. |
| 7,354,423 B2 | 4/2008 | Zelickson et al. |
| 7,412,978 B1 | 8/2008 | Keller |
| 7,621,933 B2 | 11/2009 | Bodduluri et al. |
| 7,625,384 B2 | 12/2009 | Eriksson et al. |
| 7,708,746 B2 | 5/2010 | Eriksson et al. |
| 7,846,465 B1 | 12/2010 | Keller et al. |
| 7,942,153 B2 | 5/2011 | Manstein et al. |
| 7,962,192 B2 | 6/2011 | Bodduluri et al. |
| 7,993,310 B2 | 8/2011 | Rosiello |
| 8,062,322 B2 | 11/2011 | Rassman et al. |
| 8,202,279 B2 | 6/2012 | Cole |
| 8,211,134 B2 | 7/2012 | Oostman, Jr. |
| 8,317,804 B1 | 11/2012 | Rassman et al. |
| 8,486,155 B2 | 7/2013 | McAlister et al. |
| 8,529,883 B2 | 9/2013 | Maslowski |
| 8,535,299 B2 | 9/2013 | Giovannoli |
| 8,540,731 B2 | 9/2013 | Kay et al. |
| 8,545,489 B2 | 10/2013 | Giovannoli |
| 8,690,863 B2 | 4/2014 | Chan et al. |
| 8,728,819 B2 | 5/2014 | Maslowski et al. |
| 8,765,121 B2 | 7/2014 | Maslowski |
| 8,900,181 B2 | 12/2014 | Knowlton |
| 8,986,324 B2 | 3/2015 | Bodduluri et al. |
| 9,005,218 B2 | 4/2015 | Harris |
| 9,060,803 B2 | 6/2015 | Anderson et al. |
| 9,095,368 B2 | 8/2015 | Umar et al. |
| 9,351,792 B2 | 5/2016 | Manstein et al. |
| 9,415,075 B2 | 8/2016 | Maslowski |
| 9,439,673 B2 | 9/2016 | Austen |
| 9,468,459 B2 | 10/2016 | Hall et al. |
| 9,743,949 B2 | 8/2017 | Guiles et al. |
| D797,286 S | 9/2017 | Ginggen et al. |
| 9,902,937 B2 | 2/2018 | Maslowski et al. |
| 10,098,914 B2 | 10/2018 | Maslowski |
| 10,117,721 B2 | 11/2018 | Tripathi et al. |
| 10,219,827 B2 | 3/2019 | Knowlton et al. |
| 10,251,792 B2 | 4/2019 | Levinson et al. |
| 10,335,190 B2 | 7/2019 | Knowlton |
| 10,368,904 B2 | 8/2019 | Knowlton |
| 2001/0053888 A1 | 12/2001 | Athanasiou et al. |
| 2002/0052619 A1 | 5/2002 | Transue |
| 2002/0088779 A1 | 7/2002 | Neev et al. |
| 2002/0111563 A1 | 8/2002 | Hall |
| 2002/0183688 A1 | 12/2002 | Lastovich et al. |
| 2003/0036770 A1 | 2/2003 | Markman |
| 2003/0069548 A1 | 4/2003 | Connelly et al. |
| 2003/0216719 A1 | 11/2003 | Debenedictis et al. |
| 2004/0082940 A1 | 4/2004 | Black et al. |
| 2004/0087893 A1 | 5/2004 | Kwon |
| 2004/0087992 A1 | 5/2004 | Gartstein et al. |
| 2004/0175690 A1 | 9/2004 | Mishra et al. |
| 2004/0193203 A1* | 9/2004 | Pak .................... A61B 17/3468 606/187 |
| 2004/0210214 A1 | 10/2004 | Knowlton |
| 2005/0049582 A1 | 3/2005 | Debenedictis et al. |
| 2005/0154331 A1 | 7/2005 | Christie et al. |
| 2005/0154431 A1 | 7/2005 | Quistgaard et al. |
| 2005/0171504 A1 | 8/2005 | Miller |
| 2005/0267506 A1 | 12/2005 | Harris |
| 2005/0283141 A1 | 12/2005 | Giovannoli |
| 2006/0051404 A1 | 3/2006 | Yeshurun et al. |
| 2006/0155266 A1 | 7/2006 | Manstein et al. |
| 2007/0038236 A1 | 2/2007 | Cohen |
| 2007/0073217 A1 | 3/2007 | James |
| 2007/0073327 A1 | 3/2007 | Giovannoli |
| 2007/0179481 A1 | 8/2007 | Frangineas et al. |
| 2007/0179516 A1 | 8/2007 | Mishra et al. |
| 2007/0207131 A1 | 9/2007 | Boss et al. |
| 2007/0224173 A1 | 9/2007 | Koullick et al. |
| 2007/0293884 A9 | 12/2007 | Cole et al. |
| 2008/0172047 A1 | 7/2008 | Altshuler et al. |
| 2008/0275378 A1 | 11/2008 | Herndon |
| 2009/0048558 A1 | 2/2009 | Del Vecchio |
| 2010/0114118 A1 | 5/2010 | Harris |
| 2010/0121307 A1 | 5/2010 | Lockard et al. |
| 2010/0204722 A1 | 8/2010 | Gilsdorf |
| 2010/0303770 A1 | 12/2010 | Maslowski et al. |
| 2011/0009860 A1 | 1/2011 | Chornenky et al. |
| 2011/0077664 A1 | 3/2011 | Schulz et al. |
| 2011/0177591 A1 | 7/2011 | Iwatschenko et al. |
| 2011/0208089 A1 | 8/2011 | Sundheimer et al. |
| 2011/0251602 A1 | 10/2011 | Anderson et al. |
| 2011/0257588 A1 | 10/2011 | Knowlton |
| 2011/0264115 A1 | 10/2011 | Asrani et al. |
| 2011/0282239 A1 | 11/2011 | Conlon et al. |
| 2011/0282382 A1 | 11/2011 | McAlister et al. |
| 2011/0313429 A1 | 12/2011 | Anderson et al. |
| 2012/0022510 A1 | 1/2012 | Welches et al. |
| 2012/0035599 A1 | 2/2012 | Sabir et al. |
| 2012/0041430 A1 | 2/2012 | Anderson et al. |
| 2012/0219634 A1 | 8/2012 | Maslowski et al. |
| 2012/0226214 A1 | 9/2012 | Gurtner et al. |
| 2012/0271320 A1 | 10/2012 | Hall et al. |
| 2012/0323139 A1 | 12/2012 | Richardson |
| 2012/0323325 A1 | 12/2012 | Fulton |
| 2013/0006168 A1 | 1/2013 | Del Vecchio |
| 2013/0090669 A1 | 4/2013 | Bellomo et al. |
| 2013/0096600 A1 | 4/2013 | Wesley et al. |
| 2013/0204273 A1 | 8/2013 | Sabir et al. |
| 2013/0236427 A1 | 9/2013 | Pernock |
| 2013/0287286 A1 | 10/2013 | Zingaretti et al. |
| 2013/0295061 A1 | 11/2013 | Maslowski |
| 2013/0304090 A1 | 11/2013 | Oostman, Jr. et al. |
| 2013/0345721 A1 | 12/2013 | Menke et al. |
| 2014/0031801 A1 | 1/2014 | Giovannoli |
| 2014/0099383 A1 | 4/2014 | Maslowski et al. |
| 2014/0277055 A1 | 9/2014 | Austen, Jr. |
| 2014/0296741 A1 | 10/2014 | Austen |
| 2014/0303648 A1 | 10/2014 | Knowlton |
| 2014/0343575 A1 | 11/2014 | Andreani et al. |
| 2015/0018844 A1 | 1/2015 | Harris |
| 2015/0173991 A1 | 6/2015 | Anderson et al. |
| 2015/0201955 A1 | 7/2015 | Sabir et al. |
| 2015/0216545 A1 | 8/2015 | Anderson et al. |
| 2015/0230818 A1 | 8/2015 | Knowlton |
| 2015/0238214 A1 | 8/2015 | Anderson et al. |
| 2015/0250493 A1 | 9/2015 | Umar |
| 2015/0366719 A1 | 12/2015 | Levinson et al. |
| 2016/0008515 A1 | 1/2016 | Stilwell et al. |
| 2016/0095592 A1 | 4/2016 | Levinson et al. |
| 2016/0166272 A1 | 6/2016 | Shiao |
| 2016/0192961 A1 | 7/2016 | Ginggen et al. |
| 2016/0287281 A1 | 10/2016 | Knowlton |
| 2016/0310157 A1 | 10/2016 | Guiles et al. |
| 2016/0310158 A1 | 10/2016 | Guiles et al. |
| 2016/0310159 A1 | 10/2016 | Guiles et al. |
| 2016/0310444 A1 | 10/2016 | Dobak, III |
| 2016/0317170 A1 | 11/2016 | Knowlton |
| 2016/0317721 A1 | 11/2016 | Ginggen et al. |
| 2016/0340651 A1 | 11/2016 | Maslowski et al. |
| 2016/0367280 A1 | 12/2016 | Austen |
| 2017/0042561 A1 | 2/2017 | Hall et al. |
| 2017/0079824 A1 | 3/2017 | Thompson |
| 2017/0296214 A1 | 10/2017 | Knowlton |
| 2017/0333068 A1 | 11/2017 | Knowlton |
| 2017/0367729 A1 | 12/2017 | Ginggen et al. |
| 2018/0006300 A1 | 1/2018 | Jeong et al. |
| 2018/0036029 A1 | 2/2018 | Anderson et al. |
| 2018/0078278 A1 | 3/2018 | Levinson et al. |
| 2018/0161056 A1 | 6/2018 | Kim et al. |
| 2018/0325543 A1 | 11/2018 | Skog et al. |
| 2018/0346878 A1 | 12/2018 | Maslowski et al. |

(56) References Cited

U.S. PATENT DOCUMENTS

| | | |
|---|---|---|
| 2019/0015255 A1 | 1/2019 | Gurtner et al. |
| 2019/0046777 A1 | 2/2019 | Knowlton |
| 2019/0099199 A1 | 4/2019 | Levinson et al. |

FOREIGN PATENT DOCUMENTS

| | | |
|---|---|---|
| KR | 20080100795 A | 11/2008 |
| WO | 0145566 A1 | 6/2001 |
| WO | 2005072181 A2 | 8/2005 |
| WO | 2008002064 A1 | 1/2008 |
| WO | 2009146068 A1 | 12/2009 |
| WO | 2012103483 A2 | 8/2012 |
| WO | 2012136904 A1 | 10/2012 |
| WO | 2013013196 A1 | 1/2013 |
| WO | 2013013199 A2 | 1/2013 |
| WO | 2014028626 A1 | 2/2014 |
| WO | 2014089488 A2 | 6/2014 |
| WO | 2015051164 A2 | 4/2015 |

OTHER PUBLICATIONS

Akan, Mithat M.D., et al.; "An Alternative Method to Minimize Pain in the Split-Thickness Skin Graft Donor Site"; From the Department of Plastic and Reconstructive Surgery, Dr. Lütfi K|rdar Kartal Education and Research Hospital, Istanbul; and the Department of Plastic and Reconstructive Surgery, Ankara Education and Research Hospital. revised Aug. 20, 2002.

Ablaza, Valerie J. M.D., et al.; "An Alternative Treatment for the Split Skin-Graft Donor Site"; Aesthetic Plastic Surgery, 21:207-209, Springer-Verlag New York, Inc. 1997, 3 pages.

Jones, Larry M. M.D.; "The Biobrane Stent"; From the Mercy Hospital of Pittsburgh, Journal of Burn Care and Rehabilitation, vol. 19, No. 4, 1998, 2 pages.

Andreassi, Andrea M.D., et al.; "Classification and Pathophysiology of Skin Grafts"; Clinics in Dermatology, vol. 23 pp. 332-337, 2005 Elsevier Inc.

Hallock, Geoffrey G. M.D.; "The Cosmetic Split-Thickness Skin Graft"; From the Division of Plastic Surgery, Lehigh Valley Hospital, vol. 104, No. 7, Feb. 1999, 3 pages.

Williamson, J. S. M.D., et al.; "Cultured Epithelial Autograft: Five Years of Clinical Experience with Twenty-Eight Patients"; The Journal of Trauma: Injury, Infection, and Critical Care, Issue: vol. 39(2), Aug. 1995, pp. 309-319.

Cirodde, Audrey, et al.; "Cultured Epithelial Autografts in Massive Burns: A Single-Center Retrospective Study with 63 Patients"; Science Direct, www.sciencedirect.com, 2011 Elsevier Ltd and ISBI, Mar. 2011, 9 pages.

Clugston, Patricia A. M.D., et al.; "Cultured Epithelial Autografts: Three Years of Clinical Experience with Eighteen Patients"; Journal of Burn Care and Rehabilitation, vol. 12, No. 6 Nov./Dec. 1991, 7 pages.

Fhourani, Vinod H. M.D., et al.; "Factors Affecting Success of Split-Thickness Skin Grafts in the Modern Burn Unit" The Journal of Trauma, Injury, Infection, and Critical Care; vol. 54 pp. 562-568, Dec. 2002.

Sheridan, Robert L., et al.; "Initial Experience with a Composite Autologous Skin Substitute"; Shriners Burn Hospital Boston MA, USA, Burns vol. 27 pp. 421-424, Nov. 2000.

Elliot, Michael and Vandervord, John; "Initial Experience with Cultured Epithelial Autografts in Massively Burnt Patients"; Department of Plastic Surgery, Royal North Shore Hospital, Sydney, Australia, ANZ J. Surg. vol. 72 pp. 893-895, Aug. 2002.

Hansbrough, Wendy BS, RN, et al. "Management of Skin-Grafted Bum Wounds with Xeroform* and Layers of Dry Coarse-Mesh Gauze Dressing Results in Excellent Graft Take and Minimal Nursing Time"; From the University of California, San Diego, Regional Burn Center and Medical Center; Jul. 1994, Copyright 1995 by Burn Science Publishers, Inc. 4 pages.

Wells, Mark D. M.D., Kim, David S. M.D.; "A New Method of Skin-Graft Stabilization: The Reston Technique"; From the Division of Plastic Surgery, Department of Surgery, University of Kentucky Chandler Medical Center, Lexington KY, Dec. 1994, 3 pages, Copyright by Little, Brown and Company 1995.

Hiazani, Ron M.D. et al., "Optimizing Aesthetic Results in Skin Grafting"; From the Department of Surgery, Division of Plastic Surgery, University of Louisville, Louisville, Kentucky, The American Surgeon, vol. 78, Feb. 2012, 4 pages.

Lee, Haguen; "Outcomes of Sprayed Cultured Epithelial Autografts for Full-Thickness Wounds"; A Single-Centre Experience, Science Direct, www.sciencedirect.com, 2012 Elsevier Ltd and ISBI, Jan. 2012, 6 pages.

Greenwood, John M.D., et ; "Real-Time Demonstration of Split Skin Graft Inosculation and Integra Dermal Matrix Neovascularization Using Confocal Laser Scanning Microscopy"; Burns Unit, Royal Adelaide Hospital, North Terrace Adelaide, SA 5000, Australia, published Aug. 2009, Journal of Plastic Surgery, vol. 9.

Lindenblatt, Nicole, M.D., et al.; "A New Model for Studying the Revascularization of Skin Grafts In Vivo: The Role of Angiogenesis"; From the Division of Plastic and Reconstructive Surgery, University Hospital Zurich; the Institute for Clinical andExperimental Surgery, University of Saarland; and the Institute for Experimental Surgery, University of Rostock. accepted May 28, 2008. www.PRSJournal.com, 12 pages.

Dornseifer, Ulf M.D., et al.; "The Ideal Split-Thickness Skin Graft Donor Site Dressing"; From the Department of Plastic, Reconstructive, Hand, and Burn Surgery, Clinic Bogenhausen, Technical University, Munich, Germany, Annals of Plastic Surgery, vol. 63, No. Aug. 2, 2009, 3 pages.

Dornseifer, Ulf M.D., et al.; "The Ideal Split-Thickness Skin Graft Donor-Site Dressing: A Clinical Comparative Trial of a Modified Polyurethane Dressing and Aquacel"; Burn Surgery, Academic Hospital Munich Bogenhausen, Technical University Munich, and the Institute of Medical Statistics and Epidemiology, Technical University Munich. accepted Mar. 2011. Copyright © 2011 by the American Society of Plastic Surgeons. WWW. PRSJournal.com, 7 pages.

Penington, Anthony, Morrison, Wayne A.; "Skin Graft Failure Is Predicted By Waist-Hip Ratio: a Marker for Metabolic Syndrome"; Department of Surgery, St. Vincent's Hospital, University of Melbourne, Melbourne, Victoria, Australia; Jun. 2006, copyright 2007 Royal Australasian College of Surgeons, 3 pages.

Wendt, James Robert M.D., et al.; "Long-Term Survival of Human Skin Allografts in Patients with Immunosuppression"; From the Department of Plastic Surgery, Hoag Memorial Hospital Presbyterian; Amgen; and Department of Pathology and Laboratory Medicine, UCLA Clinical Cytogenetics Laboratory. 8 pages.

Mimoun, Maurice M.D. et al.; "The Scalp Is an Advantageous Donor Site for Thin-Skin Grafts: A Report on 945 Harvested Samples"; From the Plastic, Aesthetic, Reconstructive and Burn Surgery Unit, Rothschild Hospital, and the Burn Unit, Saint-Antoine Hospital. accepted Apr. 2005. Copyright © 2006 by the American Society of Plastic Surgeons, 5 pages.

Wood, F.M., et al.; "The Use of Cultured Epithelial Autograft in the Treatment of Major Burn Injuries: A Critical Review of the Literature"; Burn Service WA, Royal Perth Hospital, Princess Margaret Hospital for Children,University of Western Australia, GPO Box X2213, Perth Western Australia 6847, Australia Clinical Cell Culture, Australia, accepted Jan. 2006, copyright 2006 Elsevier Ltd and ISBI, 7 pages.

Bello, Ysabel M., et al.; "Tissue-Engineered Skin, Current Status in Wound Healing"; American Journal Clinical Dermatology, vol. 2 (5), 2001, pp. 305-313, Miami FL USA.

Kogan, Leonid, M.D.,PhD, Govrin-Yehudain, Jacky, M.D.; "Vertical (Two-Layer) Skin Grafting: New Reserves for Autologic Skin"; From Plastic Surgery Unit, Western Galilee Hospital, Nahariya, Israel. Accepted Oct. 2002, 3 pages.

Fischer, John P. M.D., et al. "Complications in Body Contouring Procedures: An Analysis of 1797 Patients from the 2005 to 2010 American College of Surgeons National Surgical Quality Improvement Program Databases"; From the Division of Plastic Surgery,

(56) References Cited

OTHER PUBLICATIONS

Hospital of the University of Pennsylvania. accepted Jul. 2013, WWW.PRSJournal.com, 10 pages.
Motttura, A. Aldo, M.D.; "Open Frontal Lift: A Conservative Approach"; Aesthetic Plastic Surgery, vol. 30 pp. 381-389, copyright 2006 Springer Science Business Media, Inc.
Polder, Kristel D. M.D., Bruce, Suzanne, M.D.; "Radiofrequency: Thermage"; Facial Plastic Surgery Clinics, Apr. 2011, pp. 347-359, copyright 2011 Elsevier Inc. All rights reserved.
Pallua, N., Wolter, ; "The Lipo-Facelift: Merging the Face-Lift and Liposculpture: Eight Years Experience and a Preliminary Observational Study"; Accepted: Apr. 30, 2013 / Published online: Oct. 2013 Springer Science+Business Media New York and International Society of Aesthetic Plastic Surgery 2013, 7 pages.
Burns, Jay A.; "Thermage: Monopolar Radiofrequency"; Aesthetic Surgery Journal, Nov./Dec. 2005, vol. 25, No. 6, 5 pages.
Sukal, Sean A. M.D., Geronemus, Roy G. M.D.; "Thermage: The Nonablative Radiofrequency for Rejuvenation" Laser and Skin Surgery Center of New York, New York, NY, USA, Clinics in Dermatology vol. 26, pp. 602-607, 2008, copyright 2008 Elsevier Inc., 6 pages.
Sklar, Lindsay, et al.; "Use of Transcutaneous Ultrasound for Lipolysis and Skin Tightening: A Review"; Accepted: Jan. 2014, copyright Springer Science+Business Media New York and International Society of Aesthetic Plastic Surgery 2014, 13 pages.
Alguire P.C et al., "Skin Biopsy Techniques for the Internist," Journal of General Internal Medicine, Jan. 1998, vol. 13 (1), pp. 46-54.
Cooperman L.S., et al., "Injectable Collagen: A Six-Year Clinical Investigation," Aesthetic Plastic Surgery, Jun. 1985, vol. 9 (2), pp. 145-151.
Extended European Search Report for Application No. EP05027935 dated Jun. 12, 2009, 4 pages.
Ford C.N., et al., "A Preliminary Study of Injectable Collagen in Human Vocal Fold Augmentation," Otolaryngology—Head and Neck Surgery, Jan. 1986, vol. 94 (1), pp. 104-112.
Ford C.N., et al., "Autologous Collagen Vocal Fold Injection: A Preliminary Clinical Study," Laryngoscope, Sep. 1995, vol. 105 (9 Pt 1), pp. 944-998.
Ford C.N., et al., "Clinical Experience with Injectable Collagen for Vocal Fold Augmentation," Larynscope, Aug. 1986, vol. 96 (8), pp. 863-869.
Ford C.N., et al., "Role of Injectable Collagen in the Treatment of Glottic Insufficiency: A Study of 119 Patients," The Annals of otology, Rhinology and Laryngology, Mar. 1992, vol. 101 (3), pp. 237-247.
Frey P., et al., "Subureteral Collagen Injection for the Endoscopic Treatment of Vesicoureteral Reflux in Children. Followup Study of 97 Treated Ureters and Histological Analysis of Collagen Implants," The Journal of Urology, Aug. 1992, vol. 148 (2 Pt 2), pp. 718-723.
Giordano A., et al., "From the Laboratory Bench to the Patient's Bedside: An Update on Clinical Trials with Mesenchymal Stem Cells," Department of Experimental Medicine of Biotechnology and Molecular Biology, Second University of Naples, Oct. 2006, 10 pages.
International Search Report and Written Opinion for Application No. PCT/US2017/017683, dated Jul. 27, 2017, 10 pages.
International Search Report and Written Opinion for Application No. PCT/US2017/030840, dated Oct. 3, 2017, 15 pages.
International Search Report and Written Opinion for Application No. PCT/US2018/017100, dated Sep. 12, 2018, 18 pages.
International Search Report and Written Opinion for Application No. PCT/US2018/32387, dated Jan. 7, 2019, 15 pages.
International Search Report and Written Opinion for Application No. PCT/US2019/037484, dated Jan. 7, 2020, 15 pages.
International Search Report and Written Opinion for Application No. PCT/US2013/073678, dated May 27, 2014, 18 pages.
International Search Report and Written Opinion for Application No. PCT/US2014/058886, dated Mar. 3, 2015, 22 pages.
International Search Report and Written Opinion for Application No. PCT/US2015/047695, dated Jan. 28, 2016, 40 pages.
International Search Report and Written Opinion for Application No. PCT/US2015/047721, dated Feb. 3, 2016, 20 pages.
International Search Report and Written Opinion for Application No. PCT/US2016/016834, dated May 17, 2016, 11 pages.
Ito K., et al., "Biology of Fracture Healing," AO Principles of Fracture Management, AO Foundation Publishing, Jan. 2013, 5 pages.
Kaplan E.N., et al., "Clinical Utilization of Injectable Collagen," Annals of Plastic Surgery, Jun. 1983, vol. 10 (6), pp. 437-451.
Klein A.W., et al., "Implantation Technics for Injectable Collagen," Journal of the American Academy of Dermatology, Aug. 1983, vol. 9 (2), pp. 224-228.
Matton G., et al., "The History of Injectable Biomaterials and the Biology of Collagen," Aesthetic Plastic Surgery, Jun. 1985, vol. 9 (2), pp. 133-140.
O'Connor K.W., et al., "Endoscopic Placement of Collagen at the Lower Esophageal Sphincter to Inhibit Gastroesophageal Reftux: a Pilot Study of 10 Medically Intractable Patients," Gastrointestinal Endoscopy, 1988, vol. 34(2), pp. 106-112.
Russe E et al., "Micro-Fractional, Direction Skin Tightening: A Porcine Model," Lasers in Surgery and Medicine, Mar. 2016, vol. 48 (3), pp. 264-269.
Shortliffe L.M., et al., "Treatment of Urinary Incontinence by the Periurethral Implantation of Glutaraldehyde Cross-Linked Collagen," The Journal of Urology, Mar. 1989, vol. 141 (3), pp. 538-541.
Supplementary European Search Report for Application No. EP14850567 dated May 4, 2017, 4 pages.
Supplementary European Search Report for Application No. EP15836045 dated Jan. 8, 2018, 7 pages.
Supplementary European Search Report for Application No. EP17750972 dated Sep. 13, 2019, 8 pages.
Supplementary European Search Report for Application No. EP17793252 dated Nov. 22, 2019, 7 pages.
Supplementary European Search Report for Application No. EP13859972, dated Jun. 10, 2016, 6 pages.
Zuber T.J., "Fusiform Exision," American Family Physician, Apr. 2003, vol. 67 (7), pp. 1539-1544.

\* cited by examiner

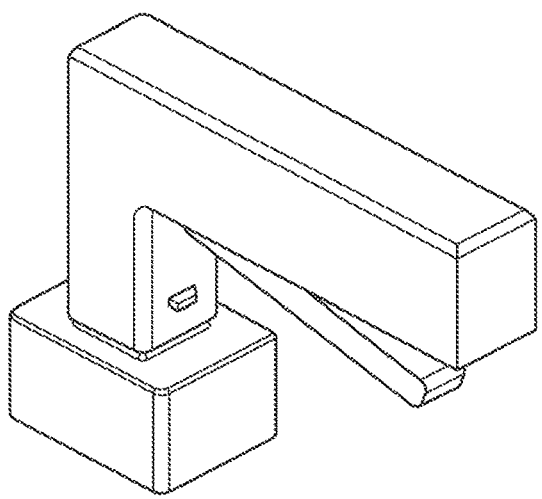
FIG. 18
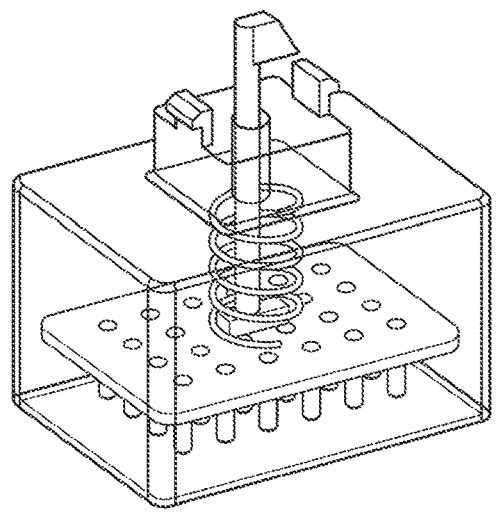 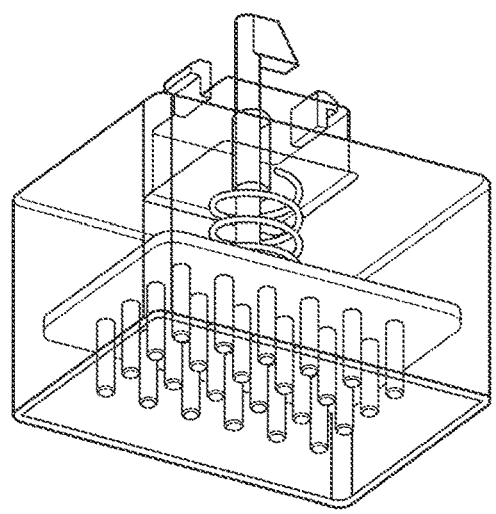
FIG. 19A  FIG. 19B
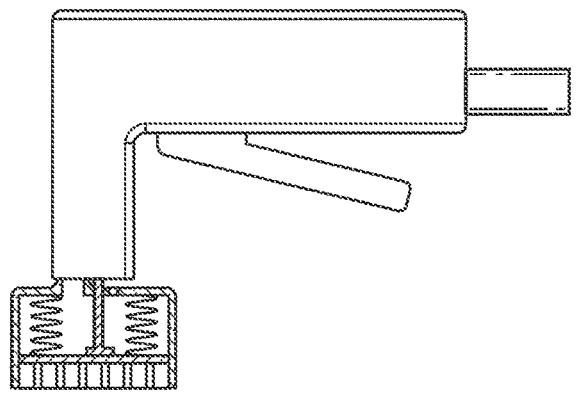
FIG. 20

Donor Hair Transplant Site

Recipient Hair Transplant Site

"Dog Ear" Redundancy

Elliptical Excision without "Dog Ear" but length of incision is increased

Fractional Resection of "Dog Ear"
Shorter incision without "Dog Ear"

Elliptical Excision of Lesion

Excision of Lesion with FR

Inframammary Incision Extended Beyond Inframammary Fold

Fractional Resection with Incision Kept within Inframammary Fold

Fractional Skin Graft Harvest

⇩ Directed Chose of Donor Site

PIXEL ARRAY MEDICAL SYSTEMS, DEVICES AND METHODS

RELATED APPLICATIONS

This application claims the benefit of U.S. Patent Application 62/456,775, filed Feb. 9, 2017.

This application claims the benefit of U.S. Patent Application No. 62/504,844, filed May 11, 2017.

This application is a continuation in part of U.S. patent application Ser. No. 14/556,648, filed Dec. 1, 2014, which is a continuation of U.S. patent application Ser. No. 12/972,013, filed Dec. 17, 2010, now U.S. Pat. No. 8,900,181.

This application is a continuation in part of U.S. patent application Ser. No. 15/812,952, filed Nov. 14, 2017.

This application is a continuation in part of U.S. patent application Ser. No. 14/099,380, filed Dec. 6, 2013.

This application is a continuation in part of U.S. patent application Ser. No. 15/821,258, filed Nov. 22, 2017.

This application is a continuation in part of U.S. patent application Ser. No. 14/505,090, filed Oct. 2, 2014.

This application is a continuation in part of U.S. patent application Ser. No. 14/505,183, filed Oct. 2, 2014.

This application is a continuation in part of U.S. patent application Ser. No. 15/821,325, filed Nov. 22, 2017.

This application is a continuation in part of U.S. patent application Ser. No. 14/840,274, filed Aug. 31, 2015.

This application is a continuation in part of U.S. patent application Ser. No. 14/840,284, filed Aug. 31, 2015.

This application is a continuation in part of U.S. patent application Ser. No. 14/840,267, filed Aug. 31, 2015.

This application is a continuation in part of U.S. patent application Ser. No. 14/840,290, filed Aug. 31, 2015.

This application is a continuation in part of U.S. patent application Ser. No. 14/840,307, filed Aug. 31, 2015.

This application is a continuation in part of U.S. patent application Ser. No. 15/016,954, filed Feb. 5, 2016.

This application is a continuation in part of U.S. patent application Ser. No. 15/017,007, filed Feb. 5, 2016.

This application is a continuation in part of U.S. patent application Ser. No. 15/431,230, filed Feb. 13, 2017.

This application is a continuation in part of U.S. patent application Ser. No. 15/431,247, filed Feb. 13, 2017.

TECHNICAL FIELD

The embodiments herein relate to medical systems, instruments or devices, and methods and, more particularly, to medical instrumentation and methods applied to the surgical management of burns, skin defects, and hair transplantation.

BACKGROUND

The aging process is most visibly depicted by the development of dependent skin laxity. This life long process may become evident as early as the third decade of life and will progressively worsen over subsequent decades. Histological research has shown that dependent stretching or age related laxity of the skin is due in part to progressive dermal atrophy associated with a reduction of skin tensile strength. When combined with the downward force of gravity, age related dermal atrophy will result in the two dimensional expansion of the skin envelope. The clinical manifestation of this physical-histological process is redundant skin laxity. The most affected areas are the head and neck, upper arms, thighs, breasts, lower abdomen and knee regions. The most visible of all areas are the head and neck. In this region, prominent "turkey gobbler" laxity of neck and "jowls" of the lower face are due to an unaesthetic dependency of skin in these areas.

Plastic surgery procedures have been developed to resect the redundant lax skin. These procedures must employ long incisions that are typically hidden around anatomical boundaries such as the ear and scalp for a facelift and the inframammary fold for a breast uplift (mastopexy). However, some areas of skin laxity resection are a poor tradeoff between the aesthetic enhancement of tighter skin and the visibility of the surgical incision. For this reason, skin redundancies of the upper arm, suprapatellar knees, thighs and buttocks are not routinely resected due to the visibility of the surgical scar.

The frequency and negative societal impact of this aesthetic deformity has prompted the development of the "Face Lift" surgical procedure. Other related plastic surgical procedures in different regions are the Abdominoplasty (Abdomen), the Mastopexy (Breasts), and the Brachioplasty (Upper Arms). Inherent adverse features of these surgical procedures are post-operative pain, scarring and the risk of surgical complications. Even though the aesthetic enhancement of these procedures is an acceptable tradeoff to the significant surgical incisions required, extensive permanent scarring is always an incumbent part of these procedures. For this reason, plastic surgeons design these procedures to hide the extensive scarring around anatomical borders such as the hairline (Facelift), the inframmary fold (Mastopexy), and the inguinal crease (Abdominoplasty). However, many of these incisions are hidden distant to the region of skin laxity, thereby limiting their effectiveness. Other skin laxity regions such as the Suprapatellar (upper-front) knee are not amendable to plastic surgical resections due to the poor tradeoff with a more visible surgical scar.

More recently, electromagnetic medical devices that create a reverse thermal gradient (i.e., Thermage) have attempted with variable success to tighten skin without surgery. At this time, these electromagnetic devices are best deployed in patients with a moderate amount of skin laxity. Because of the limitations of electromagnetic devices and potential side effects of surgery, a minimally invasive technology is needed to circumvent surgically related scarring and the clinical variability of electromagnetic heating of the skin. For many patients who have age related skin laxity (neck and face, arms, axillas, thighs, knees, buttocks, abdomen, bra line, ptosis of the breast), fractional resection of excess skin could augment a significant segment of traditional plastic surgery.

Even more significant than aesthetic modification of the skin envelope is the surgical management of burns and other trauma related skin defects. Significant burns are classified by the total body surface burned and by the depth of thermal destruction. First-degree and second-degree burns are generally managed in a non-surgical fashion with the application of topical creams and burn dressings. Deeper third-degree burns involve the full thickness thermal destruction of the skin. The surgical management of these serious injuries involves the debridement of the burn eschar and the application of split thickness grafts.

Any full thickness skin defect, most frequently created from burning, trauma, or the resection of a skin malignancy, can be closed with either skin flap transfers or skin grafts using current commercial instrumentation. Both surgical approaches require harvesting from a donor site. The use of a skin flap is further limited by the need of to include a pedicle blood supply and in most cases by the need to directly close the donor site.

The split thickness skin graft procedure, due to immunological constraints, requires the harvesting of autologous skin grafts, that is, from the same patient. Typically, the donor site on the burn patient is chosen in a non-burned area and a partial thickness sheet of skin is harvested from that area. Incumbent upon this procedure is the creation of a partial thickness skin defect at the donor site. This donor site defect is itself similar to a deep second-degree burn. Healing by re-epithelialization of this site is often painful and may be prolonged for several days. In addition, a visible donor site deformity is created that is permanently thinner and more de-pigmented than the surrounding skin. For patients who have burns over a significant surface area, the extensive harvesting of skin grafts may also be limited by the availability of non-burned areas.

For these reasons, there is a need in the rapidly expanding aesthetic market for instrumentation and procedures for aesthetic surgical skin tightening. There is also a need for systems, instruments or devices, and procedures that enable the repeated harvesting of skin grafts from the same donor site while eliminating donor site deformity.

INCORPORATION BY REFERENCE

Each patent, patent application, and/or publication mentioned in this specification is herein incorporated by reference in its entirety to the same extent as if each individual patent, patent application, and/or publication was specifically and individually indicated to be incorporated by reference.

BRIEF DESCRIPTION OF THE DRAWINGS

FIG. 18 shows a side perspective view of the PAD assembly, under an embodiment.

FIG. 19A shows a top perspective view of the scalpet device for use with the PAD assembly, under an embodiment.

FIG. 19B shows a bottom perspective view of the scalpet device for use with the PAD assembly, under an embodiment.

FIG. 20 shows a side view of the punch impact device including a vacuum component, under an embodiment.

FIG. 96 is an example depiction of "dog ear" skin redundancies in breast reduction and abdominoplasty.

FIG. 97 is a sPAD including a skived single scalpet with depth control, under an embodiment.

FIG. 98 is a sPAD including a standard single scalpet, under an embodiment.

FIG. 99 is a sPAD including a pencil-style gear reducing handpiece, under an embodiment.

FIG. 100 is a sPAD including a 3×3 centerless array, under an embodiment.

FIG. 101 is a sPAD including a cordless surgical drill for large arrays, under an embodiment.

FIG. 102 is a sPAD comprising a drill mounted 5×5 centerless array, under an embodiment.

FIG. 103 is a sPAD including a vacuum assisted pneumatic resection sPAD, under an embodiment.

FIG. 104 is a VAPR sPAD coupled to a drill via a DAC, under an embodiment.

FIG. 105 depicts the VAPR sPAD in a ready state (left), and an extended treatment state (right), under an embodiment.

FIG. 106 depicts the SAVR sPAD in a ready state (left), and a retracted state (right), under an embodiment.

FIG. 107A is a cross-sectional side view of a carrier including a vacuum manifold, under an embodiment.

Figure 107A:
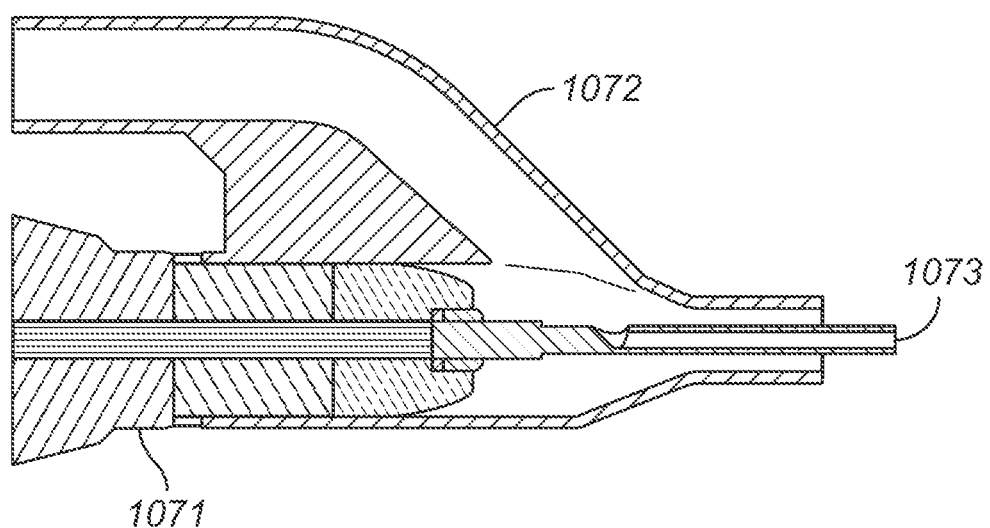
Figure 107B:
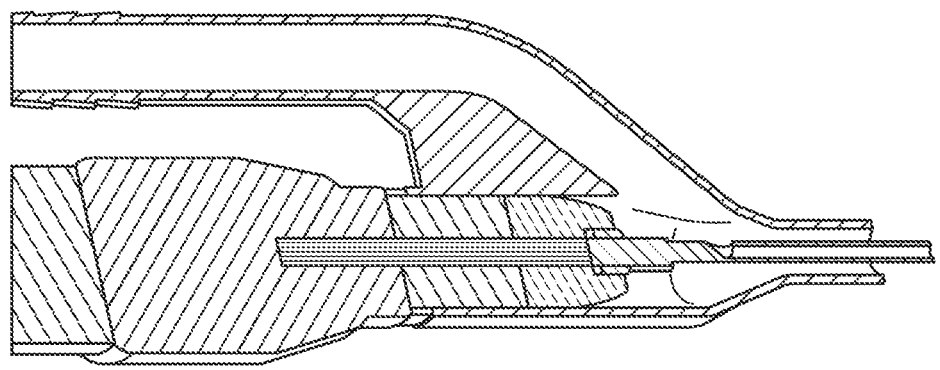

FIG. 107B is an isometric cross-sectional side view of the carrier including the vacuum manifold, under an embodiment.

Figure 107C:
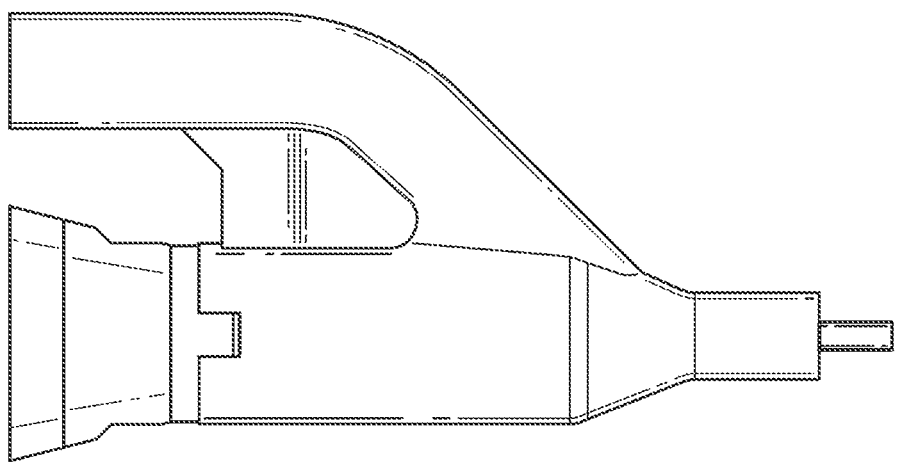

FIG. 107C is a side view of the carrier including the vacuum manifold, under an embodiment.

Figure 108:
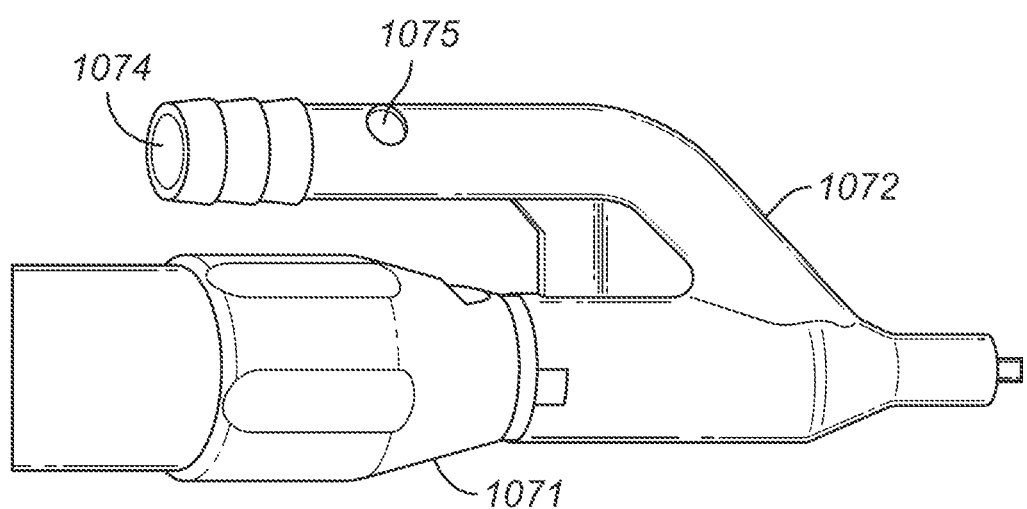

FIG. 108 is a solid side view of the carrier with the vacuum manifold configured for manual control via an aperture, under an embodiment.

Figure 109A:
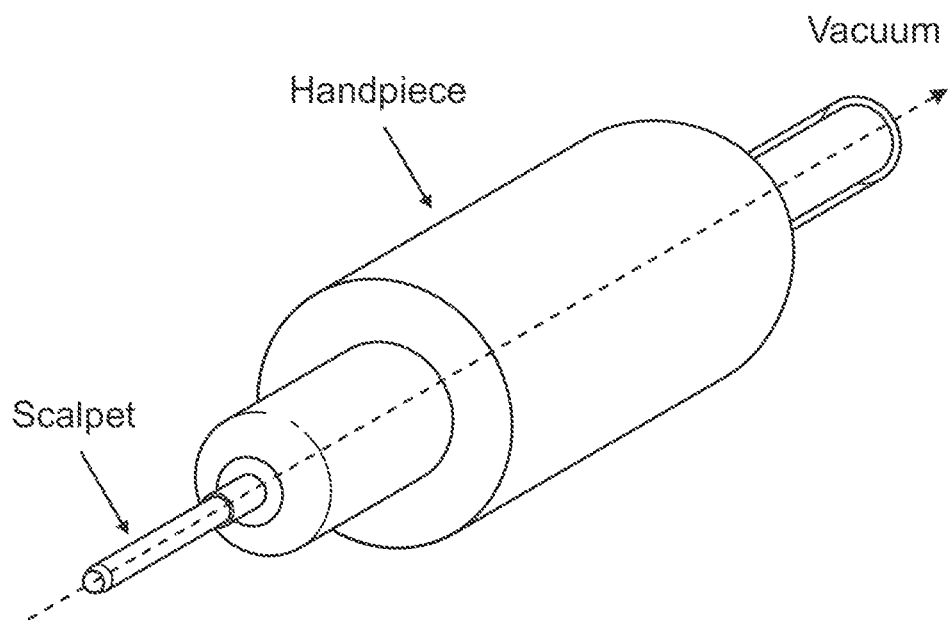

FIG. 109A is an isometric view of a handpiece configured to include or incorporate vacuum, under an embodiment.

Figure 109B:
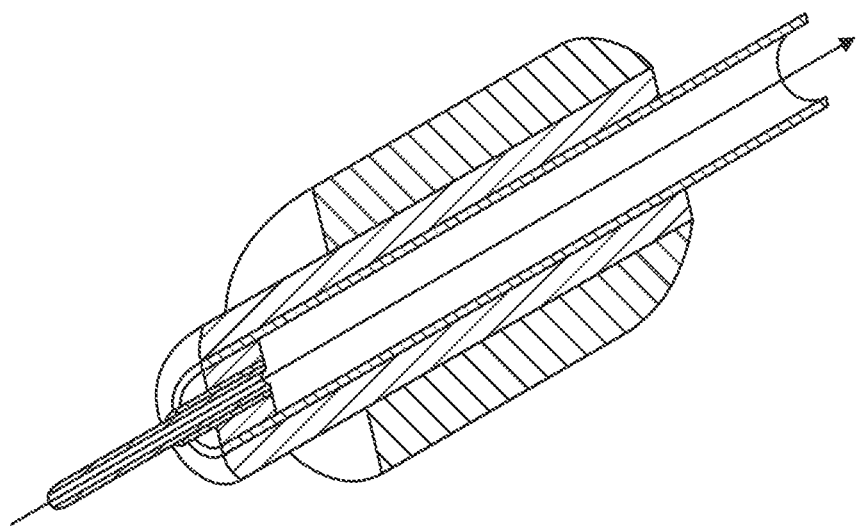

FIG. 109B is an isometric cutaway view of the handpiece configured to include or incorporate vacuum, under an embodiment.

Figure 110A:
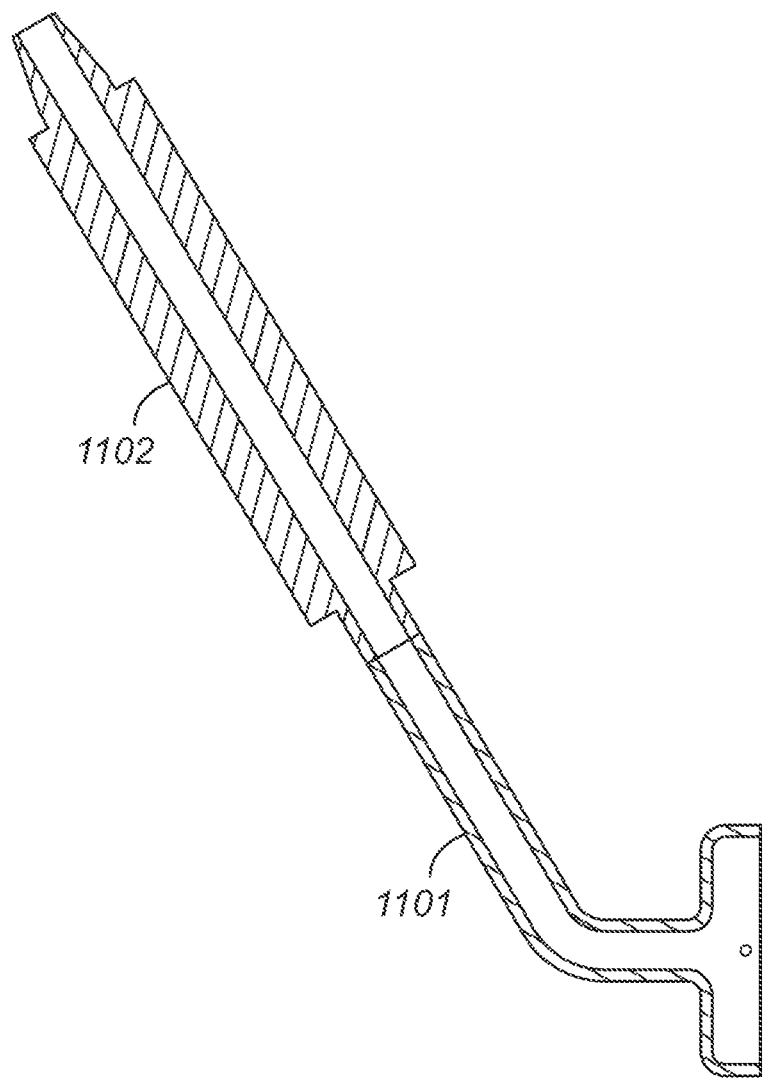

FIG. 110A is a cross-sectional side view of a vacuum manifold configured to be coupled or connected to an in-line vacuum component, under an embodiment.

Figure 110B:
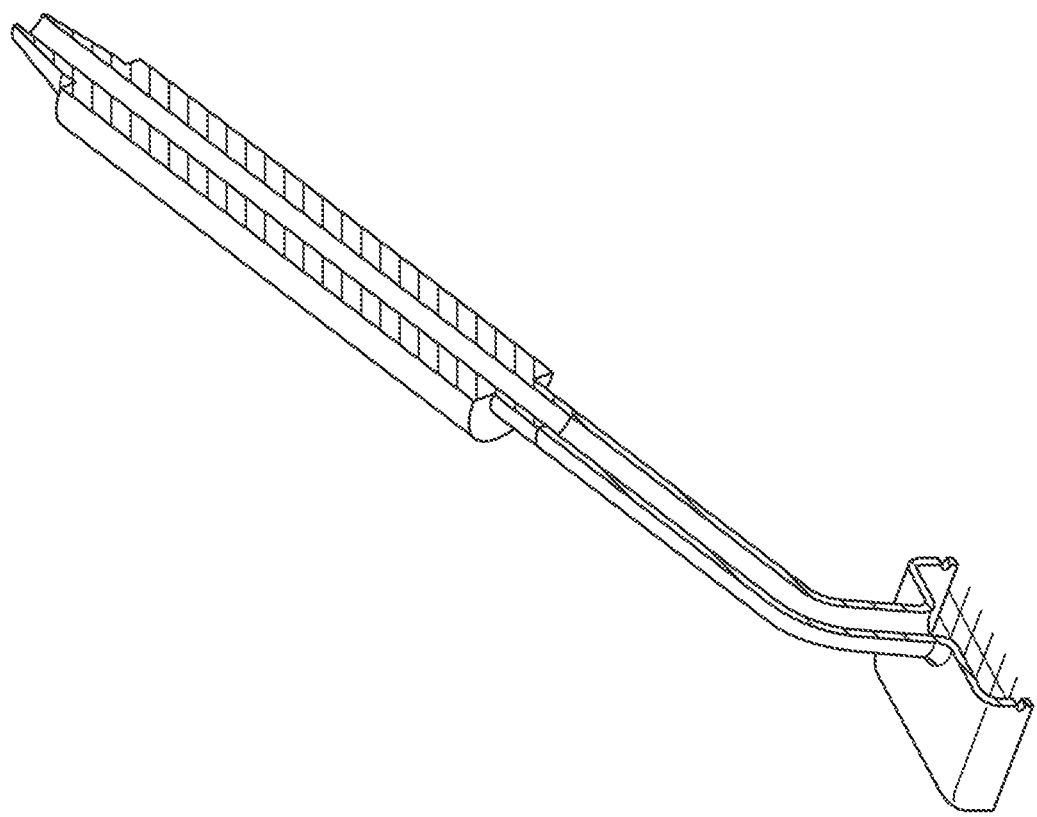

FIG. 110B is an isometric cross-sectional view of a vacuum manifold configured to be coupled or attached to an in-line vacuum component, under an embodiment.

Figure 110C:
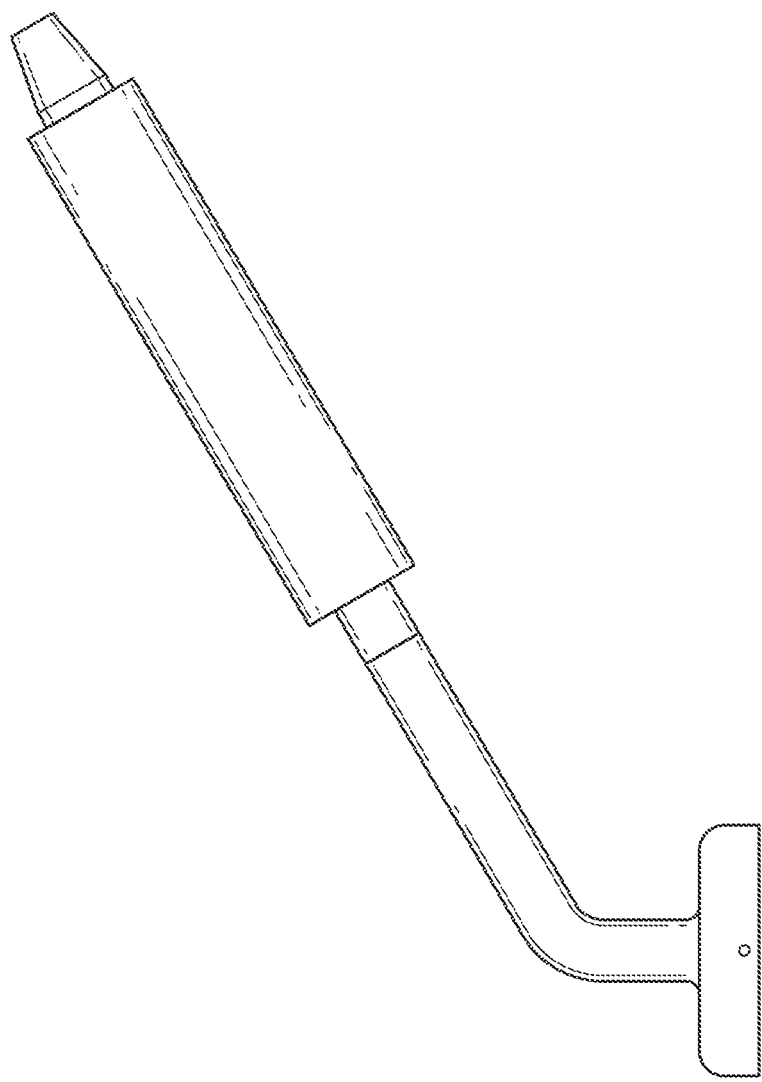

FIG. 110C is a solid side view of a vacuum manifold configured to be coupled or attached to an in-line vacuum component, under an embodiment.

Figure 111A:
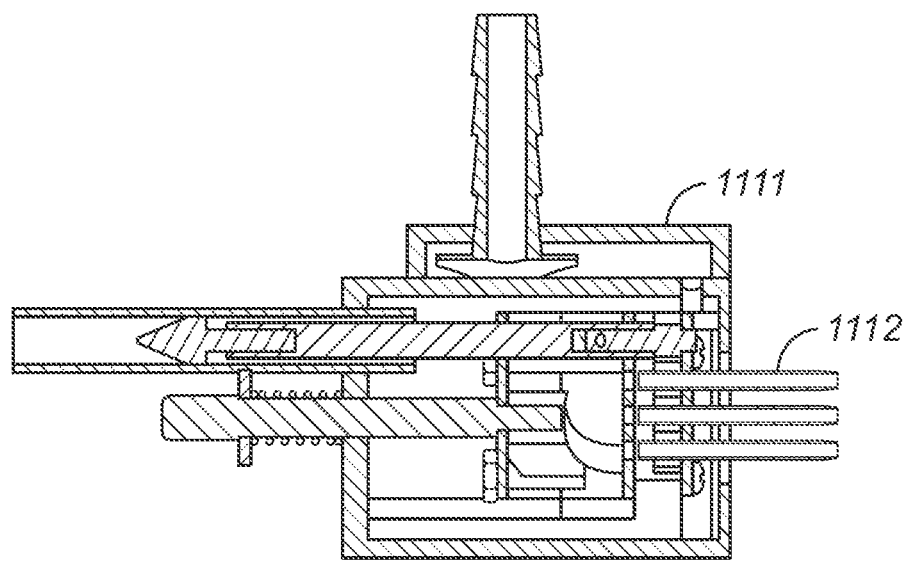

FIG. 111A is a cross-sectional side view of a scalpet array used with a vacuum aspirator, under an alternative embodiment.

Figure 111B:
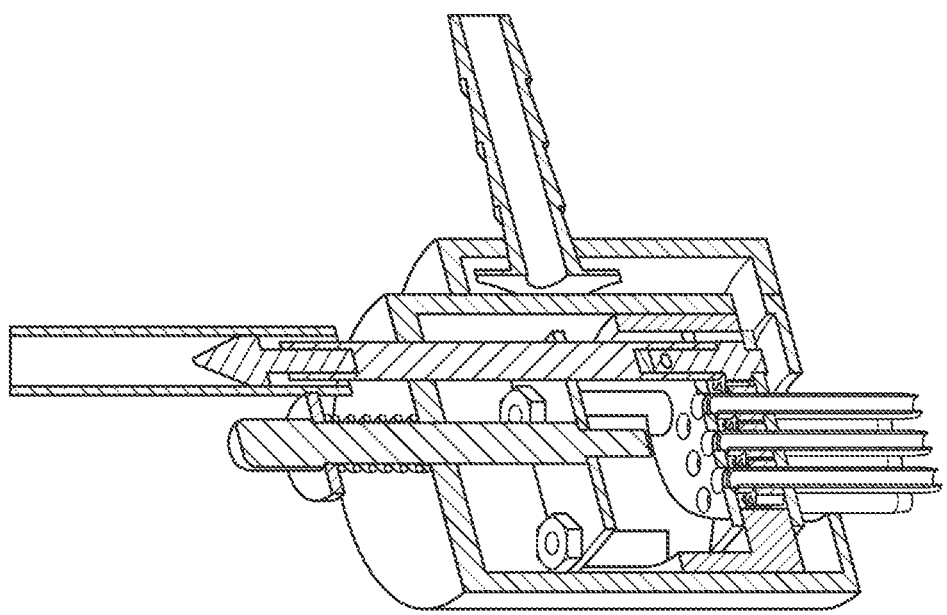

FIG. 111B is an isometric cross-sectional view of a scalpet array used with a vacuum aspirator, under an embodiment.

Figure 111C:
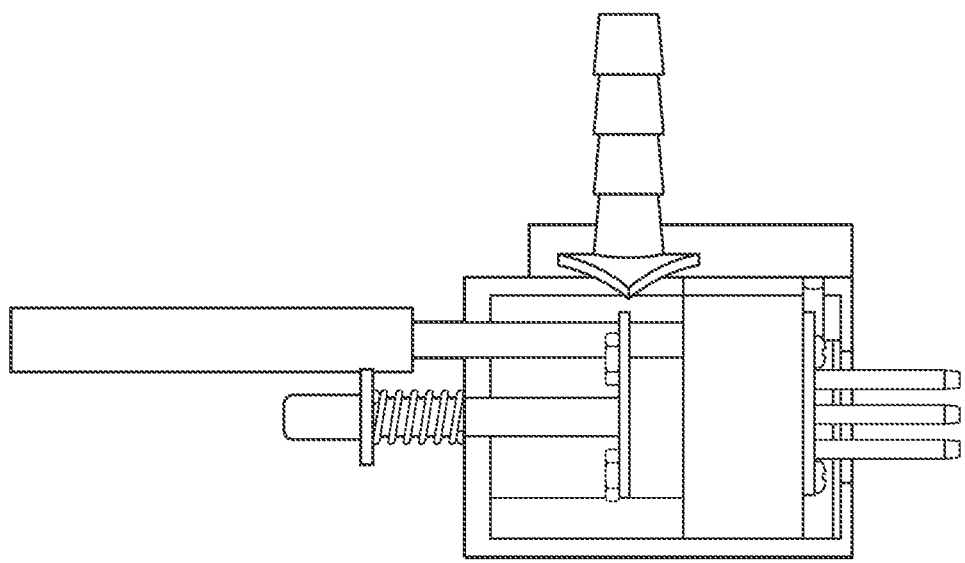

FIG. 111C is a side view of a scalpet array used with a vacuum aspirator, under an embodiment.

Figure 112:
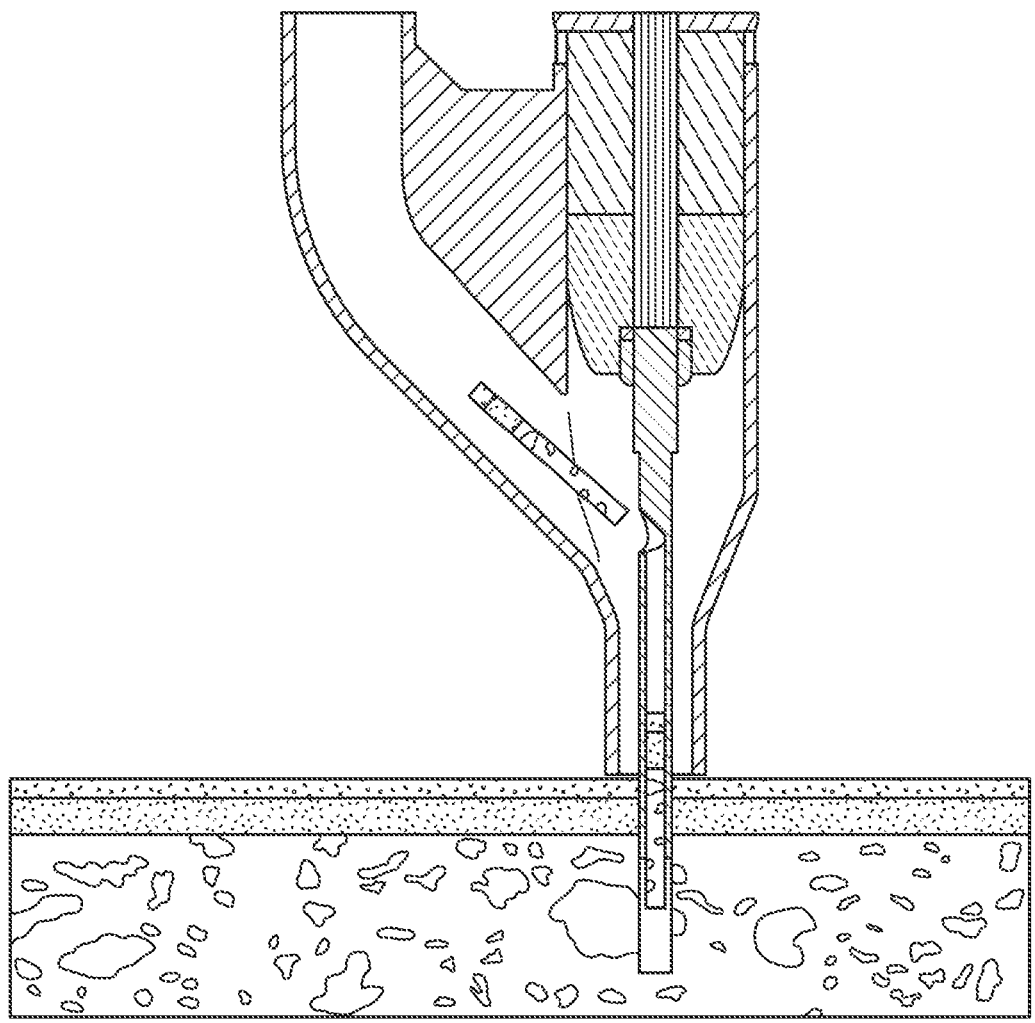

FIG. 112 is a cross-sectional side view of a single-scalpet device applied to a target tissue site, under an embodiment.

Figure 113:
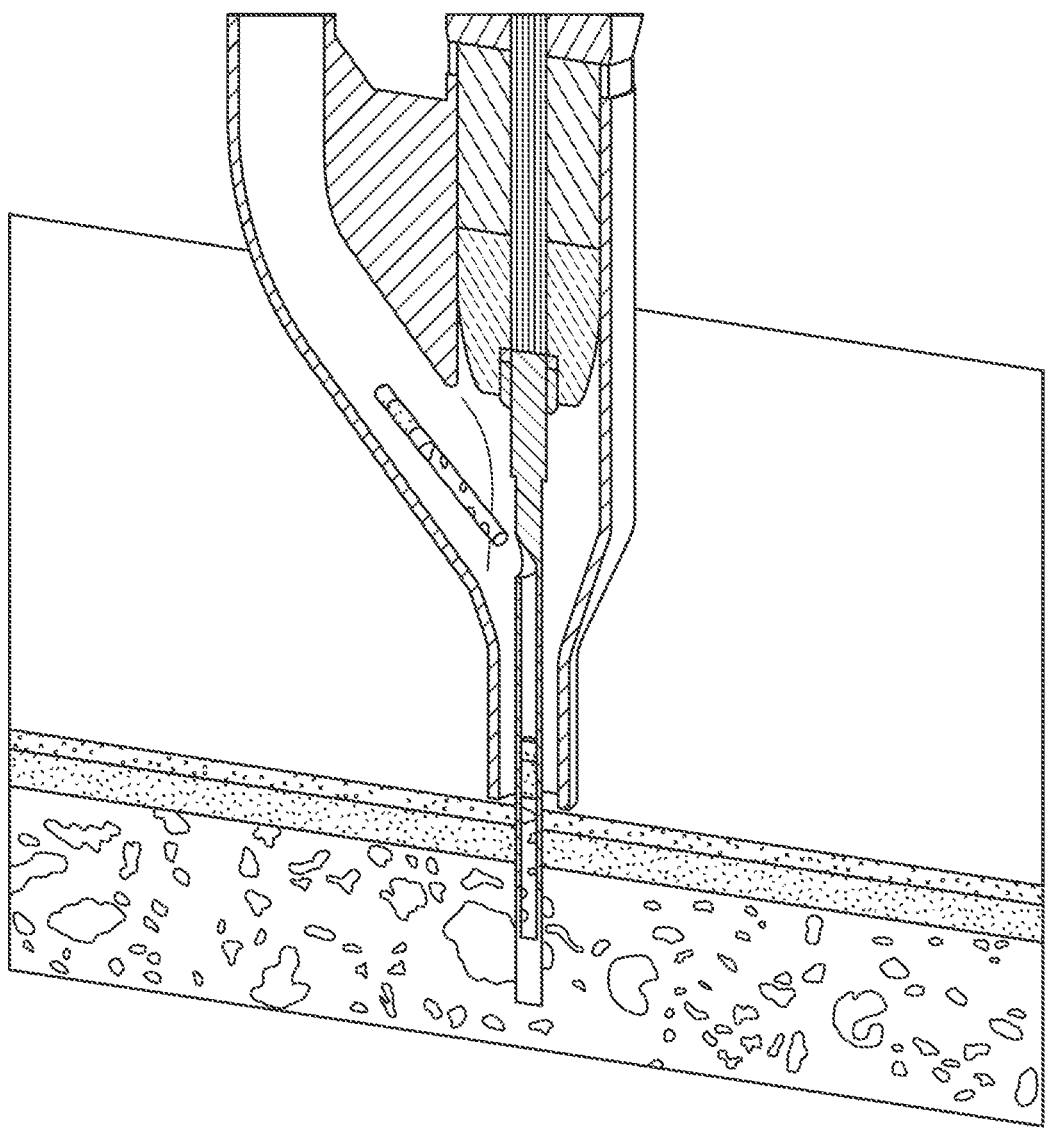

FIG. 113 is an isometric cross-sectional view of a single-scalpet device applied to a target tissue site, under an embodiment.

Figure 114A:
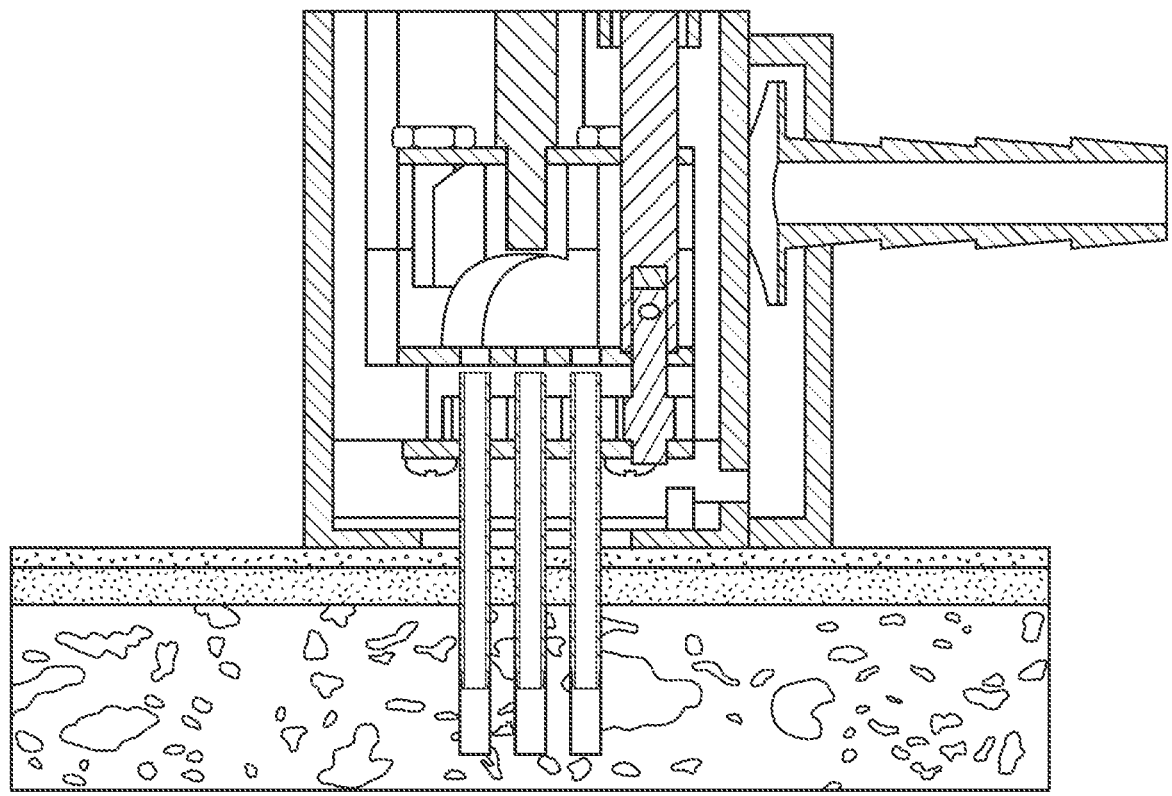

FIG. 114A is a cross-sectional side view of a multi-scalpet device applied to a target tissue site, under an embodiment.

Figure 114B:
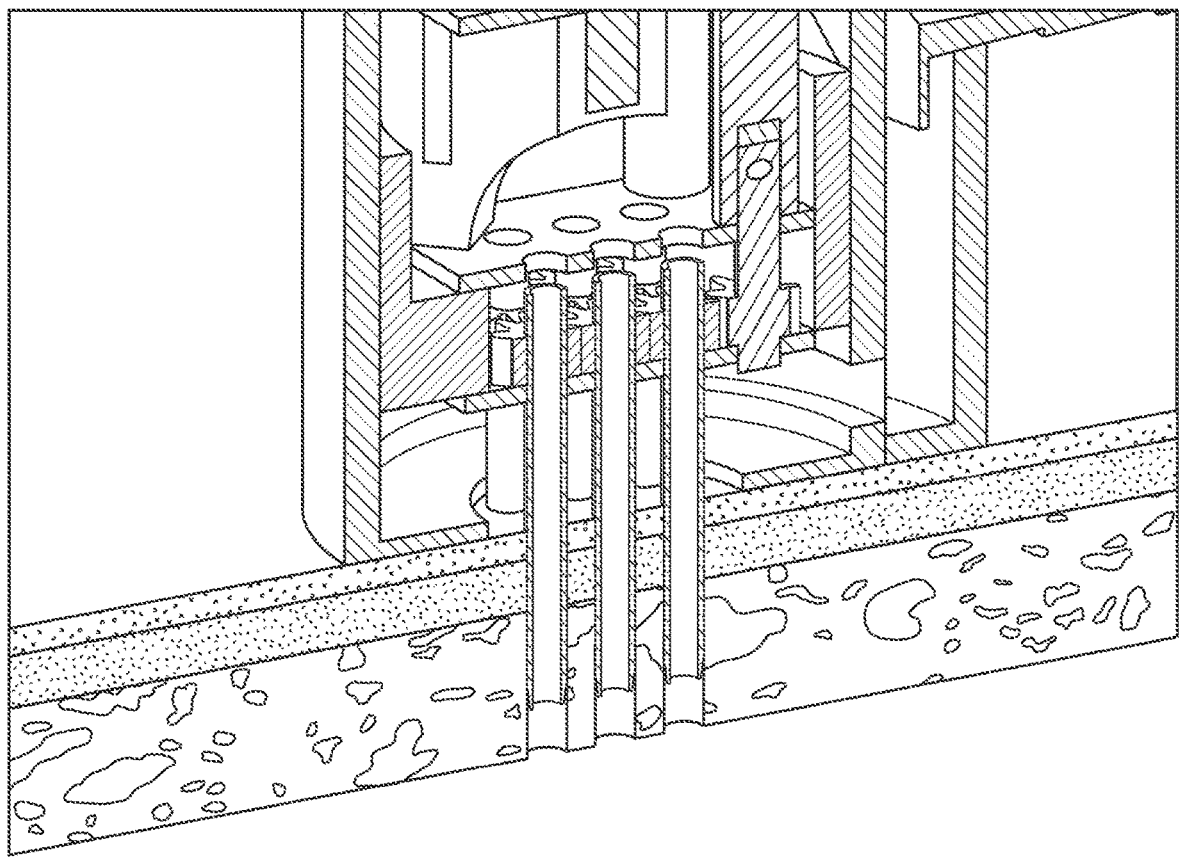

FIG. 114B is an isometric cross-sectional view of a multi-scalpet device applied to a target tissue site, under an embodiment.

Figure 115:
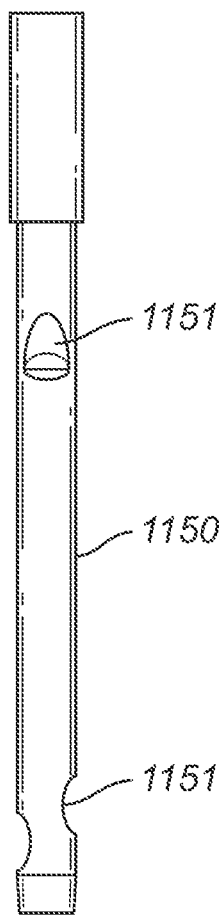

FIG. 115 is an example scalpet including apertures or slots, under an embodiment.

Figure 116:
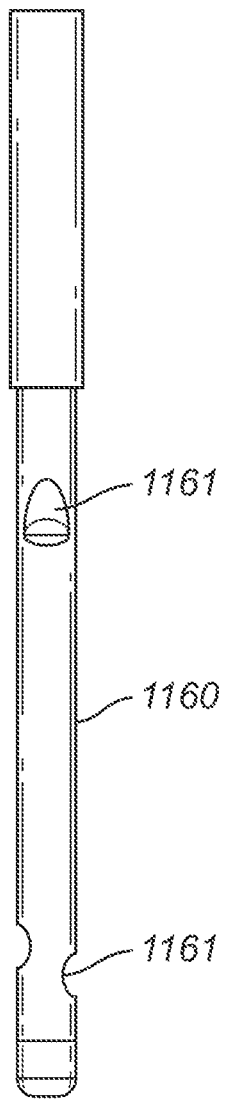

FIG. 116 is an example blunt micro-tip scalpet or cannula including apertures or slots, under an embodiment.

Figure 117:
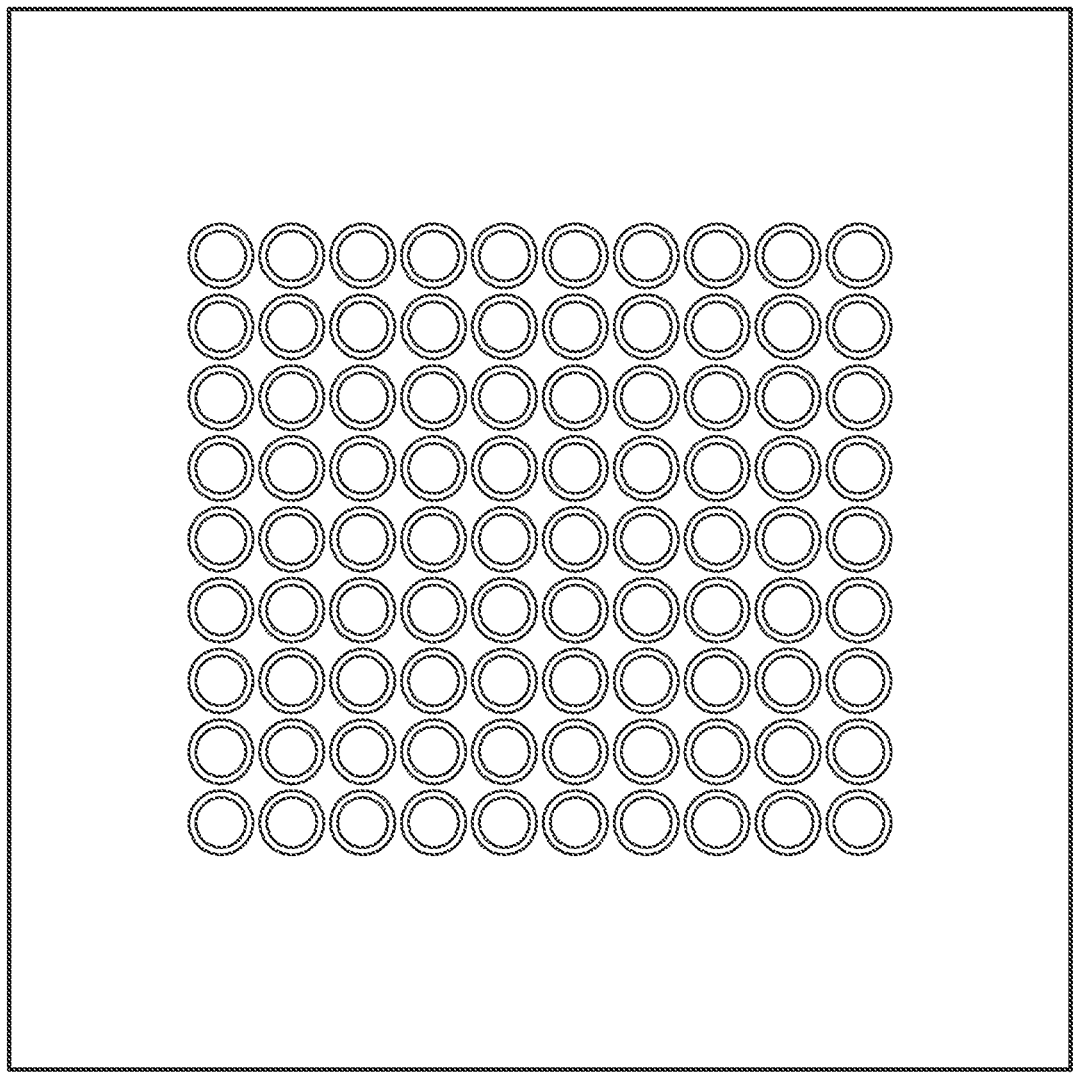

FIG. 117 is an example negative stencil marking system, under an embodiment.

Figure 118:
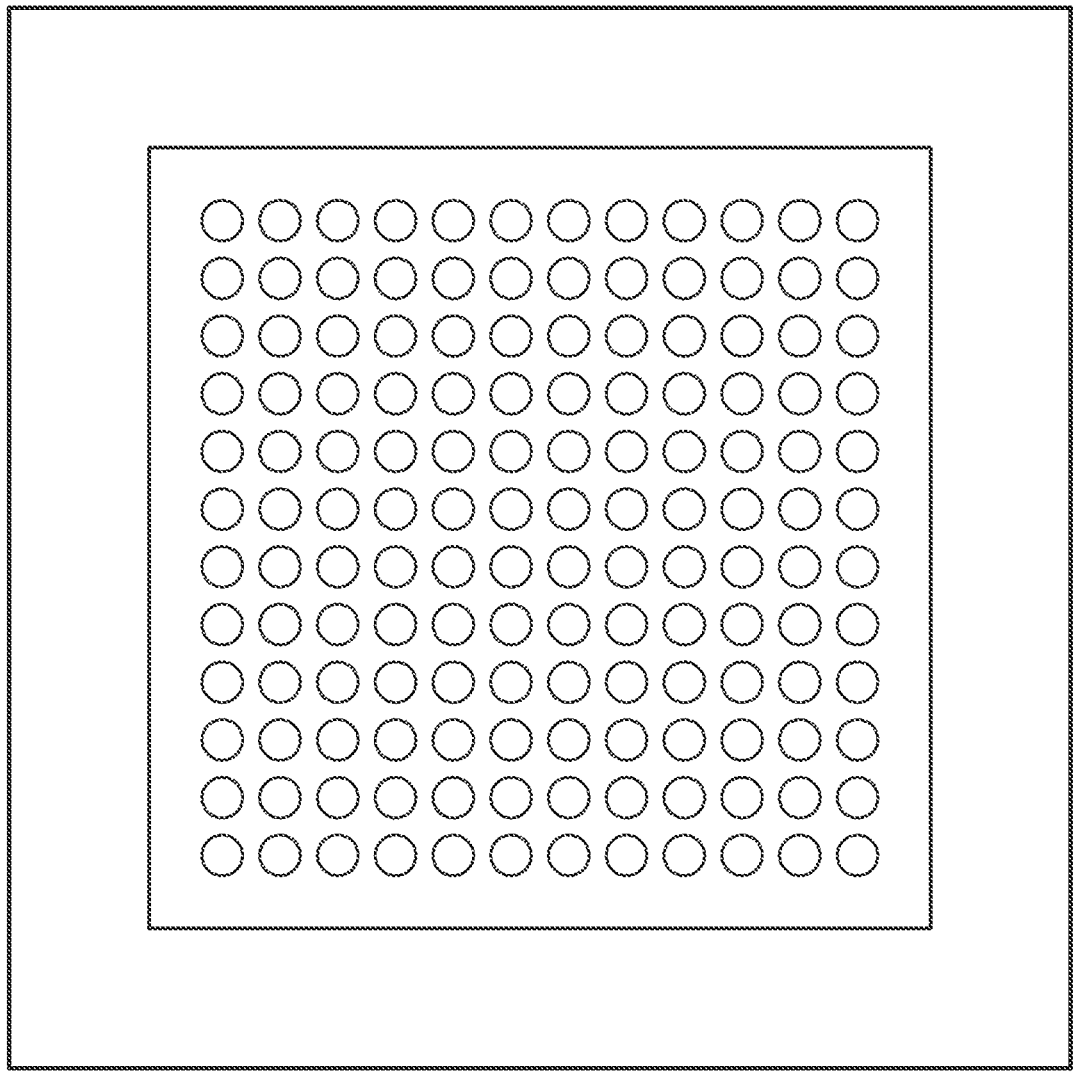

FIG. 118 is an example positive stencil marking system, under an embodiment.

Figure 119A:
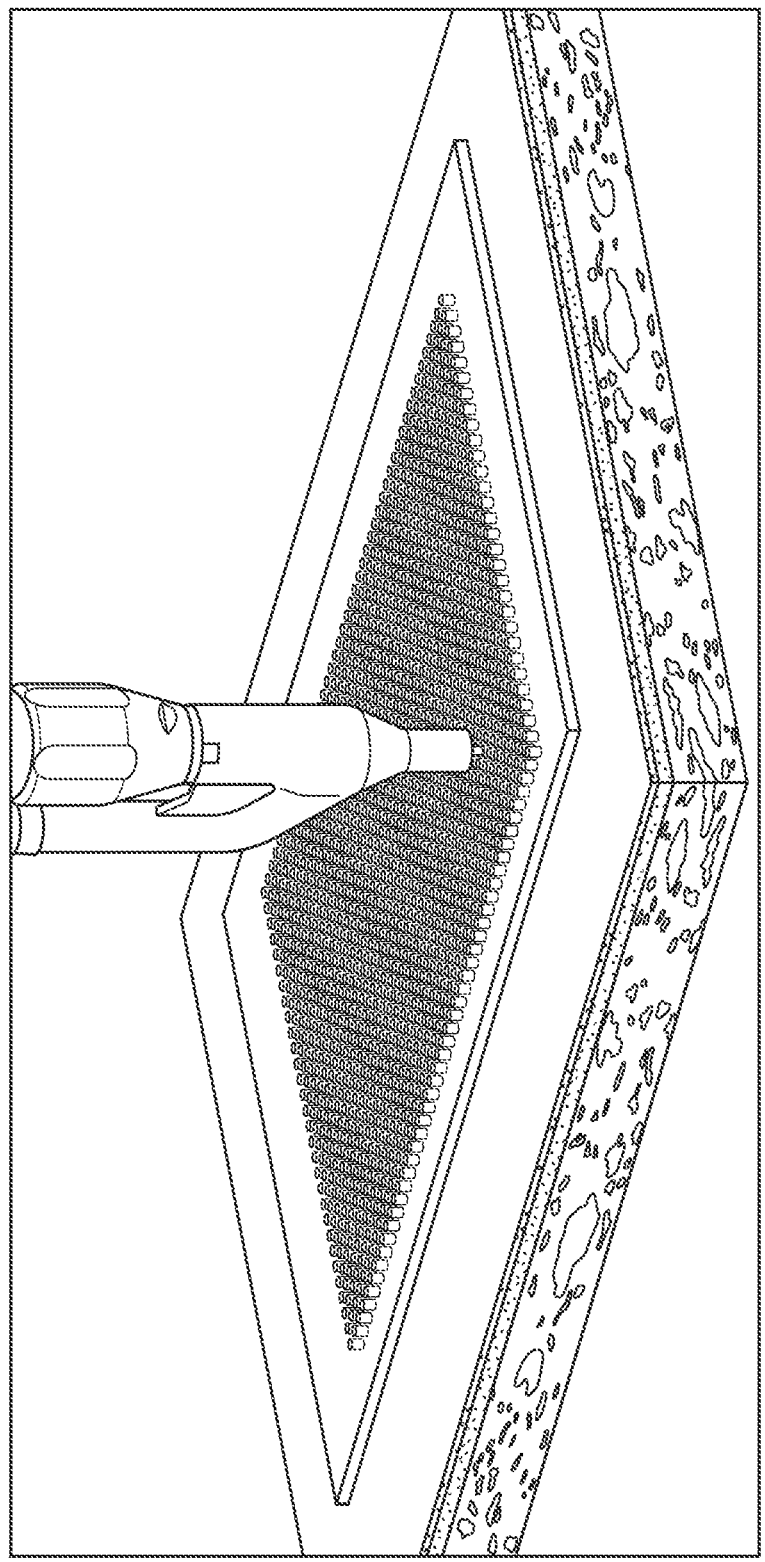

FIG. 119A shows a side view of the ASPPMP in use as a depth guide with the single-scalpet device, under an embodiment.

Figure 119B:
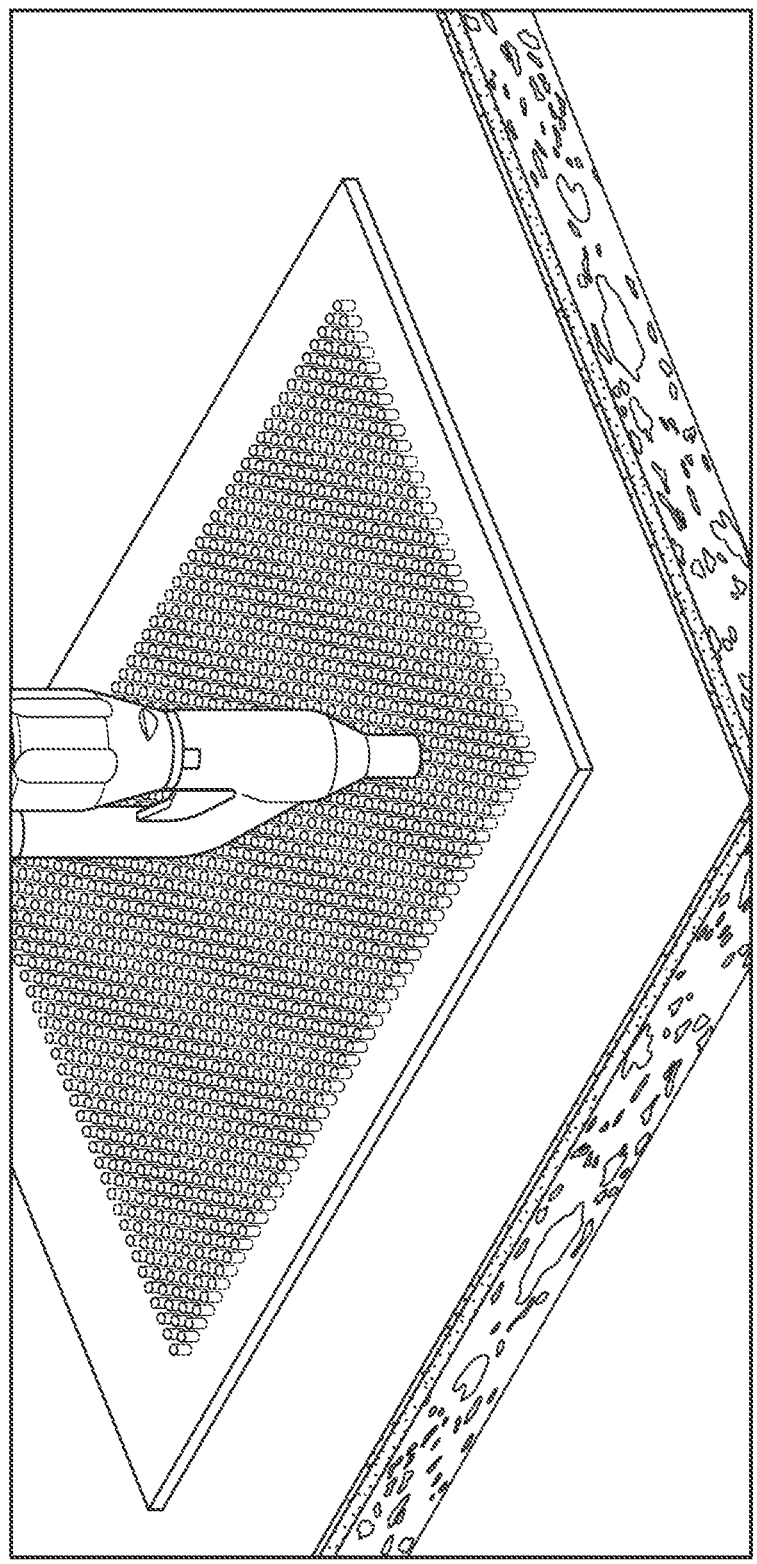

FIG. 119B shows a top isometric view of the ASPPMP in use as a depth guide with the single-scalpet device, under an embodiment.

Figure 120:
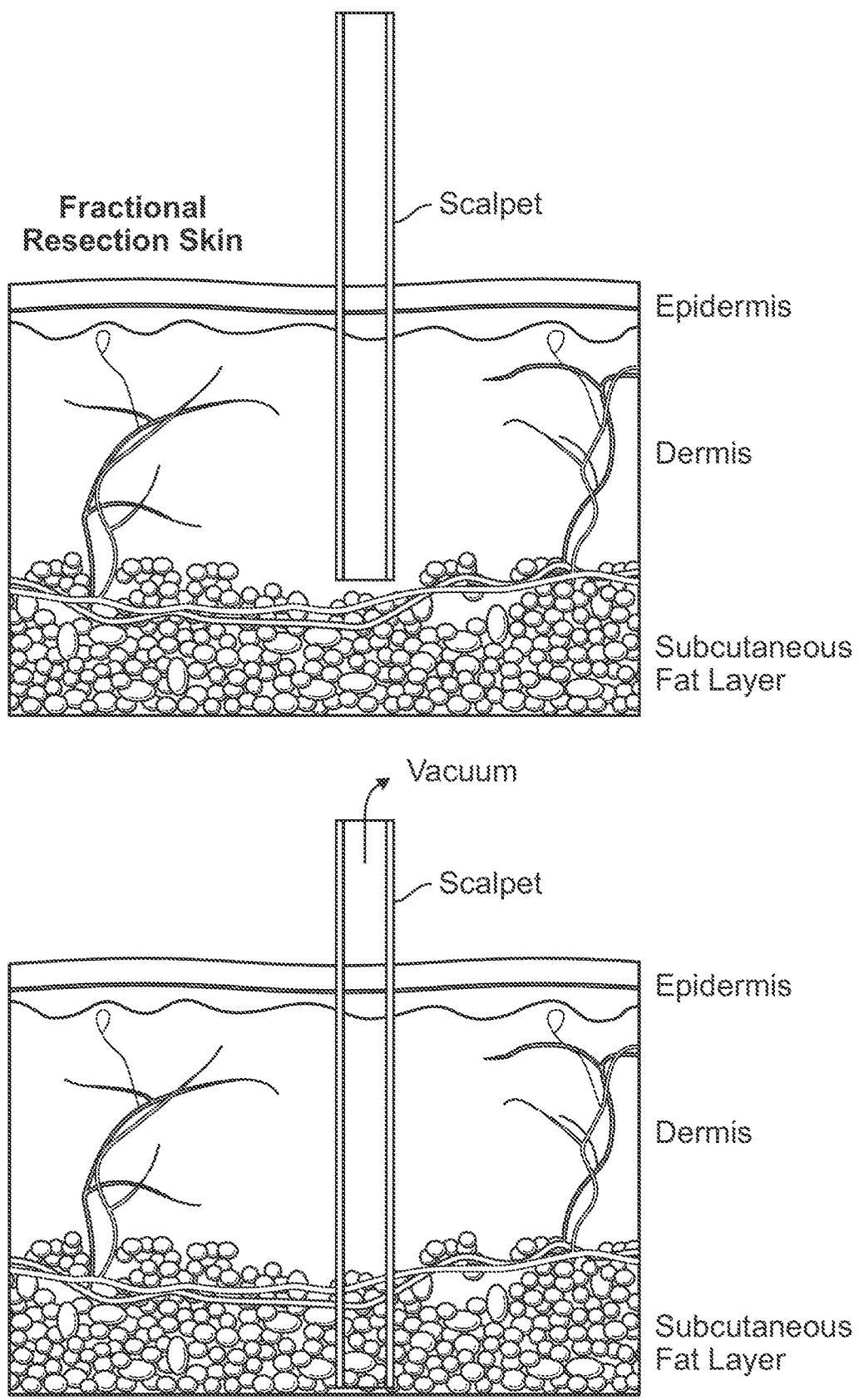

FIG. 120 shows fractional resection of skin and fractional subdermal/subcutaneous lipectomy, under an embodiment.

Figure 121:
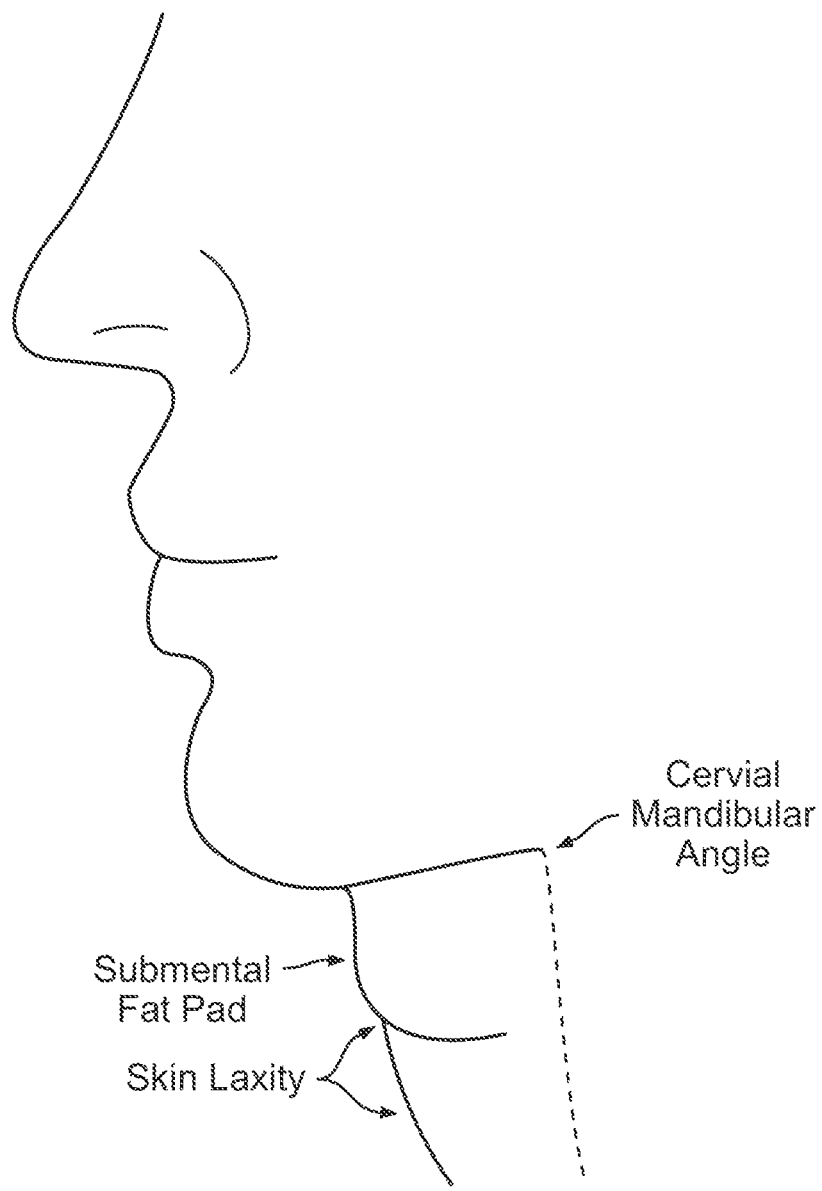

FIG. 121 shows a side view of the submentum as a target area for fractional resection of skin and fractional subdermal/subcutaneous lipectomy, under an embodiment.

Figure 122:
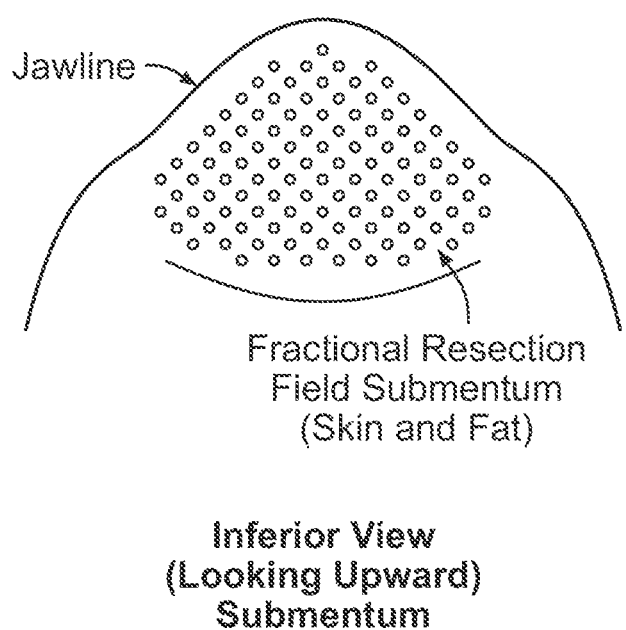

FIG. 122 shows an inferior view (looking upward) of the fractional resection field submentum as a target area for fractional resection of skin and fractional subdermal/subcutaneous lipectomy, under an embodiment.

Figure 123:
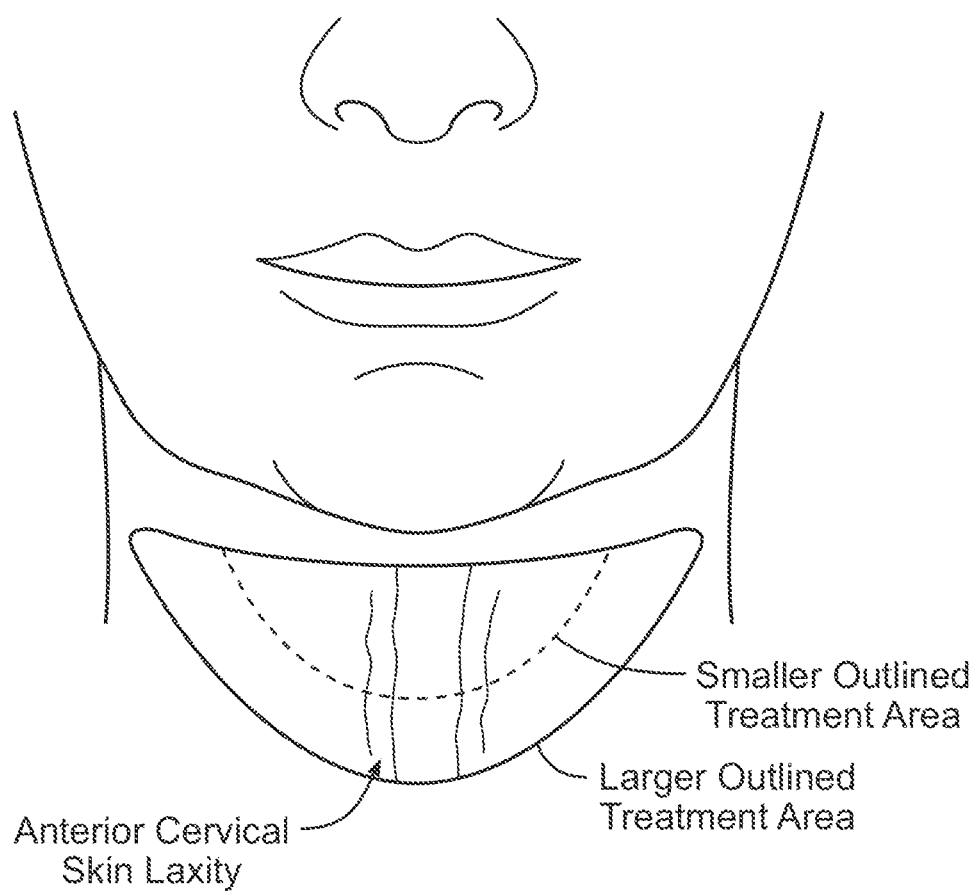

FIG. 123 shows a horizontally aligned treatment area in the submentum and lateral neck for severe skin laxity, under an embodiment.

Figure 124:
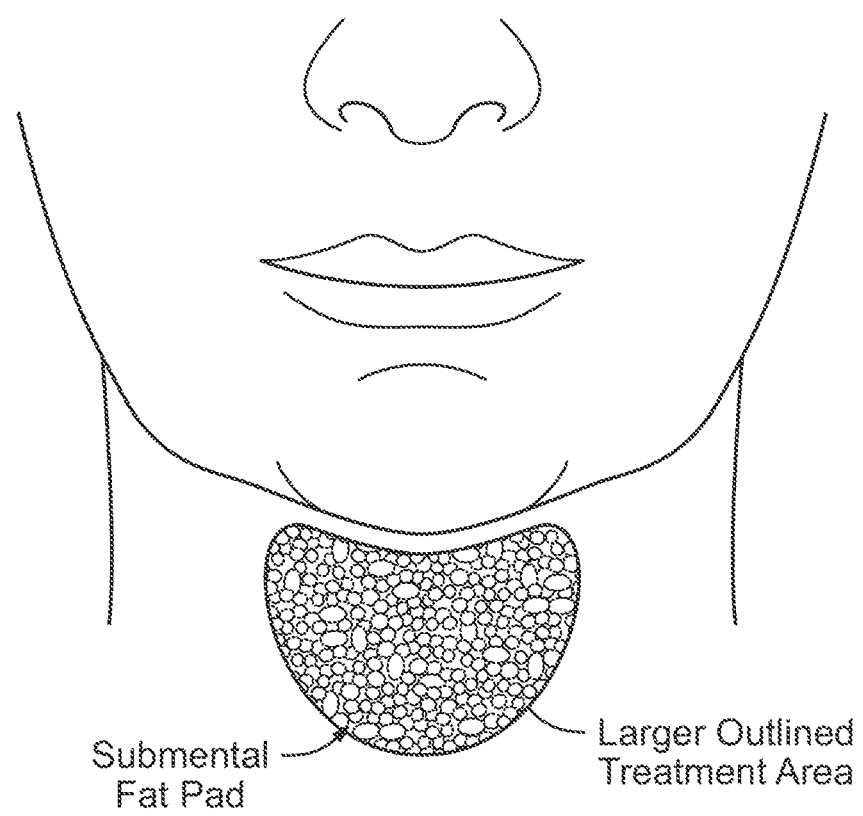

FIG. 124 shows broader fractional lipectomy in the submentum for severe lipodystrophy, under an embodiment.

Figure 125:
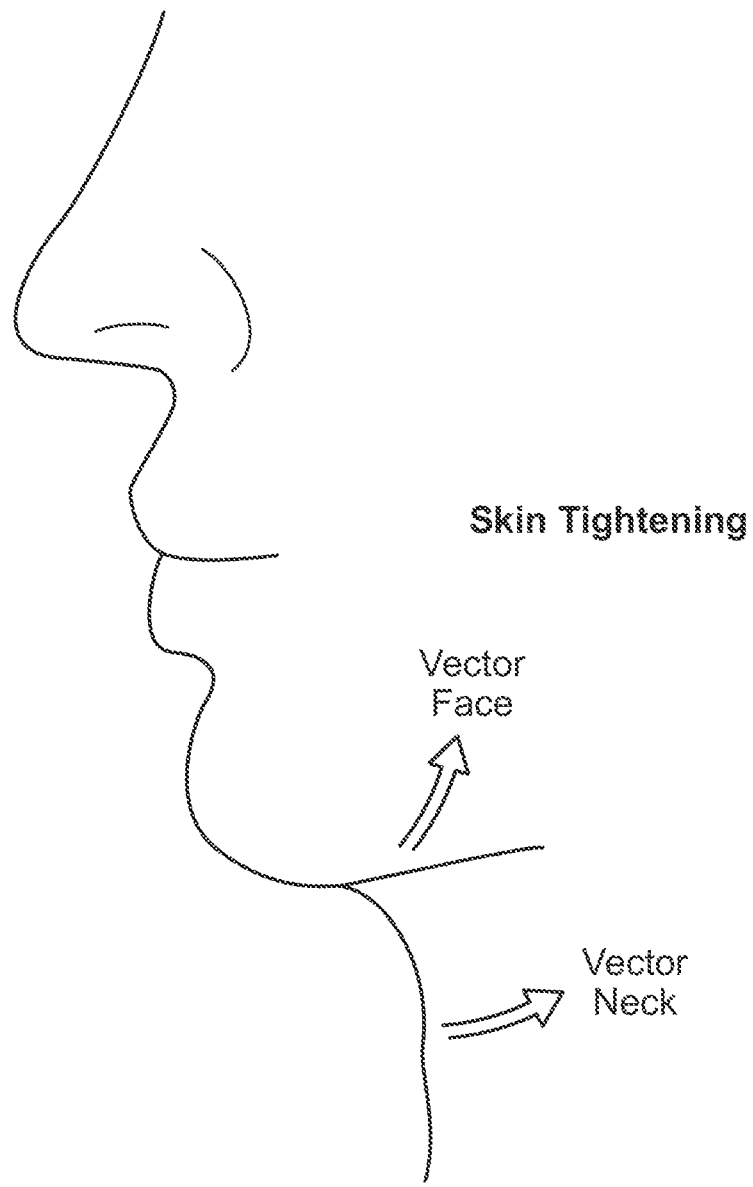

FIG. 125 shows example face vector and neck vector directed closures, under an embodiment.

Figure 126:
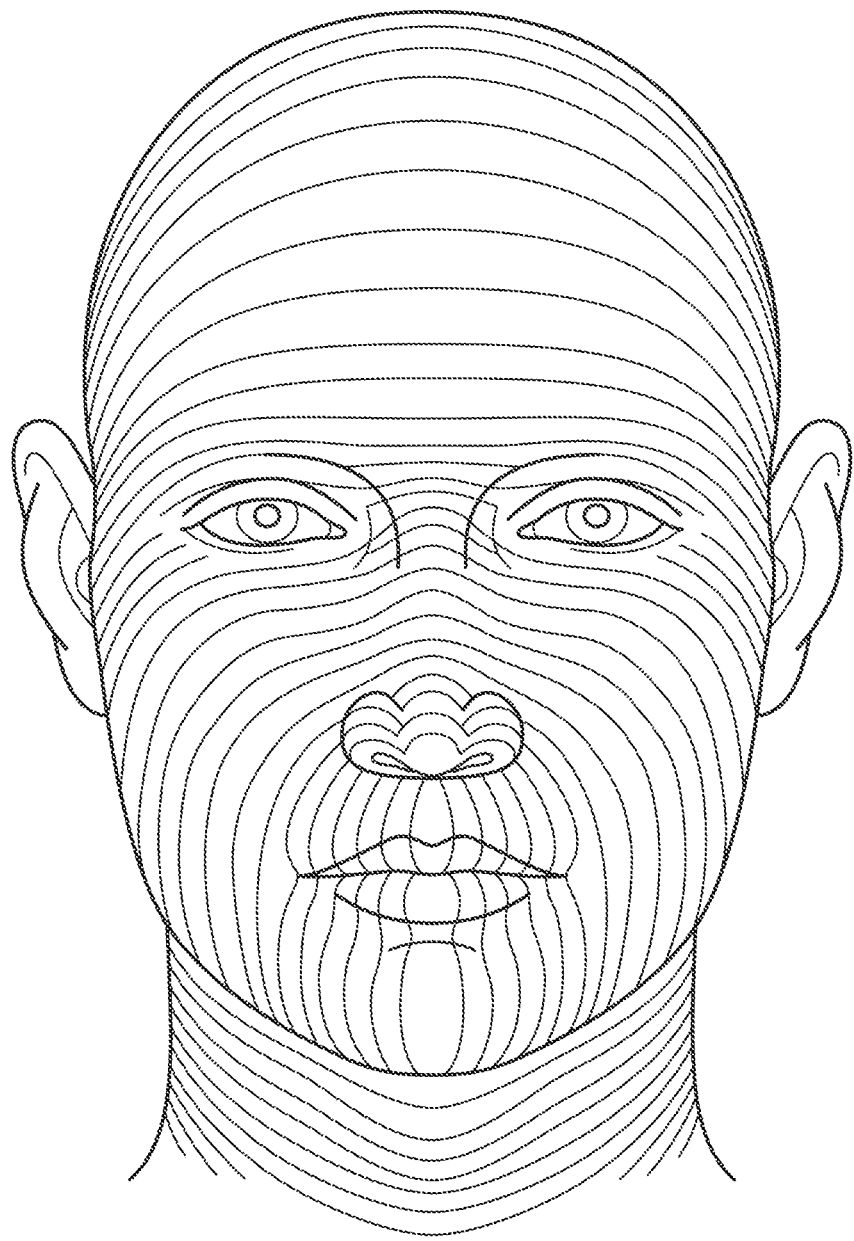

FIG. 126 shows Langer's lines of closure.

Figure 127:
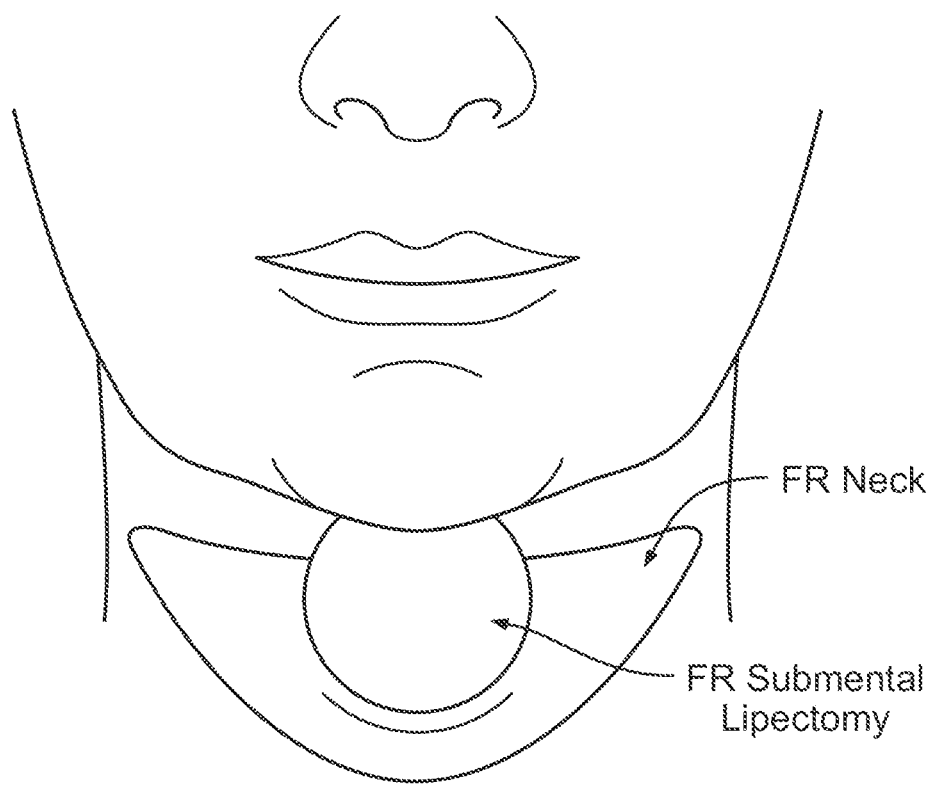

FIG. 127 shows marked target areas for fractional resection of neck and submental lipectomy, under an embodiment.

Figure 128:
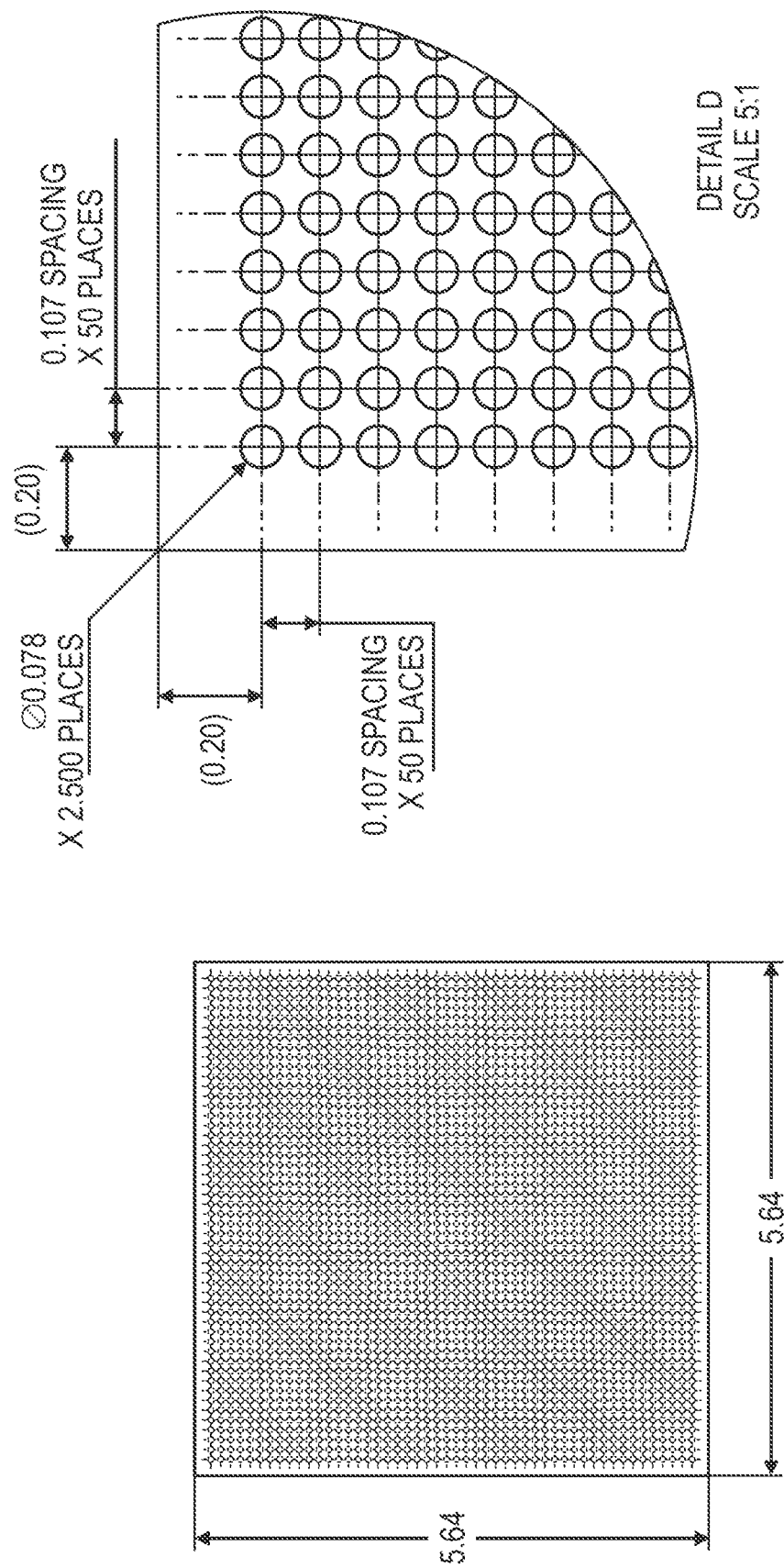

FIG. 128 shows an example stencil, under an embodiment.

Figure 129:
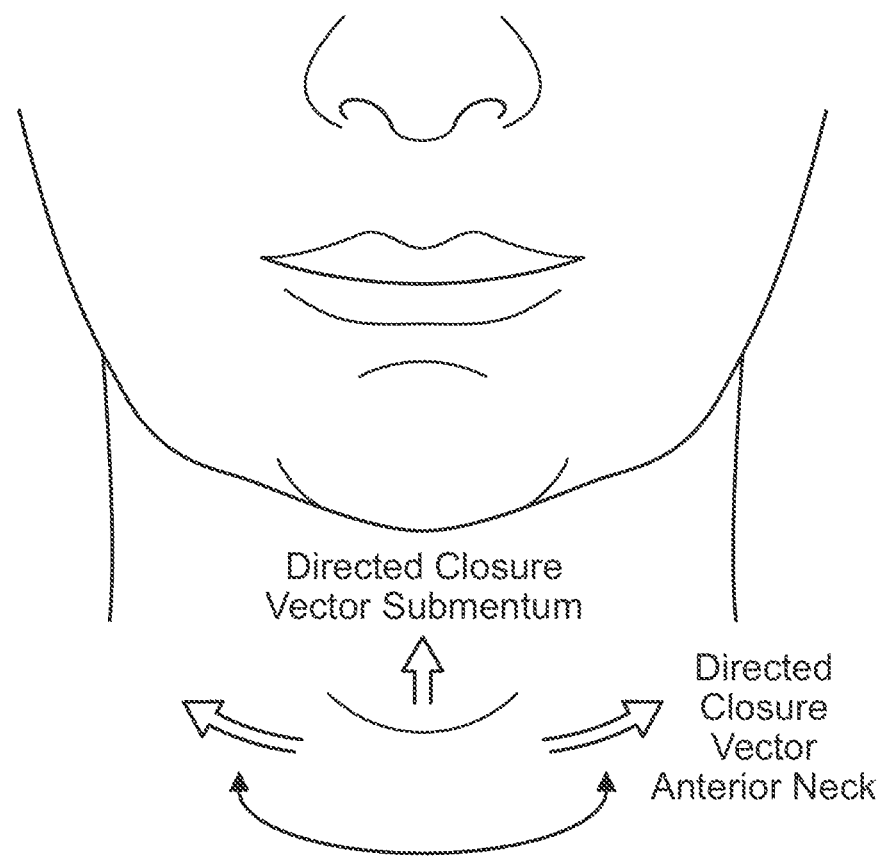

FIG. 129 shows example directed closure vectors of the submentum and anterior neck, under an embodiment.

Figure 130:
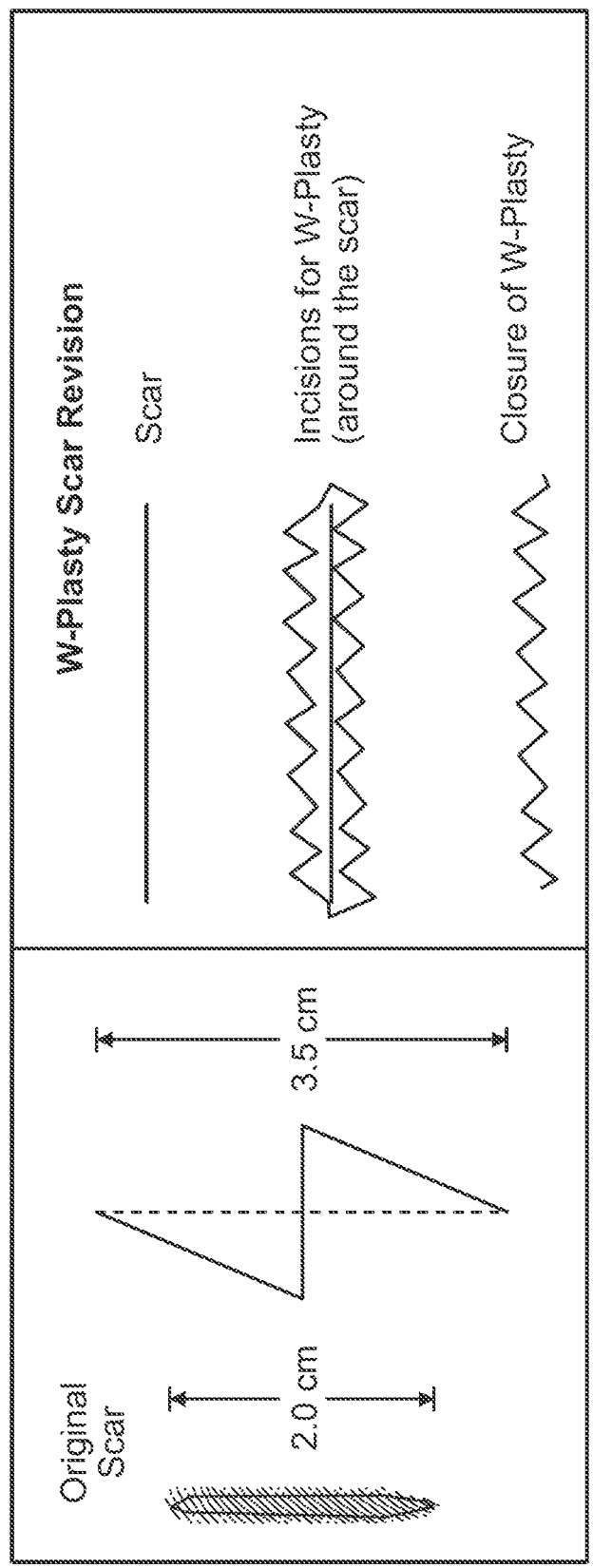

FIG. 130 depicts Z-plasty and W-plasty scar revision.

Figure 131:
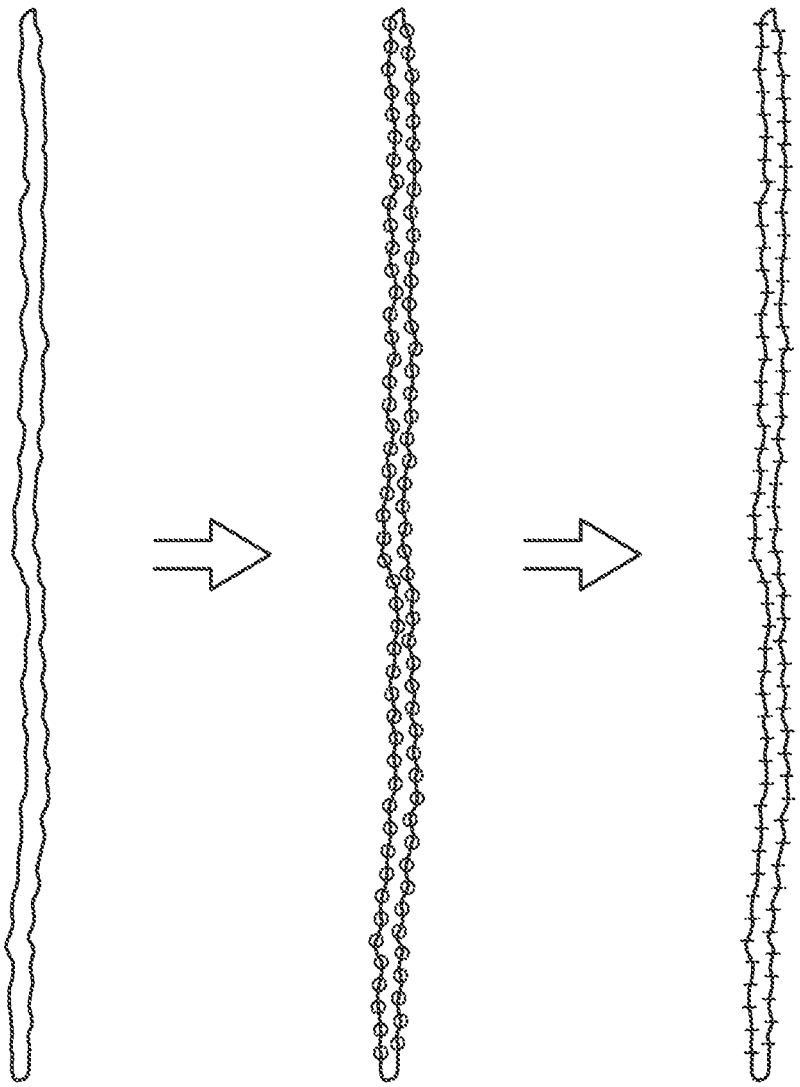

FIG. 131 shows an example of the fractional de-delineation technique of scar resection, under an embodiment.

Figure 132:
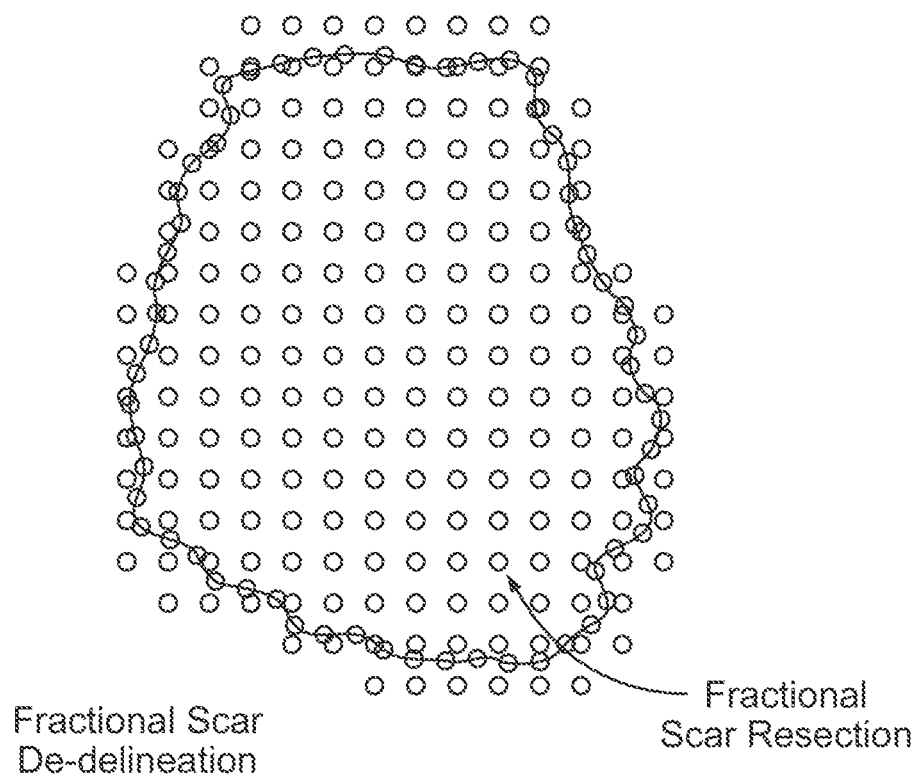

FIG. 132 shows an example of the fractional scar resection for broad hypotrophic scars, under an embodiment.

Figure 133:
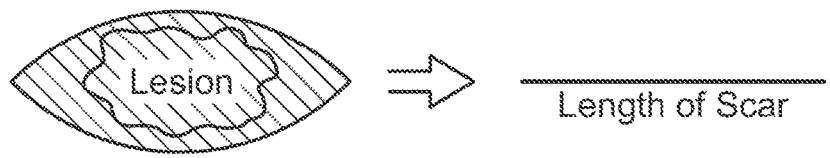
Figure 133:
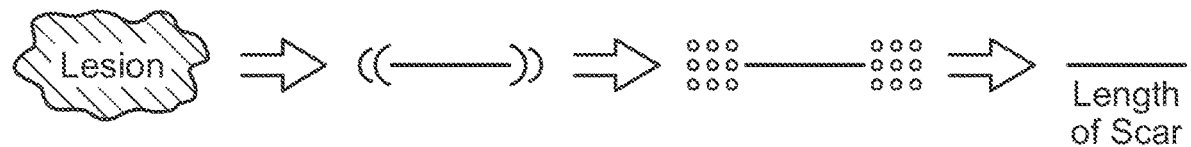
Figure 133:
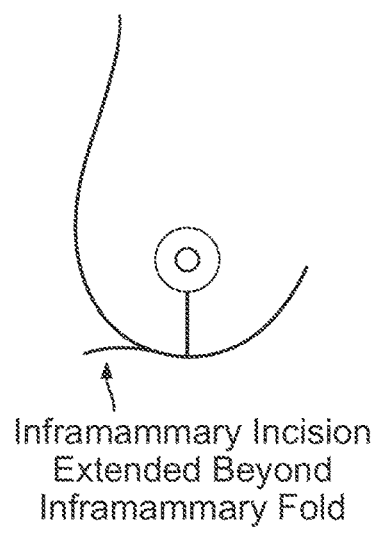
Figure 133:
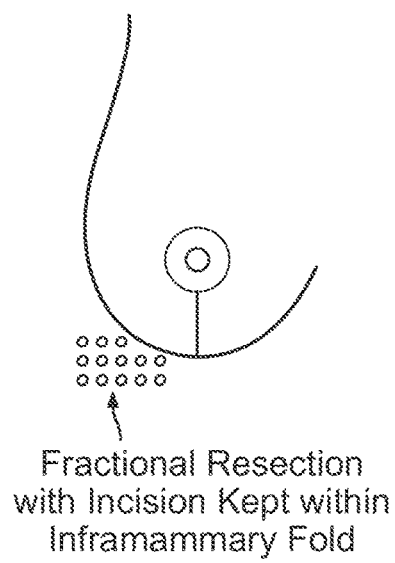

FIG. 133 shows an example comprising shortening of the inframammary incision as applied to breast reduction and/or breast repositioning, under an embodiment.

Figure 134:
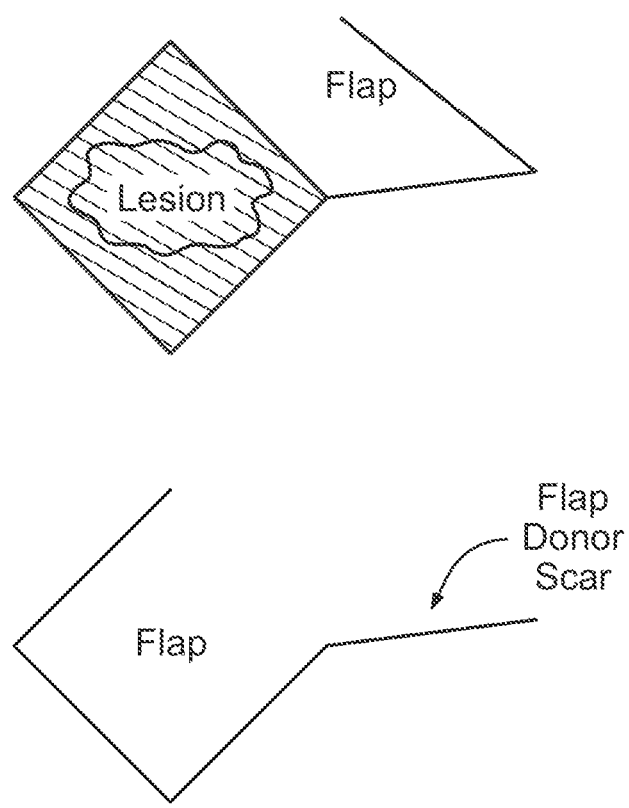

FIG. 134 shows an example flap closure.

Figure 135:
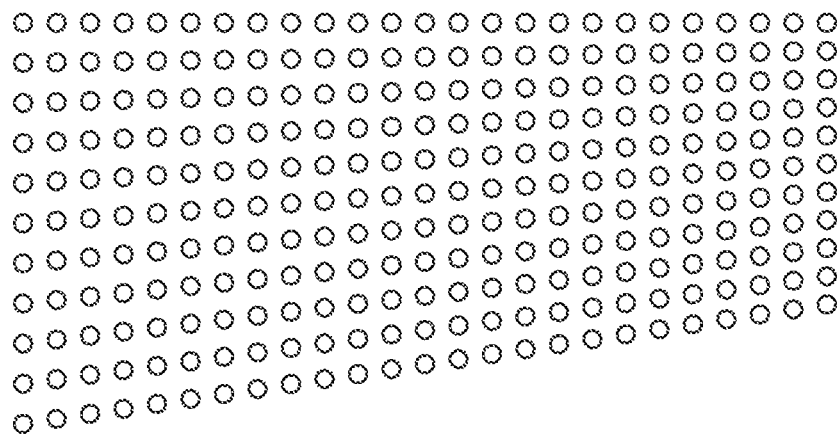
Figure 135:
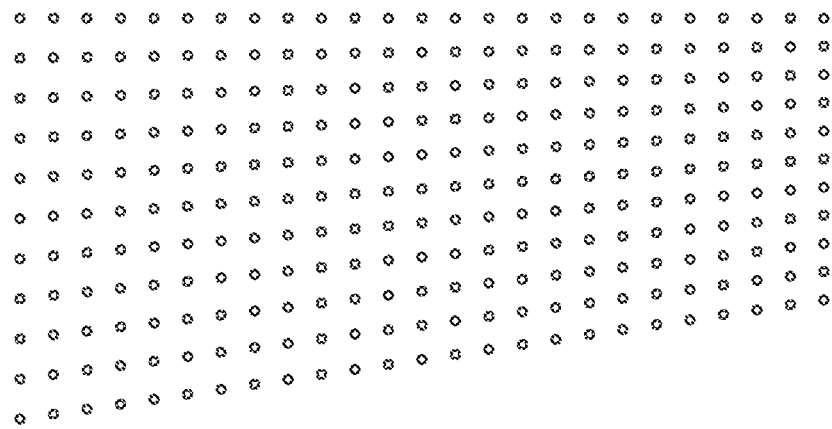

FIG. 135 shows an example comprising fractional skin graft harvesting to be applied to a donor site, under an embodiment.

Figure 136:
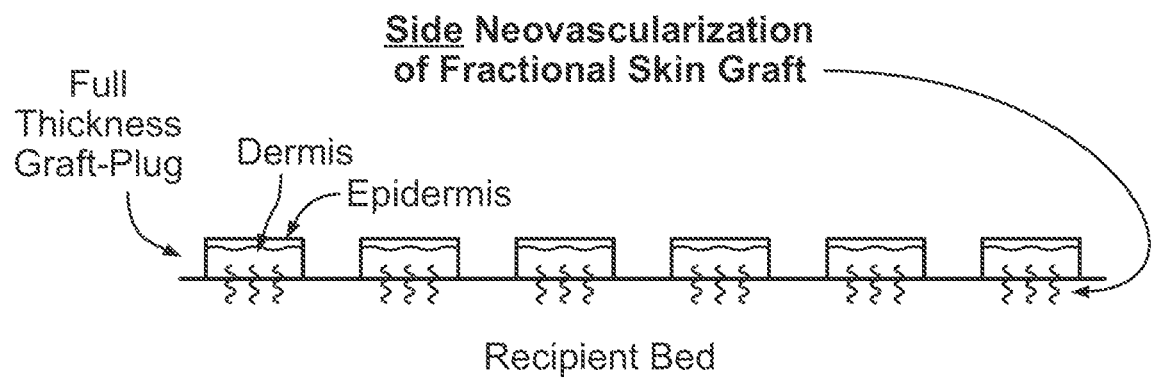
Figure 136:
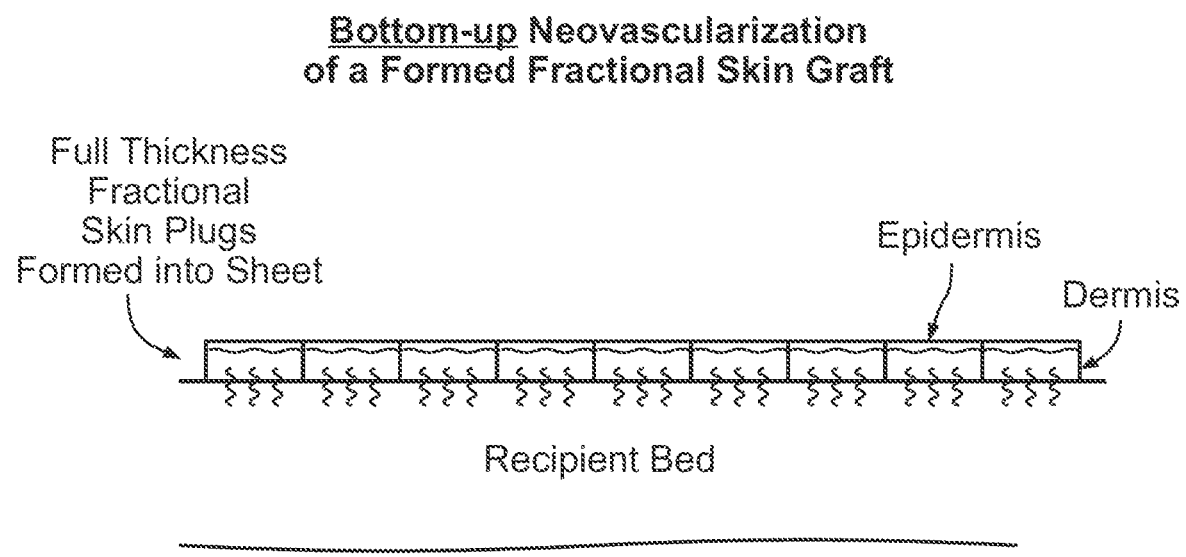

FIG. 136 shows an example comprising neovascularization of a fractional skin graft at a recipient site, under an embodiment.

Figure 137:
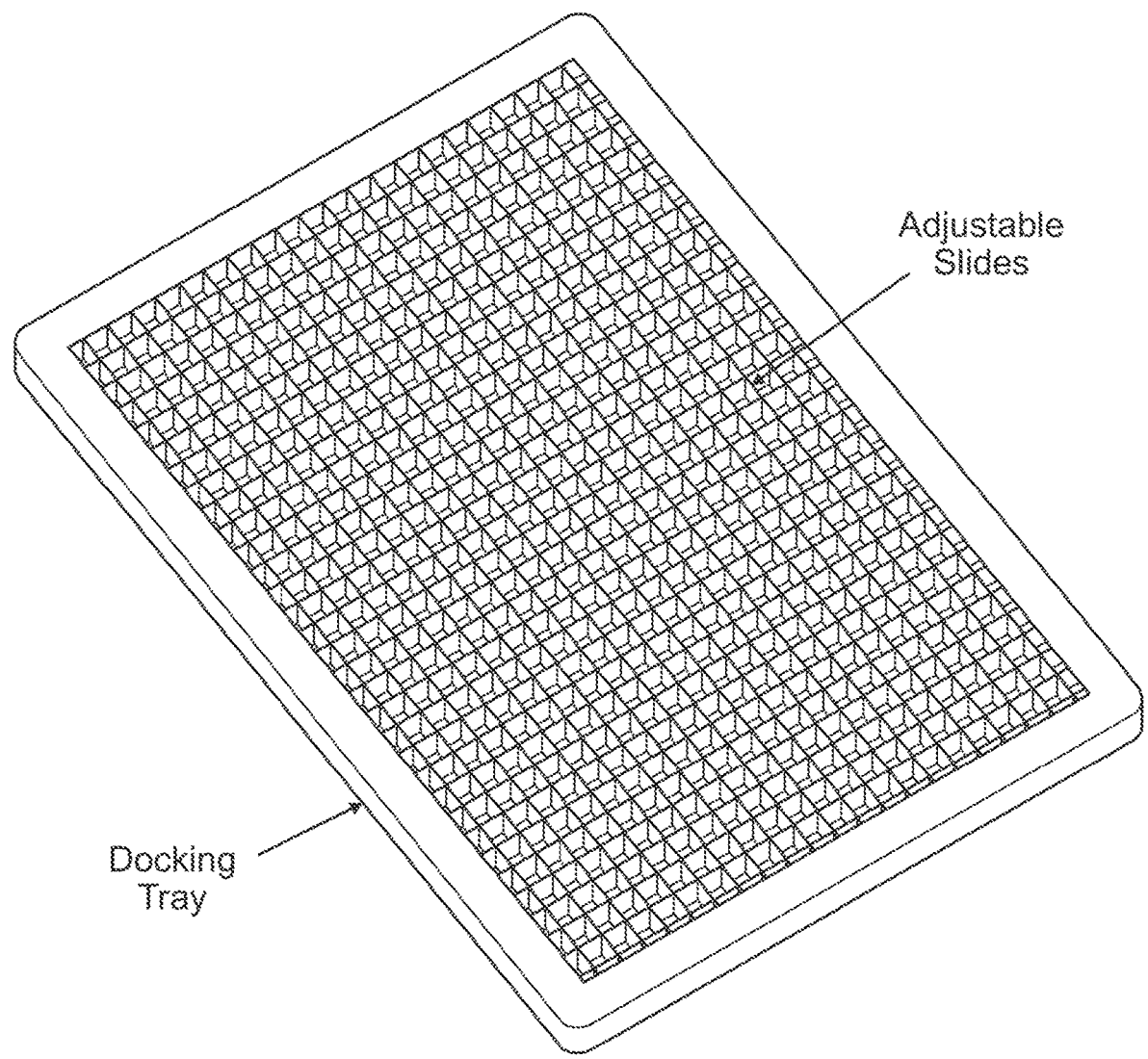

FIG. 137 shows an example docking station comprising a docking tray and adjustable slides, under an embodiment.

DETAILED DESCRIPTION

Systems, instruments, and methods for minimally invasive procedures including one or more of fractional resection, fractional lipectomy, fractional skin grafting, and/or fractional scar revision are described. Embodiments include instrumentation comprising a scalpet assembly coupled to a carrier, and the scalpet assembly includes a scalpet array. The scalpet array includes one or more scalpets configured for fractional resection, fractional lipectomy, fractional skin grafting, and/or fractional scar revision. The system includes a vacuum component coupled to the scalpet assembly and configured to evacuate tissue from the a site. The carrier is configured to control application of a rotational force and/or a vacuum force to the scalpet assembly.

The scalpet device described herein satisfies the expanding aesthetic market for instrumentation and procedures for aesthetic surgical skin tightening. Additionally, the embodiments enable the repeated harvesting of skin grafts from the same donor site while eliminating donor site deformity. The embodiments described herein are configured to resect redundant lax skin without visible scarring so that all areas of redundant skin laxity can be resected by the pixel array dermatome and procedures may be performed in areas that were previously off limits due to the visibility of the surgical incision. The technical effects realized through the embodiments described herein include smooth, tightened skin without visible scarring or long scars along anatomical borders.

Embodiments described in detail herein, which include pixel skin grafting instrumentation and methods, are configured to provide the capability to repeatedly harvest split thickness skin grafts without visible scarring of the donor site. During the procedure, a Pixel Array Dermatome (PAD) is used to harvest the skin graft from the chosen donor site. During the harvesting procedure, a pixilated skin graft is deposited onto a flexible, semi-porous, adherent membrane. The harvested skin graft/membrane composite is then applied directly to the recipient skin defect site. The fractionally resected donor site is closed with the application of an adherent sheeting or bandage (e.g., Flexzan® sheeting, etc.) that functions for a period of time (e.g., one week, etc.) as a large butterfly bandage. The intradermal skin defects generated by the PAD are closed to promote a primary healing process in which the normal epidermal-dermal architecture is realigned in an anatomical fashion to minimize scarring. Also occurring postoperatively, the adherent membrane is desquamated (shed) with the stratum corneum of the graft; the membrane can then be removed without disruption of the graft from the recipient bed.

Numerous effects realized by the pixel skin grafting procedure deserve explanation. Because the skin graft is pixelated it provides interstices for drainage between skin plug components, which enhances the percentage of "takes," compared to sheet skin grafts. During the first post-operative week, the skin graft "takes" at the recipient site by a process of neovascularization in which new vessels from the recipient bed of the skin defect grow into the new skin graft. The semiporous membrane conducts the exudate into the dressing.

The flexible membrane is configured with an elastic recoil property that promotes apposition of component skin plugs within the graft/membrane composite; promoting primary adjacent healing of the skin graft plugs and converting the pixilated appearance of the skin graft into a more uniform sheet morphology. Furthermore, the membrane aligns the micro-architectural components skin plugs, so epidermis aligns with epidermis and dermis aligns with dermis, promoting a primary healing process that reduces scarring.

There are numerous major clinical applications for the dermatomes described in detail herein, including fractional skin resection for skin tightening, fractional hair grafting for alopecia, and fractional skin harvesting for skin grafting. Fractional skin resection of an embodiment comprises harvesting skin plugs using an adherent membrane, however the fractionally incised skin plugs can be evacuated without harvesting. The paradigm of incising, evacuating and closing is most descriptive of the clinical application of skin tightening. The embodiments described herein are configured to facilitate incising and evacuating and, in order to provide for a larger scalpet array with a greater number of scalpets, the embodiments include a novel means of incising the skin surface.

Pixel array medical systems, instruments or devices, and methods are described for skin grafting and skin resection procedures, and hair transplantation procedures. In the following description, numerous specific details are introduced to provide a thorough understanding of, and enabling description for, embodiments herein. One skilled in the relevant art, however, will recognize that these embodiments can be practiced without one or more of the specific details, or with other components, systems, etc. In other instances, well-known structures or operations are not shown, or are not described in detail, to avoid obscuring aspects of the disclosed embodiments.

The following terms are intended to have the following general meaning as they may be used herein. The terms are not however limited to the meanings stated herein as the meanings of any term can include other meanings as understood or applied by one skilled in the art.

"First degree burn" as used herein includes a superficial thermal injury in which there is no disruption of the epidermis from the dermis. A first-degree burn is visualized as erythema (redness) of the skin.

"Second degree burn" as used herein includes a relatively deeper burn in which there is disruption of the epidermis from the dermis and where a variable thickness of the dermis is also denatured. Most second-degree burns are associated with blister formation. Deep second-degree burns may convert to full thickness third degree burns, usually by oxidation or infection.

"Third degree burn" as used herein includes a burn associated with the full thickness thermal destruction of the skin including the epidermis and the dermis. A third degree burn may also be associated with thermal destruction of deeper, underlying tissues (subcutaneous and muscle layers).

"Ablation" as used herein includes the removal of tissue by destruction of the tissue e.g., thermal ablation of a skin lesion by a laser.

"Autograft" as used herein includes a graft taken from the same patient.

"Backed Adherent Membrane" as used herein includes the elastic adherent membrane that captures the transected skin plugs. The Backed Adherent Membrane of an embodiment is backed on the outer surface to retain alignment of the skin plugs during harvest. After harvesting of the skin plugs, the backing is removed from the adherent membrane with harvested skin plugs. The membrane of an embodiment is porous to allow for drainage when placed at the recipient site. The membrane of an embodiment also possesses an elastic recoil property, so that when the backing is removed, it brings the sides of the skin plugs closer to each other to promote healing at the recipient site as a sheet graft.

"Burn Scar Contraction" as used herein includes the tightening of scar tissue that occurs during the wound healing process. This process is more likely to occur with an untreated third degree burn.

"Burn Scar Contracture" as used herein includes a band of scar tissue that either limits the range of motion of a joint or band of scar tissue that distorts the appearance of the patient i.e., a burn scar contracture of the face.

"Dermatome" as used herein includes an instrument that "cuts skin" or harvests a sheet split thickness skin graft. Examples of drum dermatomes include the Padgett and Reese dermatomes. Electrically powered dermatomes are the Zimmer dermatome and one electric version of the Padgett dermatome.

"Dermis" as used herein includes the deep layer of skin that is the main structural support and primarily comprises non-cellular collagen fibers. Fibroblasts are cells in the dermis that produce the collagen protein fibers.

"Donor Site" as used herein includes the anatomical site from which a skin graft is harvested.

"Epidermis" as used herein includes the outer layer of skin comprising viable epidermal cells and nonviable stratum corneum that acts as a biological barrier.

"Excise" as used herein includes the surgical removal of tissue.

"Excisional Skin Defect" as used herein includes a partial thickness or, more typically, a full thickness defect that results from the surgical removal (excision/resection) of skin (lesion).

"FTSG" as used herein includes a Full Thickness Skin Graft in which the entire thickness of the skin is harvested. With the exception of an instrument as described herein, the donor site is closed as a surgical incision. For this reason, FTSG is limited in the surface area that can be harvested.

"Granulation Tissue" as used herein includes highly vascularized tissue that grows in response to the absence of skin in a full-thickness skin defect. Granulation Tissue is the ideal base for a skin graft recipient site.

"Healing by primary intention" as used herein includes the wound healing process in which normal anatomical structures are realigned with a minimum of scar tissue formation. Morphologically the scar is less likely to be visible.

"Healing by secondary intention" as used herein includes a less organized wound healing process wherein healing occurs with less alignment of normal anatomical structures and with an increased deposition of scar collagen. Morphologically, the scar is more likely to be visible.

"Homograft" as used herein includes a graft taken from a different human and applied as a temporary biological dressing to a recipient site on a patient. Most homografts are harvested as cadaver skin. A temporary "take" of a homograft can be partially achieved with immunosuppression but homografts are eventually replaced by autografts if the patient survives.

"Incise" as used herein includes the making of a surgical incision without removal of tissue.

"Mesh Split Thickness Skin Graft" as used herein includes a split thickness skin graft that is expanded in its surface area by repetitiously incising the harvested skin graft with an instrument called a "mesher". A meshed split thickness skin graft has a higher percentage of "take" than a sheet graft because it allows drainage through the graft and conforms better to the contour irregularities of the recipient site. However, it does result in an unsightly reticulated appearance of the graft at the recipient site.

"PAD" as used herein includes a Pixel Array Dermatome, the class of instruments for fractional skin resection.

"PAD Kit" as used herein includes the disposable single use procedure kit comprising the perforated guide plate, scalpet stamper, the guide plate frame, the backed adherent membrane and the transection blade.

"Perforated Guide Plate" as used herein includes a perforated plate comprising the entire graft harvest area in which the holes of the guide plate are aligned with the scalpets of the handled stamper or the Slip-on PAD. The plate will also function as a guard to prevent inadvertent laceration of the adjacent skin. The perforations of the Guide Plate can be different geometries such as, but not limited to, round, oval, square. rectangular, and/or triangular.

"Pixelated Full Thickness Skin Graft" as used herein includes a Full Thickness Skin Graft that has been harvested with an instrument as described herein without reduced visibly apparent scarring at the donor site. The graft will also possess an enhanced appearance at the recipient site similar to a sheet FTSG but will conform better to recipient site and will have a higher percentage of 'take' due to drainage interstices between skin plugs. Another significant advantage of the pixelated FTSG in comparison to a sheet FTSG is the ability to graft larger surface areas that would otherwise require a STSG. This advantage is due to the capability to harvest from multiple donor sites with reduced visible scarring.

"Pixelated Graft Harvest" as used herein includes the skin graft harvesting from a donor site by an instrument as described in detail herein.

"Pixelated Spilt Thickness Skin Graft" as used herein includes a partial thickness skin graft that has been harvested with an SRG instrument. The skin graft shares the advantages of a meshed skin graft without unsightly donor and recipient sites.

"Recipient Site" as used herein includes the skin defect site where a skin graft is applied.

"Resect" as used herein includes excising.

"Scalpel" as used herein includes the single-edged knife that incises skin and soft tissue.

"Scalpet" as used herein includes the term that describes the small geometrically-shaped (e.g., circle, ellipse, rectangle, square, etc.) scalpel that incises a plug of skin.

"Scalpet Array" as used herein includes the arrangement or array of multiple scalpets secured to a substrate (e.g., a base plate, stamper, handled stamper, tip, disposable tip, etc.).

"Scalpet Stamper" as used herein includes a handled scalpet array instrument component of the PAD Kit that incises skin plugs through the perforated guide plate.

"Scar" as used herein includes the histological deposition of disorganized collagen following wounding, or the morphological deformity that is visually apparent from the histological deposition of disorganized collagen following wounding.

"Sheet Full Thickness Skin Graft" as used herein includes reference to application of the FTSG at the recipient site as continuous sheet. The appearance of an FTSG is superior to the appearance of a STSG and for this reason it is primarily used for skin grafting in visually apparent areas such as the face.

"Sheet Split Thickness Skin Graft" as used herein includes a partial thickness skin graft that is a continuous sheet and is associated with the typical donor site deformity.

"Skin Defect" as used herein includes the absence of the full thickness of skin that may also include the subcutaneous fat layer and deeper structures such as muscle. Skin defects can occur from a variety of causes i.e., burns, trauma, surgical excision of malignancies and the correction of congenital deformities.

"Skin Pixel" as used herein includes a piece of skin comprising epidermis and a partial or full thickness of the dermis that is cut by the scalpet; the skin pixel may include skin adnexa such as a hair follicle with or without a cuff of subcutaneous fat; also includes Skin Plug.

"Skin Plug" as used herein includes a circular (or other geometric shaped) piece of skin comprising epidermis and a partial or full thickness of the dermis that is incised by the scalpet, transected by the transection blade and captured by the adherent-backed membrane.

"STSG" as used herein includes the Partial Thickness Skin Graft in which the epidermis and a portion of the dermis is harvested with the graft.

"Subcutaneous Fat Layer" as used herein includes the layer that is immediately below the skin and is principally comprised of fat cells referred to as lipocytes. This layer functions as principle insulation layer from the environment.

"Transection Blade" as used herein includes a horizontally-aligned single edged blade that can be either slotted to the frame of the perforated plate or attached to the outrigger arm of the drum dermatome as described in detail herein. The transection blade transects the base of the incised skin plugs.

"Wound Healing" as used herein includes the obligate biological process that occurs from any type of wounding whether it be one or more of thermal, kinetic and surgical.

"Xenograft" as used herein includes a graft taken from a different species and applied as a temporary biological dressing to a recipient site on a patient.

Multiple embodiments of pixel array medical systems, instruments or devices, and methods for use are described in detail herein. The systems, instruments or devices, and methods described herein comprise minimally invasive surgical approaches for skin grafting and for skin resection that tightens lax skin without visible scarring via a device used in various surgical procedures such as plastic surgery procedures, and additionally for hair transplantation. In some embodiments, the device is a single use disposable instrument. The embodiments herein circumvent surgically related scarring and the clinical variability of electromagnetic heating of the skin and perform small multiple pixilated resections of skin as a minimally invasive alternative to large plastic surgical resections of skin. The embodiments herein can also be employed in hair transplantation, and in areas of the body that may be off limits to plastic surgery due to the visibility of the surgical scar. In addition, the approach can perform a skin grafting operation by harvesting the transected incisions of skin from a tissue site of a donor onto a skin defect site of a recipient with reduced scarring of the patient's donor site.

For many patients who have age related skin laxity (for non-limiting examples, neck and face, arms, axillas, thighs, knees, buttocks, abdomen, bra line, ptosis of the breast, etc.), the minimally invasive pixel array medical devices and methods herein perform pixilated transection/resection of excess skin, replacing plastic surgery with its incumbent scarring. Generally, the procedures described herein are performed in an office setting under a local anesthetic with minimal perioperative discomfort, but are not so limited. In comparison to a prolonged healing phase from plastic surgery, only a short recovery period is required, preferably applying a dressing and a support garment worn over the treatment area for a pre-specified period of time (e.g., 5 days, 7 days, etc.). There will be minimal or no pain associated with the procedure.

The relatively small (e.g., in a range of approximately 0.5 mm to 4.0 mm) skin defects generated by the instrumentation described herein are closed with the application of an adherent Flexan® sheet. Functioning as a large butterfly bandage, the Flexan® sheet can be pulled in a direction ("vector") that maximizes the aesthetic contouring of the treatment area. A compressive elastic garment is applied over the dressing to further assist aesthetic contouring. After completion of the initial healing phase, the multiplicity of small linear scars within the treatment area will have reduced visibility in comparison to larger plastic surgical incisions on the same area. Additional skin tightening is likely to occur over several months due to the delayed wound healing response. Other potential applications of the embodiments described herein include hair transplantation as well as the treatment of Alopecia, Snoring/Sleep apnea, Orthopedics/Physiatry, Vaginal Tightening, Female Urinary incontinence, and tightening of gastrointestinal sphincters.

Significant burns are classified by the total body surface burned and by the depth of thermal destruction, and the methods used to manage these burns depend largely on the classification. First-degree and second-degree burns are usually managed in a non-surgical fashion with the application of topical creams and burn dressings. Deeper third-degree burns involve the full thickness thermal destruction of the skin, creating a full thickness skin defect. The surgical management of this serious injury usually involves the debridement of the burn eschar and the application of split thickness grafts.

A full thickness skin defect, most frequently created from burning, trauma, or the resection of a skin malignancy, can be closed with either skin flap transfers or skin grafts using conventional commercial instrumentation. Both surgical approaches require harvesting from a donor site. The use of a skin flap is further limited by the need of to include a pedicle blood supply and in most cases by the need to directly close the donor site.

The split thickness skin graft procedure, due to immunological constraints, requires the harvesting of autologous skin grafts from the same patient. Typically, the donor site on the burn patient is chosen in a non-burned area and a partial thickness sheet of skin is harvested from that area. Incumbent upon this procedure is the creation of a partial thickness skin defect at the donor site. This donor site defect itself is similar to a deep second-degree burn. Healing by re-epithelialization of this site is often painful and may be prolonged for several days. In addition, a visible donor site deformity is typically created that is permanently thinner and more de-pigmented than the surrounding skin. For patients who have burns over a significant surface area, the extensive harvesting of skin grafts may also be limited by the availability of non-burned areas.

Both conventional surgical approaches to close skin defects (flap transfer and skin grafting) are not only associated with significant scarring of the skin defect recipient site but also with the donor site from which the graft is harvested. In contrast to the conventional procedures, embodiments described herein comprise Pixel Skin Grafting Procedures, also referred to as a pixel array procedures, that eliminate this donor site deformity and provide a method to re-harvest skin grafts from any pre-existing donor site including either sheet or pixelated donor sites. This ability to re-harvest skin grafts from pre-existing donor sites will reduce the surface area requirement for donor site skin and provide additional skin grafting capability in severely burned patients who have limited surface area of unburned donor skin.

The Pixel Skin Grafting Procedure of an embodiment is used as a full thickness skin graft. Many clinical applications such as facial skin grafting, hand surgery, and the repair of congenital deformities are best performed with full thickness skin grafts. The texture, pigmentation and overall morphology of a full thickness skin graft more closely resembles the skin adjacent to a defect than a split thickness skin graft. For this reason, full thickness skin grafting in visibly apparent areas is superior in appearance than split thickness skin grafts. The main drawback to full thickness skin grafts under conventional procedures is the extensive linear scarring created from the surgical closure of the full thickness donor site defect; this scarring limits the size and utility of full thickness skin grafting.

In comparison, the full thickness skin grafting of the Pixel Skin Grafting Procedure described herein is less limited by size and utility as the linear donor site scar is eliminated. Thus, many skin defects routinely covered with split thickness skin grafts will instead be treated using pixelated full thickness skin grafts.

The Pixel Skin Grafting Procedure provides the capability to harvest split thickness and full thickness skin grafts with minimal visible scarring of the donor site. During the procedure, a Pixel Array Dermatome (PAD) device is used to harvest the skin graft from a chosen donor site. During the harvesting procedure, the pixilated skin graft is deposited onto an adherent membrane. The adherent membrane of an embodiment includes a flexible, semi-porous, adherent membrane, but the embodiment is not so limited. The harvested skin graft/membrane composite is then applied directly to the recipient skin defect site. The fractionally resected donor site is closed with the application of an adherent Flexan® sheeting that functions for one week as a large butterfly bandage. The relatively small (e.g., 1.5 mm) intradermal circular skin defects are closed to promote a primary healing process in which the normal epidermal-dermal architecture is realigned in an anatomical fashion to minimize scarring. Also occurring approximately one week postoperatively, the adherent membrane is desquamated (shed) with the stratum corneum of the graft; the membrane can then be removed without disruption of the graft from the recipient bed. Thus, healing of the donor site occurs rapidly with minimal discomfort and scarring.

Because the skin graft at the recipient defect site using the Pixel Skin Grafting Procedure is pixelated it provides interstices for drainage between skin pixel components, which enhances the percentage of "takes," compared to sheet skin grafts. During the first post-operative week (approximate), the skin graft will "take" at the recipient site by a process of neovascularization in which new vessels from the recipient bed of the skin defect grow into the new skin graft. The semi-porous membrane will conduct the transudate (fluid) into the dressing. Furthermore, the flexible membrane is designed with an elastic recoil property that promotes apposition of component skin pixels within the graft/membrane composite and promotes primary adjacent healing of the skin graft pixels, converting the pixilated appearance of the skin graft to a uniform sheet morphology. Additionally, the membrane aligns the micro-architectural component skin pixels, so epidermis aligns with epidermis and dermis aligns with dermis, promoting a primary healing process that reduces scarring. Moreover, pixelated skin grafts more easily conform to an irregular recipient site.

Embodiments described herein also include a Pixel Skin Resection Procedure, also referred to herein as the Pixel Procedure. For many patients who have age related skin laxity (neck and face, arms, axillas, thighs, knees, buttocks, abdomen, bra line, ptosis of the breast, etc.), fractional resection of excess skin could replace a significant segment of plastic surgery with its incumbent scarring. Generally, the Pixel Procedure will be performed in an office setting under a local anesthetic. The post procedure recovery period includes wearing of a support garment over the treatment area for a pre-specified number (e.g., five, seven, etc.) of days (e.g., five days, seven days, etc.). Relatively little or no pain is anticipated to be associated with the procedure. The small (e.g., 1.5 mm) circular skin defects will be closed with the application of an adherent Flexan® sheet. Functioning as a large butterfly bandage, the Flexan® sheet is pulled in a direction ("vector") that maximizes the aesthetic contouring of the treatment area. A compressive elastic garment is then applied over the dressing to further assist aesthetic contouring. After completion of the initial healing phase, the multiplicity of small linear scars within the treatment area will not be visibly apparent. Furthermore, additional skin tightening will subsequently occur over several months due to the delayed wound healing response. Consequently, the Pixel Procedure is a minimally invasive alternative to the extensive scarring of Plastic Surgery.

Figure 1:
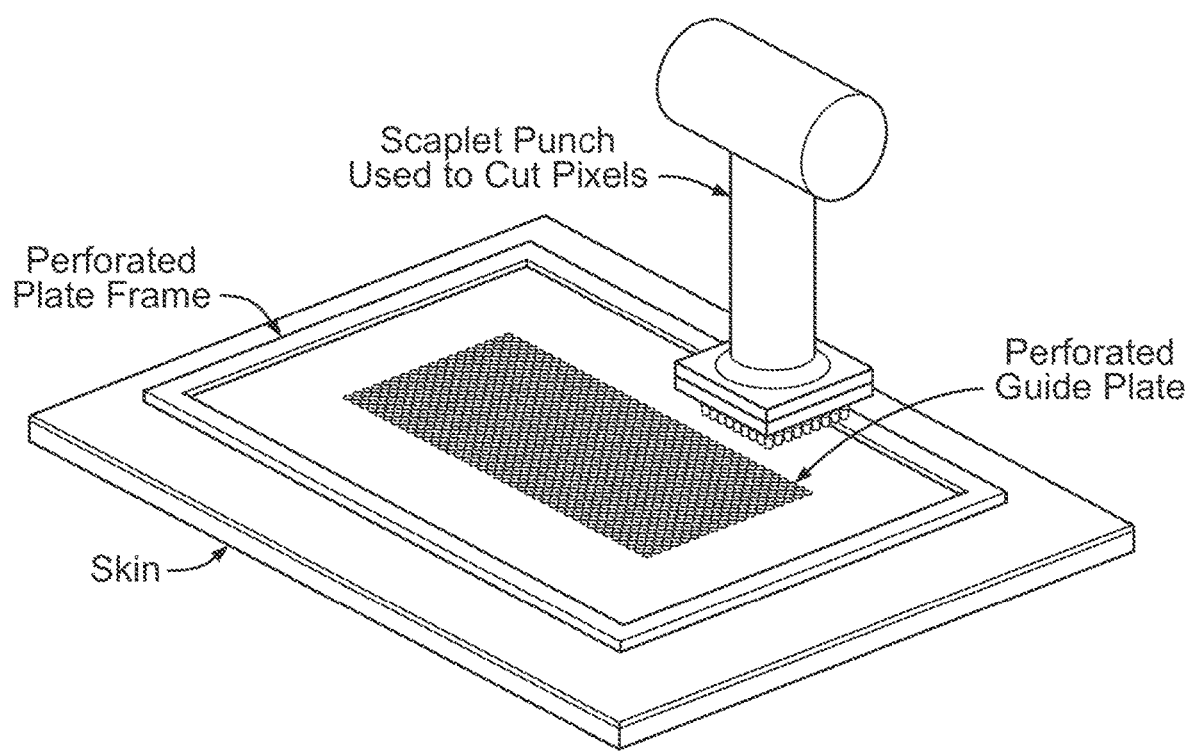
FIG. 1 shows the PAD Kit placed at a target site, under an embodiment.

The pixel array medical devices of an embodiment include a PAD Kit. FIG. 1 shows the PAD Kit placed at a target site, under an embodiment. The PAD Kit comprises a flat perforated guide plate (guide plate), a scalpet punch or device that includes a scalpet array (FIGS. 1-3), a backed adhesive membrane or adherent substrate (FIG. 4), and a skin pixel transection blade (FIG. 5), but is not so limited. The scalpet punch of an embodiment is a handheld device but is not so limited. The guide plate is optional in an alternative embodiment, as described in detail herein.

Figure 2:
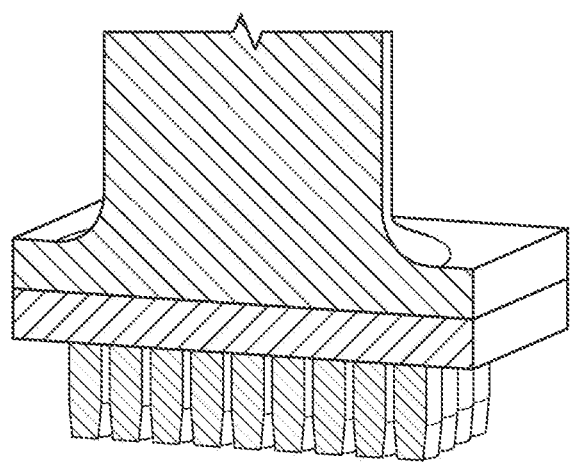
FIG. 2 is a cross-section of a scalpet punch or device including a scalpet array, under an embodiment.
Figure 3:
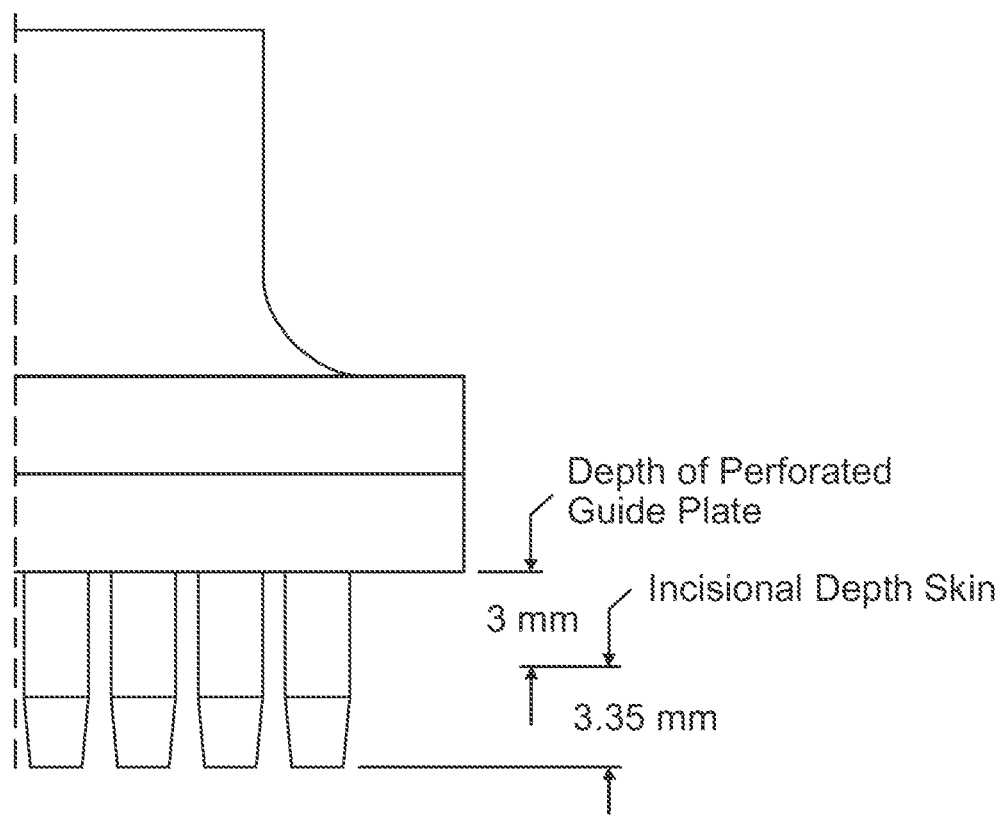
FIG. 3 is a partial cross-section of a scalpet punch or device including a scalpet array, under an embodiment.

FIG. 2 is a cross-section of a PAD Kit scalpet punch including a scalpet array, under an embodiment. The scalpet array includes one or more scalpets. FIG. 3 is a partial cross-section of a PAD Kit scalpet punch including a scalpet array, under an embodiment. The partial cross-section shows the total length of the scalpets of the scalpet array is determined by the thickness of the perforated guide plate and the incisional depth into the skin, but the embodiment is not so limited.

Figure 4:
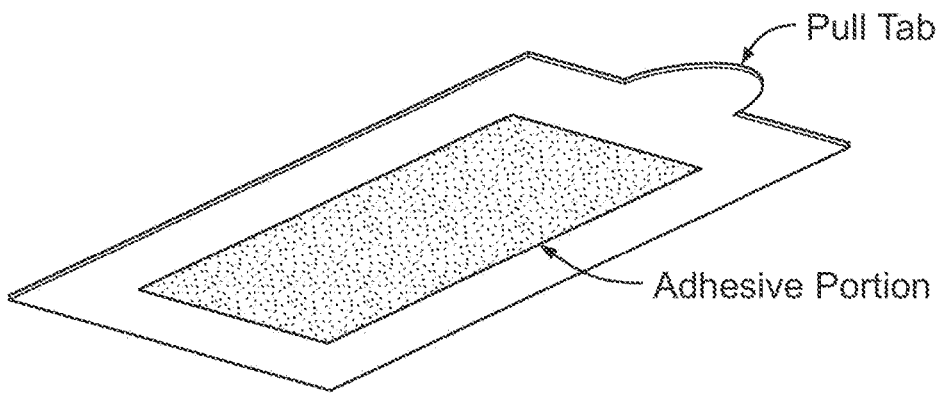
FIG. 4 shows the adhesive membrane with backing (adherent substrate) included in a PAD Kit, under an embodiment.

FIG. 4 shows the adhesive membrane with backing (adherent substrate) included in a PAD Kit, under an embodiment. The undersurface of the adhesive membrane is applied to the incised skin at the target site.

Figure 5:
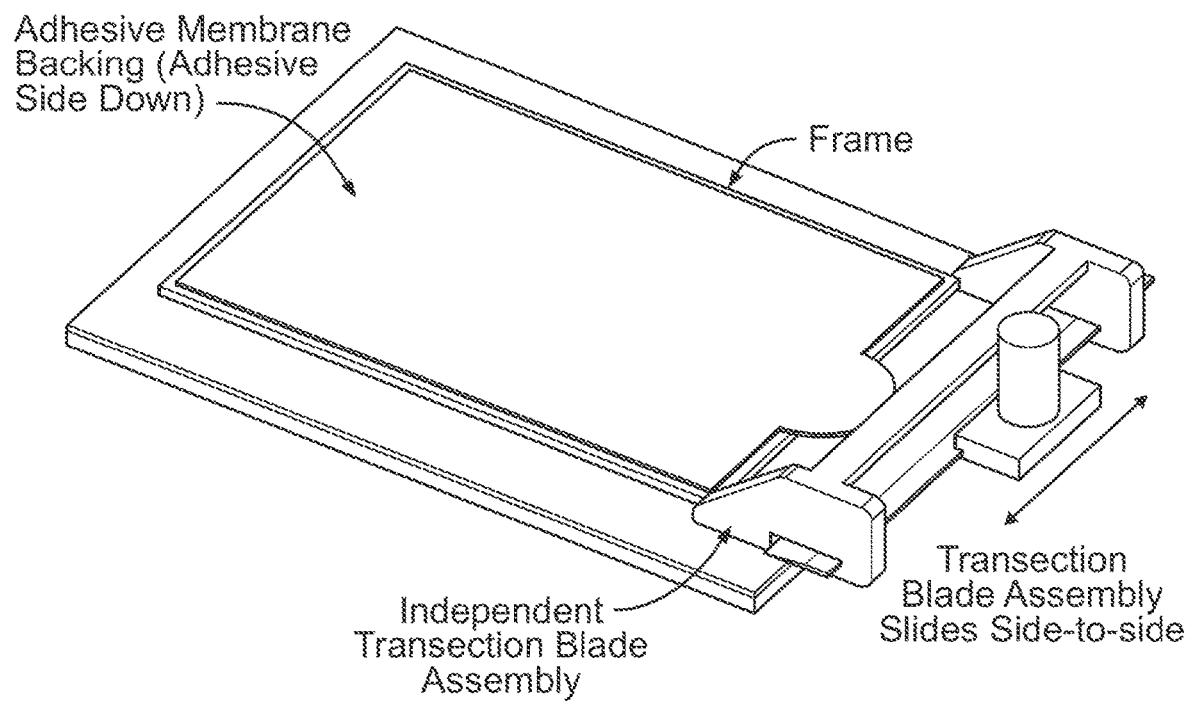
FIG. 5 shows the adhesive membrane (adherent substrate) when used with the PAD Kit frame and blade assembly, under an embodiment.

FIG. 5 shows the adhesive membrane (adherent substrate) when used with the PAD Kit frame and blade assembly, under an embodiment. The top surface of the adhesive membrane is oriented with the adhesive side down inside the frame and then pressed over the perforated plate to capture the extruded skin pixels, also referred to herein as plugs or skin plugs.

With reference to FIG. 1, the perforated guide plate is applied to the skin resection/donor site during a procedure using the PAD Kit. The scalpet punch is applied through at least a set of perforations of the perforated guide plate to incise the skin pixels. The scalpet punch is applied numerous times to a number of sets of perforations when the scalpet array of the punch includes fewer scalpets then the total number of perforations of the guide plate. Following one or more serial applications with the scalpet punch, the incised skin pixels or plugs are captured onto the adherent substrate. The adherent substrate is then applied in a manner so the adhesive captures the extruded skin pixels or plugs. As an example, the top surface of the adherent substrate of an embodiment is oriented with the adhesive side down inside the frame (when the frame is used) and then pressed over the perforated plate to capture the extruded skin pixels or plugs. As the membrane is pulled up, the captured skin pixels are transected at their base by the transection blade.

Figure 6:
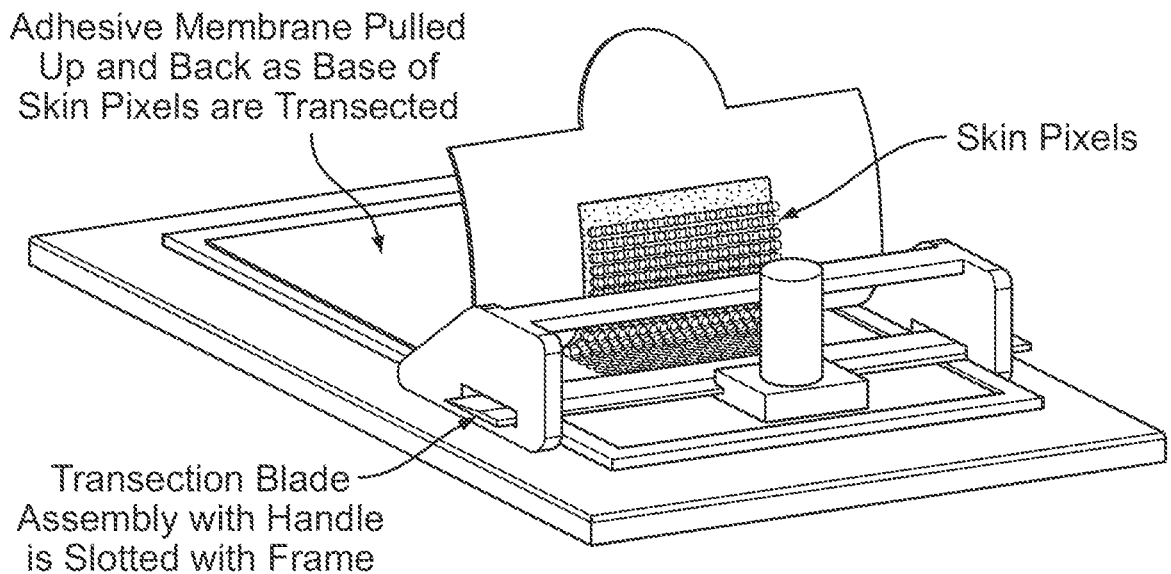
FIG. 6 shows the removal of skin pixels, under an embodiment.
Figure 7:
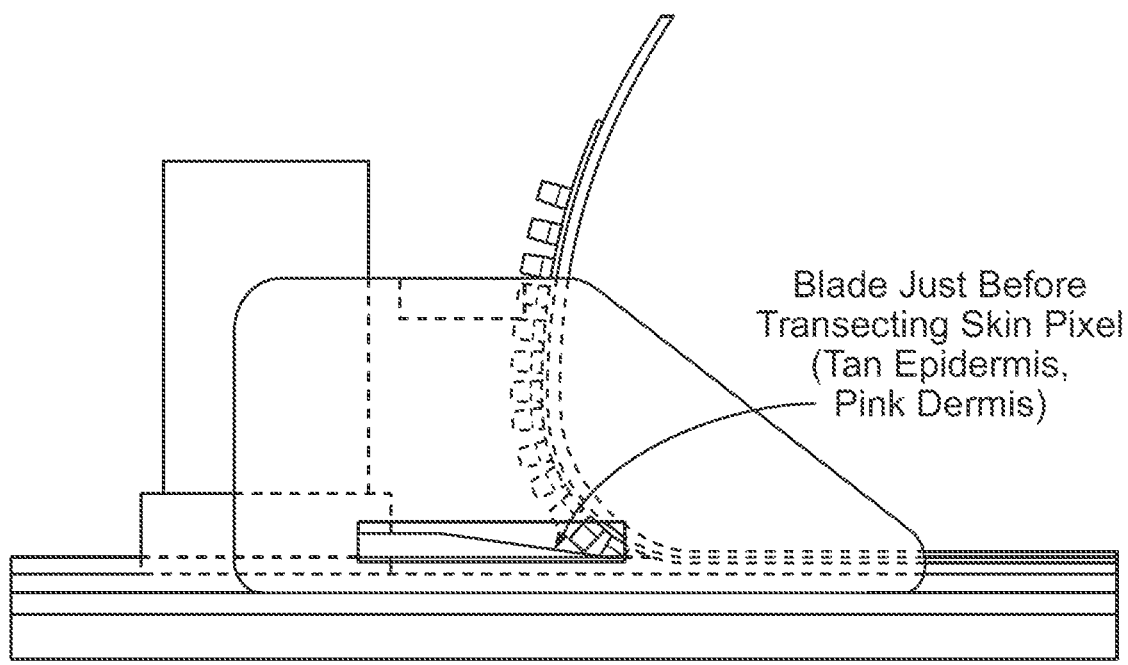
FIG. 7 is a side view of blade transection and removal of incised skin pixels with the PAD Kit, under an embodiment.
Figure 8:
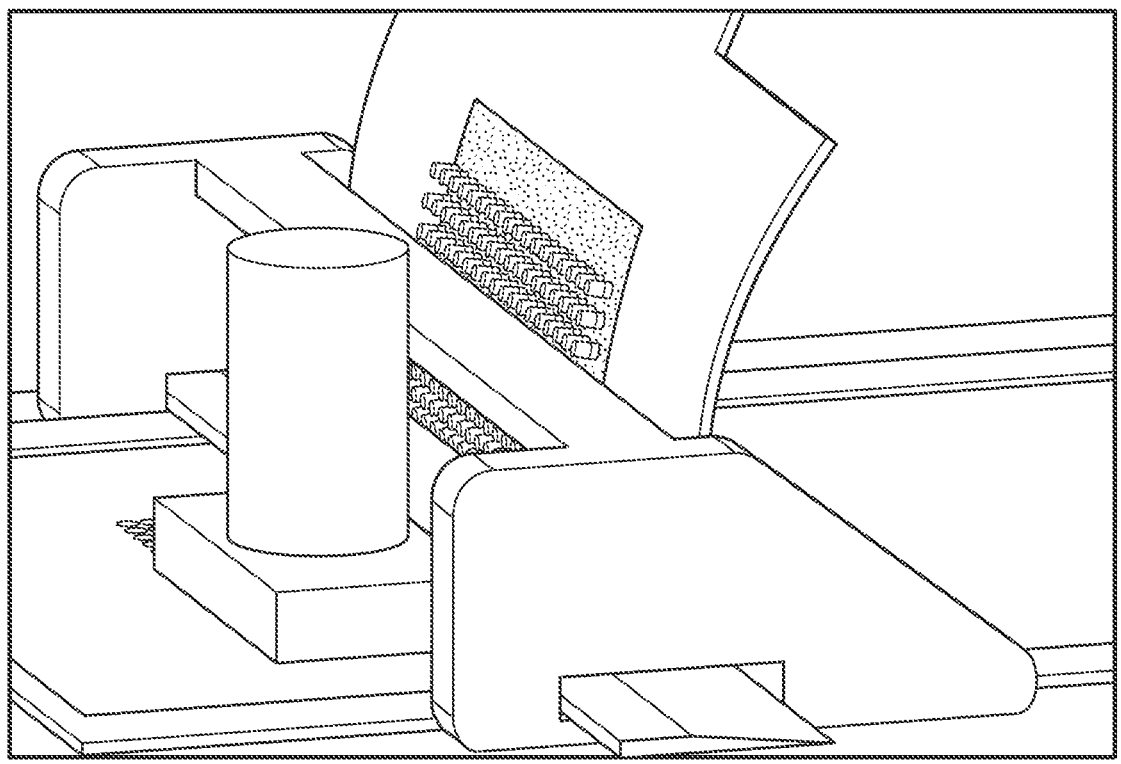
FIG. 8 is an isometric view of blade/pixel interaction during a procedure using the PAD Kit, under an embodiment.
Figure 9:
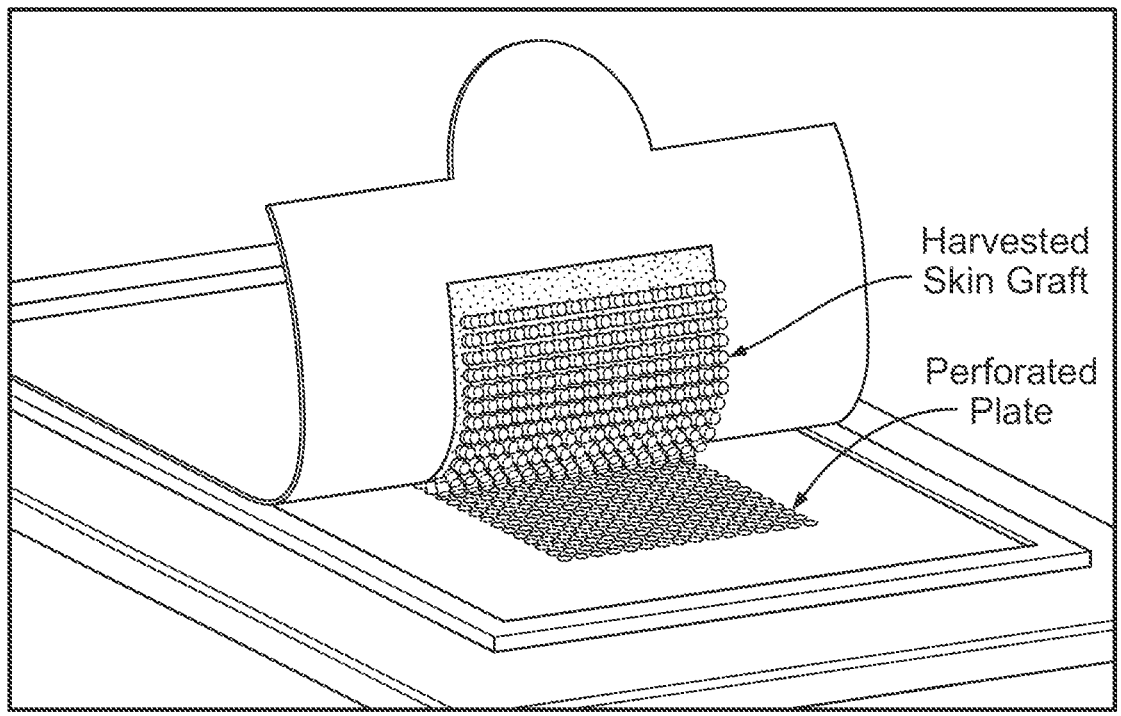
FIG. 9 is another view during a procedure using the PAD Kit (blade removed for clarity) showing both harvested skin pixels or plugs transected and captured and non-transected skin pixels or plugs prior to transection, under an embodiment.

FIG. 6 shows the removal of skin pixels, under an embodiment. The adherent substrate is pulled up and back (away) from the target site, and this act lifts or pulls the incised skin pixels or plugs. As the adherent substrate is being pulled up, the transection blade is used to transect the bases of the incised skin pixels. FIG. 7 is a side view of blade transection and removal of incised skin pixels with the PAD Kit, under an embodiment. Pixel harvesting is completed with the transection of the base of the skin pixels or plugs. FIG. 8 is an isometric view of blade/pixel interaction during a procedure using the PAD Kit, under an embodiment. FIG. 9 is another view during a procedure using the PAD Kit (blade removed for clarity) showing both harvested skin pixels or plugs transected and captured and non-transected skin pixels or plugs prior to transection, under an embodiment. At the donor site, the pixelated skin resection sites are closed with the application of Flexan® sheeting.

The guide plate and scalpet device are also used to generate skin defects at the recipient site. The skin defects are configured to receive the skin pixels harvested or captured at the donor site. The guide plate used at the recipient site can be the same guide plate used at the donor site, or can be different with a different pattern or configuration of perforations.

The skin pixels or plugs deposited onto the adherent substrate during the transection can next be transferred to the skin defect site (recipient site) where they are applied as a pixelated skin graft at a recipient skin defect site. The adherent substrate has an elastic recoil property that enables closer alignment of the skin pixels or plugs within the skin graft. The incised skin pixels can be applied from the adherent substrate directly to the skin defects at the recipient site. Application of the incised skin pixels at the recipient site includes aligning the incised skin pixels with the skin defects, and inserting the incised skin pixels into corresponding skin defects at the recipient site.

Figure 10A:
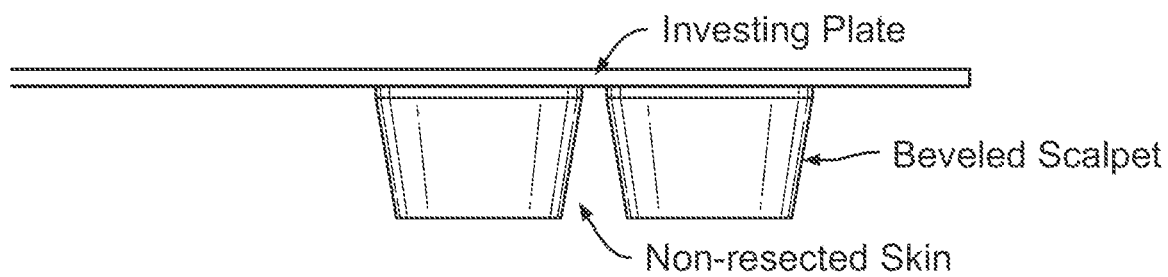
FIG. 10A is a side view of a portion of the pixel array showing scalpets secured onto an investing plate, under an embodiment.
Figure 10B:
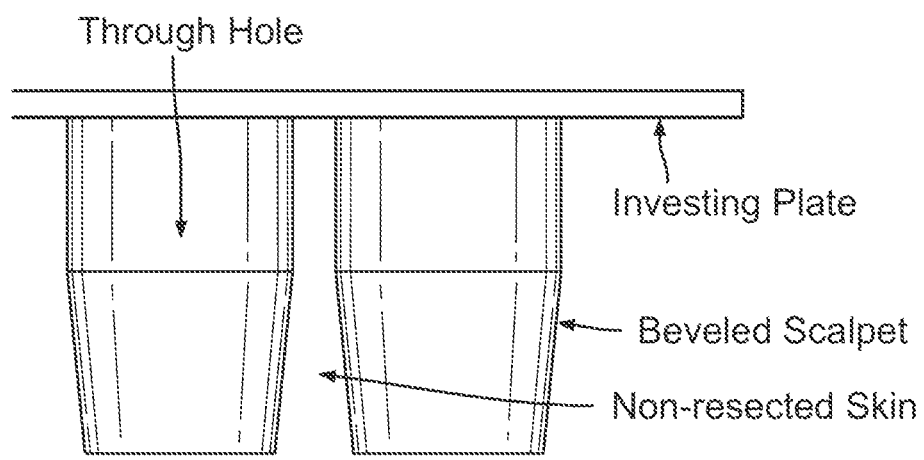
FIG. 10B is a side view of a portion of the pixel array showing scalpets secured onto an investing plate, under an alternative embodiment.
Figure 10C:
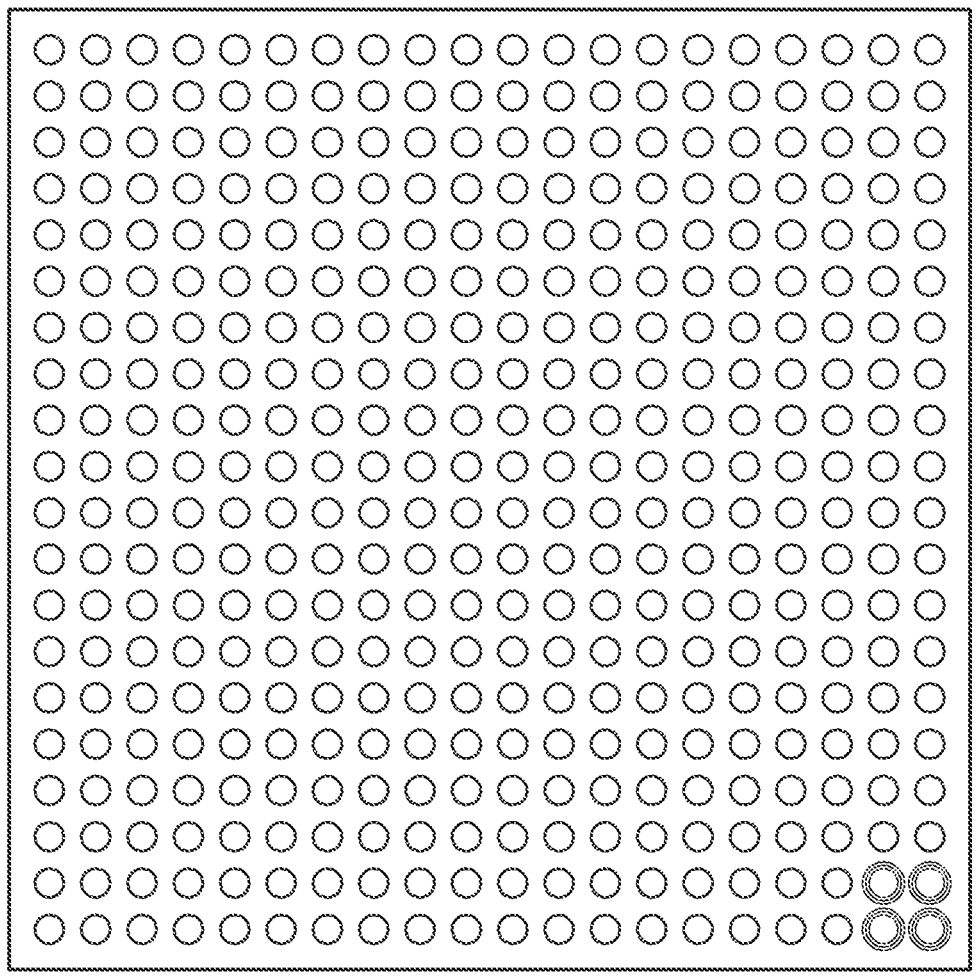
FIG. 10C is a top view of the scalpet plate, under an embodiment.
Figure 10D:
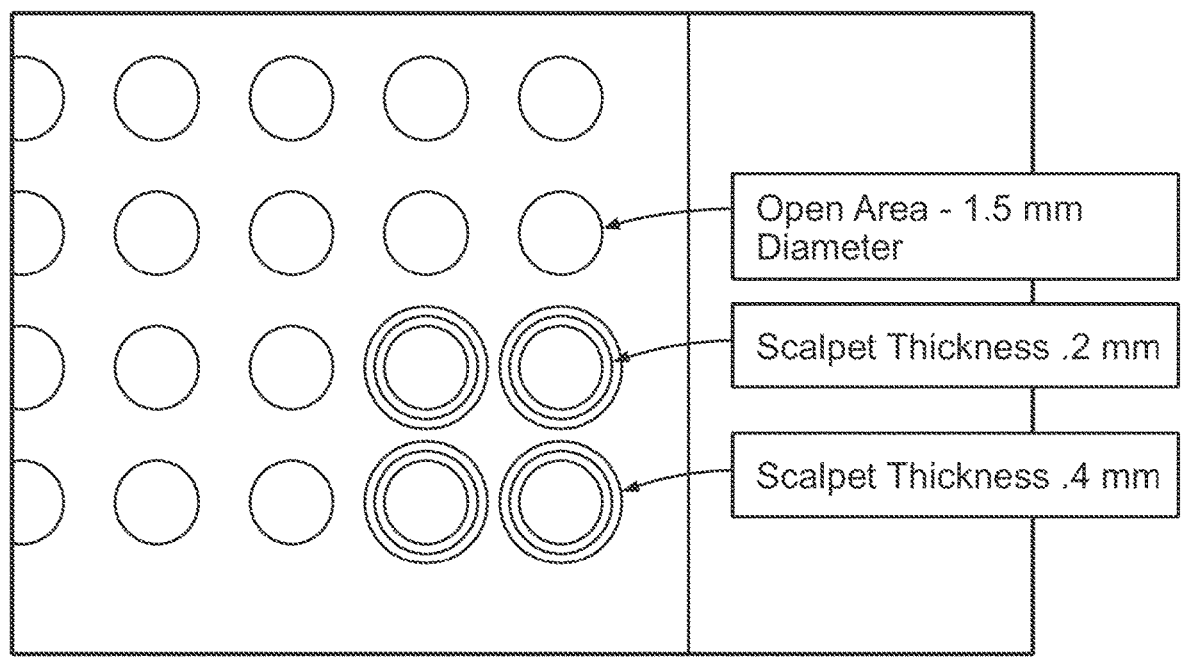
FIG. 10D is a close view of a portion of the scalpet plate, under an embodiment.

The pixel array medical devices of an embodiment include a Pixel Array Dermatome (PAD). The PAD comprises a flat array of relatively small circular scalpets that are secured onto a substrate (e.g., investing plate), and the scalpets in combination with the substrate are referred to herein as a scalpet array, pixel array, or scalpet plate. FIG. 10A is a side view of a portion of the pixel array showing scalpets secured onto an investing plate, under an embodiment. FIG. 10B is a side view of a portion of the pixel array showing scalpets secured onto an investing plate, under an alternative embodiment. FIG. 10C is a top view of the scalpet plate, under an embodiment. FIG. 10D is a close view of a portion of the scalpet plate, under an embodiment. The scalpet plate is applied directly to the skin surface. One or more scalpets of the scalpet array include one or more of a pointed surface, a needle, and a needle including multiple points.

Embodiments of the pixel array medical devices and methods include use of a harvest pattern instead of the guide plate. The harvest pattern comprises indicators or markers on a skin surface on at least one of the donor site and the recipient site, but is not so limited. The markers include any compound that may be applied directly to the skin to mark an area of the skin. The harvest pattern is positioned at a donor site, and the scalpet array of the device is aligned with or according to the harvest pattern at the donor site. The skin pixels are incised at the donor site with the scalpet array as described herein. The recipient site is prepared by positioning the harvest pattern at the recipient site. The harvest pattern used at the recipient site can be the same harvest pattern used at the donor site, or can be different with a different pattern or configuration of markers. The skin defects are generated, and the incised skin pixels are applied at the recipient site as described herein. Alternatively, the guide plate of an embodiment is used in applying the harvest pattern, but the embodiment is not so limited.

To leverage established surgical instrumentation, the array of an embodiment is used in conjunction with or as a modification to a drum dermatome, for example a Padget dermatome or a Reese dermatome, but is not so limited. The Padget drum dermatome referenced herein was originally developed by Dr. Earl Padget in the 1930s, and continues to be widely utilized for skin grafting by plastic surgeons throughout the world. The Reese modification of the Padget dermatome was subsequently developed to better calibrate the thickness of the harvested skin graft. The drum dermatome of an embodiment is a single use (per procedure) disposable, but is not so limited.

Figure 11A:
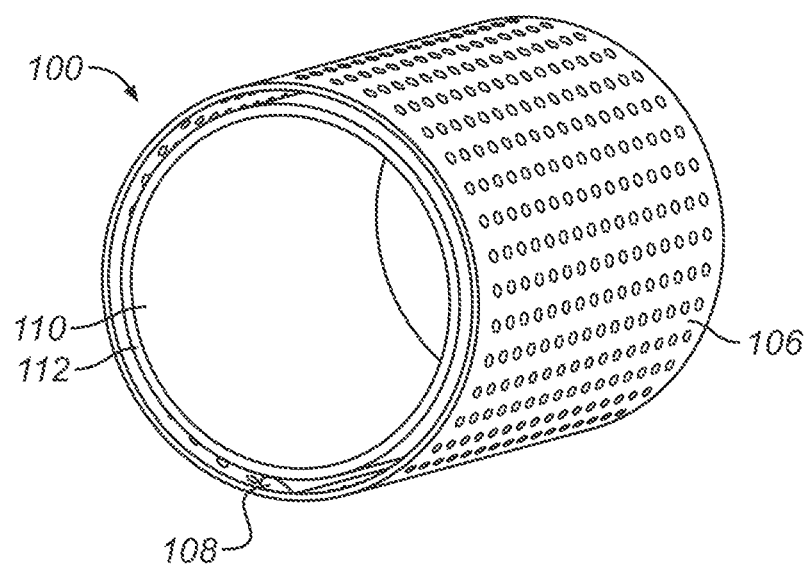
FIG. 11A shows an example of rolling pixel drum, under an embodiment.
Figure 11B:
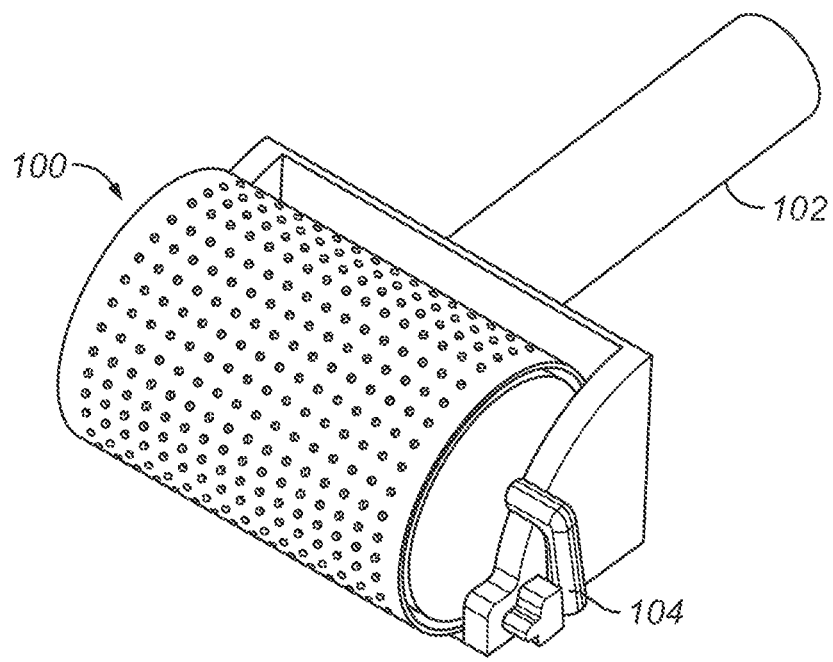
FIG. 11B shows an example of a rolling pixel drum assembled on a handle, under an embodiment.
Figure 11C:
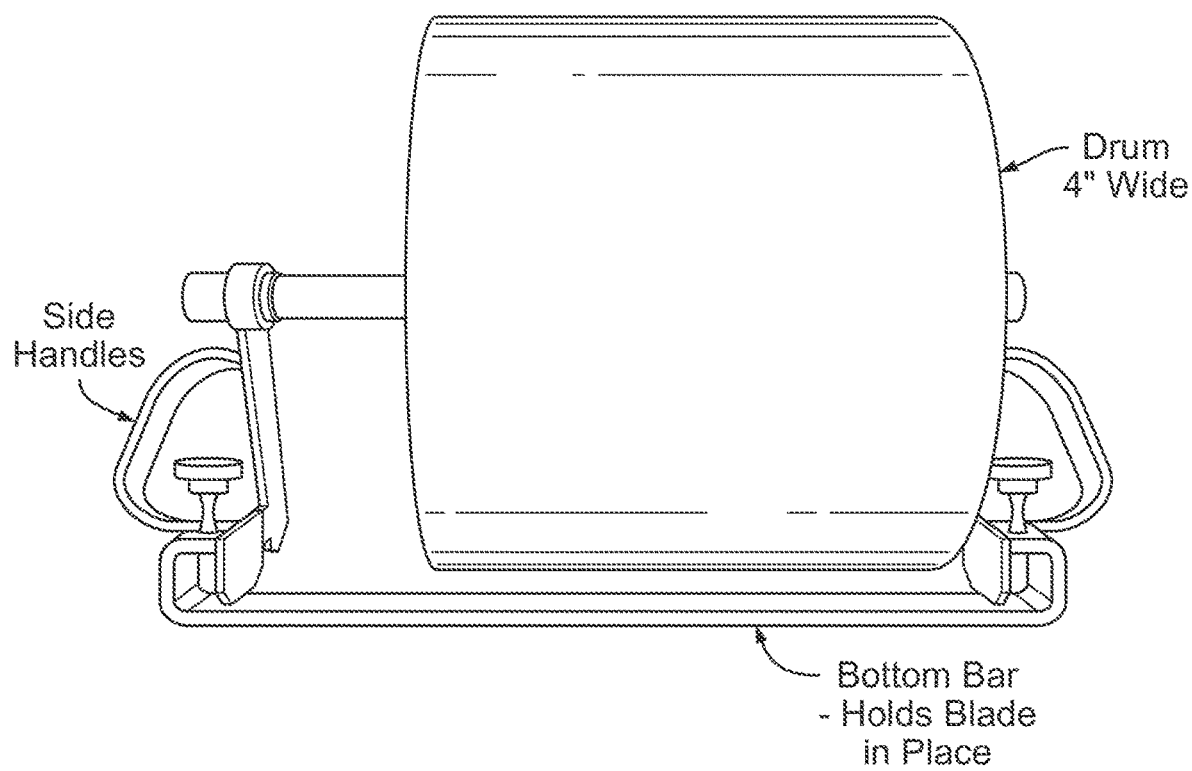
FIG. 11C depicts a drum dermatome for use with the scalpet plate, under an embodiment.

Generally, FIG. 11A shows an example of a rolling pixel drum 100, under an embodiment. FIG. 11B shows an example of a rolling pixel drum 100 assembled on a handle, under an embodiment. More specifically, FIG. 11C depicts a drum dermatome for use with the scalpet plate, under an embodiment.

Generally, as with all pixel devices described herein, the geometry of the pixel drum 100 can be a variety of shapes without limitation e.g., circular, semicircular, elliptical, square, flat, or rectangular. In some embodiments, the pixel drum 100 is supported by an axel/handle assembly 102 and rotated around a drum rotational component 104 powered by, e.g., an electric motor. In some embodiments, the pixel drum 100 can be placed on stand (not shown) when not in use, wherein the stand can also function as a battery recharger for the powered rotational component of the drum or the powered component of the syringe plunger. In some embodiments, a vacuum (not shown) can be applied to the skin surface of the pixel drum 100 and outriggers (not shown) can be deployed for tracking and stability of the pixel drum 100.

In some embodiments, the pixel drum 100 incorporates an array of scalpets 106 on the surface of the drum 100 to create small multiple (e.g., 0.5-1.5 mm) circular incisions referred to herein as skin plugs. In some embodiments, the border geometry of the scalpets can be designed to reduce pin cushioning ("trap door") while creating the skin plugs. The perimeter of each skin plug can also be lengthened by the scalpets to, for a non-limiting example, a, semicircular, elliptical, or square-shaped skin plug instead of a circular-shaped skin plug. In some embodiments, the length of the scalpets 106 may vary depending upon the thickness of the skin area selected by the surgeon for skin grafting purposes, i.e., partial thickness or full thickness.

When the drum 100 is applied to a skin surface, a blade 108 placed internal of the drum 100 transects the base of each skin plug created by the array of scalpets, wherein the internal blade 108 is connected to the central drum axel/handle assembly 102 and/or connected to outriggers attached to the central axel assembly 102. In some alternative embodiments, the internal blade 108 is not connected to the drum axel assembly 102 where the base of the incisions of skin is transected. In some embodiments, the internal blade 108 of the pixel drum 100 may oscillate either manually or be powered by an electric motor. Depending upon the density of the circular scalpets on the drum, a variable percentage of skin (e.g., 20%, 30%, 40%, etc.) can be transected within an area of excessive skin laxity.

In some embodiments, an added pixel drum harvester 112 is placed inside the drum 100 to perform a skin grafting operation by harvesting and aligning the transected/pixilated skin incisions/plugs (pixel graft) from tissue of a pixel donor onto an adherent membrane 110 lined in the interior of the pixel drum 100. A narrow space is created between the array of scalpets 106 and the adherent membrane 110 for the internal blade 108.

In an embodiment, the blade 108 is placed external to the drum 100 and the scalpet array 106 where the base of the incised circular skin plugs is transected. In another embodiment, the external blade 108 is connected to the drum axel assembly 102 when the base of the incisions of skin is transected. In an alternative embodiment, the external blade 108 is not connected to the drum axel assembly 102 when the base of the incisions of skin is transected. The adherent membrane 110 that extracts and aligns the transected skin segments is subsequently placed over a skin defect site of a patient. The blade 108 (either internal or external) can be a fenestrated layer of blade aligned to the scalpet array 106, but is not so limited.

The conformable adherent membrane 110 of an embodiment can be semi-porous to allow for drainage at a recipient skin defect when the membrane with the aligned transected skin segments is extracted from the drum and applied as a skin graft. The adherent semi-porous drum membrane 110 can also have an elastic recoil property to bring the transected/pixilated skin plugs together for grafting onto the skin defect site of the recipient, i.e., the margins of each skin plug can be brought closer together as a more uniform sheet after the adherent membrane with pixilated grafts extracted from the drum 100. Alternatively, the adherent semi-porous drum membrane 110 can be expandable to cover a large surface area of the skin defect site of the recipient. In some embodiments, a sheet of adhesive backer 111 can be applied between the adherent membrane 110 and the drum harvester 112. The drum array of scalpets 106, blade 108, and adherent membrane 110 can be assembled together as a sleeve onto a preexisting drum 100, as described in detail herein.

The internal drum harvester 112 of the pixel drum 110 of an embodiment is disposable and replaceable. Limit and/or control the use of the disposable components can be accomplished by means that includes but is not limited to electronic, EPROM, mechanical, durability. The electronic and/or mechanical records and/or limits of number of drum rotations for the disposable drum as well as the time of use for the disposable drum can be recorded, controlled and/or limited either electronically or mechanically.

During the harvesting portion of the procedure with a drum dermatome, the PAD scalpet array is applied directly to the skin surface. To circumferentially incise the skin pixels, the drum dermatome is positioned over the scalpet array to apply a load onto the subjacent skin surface. With a continuing load, the incised skin pixels are extruded through the holes of the scalpet array and captured onto an adherent membrane on the drum dermatome. The cutting outrigger blade of the dermatome (positioned over the scalpet array) transects the base of extruded skin pixels. The membrane and the pixelated skin composite are then removed from the dermatome drum, to be directly applied to the recipient skin defect as a skin graft.

Figure 12A:
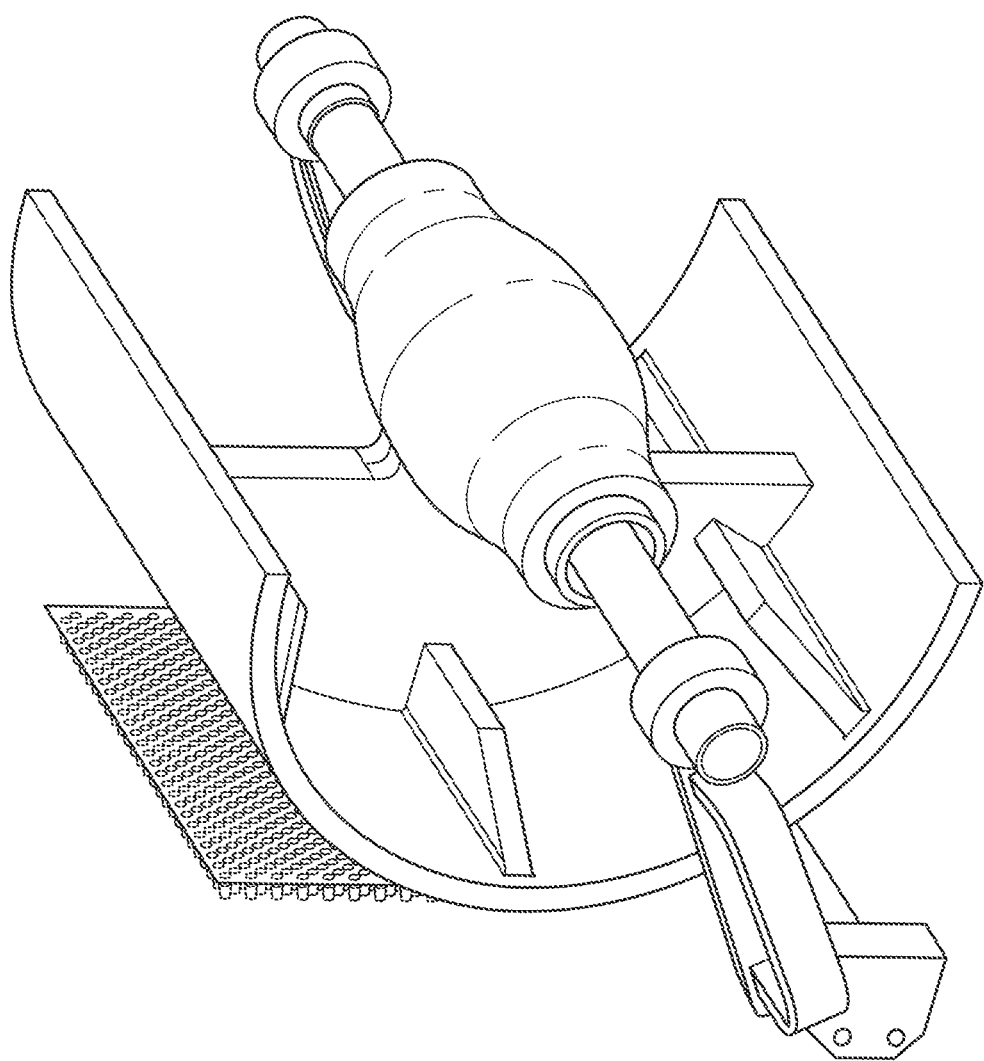
FIG. 12A shows the drum dermatome positioned over the scalpet plate, under an embodiment.
Figure 12B:
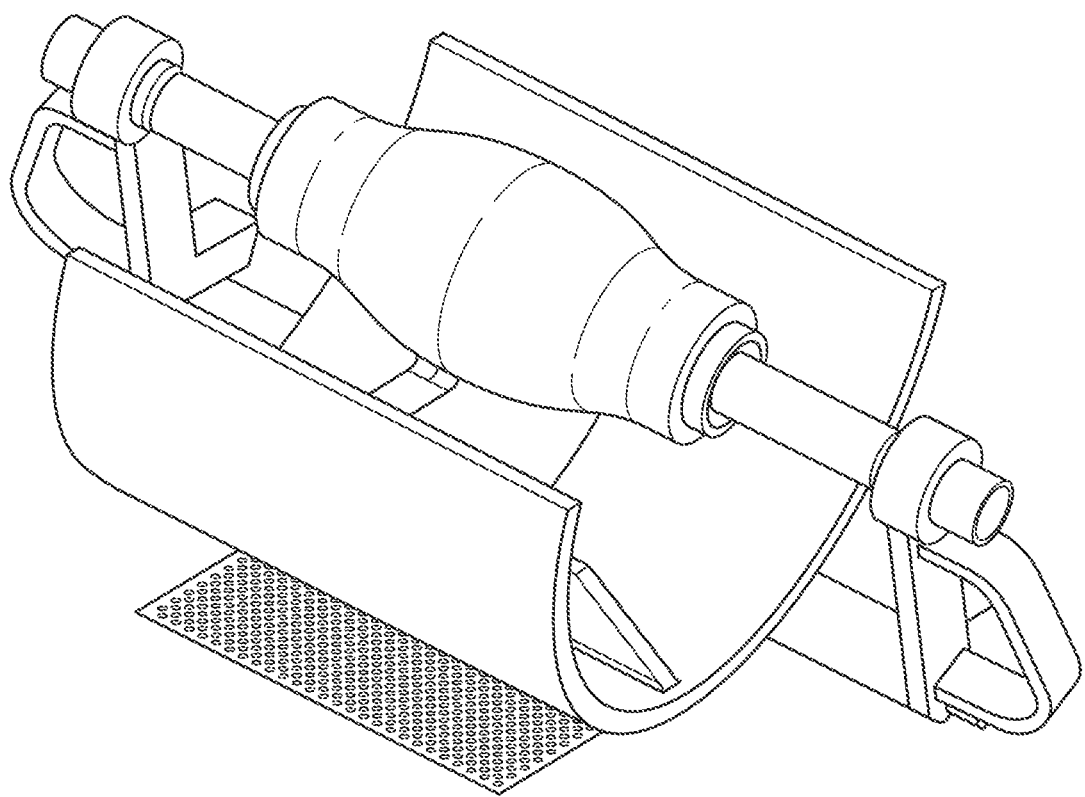
FIG. 12B is an alternative view of the drum dermatome positioned over the scalpet plate, under an embodiment.

With reference to FIG. 11C, an embodiment includes a drum dermatome for use with the scalpet plate, as described herein. More particularly, FIG. 12A shows the drum dermatome positioned over the scalpet plate, under an embodiment. FIG. 12B is an alternative view of the drum dermatome positioned over the scalpet plate, under an embodiment. The cutting outrigger blade of the drum dermatome is positioned on top of the scalpet array where the extruded skin plugs will be transected at their base.

Figure 13A:
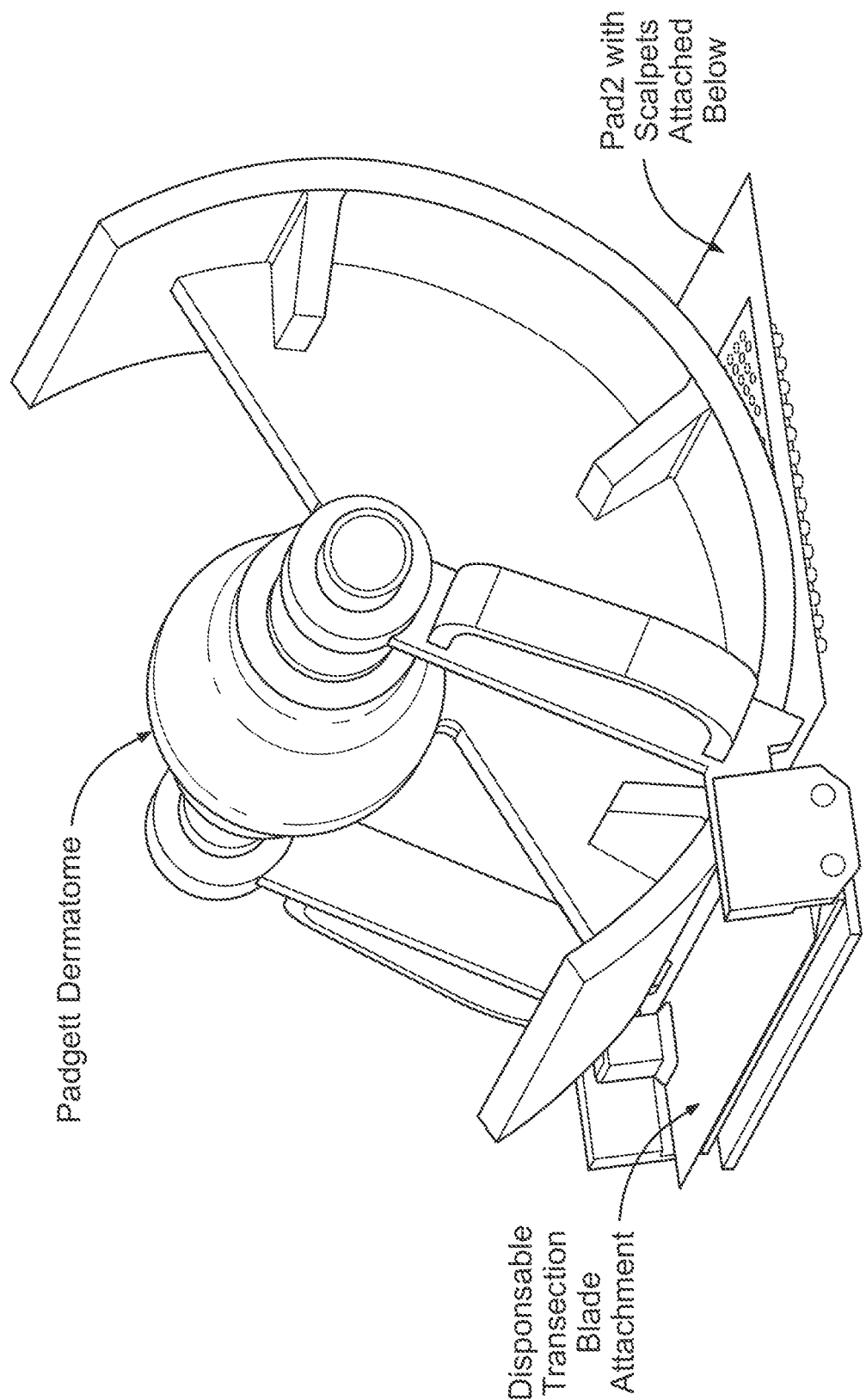
FIG. 13A is an isometric view of application of the drum dermatome (e.g., Padgett dermatome) over the scalpet plate, where the adhesive membrane is applied to the drum of the dermatome before rolling it over the investing plate, under an embodiment.
Figure 13B:
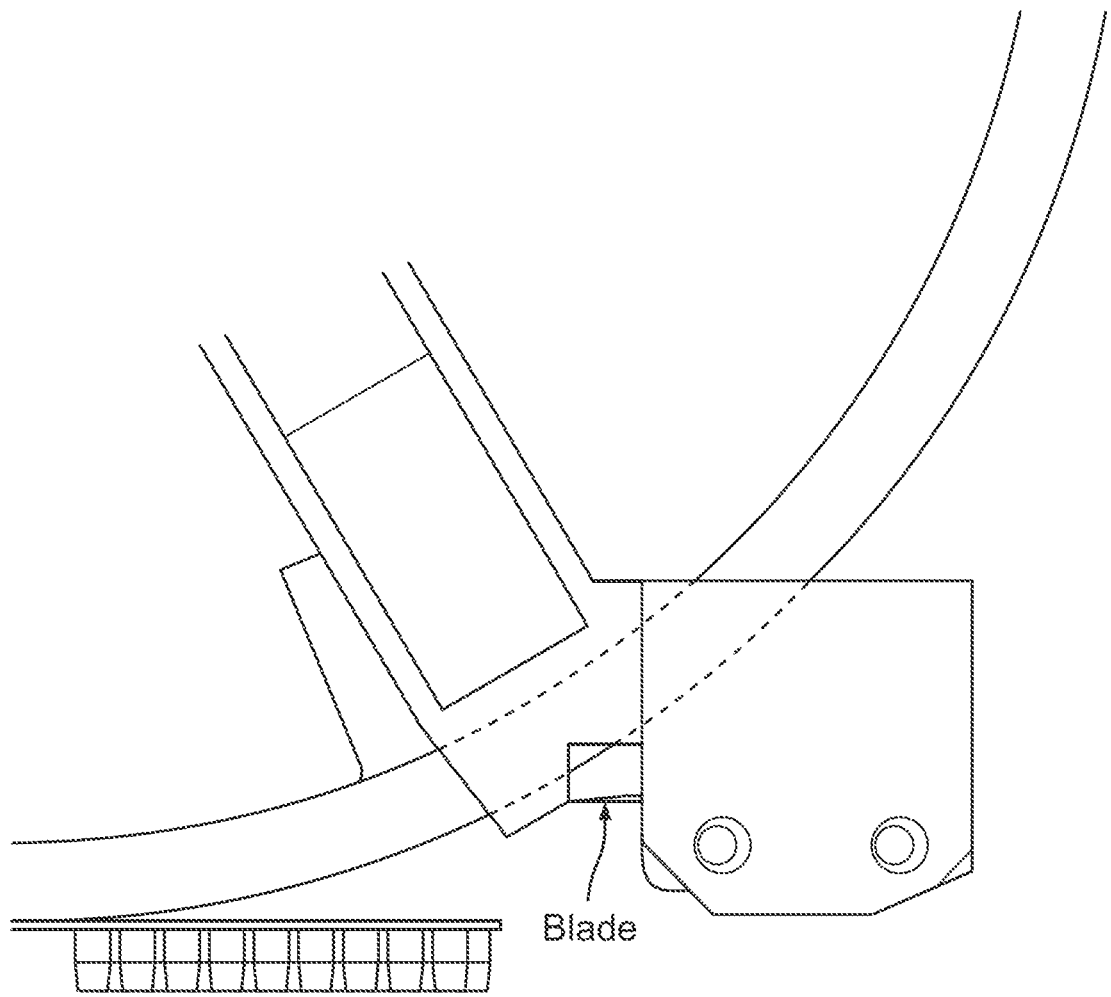
FIG. 13B is a side view of a portion of the drum dermatome showing a blade position relative to the scalpet plate, under an embodiment.
Figure 13C:
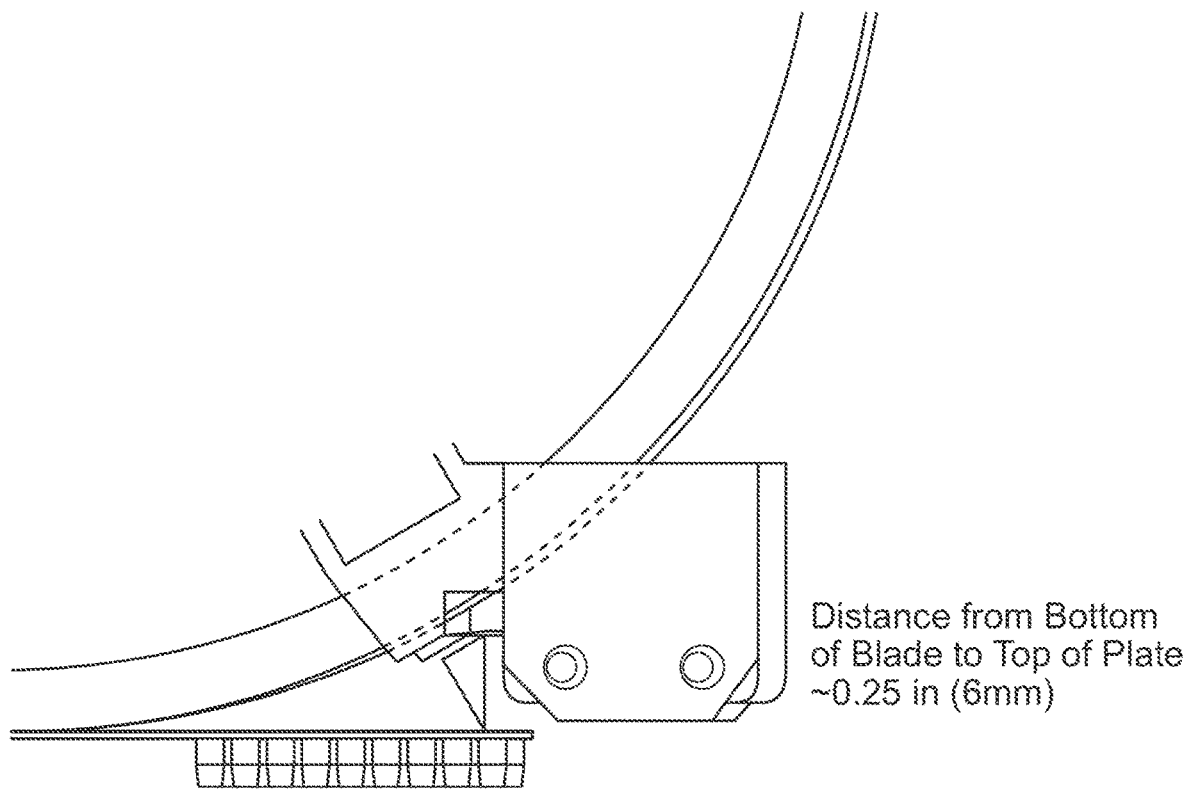
FIG. 13C is a side view of the portion of the drum dermatome showing a different blade position relative to the scalpet plate, under an embodiment.
Figure 13D:
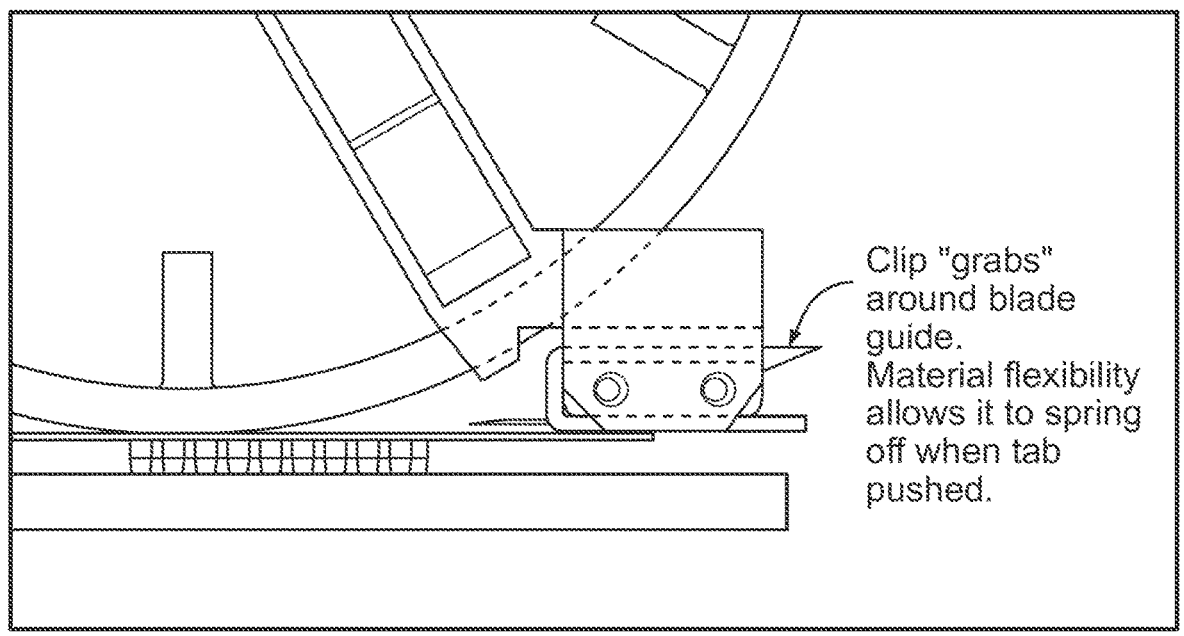
FIG. 13D is a side view of the drum dermatome with another blade position relative to the scalpet plate, under an embodiment.
Figure 13E:
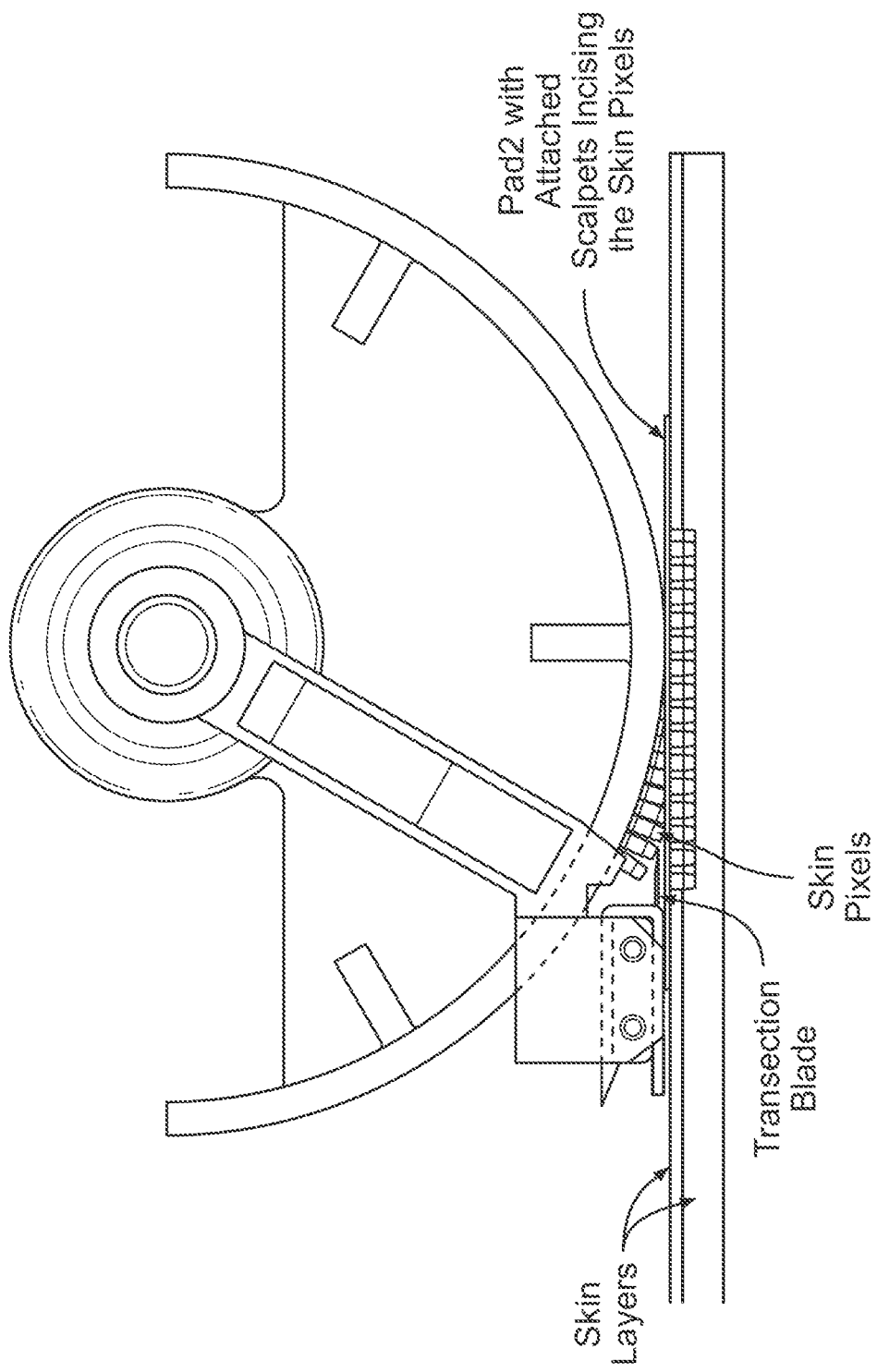
FIG. 13E is a side view of the drum dermatome with the transection blade clip showing transection of skin pixels by the blade clip, under an embodiment.
Figure 13F:
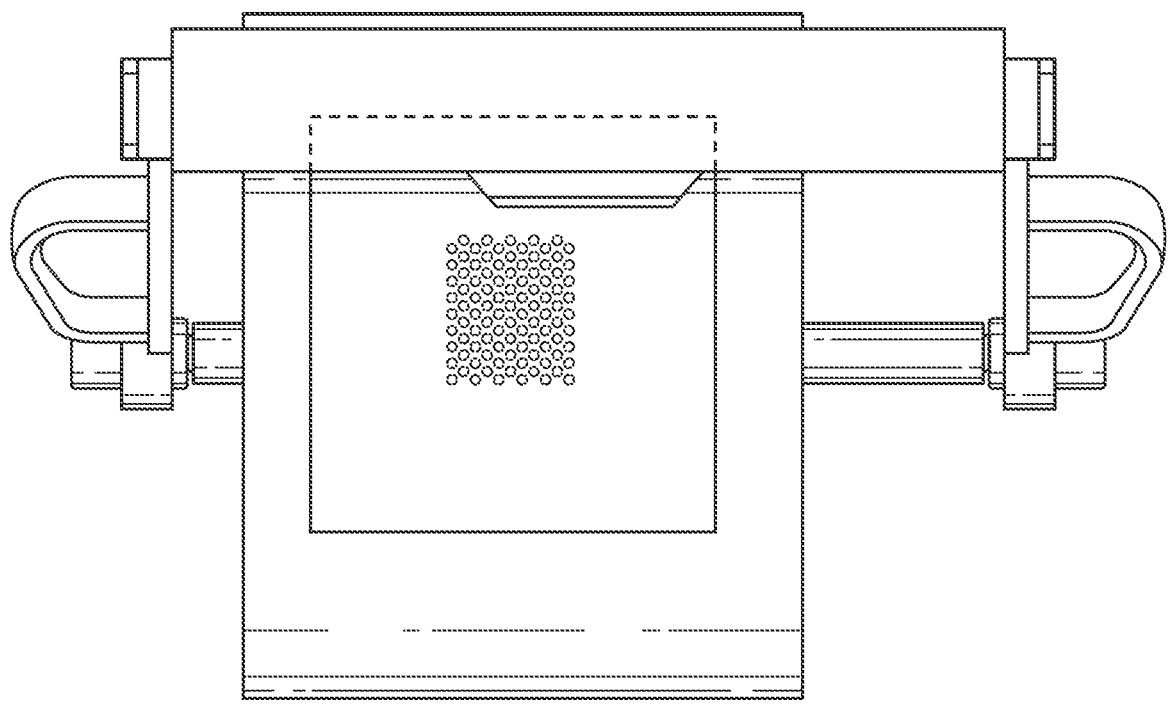
FIG. 13F is a bottom view of the drum dermatome along with the scalpet plate, under an embodiment.
Figure 13G:
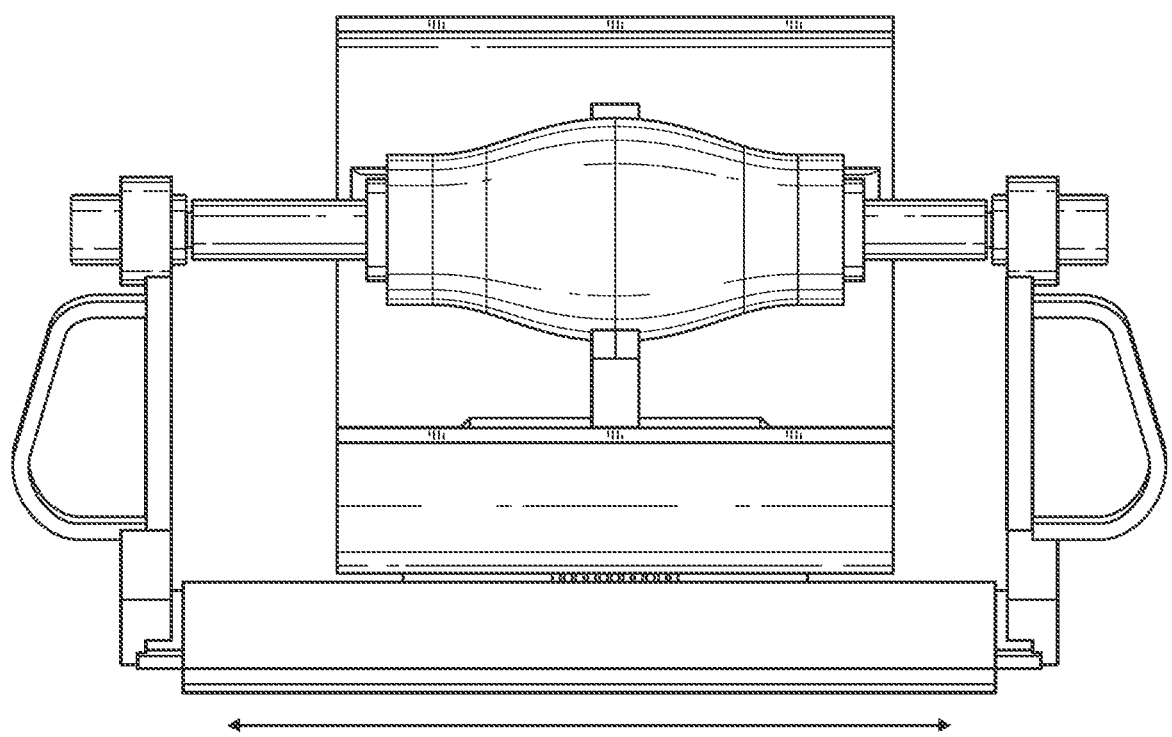
FIG. 13G is a front view of the drum dermatome along with the scalpet plate, under an embodiment.
Figure 13H:
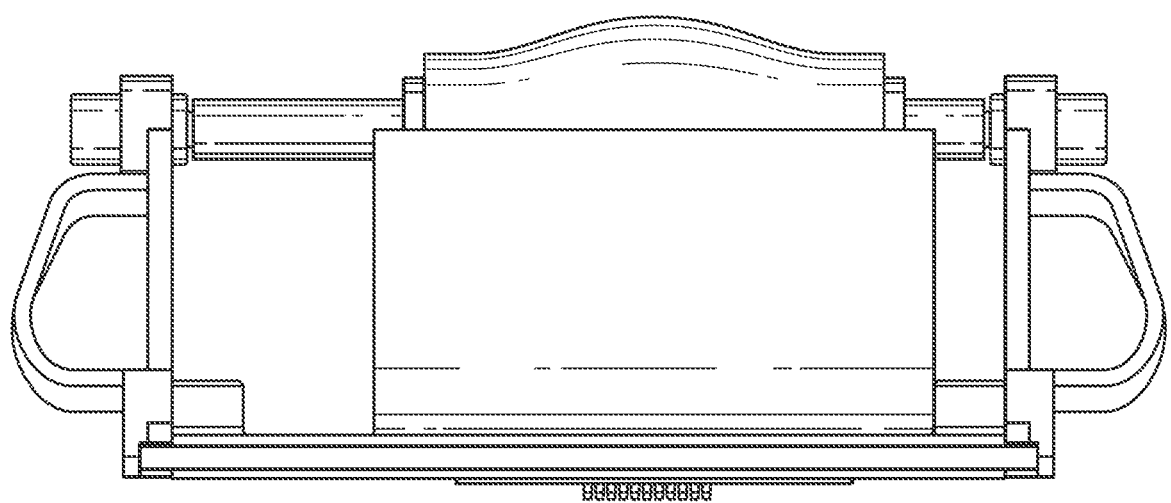
FIG. 13H is a back view of the drum dermatome along with the scalpet plate, under an embodiment.

FIG. 13A is an isometric view of application of the drum dermatome (e.g., Padgett dermatome) over the scalpet plate, where the adhesive membrane is applied to the drum of the dermatome before rolling it over the investing plate, under an embodiment. FIG. 13B is a side view of a portion of the drum dermatome showing a blade position relative to the scalpet plate, under an embodiment. FIG. 13C is a side view of the portion of the drum dermatome showing a different blade position relative to the scalpet plate, under an embodiment. FIG. 13D is a side view of the drum dermatome with another blade position relative to the scalpet plate, under an embodiment. FIG. 13E is a side view of the drum dermatome with the transection blade clip showing transection of skin pixels by the blade clip, under an embodiment. FIG. 13F is a bottom view of the drum dermatome along with the scalpet plate, under an embodiment. FIG. 13G is a front view of the drum dermatome along with the scalpet plate, under an embodiment. FIG. 13H is a back view of the drum dermatome along with the scalpet plate, under an embodiment.

Depending upon the clinical application, the disposable adherent membrane of the drum dermatome can be used to deposit/dispose of resected lax skin or harvest/align a pixilated skin graft.

Figure 14A:
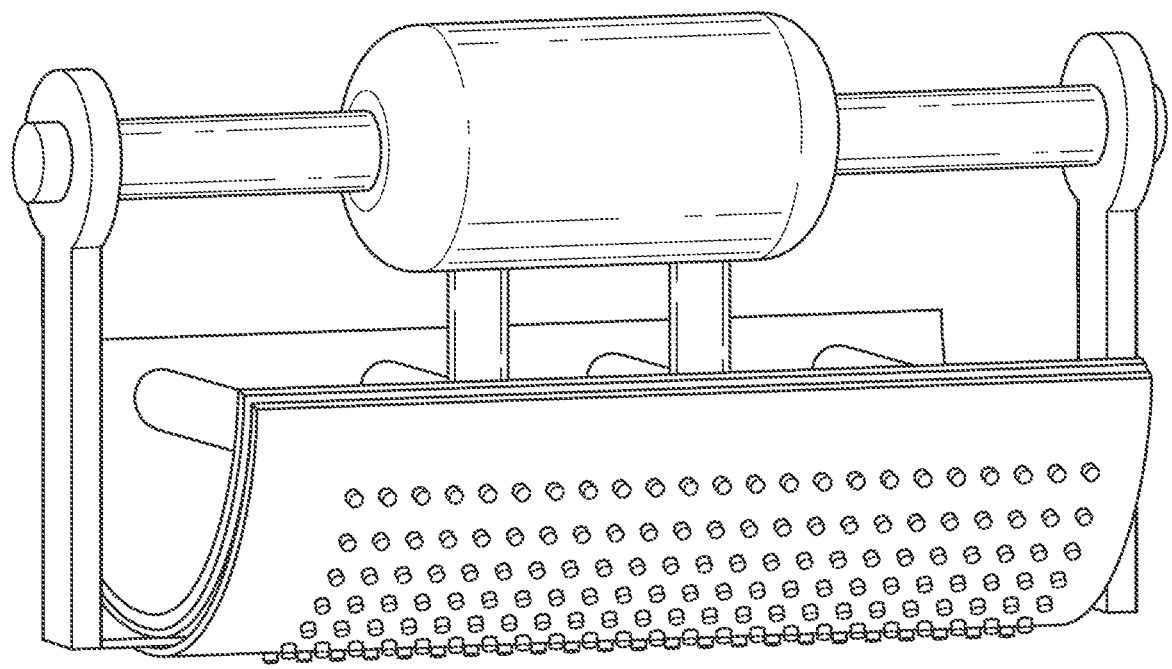
FIG. 14A shows an assembled view of the dermatome with the Pixel Onlay Sleeve (POS), under an embodiment.
Figure 14B:
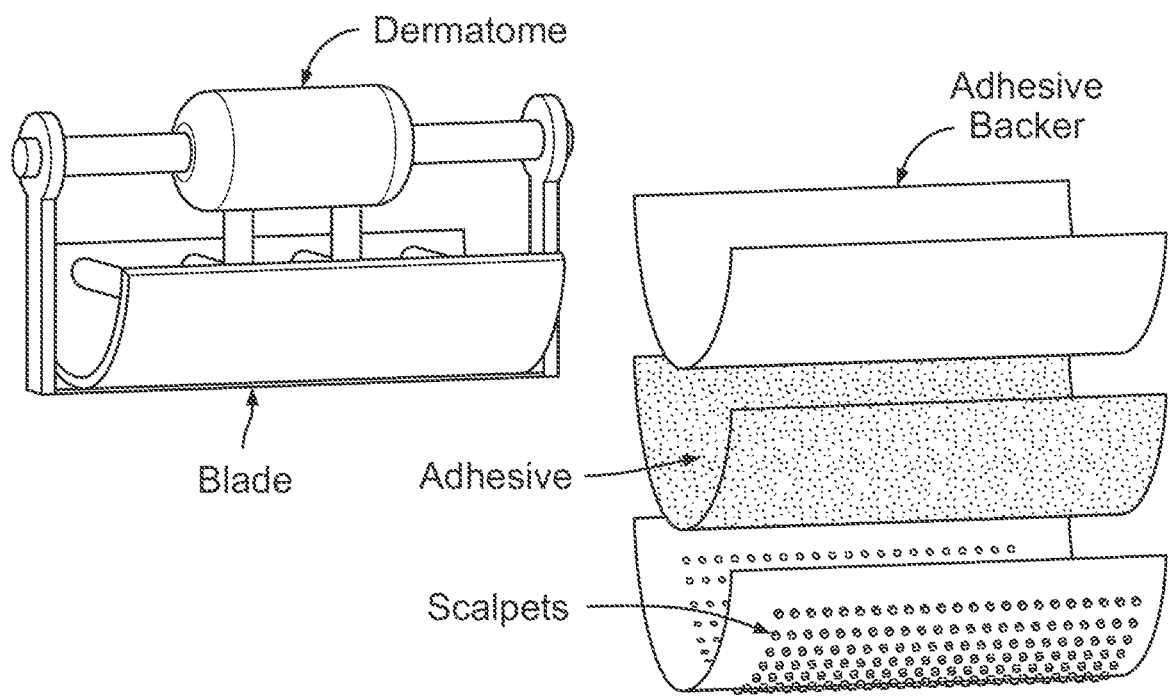
FIG. 14B is an exploded view of the dermatome with the Pixel Onlay Sleeve (POS), under an embodiment.
Figure 14C:
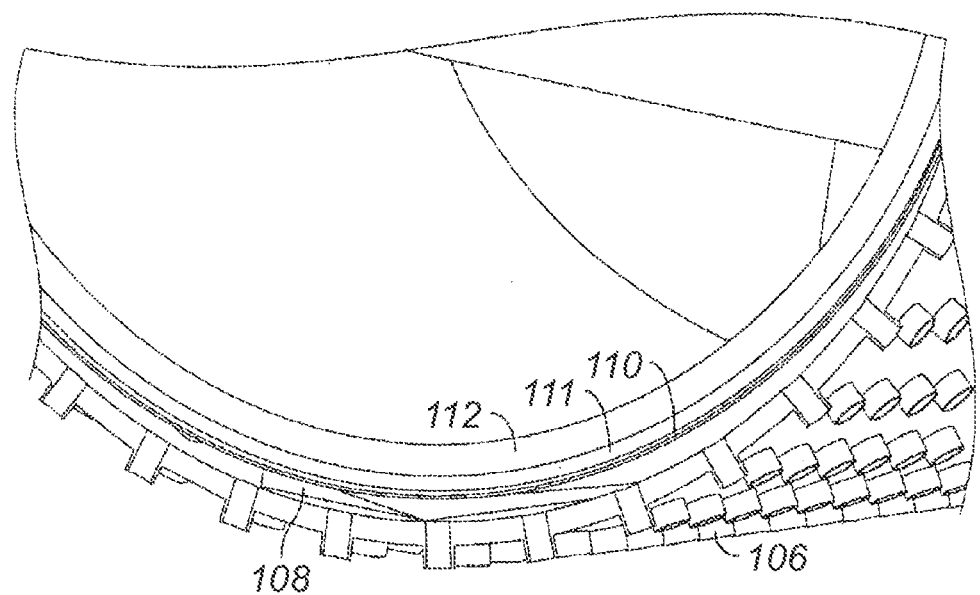
FIG. 14C shows a portion of the dermatome with the Pixel Onlay Sleeve (POS), under an embodiment.

Embodiments described herein also include a Pixel Onlay Sleeve (POS) for use with the dermatomes, for example the Padget dermatomes and Reese dermatomes. FIG. 14A shows an assembled view of the dermatome with the Pixel Onlay Sleeve (POS), under an embodiment. The POS comprises the dermatome and blade incorporated with an adhesive backer, adhesive, and a scalpet array. The adhesive backer, adhesive, and scalpet array are integral to the device, but are not so limited. FIG. 14B is an exploded view of the dermatome with the Pixel Onlay Sleeve (POS), under an embodiment. FIG. 14C shows a portion of the dermatome with the Pixel Onlay Sleeve (POS), under an embodiment.

The POS, also referred to herein as the "sleeve," provides a disposable drum dermatome onlay for the fractional resection of redundant lax skin and the fractional skin grafting of skin defects. The onlay sleeve is used in conjunction with either the Padget and Reese dermatomes as a single use disposable component. The POS of an embodiment is a three-sided slip-on disposable sleeve that slips onto a drum dermatome. The device comprises an adherent membrane and a scalpet drum array with an internal transection blade. The transection blade of an embodiment includes a single-sided cutting surface that sweeps across the internal surface of the scalpet drum array.

In an alternative blade embodiment, a fenestrated cutting layer covers the internal surface of the scalpet array. Each fenestration with its cutting surface is aligned with each individual scalpet. Instead of sweeping motion to transect the base of the skin plugs, the fenestrated cutting layer oscillates over the scalpet drum array. A narrow space between the adherent membrane and the scalpet array is created for excursion of the blade. For multiple harvesting during a skin grafting procedure, an insertion slot for additional adherent membranes is provided. The protective layer over the adherent membrane is pealed away insitu with an elongated extraction tab that is pulled from an extraction slot on the opposite side of the sleeve assembly. As with other pixel device embodiments, the adherent membrane is semi-porous for drainage at the recipient skin defect site. To morph the pixilated skin graft into a more continuous sheet, the membrane may also have an elastic recoil property to provide closer alignment of the skin plugs within the skin graft.

Figure 15A:
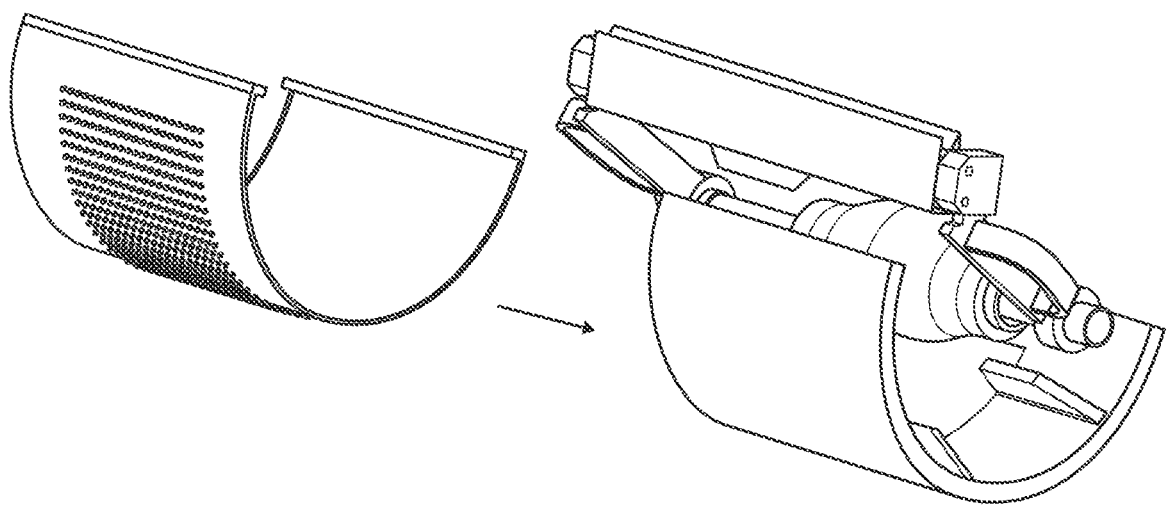
FIG. 15A shows the Slip-On PAD being slid onto a Padgett Drum Dermatome, under an embodiment.
Figure 15B:
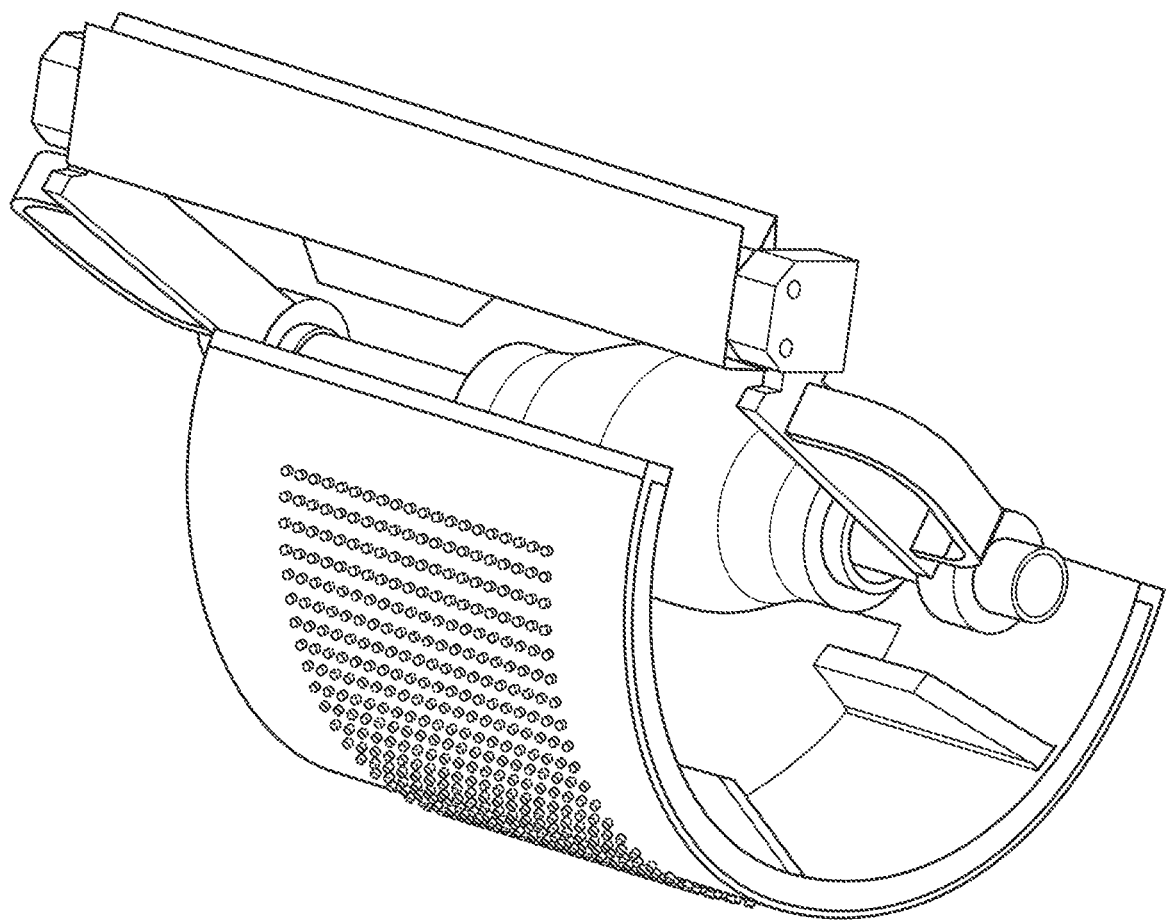
FIG. 15B shows an assembled view of the Slip-On PAD installed over the Padgett Drum Dermatome, under an embodiment.

Embodiments described herein include a Slip-On PAD that is configured as a single-use disposable device with either the Padgett or Reese dermatomes. FIG. 15A shows the Slip-On PAD being slid onto a Padgett Drum Dermatome, under an embodiment. FIG. 15B shows an assembled view of the Slip-On PAD installed over the Padgett Drum Dermatome, under an embodiment.

Figure 16A:
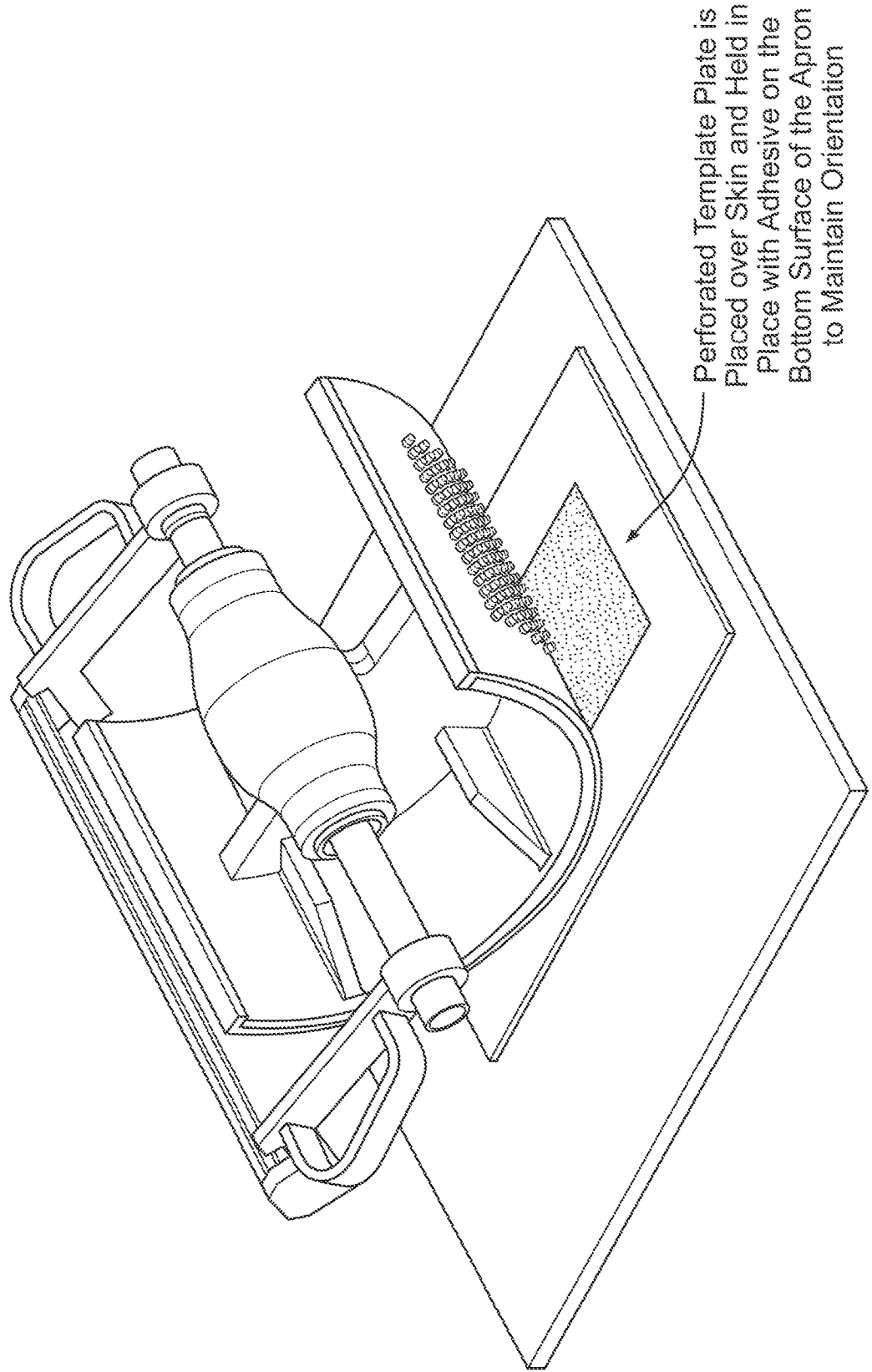
FIG. 16A shows the Slip-On PAD installed over a Padgett Drum Dermatome and used with a perforated template or guide plate, under an embodiment.

The Slip-on PAD of an embodiment is used (optionally) in combination with a perforated guide plate. FIG. 16A shows the Slip-On PAD installed over a Padgett Drum Dermatome and used with a perforated template or guide plate, under an embodiment. The perforated guide plate is placed over the target skin site and held in place with adhesive on the bottom surface of the apron to maintain orientation. The Padgett Dermatome with Slip-On PAD is rolled over the perforated guide plate on the skin.

Figure 16B:
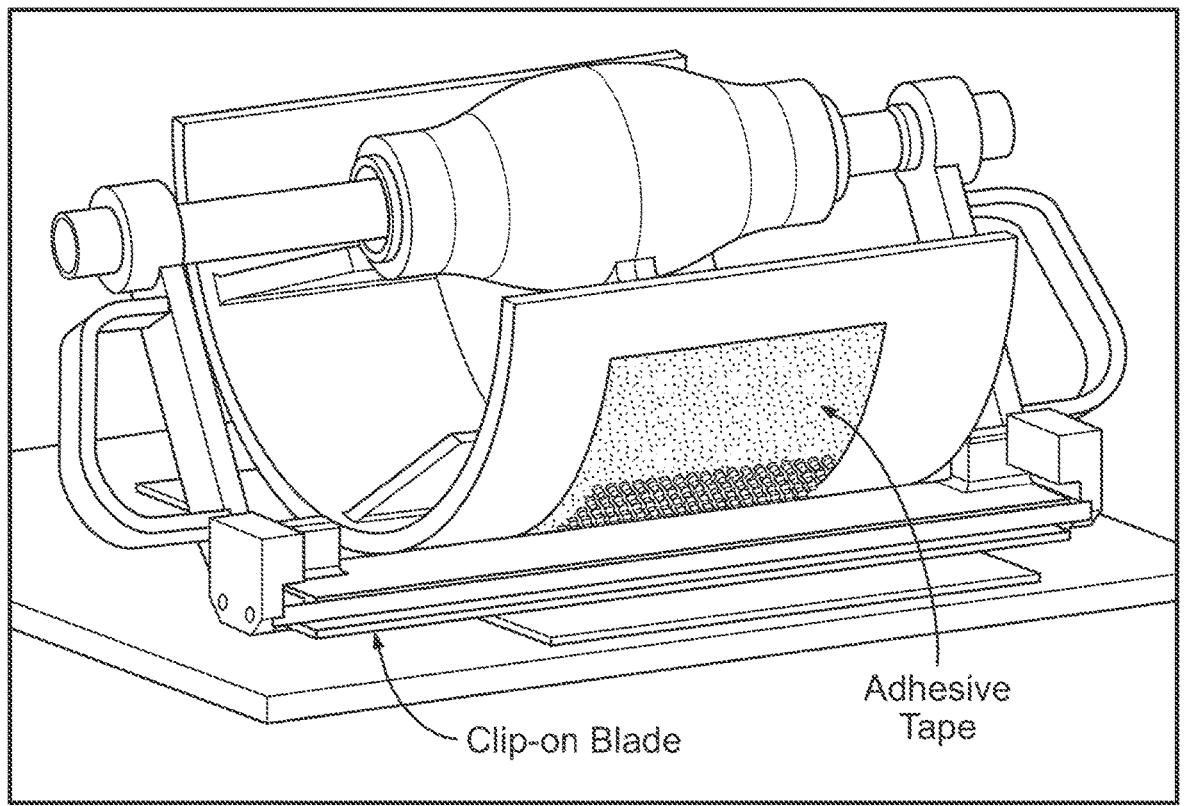
FIG. 16B shows skin pixel harvesting with a Padgett Drum Dermatome and installed Slip-On PAD, under an embodiment.

FIG. 16B shows skin pixel harvesting with a Padgett Drum Dermatome and installed Slip-On PAD, under an embodiment. For skin pixel harvesting, the Slip-On PAD is removed, adhesive tape is applied over the drum of the Padgett dermatome, and the clip-on blade is installed on the outrigger arm of the dermatome, which then is used to transect the base of the skin pixels. The Slip-on PAD of an embodiment is also used (optionally) with standard surgical instrumentation such as a ribbon retractor to protect the adjacent skin of the donor site.

Embodiments of the pixel instruments described herein include a Pixel Drum Dermatome (PD2) that is a single use disposable instrument or device. The PD2 comprises a cylinder or rolling/rotating drum coupled to a handle, and the cylinder includes a Scalpet Drum Array. An internal blade is interlocked to the drum axle/handle assembly and/or interlocked to outriggers attached to the central axle. As with the PAD and the POS described herein, small multiple pixilated resections of skin are performed directly in the region of skin laxity, thereby enhancing skin tightening with minimal visible scarring.

Figure 17A:
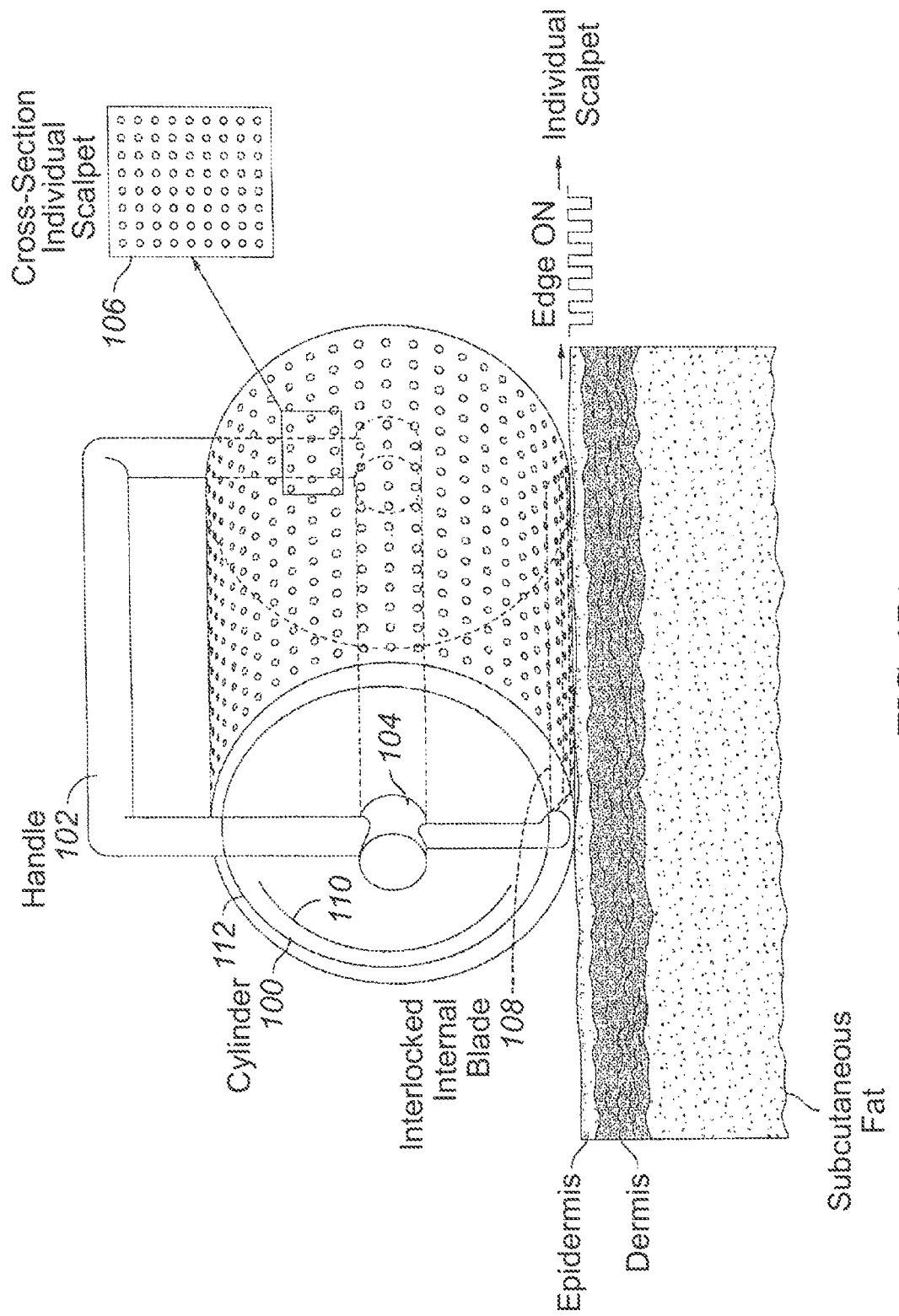
FIG. 17A shows an example of a Pixel Drum Dermatome being applied to a target site of the skin surface, under an embodiment.
Figure 17B:
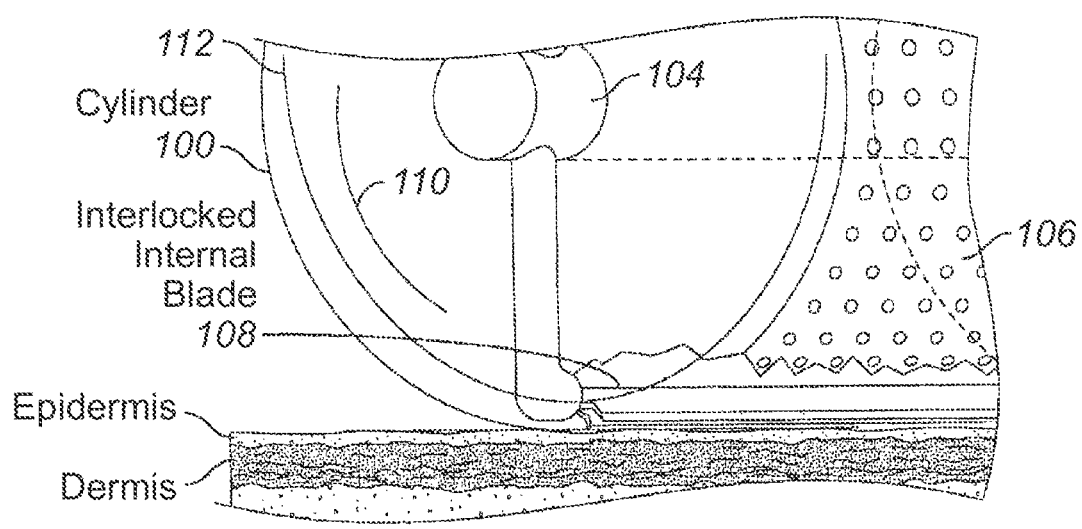
FIG. 17B shows an alternative view of a portion of the Pixel Drum Dermatome being applied to a target site of the skin surface, under an embodiment.

FIG. 17A shows an example of a Pixel Drum Dermatome being applied to a target site of the skin surface, under an embodiment. FIG. 17B shows an alternative view of a portion of the Pixel Drum Dermatome being applied to a target site of the skin surface, under an embodiment.

The PD2 device applies a full rolling/rotating drum to the skin surface where multiple small (e.g., 1.5 mm) circular incisions are created at the target site with a "Scalpet Drum Array". The base of each skin plug is then transected with an internal blade that is interlocked to the central drum axel/handle assembly and/or interlocked to outriggers attached to the central axel. Depending upon the density of the circular scalpets on the drum, a variable percentage of skin can be resected. The PD2 enables portions (e.g., 20%, 30%, 40%, etc.) of the skin's surface area to be resected without visible scarring in an area of excessive skin laxity, but the embodiment is not so limited.

Another alternative embodiment of the pixel instruments presented herein is the Pixel Drum Harvester (PDH). Similar to the Pixel Drum Dermatome, an added internal drum harvests and aligns the pixilated resections of skin onto an adherent membrane that is then placed over a recipient skin defect site of the patient. The conformable adherent membrane is semi-porous to allow for drainage at a recipient skin defect when the membrane with the aligned resected skin segments is extracted from the drum and applied as a skin graft. An elastic recoil property of the membrane allows closer approximation of the pixilated skin segments, partially converting the pixilated skin graft to a sheet graft at the recipient site.

The pixel array medical systems, instruments or devices, and methods described herein evoke or enable cellular and/or extracellular responses that are obligatory to the clinical outcomes achieved. For the pixel dermatomes, a physical reduction of the skin surface area occurs due to the pixilated resection of skin, i.e., creation of the skin plugs. In addition, a subsequent tightening of the skin results due to the delayed wound healing response. Each pixilated resection initiates an obligate wound healing sequence in multiple phases as described in detail herein.

The first phase of this sequence is the inflammatory phase in which degranulation of mast cells release histamine into the "wound". Histamine release may evoke dilatation of the capillary bed and increase vessel permeability into the extracellular space. This initial wound healing response occurs within the first day and will be evident as erythema on the skin's surface.

The second phase (of Fibroplasia) commences within three to four days of "wounding". During this phase, there is migration and mitotic multiplication of fibroblasts. Fibroplasia of the wound includes the deposition of neocollagen and the myofibroblastic contraction of the wound.

Histologically, the deposition of neocollagen can be identified microscopically as compaction and thickening of the dermis. Although this is a static process, the tensile strength of the wound significantly increases. The other feature of Fibroplasia is a dynamic physical process that results in a multi-dimensional contraction of the wound. This component feature of Fibroplasia is due to the active cellular contraction of myofibroblasts. Morphologically, myoblastic contraction of the wound will be visualized as a two dimensional tightening of the skin surface. Overall, the effect of Fibroplasia is dermal contraction along with the deposition of a static supporting scaffolding of neocollagen with a tightened framework. The clinical effect is seen as a delayed tightening of skin with smoothing of skin texture over several months. The clinical endpoint is generally a more youthful appearing skin envelope of the treatment area. A third and final phase of the delayed wound healing response is maturation.

During this phase there is a strengthening and remodeling of the treatment area due to an increased cross-linkage of the collagen fibril matrix (of the dermis). This final stage commences within six to twelve months after "wounding" and may extend for at least one to two years. Small pixilated resections of skin should preserve the normal dermal architecture during this delayed wound healing process without the creation of an evident scar that typically occurs with a larger surgical resection of skin. Lastly, there is a related stimulation and rejuvenation of the epidermis from the release of epidermal growth hormone. The delayed wound healing response can be evoked, with scar collagen deposition, within tissues (such as muscle or fat) with minimal pre-existing collagen matrix.

Other than tightening skin for aesthetic purposes, the pixel array medical systems, instruments or devices, and methods described herein may have additional medically related applications. In some embodiments, the pixel array devices can transect a variable portion of any soft tissue structure without resorting to a standard surgical resection. More specifically, the reduction of an actinic damaged area of skin via the pixel array devices should reduce the incidence of skin cancer. For the treatment of sleep apnea and snoring, a pixilated mucosal reduction (soft palate, base of the tongue and lateral pharyngeal walls) via the pixel array devices would reduce the significant morbidity associated with more standard surgical procedures. For birth injuries of the vaginal vault, pixilated skin and vaginal mucosal resection via the pixel array devices would reestablish normal pre-partum geometry and function without resorting to an A&P resection. Related female stress incontinence could also be corrected in a similar fashion.

The pixel array dermatome (PAD) of an embodiment, also referred to herein as a scalpet device assembly, includes a system or kit comprising a control device, also referred to as a punch impact hand-piece, and a scalpet device, also referred to as a tip device. The scalpet device, which is removeably coupled to the control device, includes an array of scalpets positioned within the scalpet device. The removeable scalpet device of an embodiment is disposable and consequently configured for use during a single procedure, but the embodiment is not so limited.

The PAD includes an apparatus comprising a housing configured to include a scalpet device. The scalpet device includes a substrate and a scalpet array, and the scalpet array includes a plurality of scalpets arranged in a configuration on the substrate. The substrate and the plurality of scalpets are configured to be deployed from the housing and retracted into the housing, and the plurality of scalpets is configured to generate a plurality of incised skin pixels at a target site when deployed. The proximal end of the control device is configured to be hand-held. The housing is configured to be removeably coupled to a receiver that is a component of a control device. The control device includes a proximal end that includes an actuator mechanism, and a distal end that includes the receiver. The control device is configured to be disposable, but alternatively the control device is configured to be at least one of cleaned, disinfected, and sterilized.

The scalpet array is configured to be deployed in response to activation of the actuator mechanism. The scalpet device of an embodiment is configured so the scalpet array is deployed from the scalpet device and retracted back into the scalpet device in response to activation of the actuator mechanism. The scalpet device of an alternative embodiment is configured so the scalpet array is deployed from the scalpet device in response to activation of the actuator mechanism, and retracted back into the scalpet device in response to release of the actuator mechanism.

FIG. 18 shows a side perspective view of the PAD assembly, under an embodiment. The PAD assembly of this embodiment includes a control device configured to be hand-held, with an actuator or trigger and the scalpet device comprising the scalpet array. The control device is reusable, but alternative embodiments include a disposable control device. The scalpet array of an embodiment is configured to create or generate an array of incisions (e.g., 1.5 mm, 2 mm, 3 mm, etc.) as described in detail herein. The scalpet device of an embodiment includes a spring-loaded array of scalpets configured to incise the skin as described in detail herein, but the embodiments are not so limited.

FIG. 19A shows a top perspective view of the scalpet device for use with the PAD assembly, under an embodiment. FIG. 19B shows a bottom perspective view of the scalpet device for use with the PAD assembly, under an embodiment. The scalpet device comprises a housing configured to house a substrate that is coupled to or includes a plunger. The housing is configured so that a proximal end of the plunger protrudes through a top surface of the housing. The housing is configured to be removeably coupled to the control device, and a length of the plunger is configured to protrude a distance through the top surface to contact the control device and actuator when the scalpet device is coupled to the control device.

The substrate of the scalpet device is configured to retain numerous scalpets that form the scalpet array. The scalpet array comprises a pre-specified number of scalpets as appropriate to the procedure in which the scalpet device assembly is used. The scalpet device includes at least one spring mechanism configured to provide a downward, or impact or punching, force in response to activation of the scalpet array device, and this force assists generation of incisions (pixelated skin resection sites) by the scalpet array. Alternatively, the spring mechanism can be configured to provide an upward, or retracting, force to assist in retraction of the scalpet array.

One or more of the scalpet device and the control device of an embodiment includes an encryption system (e.g., EPROM, etc.). The encryption system is configured to prevent illicit use and pirating of the scalpet devices and/or control devices, but is not so limited.

During a procedure, the scalpet device assembly is applied one time to a target area or, alternative, applied serially within a designated target treatment area of skin laxity. The pixelated skin resection sites within the treatment area are then closed with the application of Flexan sheeting, as described in detail herein, and directed closure of these pixelated resections is performed in a direction that provides the greatest aesthetic correction of the treatment site.

The PAD device of an alternative embodiment includes a vacuum component or system for removing incised skin pixels. FIG. 20 shows a side view of the punch impact device including a vacuum component, under an embodiment. The PAD of this example includes a vacuum system or component within the control device to suction evacuate the incised skin pixels, but is not so limited. The vacuum component is removeably coupled to the PAD device, and its use is optional. The vacuum component is coupled to and configured to generate a low-pressure zone within or adjacent to one or more of the housing, the scalpet device, the scalpet array, and the control device. The low-pressure zone is configured to evacuate the incised skin pixels.

The PAD device of another alternative embodiment includes a radio frequency (RF) component or system for generating skin pixels. The RF component is coupled to and configured to provide or couple energy within or adjacent to one or more of the housing, the scalpet device, the scalpet array, and the control device. The RF component is removeably coupled to the PAD device, and its use is optional. The energy provided by the RF component includes one or more of thermal energy, vibrational energy, rotational energy, and acoustic energy, to name a few.

The PAD device of yet another alternative embodiment includes a vacuum component or system and an RF component or system. The PAD of this embodiment includes a vacuum system or component within the handpiece to suction evacuate the incised skin pixels. The vacuum component is removeably coupled to the PAD device, and its use is optional. The vacuum component is coupled to and configured to generate a low-pressure zone within or adjacent to one or more of the housing, the scalpet device, the scalpet array, and the control device. The low-pressure zone is configured to evacuate the incised skin pixels. Additionally, the PAD device includes an RF component coupled to and configured to provide or couple energy within or adjacent to one or more of the housing, the scalpet device, the scalpet array, and the control device. The RF component is removeably coupled to the PAD device, and its use is optional. The energy provided by the RF component includes one or more of thermal energy, vibrational energy, rotational energy, and acoustic energy, to name a few.

As one particular example, the PAD of an embodiment includes an electrosurgical generator configured to more effectively incise donor skin or skin plugs with minimal thermo-conductive damage to the adjacent skin. For this reason, the RF generator operates using relatively high power levels with relatively short duty cycles, for example.

The RF generator is configured to supply one or more of a powered impactor component configured to provide additional compressive force for cutting, cycling impactors, vibratory impactors, and an ultrasonic transducer.

The PAD with RF of this example also includes a vacuum component, as described herein. The vacuum component of this embodiment is configured to apply a vacuum that pulls the skin up towards the scalpets (e.g., into the lumen of the scalpets, etc.) to stabilize and promote the RF mediated incision of the skin within the fractional resection field, but is not so limited. One or more of the RF generator and the vacuum appliance is coupled to be under the control of a processor running a software application. Additionally, the PAD of this embodiment can be used with the guide plate as described in detail herein, but is not so limited.

In addition to fractional incision at a donor site, fractional skin grafting includes the harvesting and deposition of skin plugs (e.g., onto an adherent membrane, etc.) for transfer to a recipient site. As with fractional skin resection, the use of a duty-driven RF cutting edge on an array of scalpets facilitates incising donor skin plugs. The base of the incised scalpets is then transected and harvested as described in detail herein.

The timing of the vacuum assisted component is processor controlled to provide a prescribed sequence with the RF duty cycle. With software control, different variations are possible to provide the optimal sequence of combined RF cutting with vacuum assistance. Without limitation, these include an initial period of vacuum prior to the RF duty cycle. Subsequent to the RF duty cycle, a period during the sequence of an embodiment includes suction evacuation of the incised skin plugs.

Other potential control sequences of the PAD include without limitation simultaneous duty cycles of RF and vacuum assistance. Alternatively, a control sequence of an embodiment includes pulsing or cycling of the RF duty cycle within the sequence and/or with variations of RF power or the use of generators at different RF frequencies.

Another alternative control sequence includes a designated RF cycle occurring at the depth of the fractional incision. A lower power longer duration RF duty cycle with insulated shaft with an insulated shaft an active cutting tip could generate a thermal-conductive lesion in the deep dermal/subcutaneous tissue interface. The deep thermal lesion would evoke a delayed wound healing sequence that would secondarily tighten the skin without burning of the skin surface.

With software control, different variations are possible to provide the optimal sequence of combined RF cutting and powered mechanical cutting with vacuum assistance. Examples include but are not limited to combinations of powered mechanical cutting with vacuum assistance, RF cutting with powered mechanical cutting and vacuum assistance, RF cutting with vacuum assistance, and RF cutting with vacuum assistance. Examples of combined software controlled duty cycles include but are not limited to precutting vacuum skin stabilization period, RF cutting duty cycle with vacuum skin stabilization period, RF cutting duty cycle with vacuum skin stabilization and powered mechanical cutting period, powered mechanical cutting with vacuum skin stabilization period, post cutting RF duty cycle for thermal conductive heating of the deeper dermal and/or subdermal tissue layer to evoke a wound healing response for skin tightening, and a post cutting vacuum evacuation period for skin tightening.

Figure 21A:
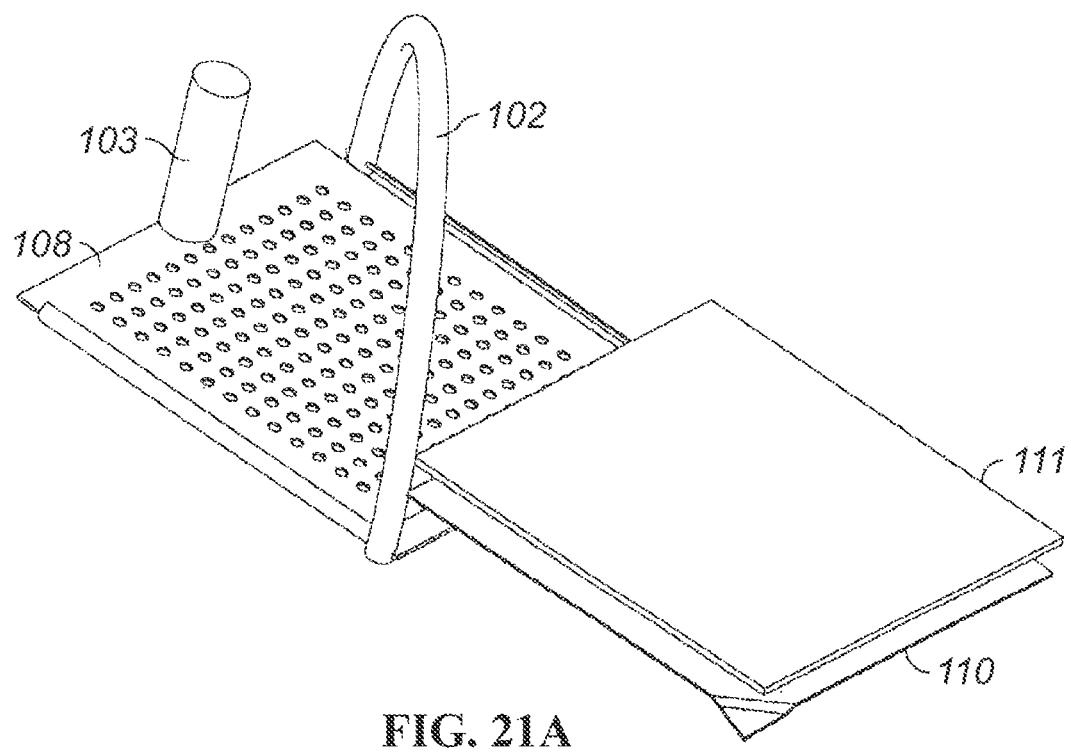
FIG. 21A shows a top view of an oscillating flat scalpet array and blade device, under an embodiment.
Figure 21B:
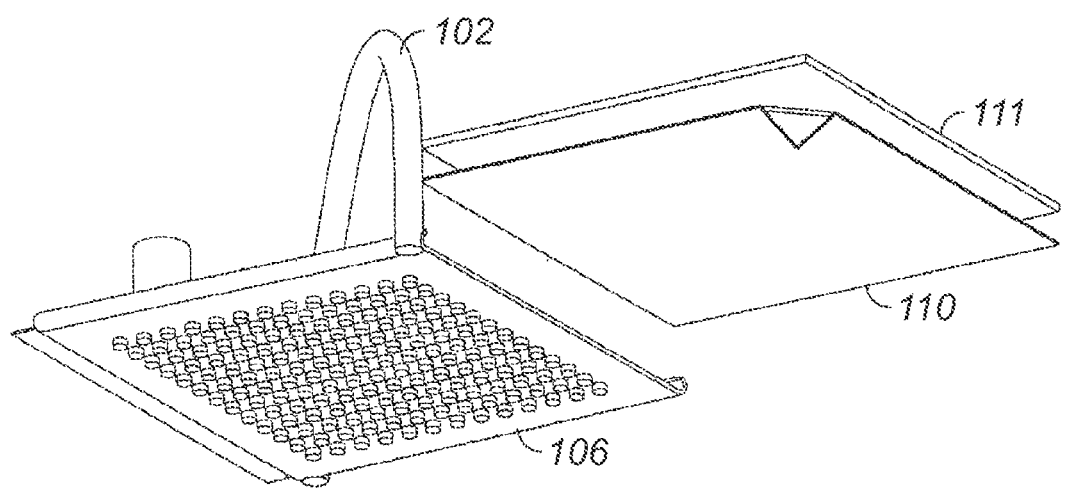
FIG. 21B shows a bottom view of an oscillating flat scalpet array and blade device, under an embodiment.
Figure 21C:
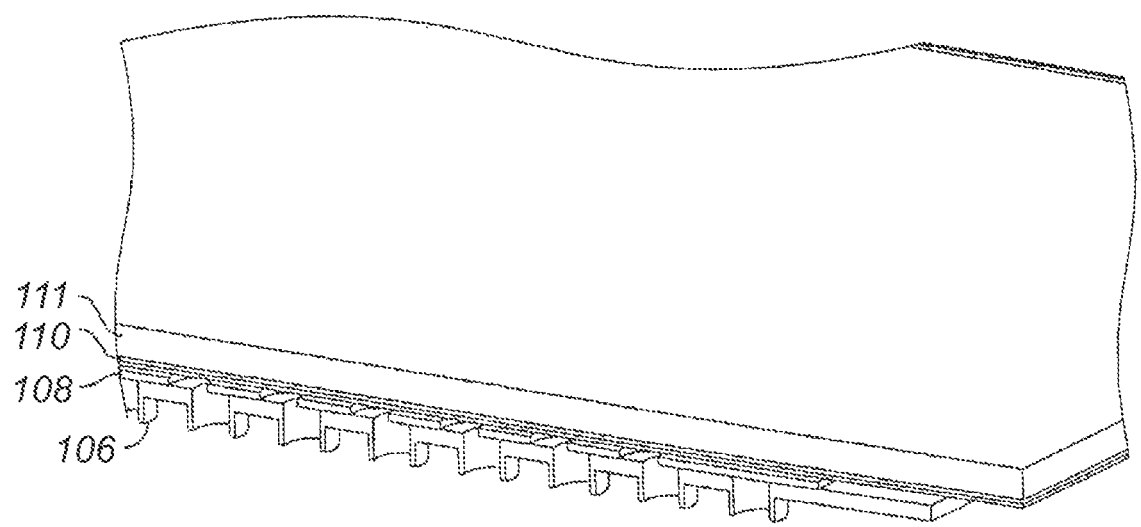
FIG. 21C is a close-up view of the flat array when the array of scalpets, blades, adherent membrane and the adhesive backer are assembled together, under an embodiment.
Figure 21D:
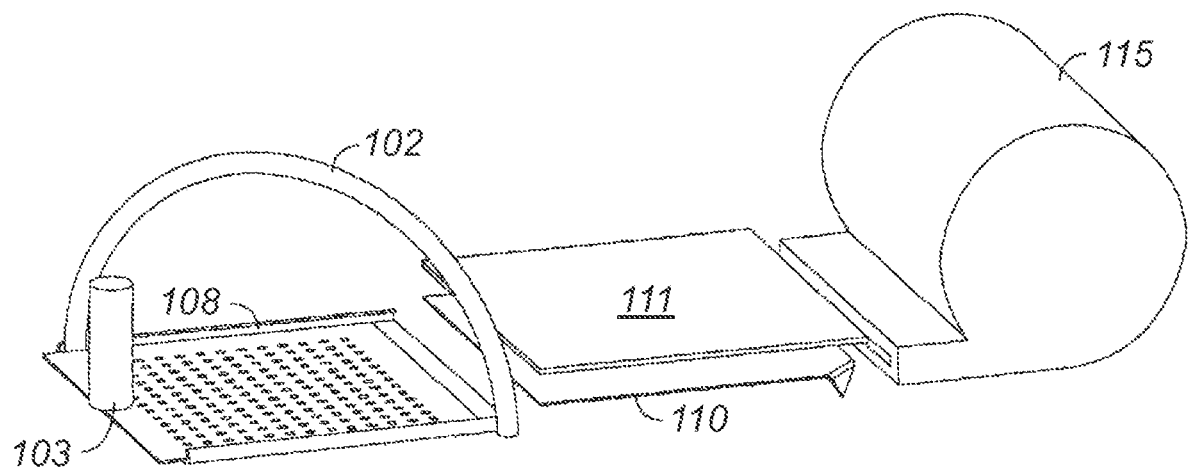
FIG. 21D is a close-up view of the flat array of scalpets with a feeder component, under an embodiment.

Another embodiment of pixel array medical devices described herein includes a device comprising an oscillating flat array of scalpets and blade either powered electrically or deployed manually (unpowered) and used for skin tightening as an alternative to the drum/cylinder described herein. FIG. 21A shows a top view of an oscillating flat scalpet array and blade device, under an embodiment. FIG. 21B shows a bottom view of an oscillating flat scalpet array and blade device, under an embodiment. Blade 108 can be a fenestrated layer of blade aligned to the scalpet array 106. The instrument handle 102 is separated from the blade handle 103 and the adherent membrane 110 can be peeled away from the adhesive backer 111. FIG. 21C is a close-up view of the flat array when the array of scalpets 106, blades 108, adherent membrane 110 and the adhesive backer 111 are assembled together, under an embodiment. As assembled, the flat array of scalpets can be metered to provide a uniform harvest or a uniform resection. In some embodiments, the flat array of scalpets may further include a feeder component 115 for the adherent harvesting membrane 110 and adhesive backer 111. FIG. 21D is a close-up view of the flat array of scalpets with a feeder component 115, under an embodiment.

Figure 22:
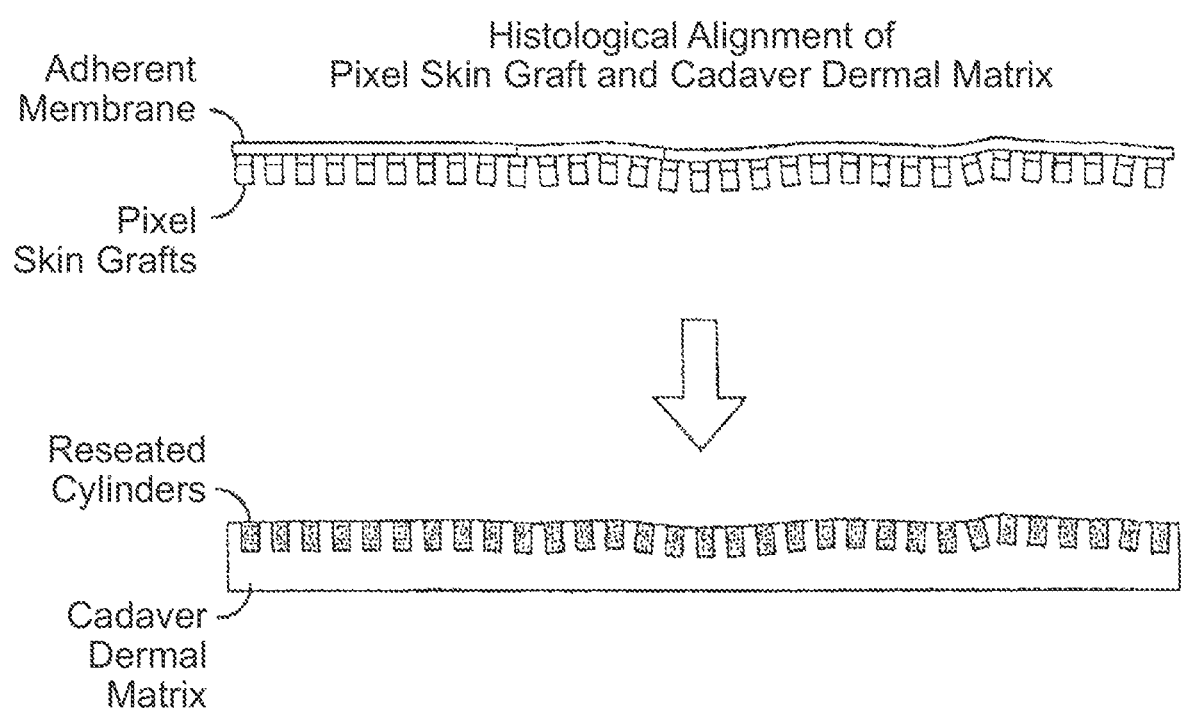
FIG. 22 shows a cadaver dermal matrix cylindrically transected similar in size to the harvested skin pixel grafts, under an embodiment.

In another skin grafting embodiment, the pixel graft is placed onto an irradiated cadaver dermal matrix (not shown). When cultured onto the dermal matrix, a graft of full thickness skin is created for the patient that is immunologically identical to the pixel donor. In embodiments, the cadaver dermal matrix can also be cylindrical transected similar in size to the harvested skin pixel grafts to provide histological alignment of the pixilated graft into the cadaver dermal framework. FIG. 22 shows a cadaver dermal matrix cylindrically transected similar in size to the harvested skin pixel grafts, under an embodiment. In some embodiments, the percentage of harvest of the donor site can be determined in part by the induction of a normal dermal histology at the skin defect site of the recipient, i.e., a normal (smoother) surface topology of the skin graft is facilitated. With either the adherent membrane or the dermal matrix embodiment, the pixel drum harvester includes the ability to harvest a large surface area for grafting with visible scarring of the patient's donor site significantly reduced or eliminated.

In addition to the pixel array medical devices described herein, embodiments include drug delivery devices. For the most part, the parenteral delivery of drugs is still accomplished from an injection with a syringe and needle. To circumvent the negative features of the needle and syringe system, the topical absorption of medication transcutaneously through an occlusive patch was developed. However, both of these drug delivery systems have significant drawbacks. The human aversion to a needle injection has not abated during the nearly two centuries of its use. The variable systemic absorption of either a subcutaneous or intramuscular drug injection reduces drug efficacy and may increase the incidence of adverse patient responses. Depending upon the lipid or aqueous carrier fluid of the drug, the topically applied occlusive patch is plagued with variable absorption across an epidermal barrier. For patients who require local anesthesia over a large surface area of skin, neither the syringe/needle injections nor topical anesthetics are ideal. The syringe/needle "field" injections are often painful and may instill excessive amounts of the local anesthetic that may cause systemic toxicity. Topical anesthetics rarely provide the level of anesthesia required for skin related procedures.

Figure 23:
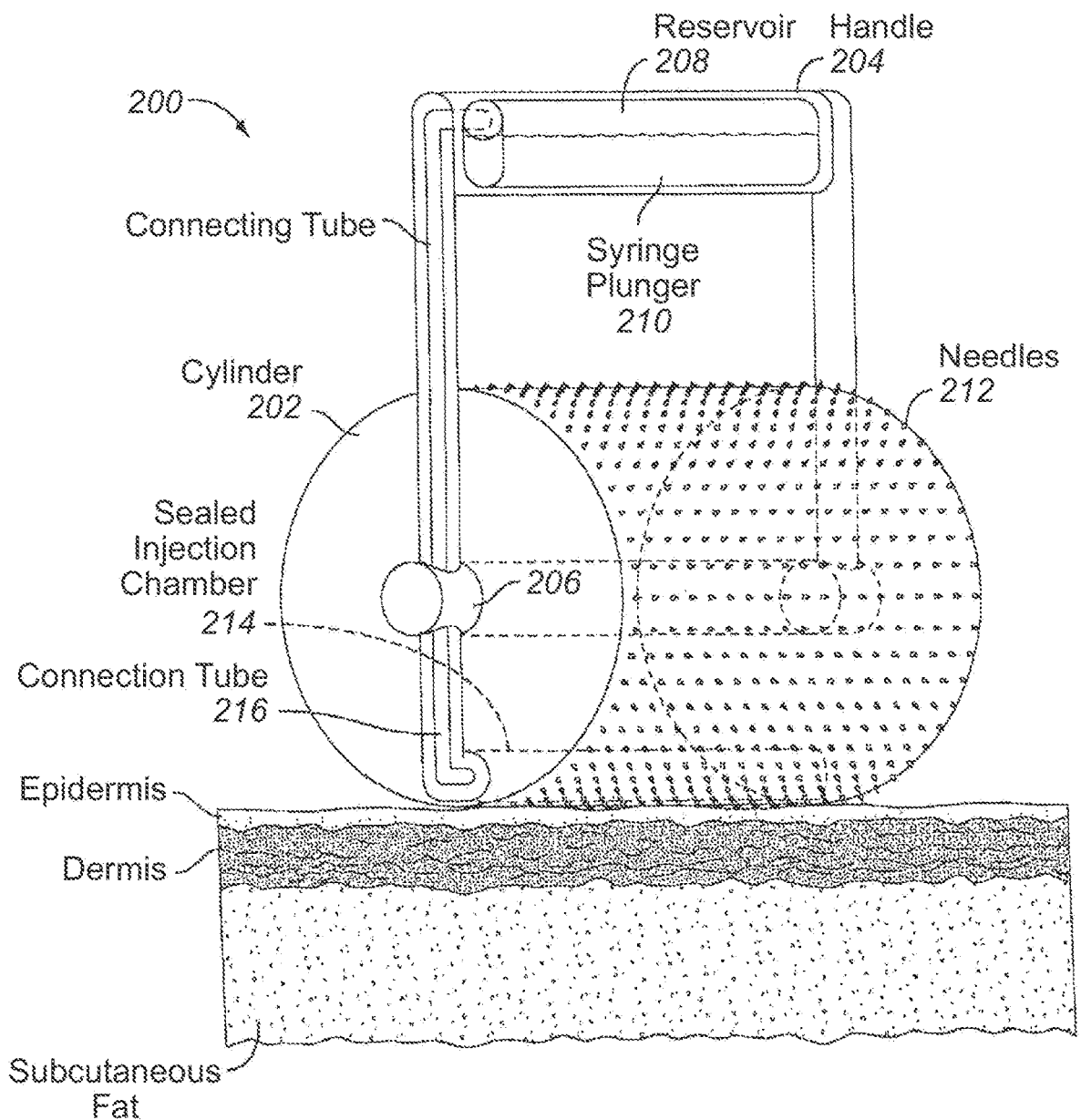
FIG. 23 is a drum array drug delivery device, under an embodiment.

FIG. 23 is a drum array drug delivery device 200, under an embodiment. The drug delivery device 200 successfully addresses the limitations and drawbacks of other drug delivery systems. The device comprises a drum/cylinder 202 supported by an axel/handle assembly 204 and rotated around a drum rotation component 206. The handle assembly 204 of an embodiment further includes a reservoir 208 of drugs to be delivered and a syringe plunger 210. The surface of the drum 202 is covered by an array of needles 212 of uniform length, which provide a uniform intradermal (or subdermal) injection depth with a more controlled volume of the drug injected into the skin of the patient. During operation, the syringe plunger 210 pushes the drug out of the reservoir 208 to be injected into a sealed injection chamber 214 inside the drum 202 via connecting tube 216. The drug is eventually delivered into the patient's skin at a uniform depth when the array of needles 212 is pushed into a patient's skin until the surface of the drum 202 hits the skin. Non-anesthetized skip area is avoided and a more uniform pattern of cutaneous anesthesia is created. The rolling drum application of the drug delivery device 200 also instills the local anesthetic faster with less discomfort to the patient.

Figure 24A:
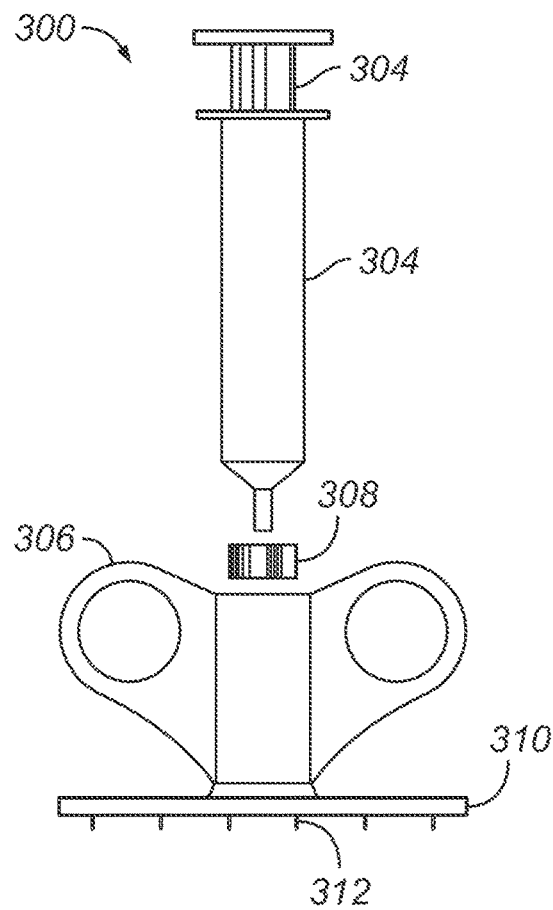
FIG. 24A is a side view of a needle array drug delivery device, under an embodiment.
Figure 24B:
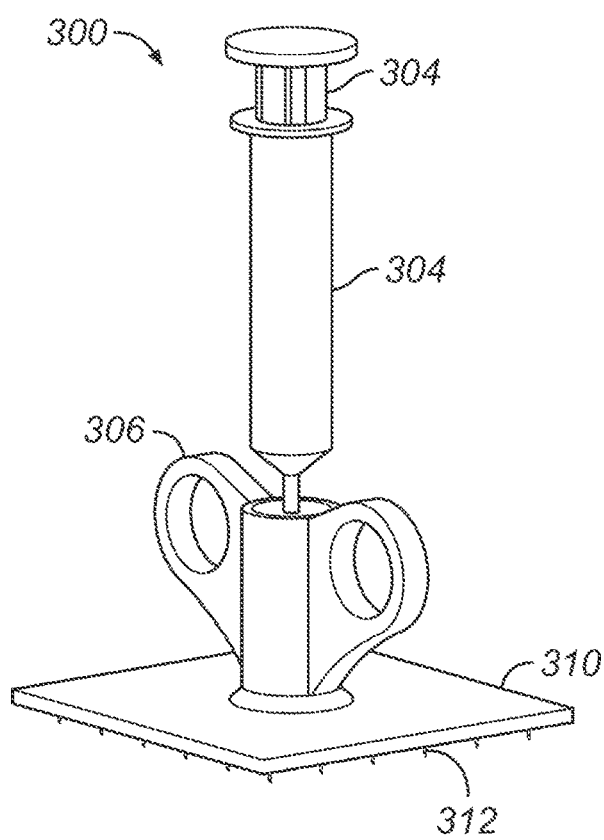
FIG. 24B is an upper isometric view of a needle array drug delivery device, under an embodiment.
Figure 24C:
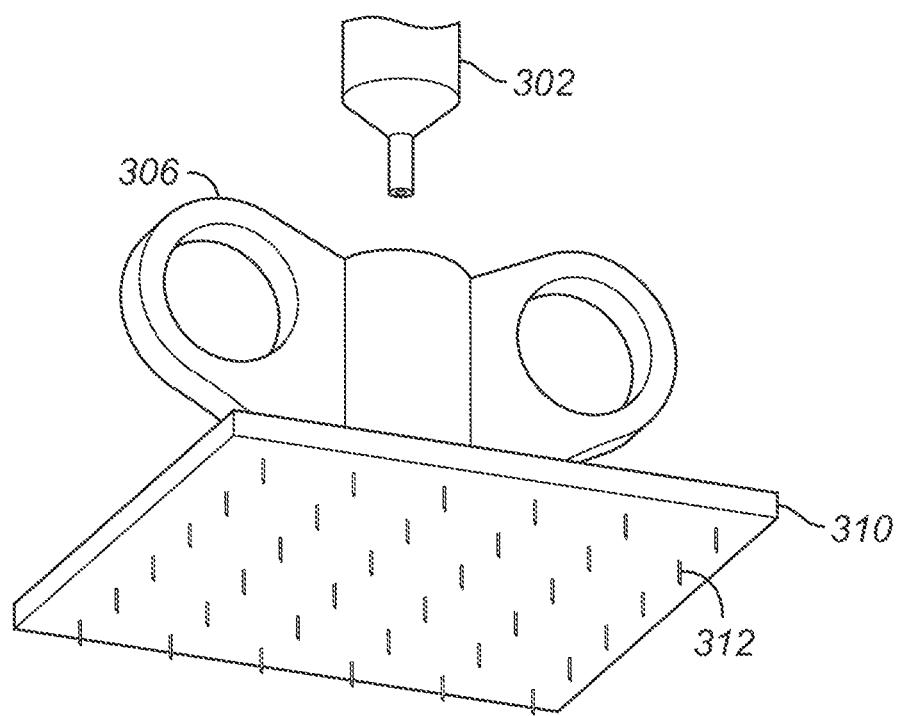
FIG. 24C is a lower isometric view of a needle array drug delivery device, under an embodiment.

FIG. 24A is a side view of a needle array drug delivery device 300, under an embodiment. FIG. 24B is an upper isometric view of a needle array drug delivery device 300, under an embodiment. FIG. 24C is a lower isometric view of a needle array drug delivery device 300, under an embodiment. The drug delivery device 300 comprises a flat array of fine needles 312 of uniform length positioned on manifold 310 can be utilized for drug delivery. In this example embodiment, syringe 302 in which drug for injection is contained can be plugged into a disposable adaptor 306 with handles, and a seal 308 can be utilized to ensure that the syringe 302 and the disposable adaptor 306 are securely coupled to each other. When the syringe plunger 304 is pushed, drug contained in syringe 302 is delivered from syringe 302 into the disposable adaptor 306. The drug is further delivered into the patient's skin through the flat array of fine needles 312 at a uniform depth when the array of needles 312 is pushed into a patient's skin until manifold 310 hits the skin.

The use of the drug delivery device 200 may have as many clinical applications as the number of pharmacological agents that require transcutaneous injection or absorption. For non-limiting examples, a few of the potential applications are the injection of local anesthetics, the injection of neuromodulators such as Botulinum toxin (Botox), the injection of insulin and the injection of replacement estrogens and corticosteroids.

In some embodiments, the syringe plunger 210 of the drug delivery device 200 can be powered by, for a non-limiting example, an electric motor. In some embodiments, a fluid pump (not shown) attached to an IV bag and tubing can be connected to the injection chamber 214 and/or the reservoir 208 for continuous injection. In some embodiments, the volume of the syringe plunger 210 in the drug delivery device 200 is calibrated and programmable.

Another application of pixel skin graft harvesting with the PAD (Pixel Array Dermatome) device as described in detail herein is Alopecia. Alopecia is a common aesthetic malady, and it occurs most frequently in the middle-aged male population, but is also observed in the aging baby boomer female population. The most common form of alopecia is Male Pattern Baldness (MPB) that occurs in the frontal-parietal region of the scalp. Male pattern baldness is a sex-linked trait that is transferred by the X chromosome from the mother to male offspring. For men, only one gene is needed to express this phenotype. As the gene is recessive, female pattern baldness requires the transfer of both X linked genes from both mother and father. Phenotypic penetrance can vary from patient to patient and is most frequently expressed in the age of onset and the amount of frontal/partial/occipital alopecia. The patient variability in the phenotypic expression of MPB is due to the variable genotypic translation of this sex-linked trait. Based upon the genotypic occurrence of MPB, the need for hair transplantation is vast. Other non-genetic related etiologies are seen in a more limited segment of the population. These non-genetic etiologies include trauma, fungal infections, lupus erythematosus, radiation and chemotherapy.

A large variety of treatment options have been proposed to the public. These include FDA approved topical medications such as Minoxidil and Finasteride which have had limited success as these agents require the conversion of dormant hair follicles into an anagen growth phase. Other remedies include hairpieces and hair weaving. The standard of practice remains surgical hair transplantation, which involves the transfer of hair plugs, strips and flaps from the hair-bearing scalp into the non hair-bearing scalp. For the most part, conventional hair transplantation involves the transfer of multiple single hair micrographs from the hair-bearing scalp to the non hair-bearing scalp of the same patient. Alternately, the donor plugs are initially harvested as hair strips and then secondarily sectioned into micrographs for transfer to the recipient scalp. Regardless, this multi-staged procedure is both tedious and expensive, involving several hours of surgery for the average patient.

The conventional hair transplantation market has been encumbered by lengthy hair grafting procedures that are performed in several stages. A typical hair grafting procedure involves the transfer of hair plugs from a donor site in the occipital scalp to a recipient site in the balding frontal-parietal scalp. For most procedures, each hair plug is transferred individually to the recipient scalp. Several hundred plugs may be transplanted during a procedure that may require several hours to perform. Post procedure "take" or viability of the transplanted hair plugs is variable due to factors that limit neovascularization at the recipient site. Bleeding and mechanical disruption due to motion are key factors that reduce neovascularization and "take" of hair grafts. Embodiments described herein include surgical instrumentation configured to transfer several hair grafts at once that are secured and aligned en masse at a recipient site on the scalp. The procedures described herein using the PAD of an embodiment reduce the tedium and time required with conventional instrumentation.

Figure 25:
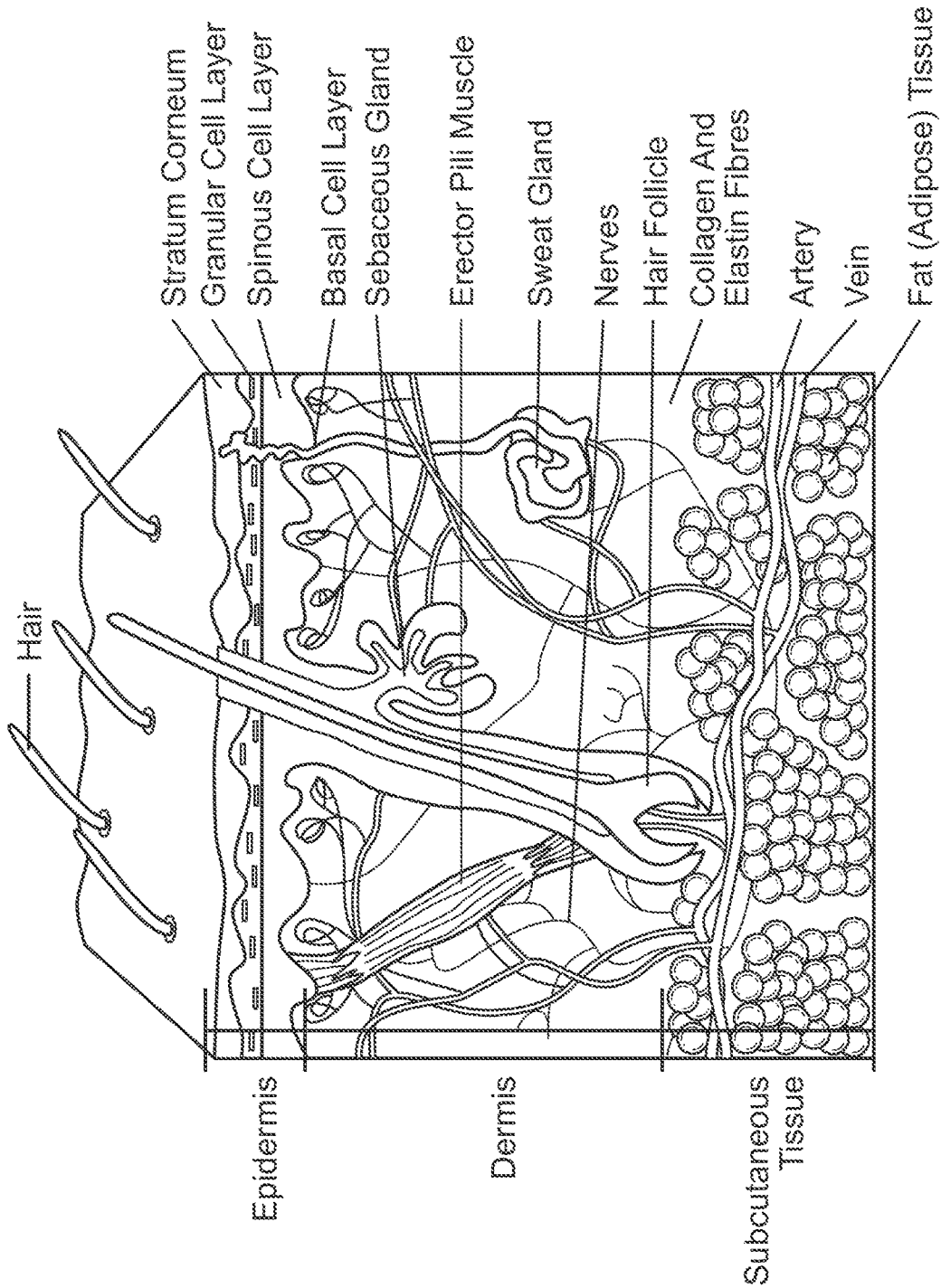
FIG. 25 shows the composition of human skin.

FIG. 25 shows the composition of human skin. Skin comprises two horizontally stratified layers, referred to as the epidermis and the dermis, acting as a biological barrier to the external environment. The epidermis is the enveloping layer and comprises a viable layer of epidermal cells that migrate upward and "mature" into a non-viable layer called the stratum corneum. The stratum corneum is a lipid-keratin composite that serves as a primary biological barrier, and this layer is continually shed and reconstituted in a process called desquamation. The dermis is the subjacent layer that is the main structural support of the skin, and is predominately extracellular and is comprised of collagen fibers.

In addition to the horizontally stratified epidermis and dermis, the skin includes vertically-aligned elements or cellular appendages including the pilosebaceous units, comprising the hair folical and sebacious gland. Pilosebaceous units each include a sebaceous oil gland and a hair follicle. The sebaceous gland is the most superficial and discharges sebum (oil) into the shaft of the hair follicle. The base of the hair follicle is called the bulb and the base of the bulb has a deep generative component called the dermal papilla. The hair follicles are typically aligned at an oblique angle to the skin surface. Hair follicles in a given region of the scalp are aligned parallel to each other. Although pilosebaceous units are common throughout the entire integument, the density and activity of these units within a region of the scalp is a key determinate as to the overall appearance of hair.

In additional to pilosebaceous units, sweat glands also course vertically through the skin. They provide a water-based transudate that assists in thermoregulation. Apocrine sweat glands in the axilla and groin express a more pungent sweat that is responsible for body odor. For the rest of the body, eccrine sweat glands excrete a less pungent sweat for thermoregulation.

Figure 26:
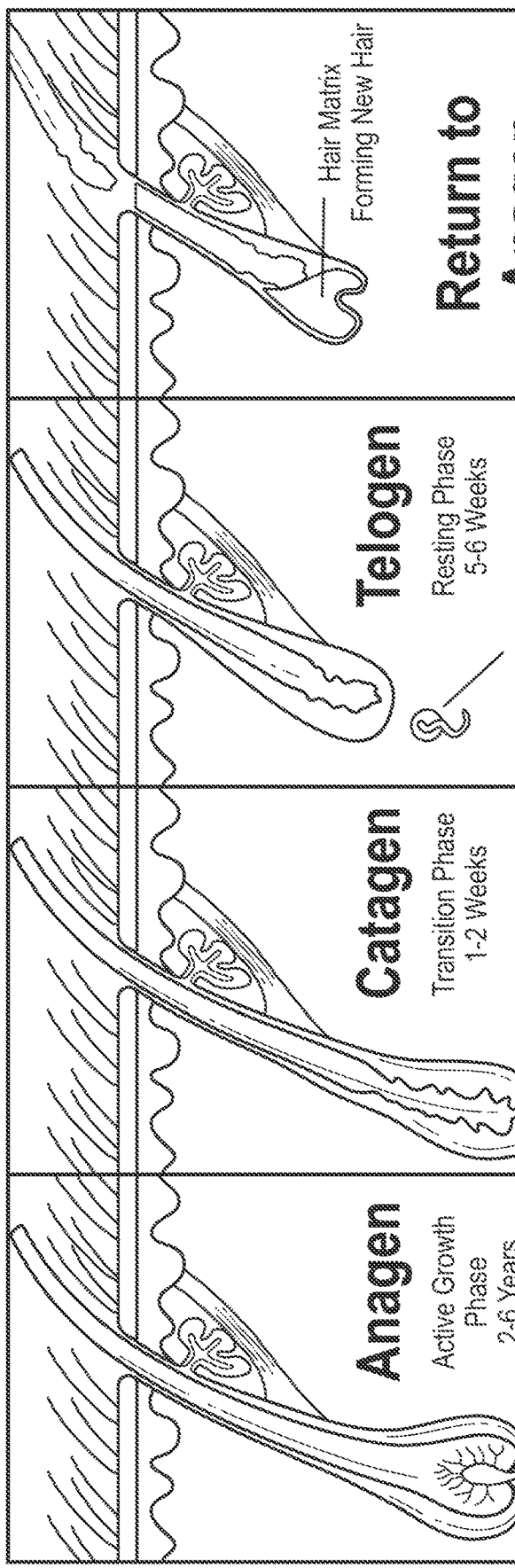
FIG. 26 shows the physiological cycles of hair growth.

Hair follicles proceed through different physiological cycles of hair growth. FIG. 26 shows the physiological cycles of hair growth. The presence of testosterone in a genetically-prone man will produce alopecia to a variable degree in the frontal-parietal scalp. Essentially, the follicle becomes dormant by entering the telogen phase without return to the anagen phase. Male Pattern Baldness occurs when the hair fails to return from the telogen phase to the anagen phase.

The PAD of an embodiment is configured for en-masse harvesting of hair-bearing plugs with en-masse transplantation of hair bearing plugs into non hair-bearing scalp, which truncates conventional surgical procedures of hair transplantation. Generally, the devices, systems and/or methods of an embodiment are used to harvest and align a large multiplicity of small hair bearing plugs in a single surgical step or process, and the same instrumentation is used to prepare the recipient site by performing a multiple pixelated resection of non hair-bearing scalp. The multiple hair-plug graft is transferred and transplanted en-masse to the prepared recipient site. Consequently, through use of an abbreviated procedure, hundreds of hair bearing plugs can be transferred from a donor site to a recipient site. Hair transplantation using the embodiments described herein therefore provides a solution that is a single surgical procedure having ease, simplicity and significant time reduction over the tedious and multiple staged conventional process.

Figure 27:
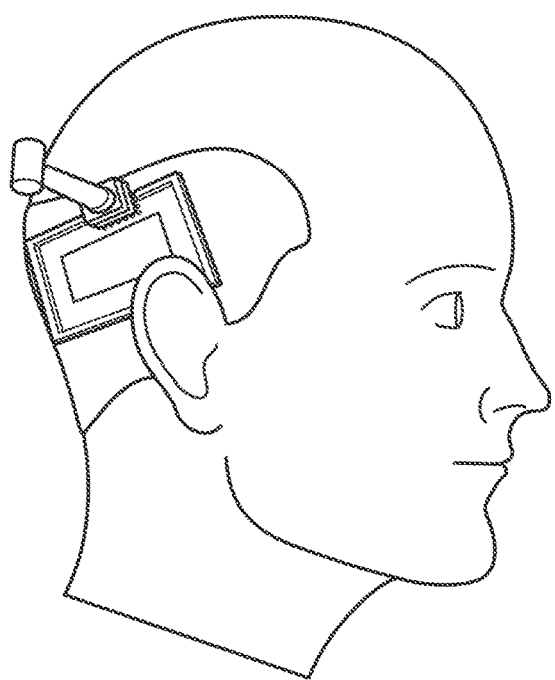
FIG. 27 shows harvesting of donor follicles, under an embodiment.

Hair transplantation using the pixel dermatome of an embodiment facilitates improvements in the conventional standard follicular unit extraction (FUT) hair transplant approach. Generally, under the procedure of an embodiment hair follicles to be harvested are taken from the Occipital scalp of the donor. In so doing, the donor site hair is partially shaved, and the perforated plate of an embodiment is located on the scalp and oriented to provide a maximum harvest. FIG. 27 shows harvesting of donor follicles, under an embodiment. The scalpets in the scalpet array are configured to penetrate down to the subcutaneous fat later to capture the hair follicle. Once the hair plugs are incised, they are harvested onto an adhesive membrane by transecting the base of the hair plug with the transection blade, as described in detail herein. Original alignment of the hair plugs with respect to each other at the donor site is maintained by applying the adherent membrane before transecting the base. The aligned matrix of hair plugs on the adherent membrane will then be grafted en masse to a recipient site on the frontal-parietal scalp of the recipient.

Figure 28:
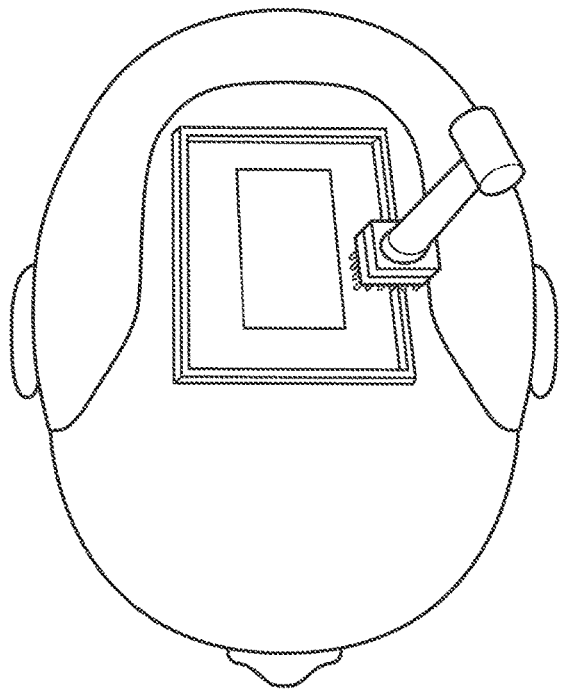
FIG. 28 shows preparation of the recipient site, under an embodiment.

FIG. 28 shows preparation of the recipient site, under an embodiment. The recipient site is prepared by resection of non-hair bearing skin plugs in a topographically identical pattern as the harvested occipital scalp donor site. The recipient site is prepared for the mass transplant of the hair plugs using the same instrumentation that was used at the donor site under an embodiment and, in so doing, scalp defects are created at the recipient site. The scalp defects created at the recipient site have the same geometry as the harvested plugs on the adherent membrane.

Figure 29:
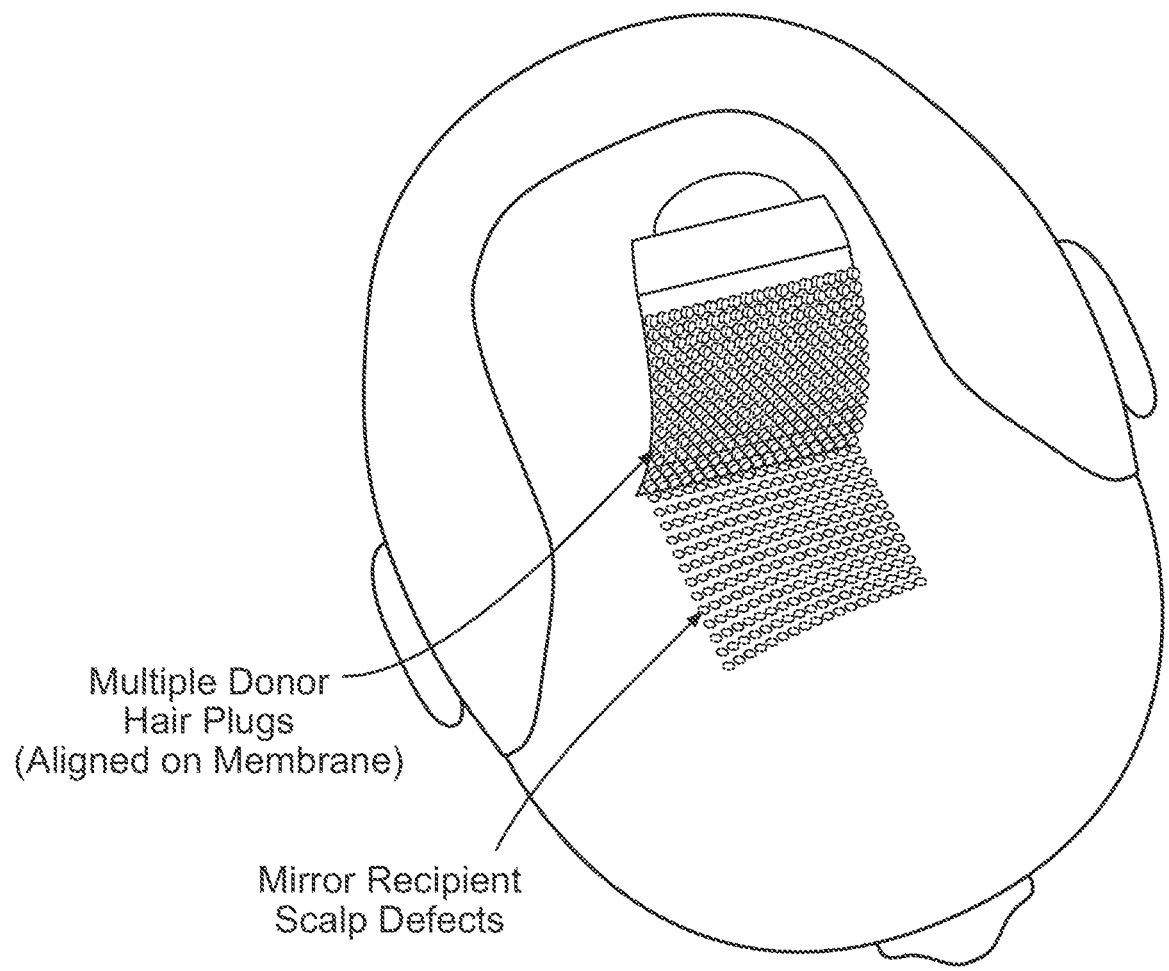
FIG. 29 shows placement of the harvested hair plugs at the recipient site, under an embodiment.

The adherent membrane laden with the harvested hair plugs is applied over the same pattern of scalp defects at the recipient site. Row-by-row, each hair-bearing plug is inserted into its mirror image recipient defect. FIG. 29 shows placement of the harvested hair plugs at the recipient site, under an embodiment. Plug-to-plug alignment is maintained, so the hair that grows from the transplanted hair plugs lays as naturally as it did at the donor site. More uniform alignment between the native scalp and the transplanted hair will also occur.

Figure 30:
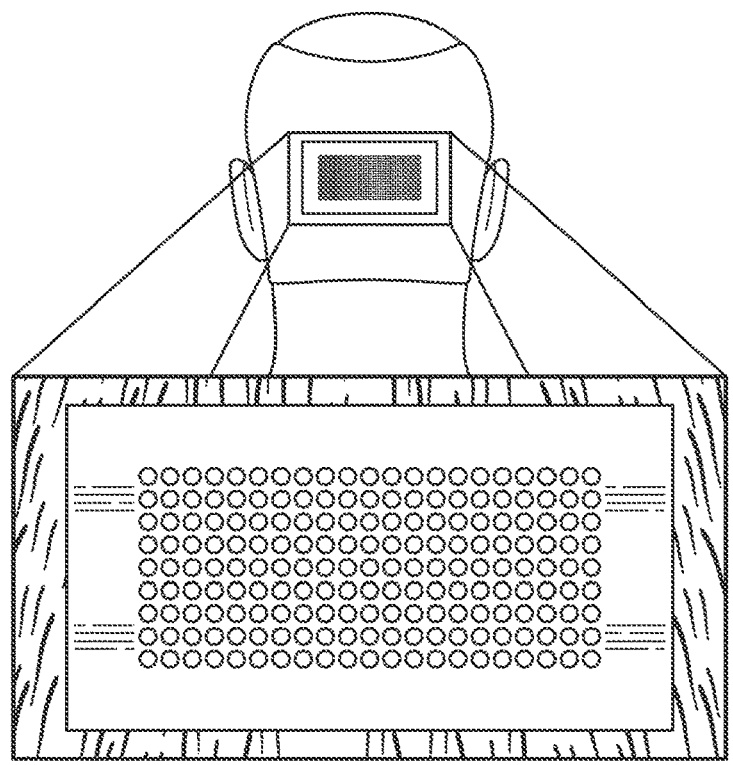
FIG. 30 shows placement of the perforated plate on the occipital scalp donor site, under an embodiment.

More particularly, the donor site hair is partially shaved to prepare for location or placement of the perforated plate on the scalp. The perforated plate is positioned on the occipital scalp donor site to provide a maximum harvest. FIG. 30 shows placement of the perforated plate on the occipital scalp donor site, under an embodiment. Mass harvesting of hair plugs is achieved using the spring-loaded pixilation device comprising the impact punch hand-piece with a scalpet disposable tip. An embodiment is configured for harvesting of individual hair plugs using off-the-shelf FUE extraction devices or biopsy punches; the holes in the perforated plates supplied are sized to accommodate off-the-shelf technology.

Figure 31:
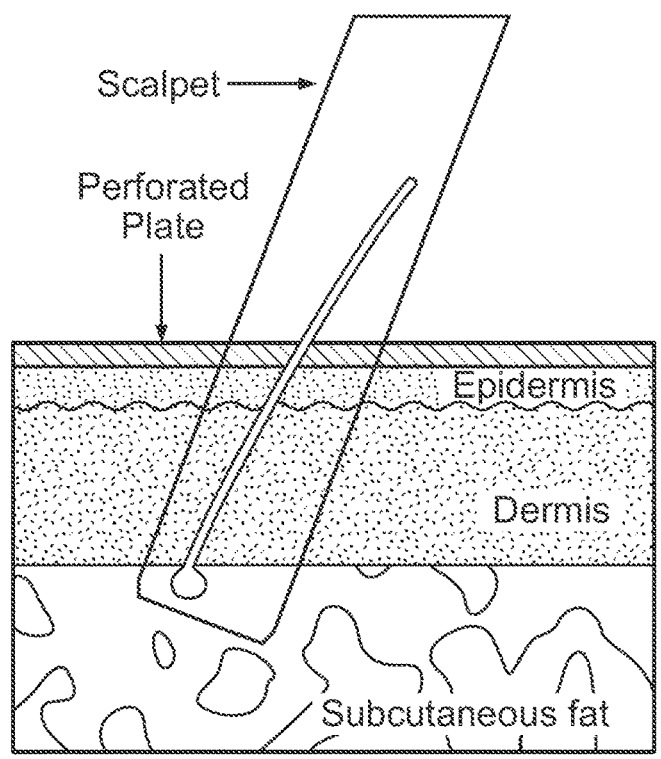
FIG. 31 shows scalpet penetration depth through skin when the scalpet is configured to penetrate to the subcutaneous fat layer to capture the hair follicle, under an embodiment.
Figure 32:
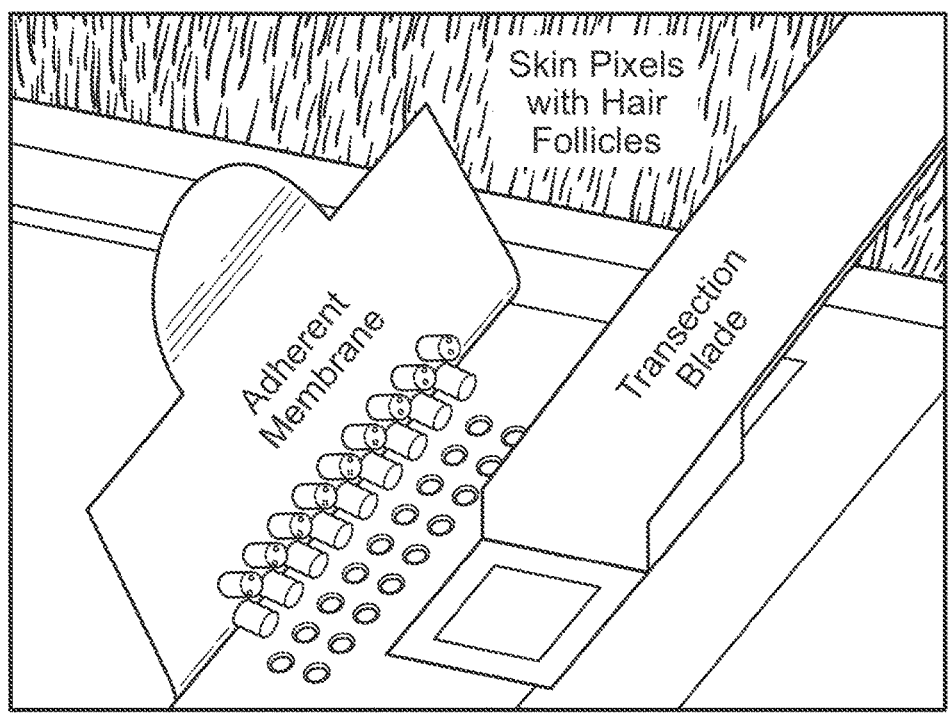
FIG. 32 shows hair plug harvesting using the perforated plate at the occipital donor site, under an embodiment.

The scalpets comprising the scalpet array disposable tip are configured to penetrate down to the subcutaneous fat later to capture the hair follicle. FIG. 31 shows scalpet penetration depth through skin when the scalpet is configured to penetrate to the subcutaneous fat layer to capture the hair follicle, under an embodiment. Once the hair plugs are incised, they are harvested onto an adhesive membrane by transecting the base of the hair plug with the transection blade, but are not so limited. FIG. 32 shows hair plug harvesting using the perforated plate at the occipital donor site, under an embodiment. The original alignment of the hair plugs with respect to each other is maintained by applying an adherent membrane of an embodiment. The adherent membrane is applied before transecting the base of the resected pixels, the embodiments are not so limited. The aligned matrix of hair plugs on the adherent membrane is subsequently grafted en masse to a recipient site on the frontal-parietal scalp.

Figure 33:
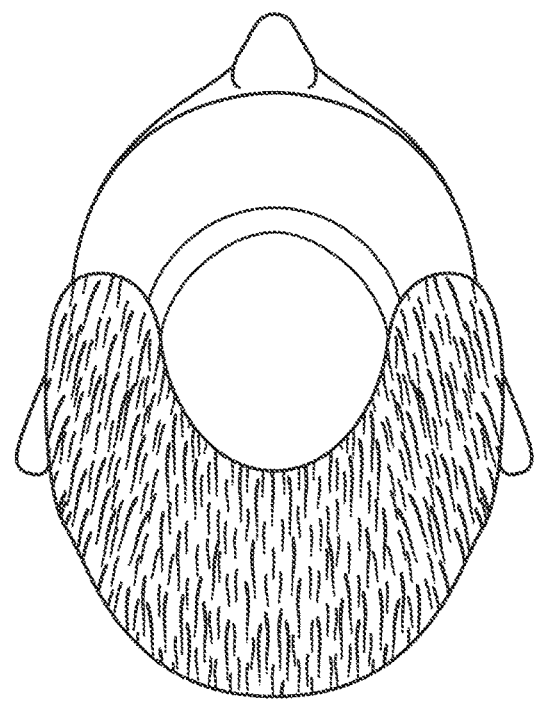
FIG. 33 shows creation of the visible hairline, under an embodiment.

Additional single hair plugs may be harvested through the perforated plate, to be used to create the visible hairline, for example. FIG. 33 shows creation of the visible hairline, under an embodiment. The visible hairline is determined and developed with a manual FUT technique. The visible hairline and the mass transplant of the vertex may be performed concurrently or as separate stages. If the visible hairline and mass transplant are performed concurrently, the recipient site is developed starting with the visible hairline.

Figure 34:
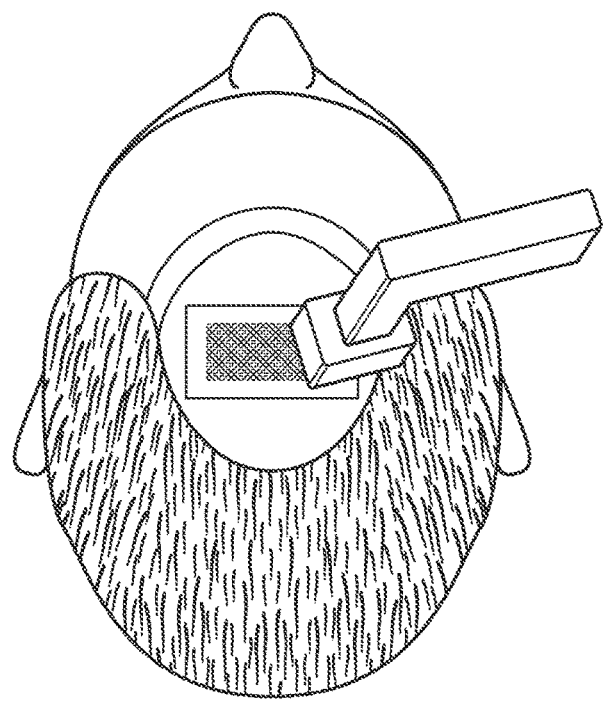
FIG. 34 shows preparation of the donor site using the patterned perforated plate and spring-loaded pixilation device to create identical skin defects at the recipient site, under an embodiment.

Transplantation of harvested hair plugs comprises preparing the recipient site is prepared by resecting non-hair bearing skin plugs in a topographically identical pattern as the pattern of the harvested occipital scalp donor site. FIG. 34 shows preparation of the donor site using the patterned perforated plate and spring-loaded pixilation device to create identical skin defects at the recipient site, under an embodiment. The recipient site of an embodiment is prepared for the mass transplant of the hair plugs using the same perforated plate and spring-loaded pixilation device that was used at the donor site. Scalp defects are created at the recipient site. These scalp defects have the same geometry as the harvested plugs on the adherent membrane.

Figure 35:
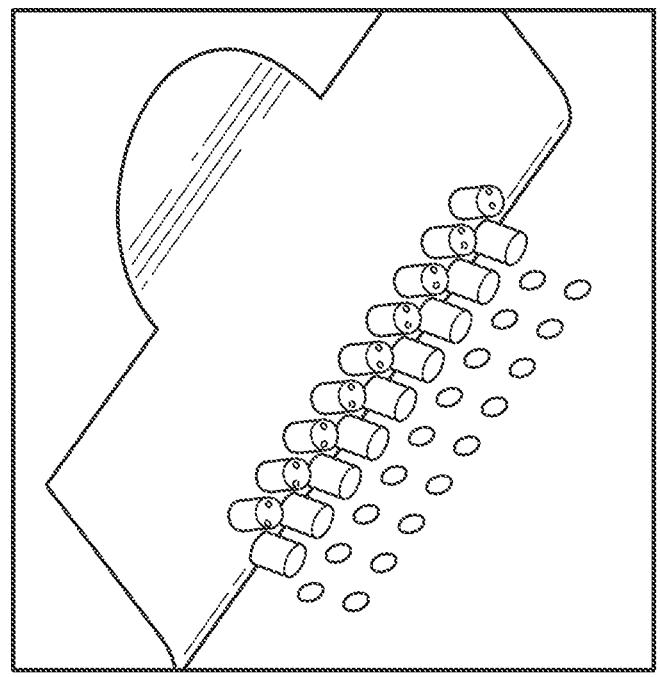
FIG. 35 shows transplantation of harvested plugs by inserting harvested plugs into a corresponding skin defect created at the recipient site, under an embodiment.

The adherent membrane carrying the harvested hair plugs is applied over the same pattern of scalp defects at recipient site. Row-by-row each follicle-bearing or hair-bearing skin plug is inserted into its mirror image recipient defect. FIG. 35 shows transplantation of harvested plugs by inserting harvested plugs into a corresponding skin defect created at the recipient site, under an embodiment. Plug-to-plug alignment is maintained, so the hair that grows from the transplanted hair plugs lays as naturally as it did at the donor site. More uniform alignment between the native scalp and the transplanted hair will also occur.

Figure 36:
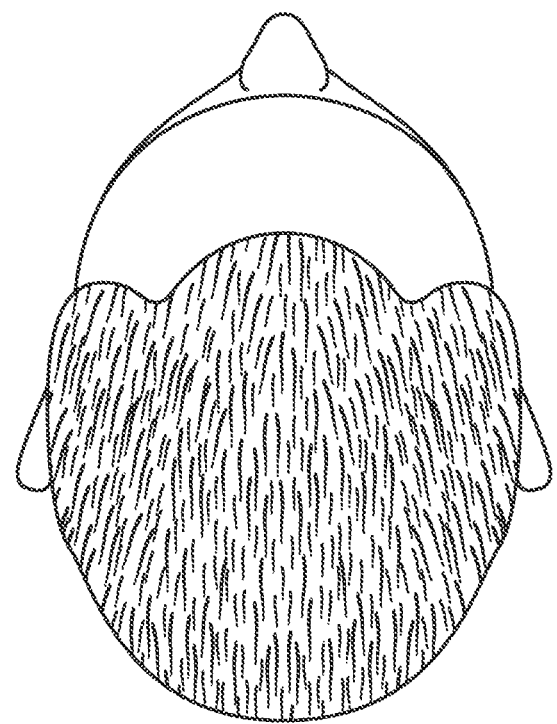
FIG. 36 shows a clinical end point using the pixel dermatome instrumentation and procedure, under an embodiment.

Clinical endpoints vary from patient to patient, but it is predicted that a higher percentage of hair plugs will "take" as a result of improved neovascularization. FIG. 36 shows a clinical end point using the pixel dermatome instrumentation and procedure, under an embodiment. The combination of better "takes", shorter procedure times, and a more natural-looking result, enable the pixel dermatome instrumentation and procedure of an embodiment to overcome the deficiencies in conventional hair transplant approaches.

Embodiments of pixelated skin grafting for skin defects and pixelated skin resection for skin laxity are described in detail herein. These embodiments remove a field of skin pixels in an area of lax skin where skin tightening is desired. The skin defects created by this procedure (e.g., in a range of approximately 1.5-3 mm-diameter) are small enough to heal per primam without visible scarring; the wound closure of the multiple skin defects is performed directionally to produce a desired contouring effect. Live animal testing of the pixel resection procedure has produced excellent results.

The pixel procedure of an embodiment is performed in an office setting under a local anesthetic but is not so limited. The surgeon uses the instrumentation of an embodiment to rapidly resect an array of skin pixels (e.g., circular, elliptical, square, etc.). Relatively little pain is associated with the procedure. The intradermal skin defects generated during the procedure are closed with the application of an adherent Flexan (3M) sheet, but embodiments are not so limited. Functioning as a large butterfly bandage, the Flexan sheet is pulled in a direction that maximizes the aesthetic contouring of the treatment area. A compressive elastic garment is then applied over the dressing to assist aesthetic contouring. During recovery, the patient wears a support garment over the treatment area for a period of time (e.g., 5 days, etc.). After initial healing, the multiplicity of small linear scars within the treatment area is not visibly apparent. Additional skin tightening will occur subsequently over several months from the delayed wound healing response. Consequently, the pixel procedure is a minimally invasive alternative for skin tightening in areas where the extensive scarring of traditional aesthetic plastic surgery is to be avoided.

The pixel procedure evokes cellular and extracellular responses that are obligatory to the clinical outcomes achieved. A physical reduction of the skin surface area occurs due to the fractional resection of skin, which physically removes a portion of skin directly in the area of laxity. In addition, a subsequent tightening of the skin is realized from the delayed wound healing response. Each pixilated resection initiates an obligate wound healing sequence. The healing response effected in an embodiment comprises three phases, as previously described in detail herein.

The first phase of this sequence is the inflammatory phase in which degranulation of mast cells releases histamine into the "wound". Histamine release evokes dilatation of the capillary bed and increases vessel permeability into the extracellular space. This initial wound healing response occurs within the first day and will be evident as erythema on the skin's surface.

Within days of "wounding", the second phase of healing, fibroplasia, commences. During fibroplasia, there is migration and mitotic multiplication of fibroblasts. Fibroplasia has two key features: the deposition of neocollagen and the myofibroblastic contraction of the wound. Histologically, the deposition of neocollagen is identified microscopically as compaction and thickening of the dermis. Although this is a static process, the tensile strength of the skin significantly increases. Myofibroblastic contraction is a dynamic physical process that results in two-dimensional tightening of the skin surface. This process is due to the active cellular contraction of myofibroblasts and the deposition of contractile proteins within the extracellular matrix. Overall, the effect of fibroplasia will be dermal contraction and the deposition of a static supporting scaffolding of neocollagen with a tightened framework. The clinical effect is realized as a delayed tightening of skin with smoothing of skin texture over some number of months. The clinical endpoint is a more youthful appearing skin envelope of the treatment area.

A third and final phase of the delayed wound healing response is maturation. During maturation, there is a strengthening and remodeling of the treatment area due to increased cross-linkage of the collagen fibril matrix (of the dermis). This final stage commences within 6 to 12 months after "wounding" and may extend for at least 1-2 years. Small pixilated resections of skin should preserve the normal dermal architecture during maturation, but without the creation of a visually evident scar that typically occurs with a larger surgical resection of skin. Lastly, there is a related stimulation and rejuvenation of the epidermis from the release of epidermal growth hormone.

Figure 38:
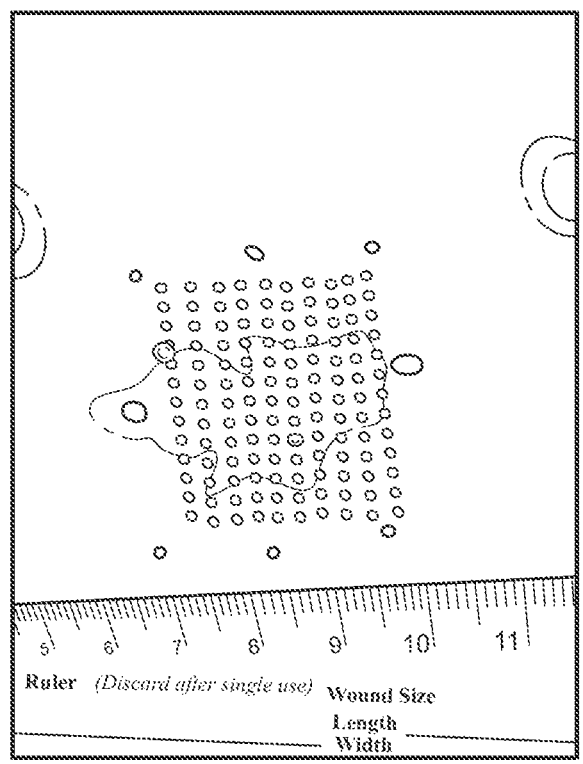
FIG. 38 is an image of the post-operative skin resection field, under an embodiment.
Figure 37:
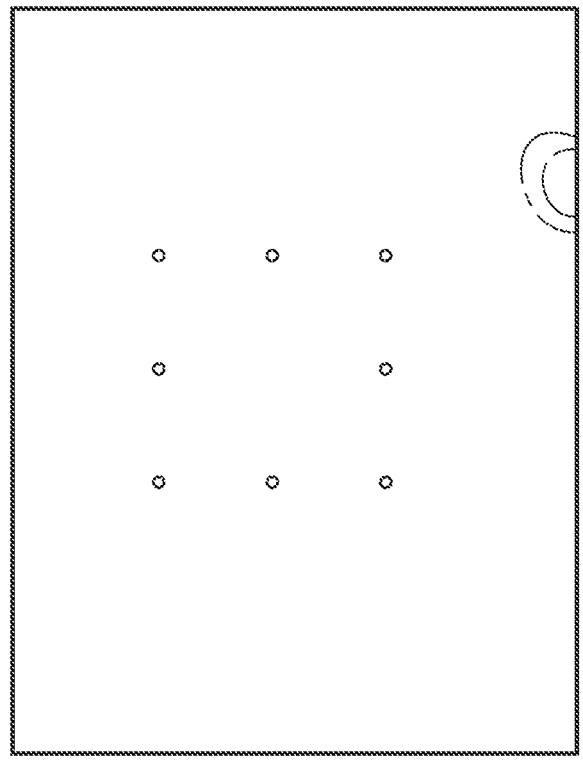
FIG. 37 is an image of the skin tattooed at the corners and midpoints of the area to be resected, under an embodiment.

FIGS. 37-42 show images resulting from a pixel procedure conducted on a live animal, under an embodiment. Embodiments described herein were used in this proof-of-concept study in an animal model that verified the pixel procedure produces aesthetic skin tightening without visible scarring. The study used a live porcine model, anesthetized for the procedure. FIG. 37 is an image of the skin tattooed at the corners and midpoints of the area to be resected, under an embodiment. The field margins of resection were demarcated with a tattoo for post-operative assessment, but embodiments are not so limited. The procedure was performed using a perforated plate (e.g., 10×10 pixel array) to designate the area for fractional resection. The fractional resection was performed using biopsy punches (e.g., 1.5 mm diameter). FIG. 38 is an image of the post-operative skin resection field, under an embodiment. Following the pixel resection, the pixelated resection defects were closed (horizontally) with Flexan membrane.

Figure 40:
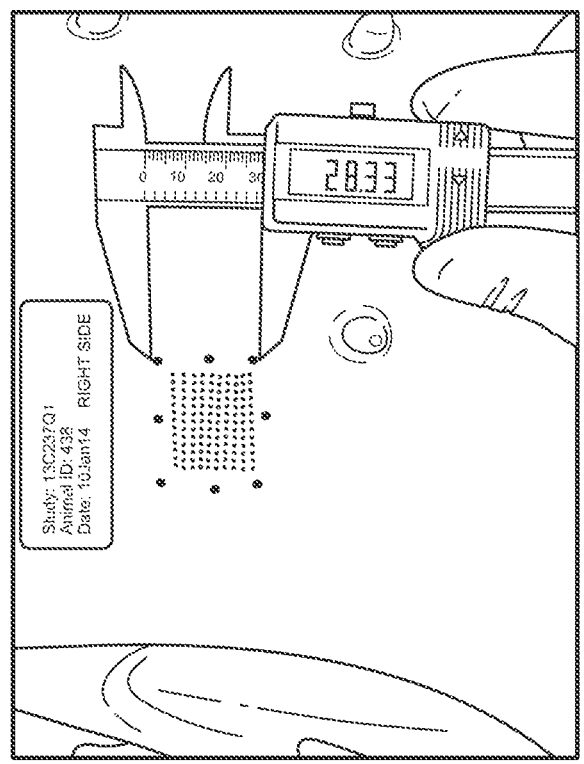
FIG. 40 is an image at 29 days following the procedure showing resections healed per primam and maturation of the resection field continuing per primam, with measured margins, under an embodiment.
Figure 39:
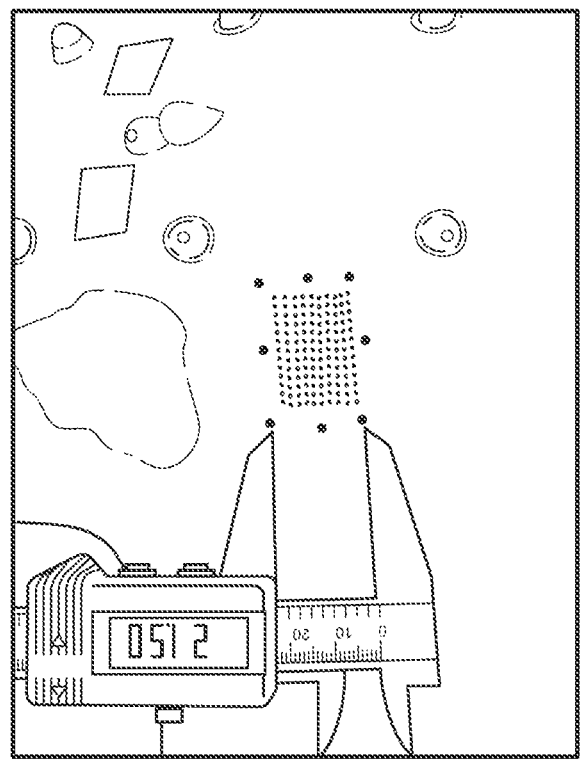
FIG. 39 is an image at 11 days following the procedure showing resections healed per primam, with measured margins, under an embodiment.
Figure 42:
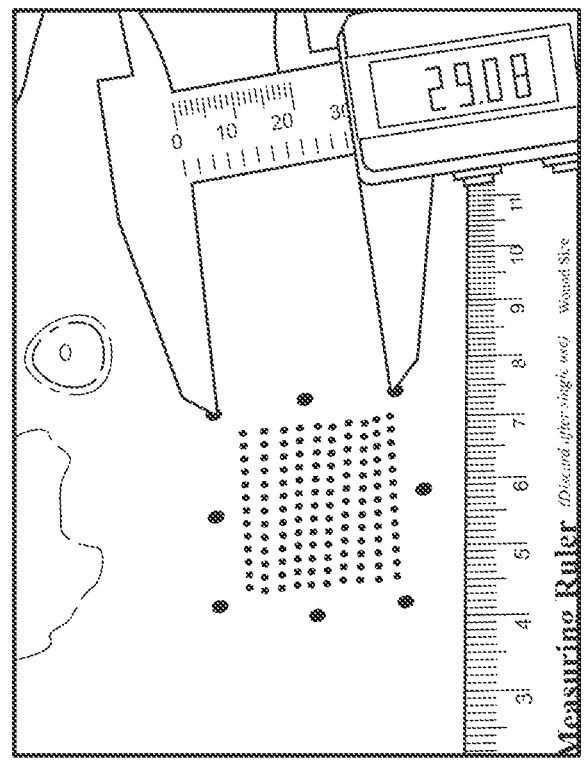
FIG. 42 is an image at 90 days post-operative showing resections healed per primam and maturation of the resection field continuing per primam, with measured lateral dimensions, under an embodiment.
Figure 41:
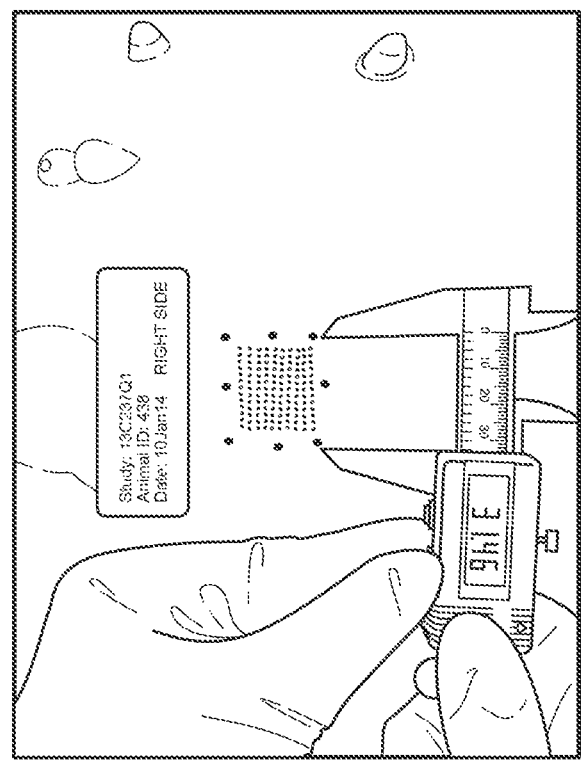
FIG. 41 is an image at 29 days following the procedure showing resections healed per primam and maturation of the resection field continuing per primam, with measured lateral dimensions, under an embodiment.

Eleven days following the procedure, all resections had healed per primam in the area designated by the tattoo, and photographic and dimensional measurements were made. FIG. 39 is an image at 11 days following the procedure showing resections healed per primam, with measured margins, under an embodiment. Photographic and dimensional measurements were subsequently made 29 days following the procedure. FIG. 40 is an image at 29 days following the procedure showing resections healed per primam and maturation of the resection field continuing per primam, with measured margins, under an embodiment. FIG. 41 is an image at 29 days following the procedure showing resections healed per primam and maturation of the resection field continuing per primam, with measured lateral dimensions, under an embodiment. Photographic and dimensional measurements were repeated 90 days post-operative, and the test area skin was completely smooth to touch. FIG. 42 is an image at 90 days post-operative showing resections healed per primam and maturation of the resection field continuing per primam, with measured lateral dimensions, under an embodiment.

Fractional resection as described herein is performed intradermally or through the entire thickness of the dermis. The ability to incise skin with a scalpet (e.g., round, square, elliptical, etc.) is enhanced with the addition of additional force(s). The additional force includes force applied to the scalpet or scalpet array, for example, where the force comprises one or more of rotational force, kinetic impact force, and vibrational force, all of which are described in detail herein for skin fractional resection.

The scalpet device of an embodiment generally includes a scalpet assembly and a housing. The scalpet assembly includes a scalpet array, which comprises a number of scalpets, and force or drive components. The scalpet assembly includes one or more alignment plates configured to retain and position the scalpets precisely according to the configuration of the scalpet array, and to transmit force (e.g., z-axis) from the operator to the subject tissue targeted for resection. The scalpet assembly includes spacers configured to retain alignment plates at a fixed distance apart and coaxial with the scalpet array, but is not so limited.

A shell is configured to retain the spacers and the alignment plates, and includes attachment point(s) for the housing and drive shaft. The alignment plates and/or the spacers are attached or connected (e.g., snapped, welded (e.g., ultrasonic, laser, etc.), heat-staked, etc.) into position in the shell, thereby providing a rigid assembly and discourages tampering or re-purposing of the scalpet array. Additionally, the shell protects the drive mechanism or gearing and scalpets from contamination during use and allows lubrication (if required) to be applied to the gearing to reduce the torque requirement and increase the life of the gears.

As an example of the application of force using the embodiments herein, the ability to incise skin with a circular scalpet is enhanced with the addition of a rotational torque. The downward axial force used to incise the skin is significantly reduced when applied in combination with a rotational force. This enhanced capability is similar to a surgeon incising skin with a standard scalpel where the surgeon uses a combination of movement across the skin (kinetic energy) with the simultaneous application of compression (axial force) to more effectively cut the skin surface.

For piercing the skin, the amount of surface compression required is significantly reduced if a vertical kinetic force is employed simultaneously. For example, a dart throwing technique for injections has previously been used by healthcare providers for piercing skin. An "impactor" action imparted on skin by a circular scalpet of an embodiment enhances this modality's cutting capability by simultaneously employing axial compressive and axial kinetic forces. The axial compressive force used to incise the skin surface is significantly reduced if applied in combination with kinetic force.

Conventional biopsy punches are intended for a single use application in the removal of tissue, which is generally achieved by pushing the punch directly into the tissue along its central axis. Similarly, the fractional resection of an embodiment uses scalpets comprising a circular configuration. While the scalpets of an embodiment can be used in a stand-alone configuration, alternative embodiments include scalpet arrays in which scalpets are bundled together in arrays of various sizes configured to remove sections of skin, but are not so limited. The force used to pierce the skin using the fractional resection scalpet is a function of the number of scalpets in the array, so that as the array size increases the force used to pierce the skin increases.

Figure 43:
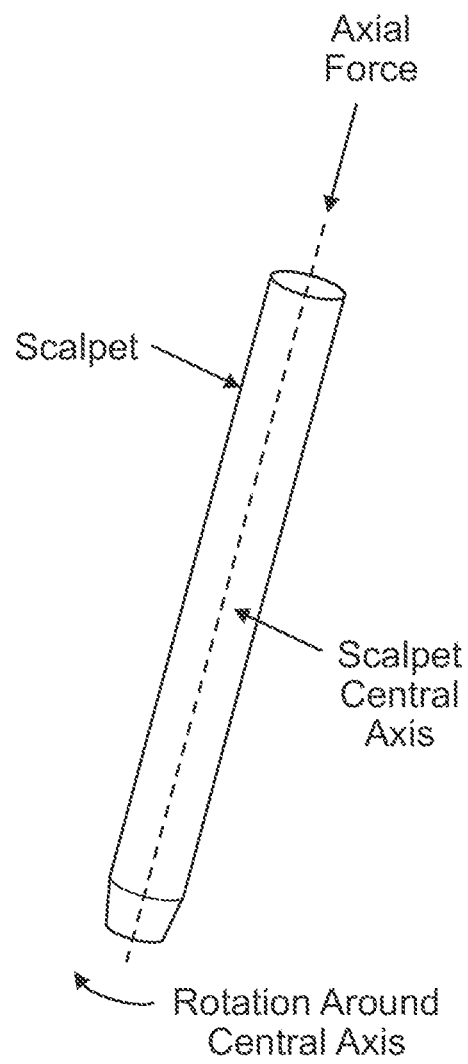
FIG. 43 is a scalpet showing the applied rotational and/or impact forces, under an embodiment.

The ability to incise skin with a circular scalpet is significantly enhanced with a reduction in the force needed to pierce the skin introduced through the addition of a rotational motion around its central axis and/or an impact force along its central axis. FIG. 43 is a scalpet showing the applied rotational and/or impact forces, under an embodiment. This enhanced rotational configuration has an affect similar to a surgeon incising skin with a standard scalpel where the surgeon uses a combination of movement across the skin (kinetic energy) with the simultaneous application of compression (axial force) to more effectively cut the skin surface. The impact force is similar to the use of a staple gun or by quickly moving a hypodermic needle prior to impacting the skin.

A consideration in the configuration of the scalpet rotation is the amount of torque used to drive multiple scalpets at a preferred speed, because the physical size and power of the system used to drive the scalpet array increases as the required torque increases. To reduce the incisional force required in a scalpet array, rows or columns or segments of the array may be individually driven or sequentially driven during an array application. Approaches for rotating the scalpets include but are not limited to geared, helical, slotted, inner helical, pin driven, and frictional (elastomeric).

The scalpet array configured for fractional resection using combined rotation and axial incision uses one or more device configurations for rotation. For example, the scalpet array of the device is configured to rotate using one or more of geared, external helical, inner helical, slotted, and pin drive rotating or oscillating mechanisms, but is not so limited. Each of the rotation mechanisms used in various embodiments is described in detail herein.

Figure 44:
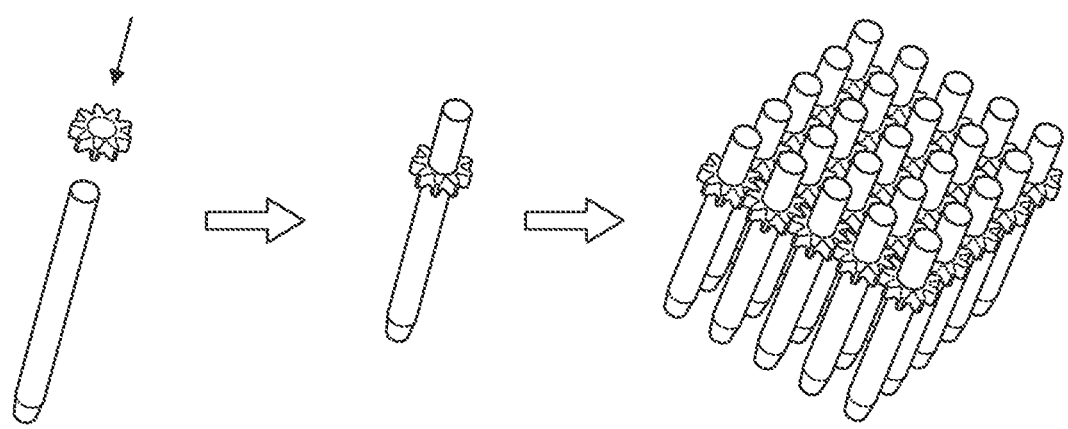
FIG. 44 shows a geared scalpet and an array including geared scalpets, under an embodiment.
Figure 45:
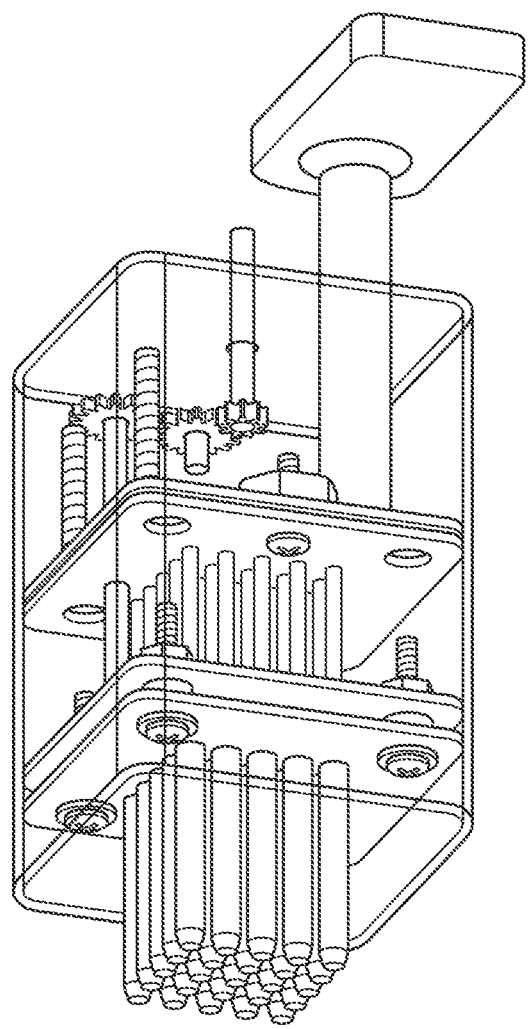
FIG. 45 is a bottom perspective view of a resection device including the scalpet assembly with geared scalpet array, under an embodiment.
Figure 46:
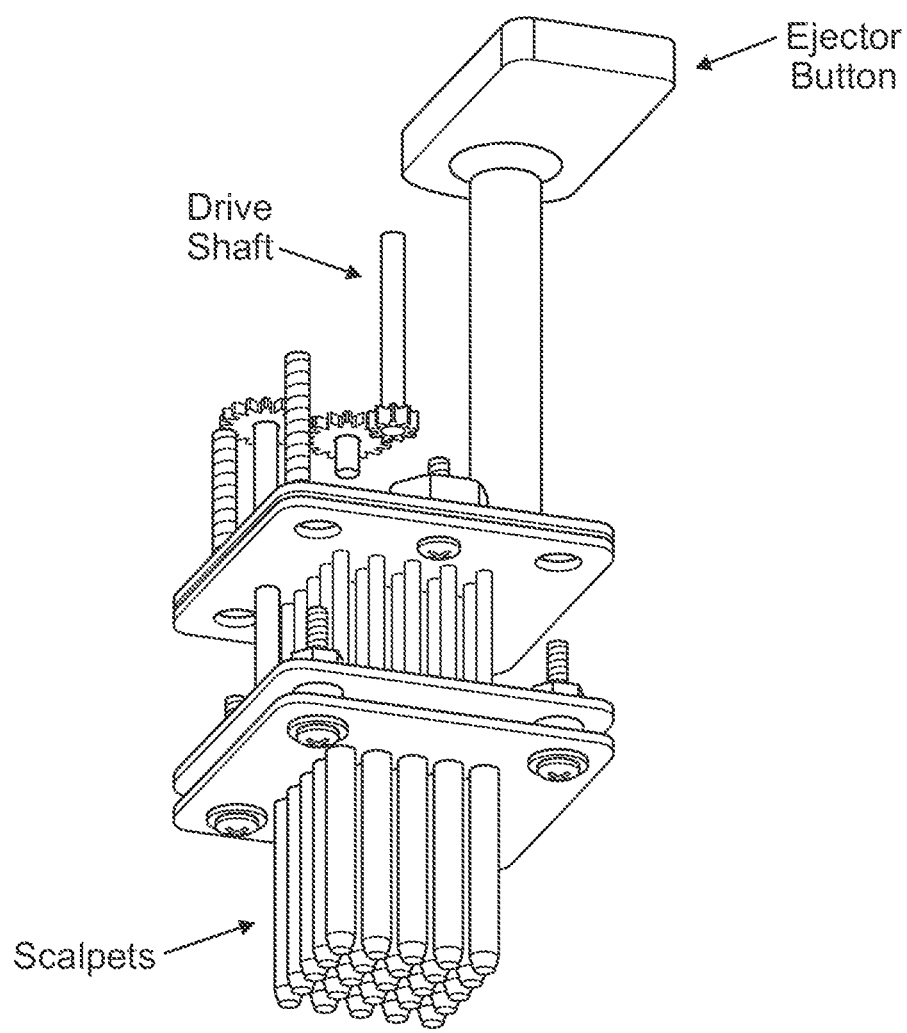
FIG. 46 is a bottom perspective view of the scalpet assembly with geared scalpet array (housing not shown), under an embodiment.
Figure 47:
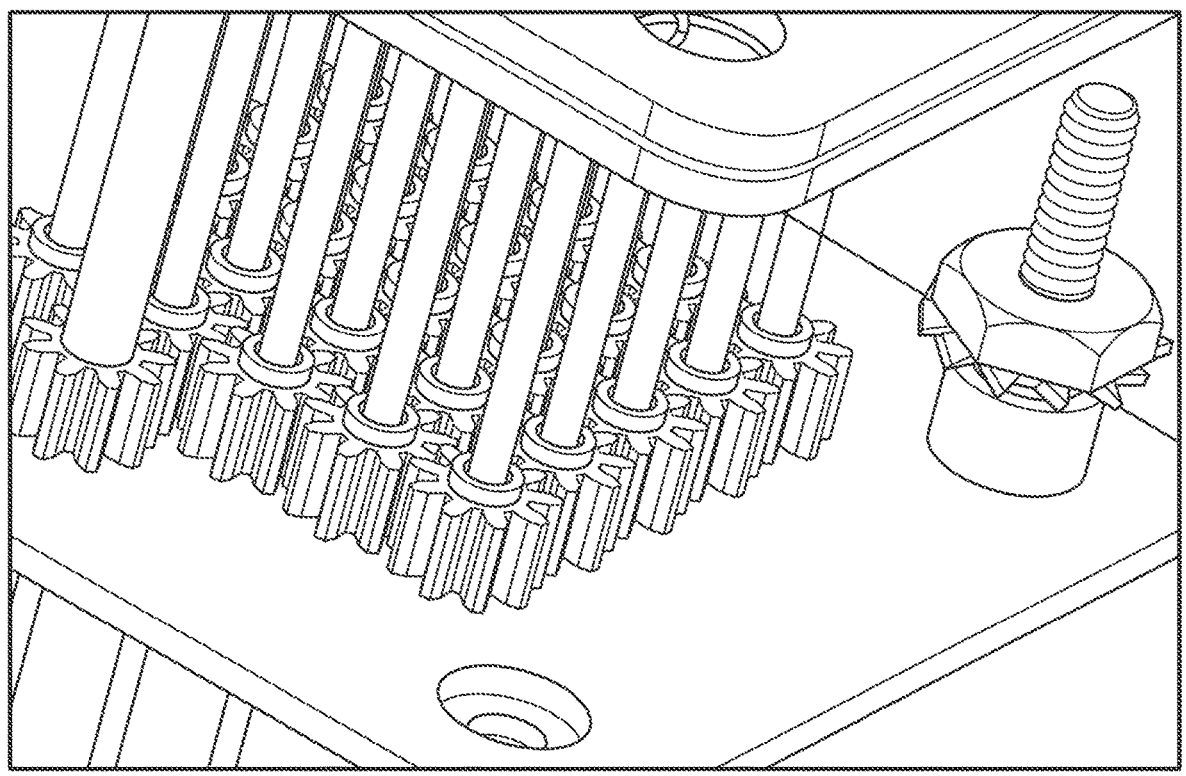
FIG. 47 is a detailed view of the geared scalpet array, under an embodiment.

FIG. 44 shows a geared scalpet and an array including geared scalpets, under an embodiment. FIG. 45 is a bottom perspective view of a resection device including the scalpet assembly with geared scalpet array, under an embodiment. The device comprises a housing (depicted as transparent for clarity of details) configured to include the geared scalpet array for the application of rotational torque for scalpet rotation. FIG. 46 is a bottom perspective view of the scalpet assembly with geared scalpet array (housing not shown), under an embodiment. FIG. 47 is a detailed view of the geared scalpet array, under an embodiment.

The geared scalpet array includes a number of scalpets as appropriate to a resection procedure in which the array is used, and a gear is coupled or connected to each scalpet. For example, the gear is fitted over or around a scalpet, but the embodiment is not so limited. The geared scalpets are configured as a unit or array so that each scalpet rotates in unison with adjacent scalpets. For example, once fit, the geared scalpets are installed together in alignment plates so that each scalpet engages and rotates in unison with its adjacent four scalpets and is thereby retained in precise alignment. The geared scalpet array is driven by at least one rotating external shaft carrying a gear at the distal end, but is not so limited. The rotational shaft(s) is configured to provide or transmit the axial force, which compresses the scalpets of the array into the skin during incision. Alternatively, axial force may be applied to the plates retaining the scalpets.

Figure 48:
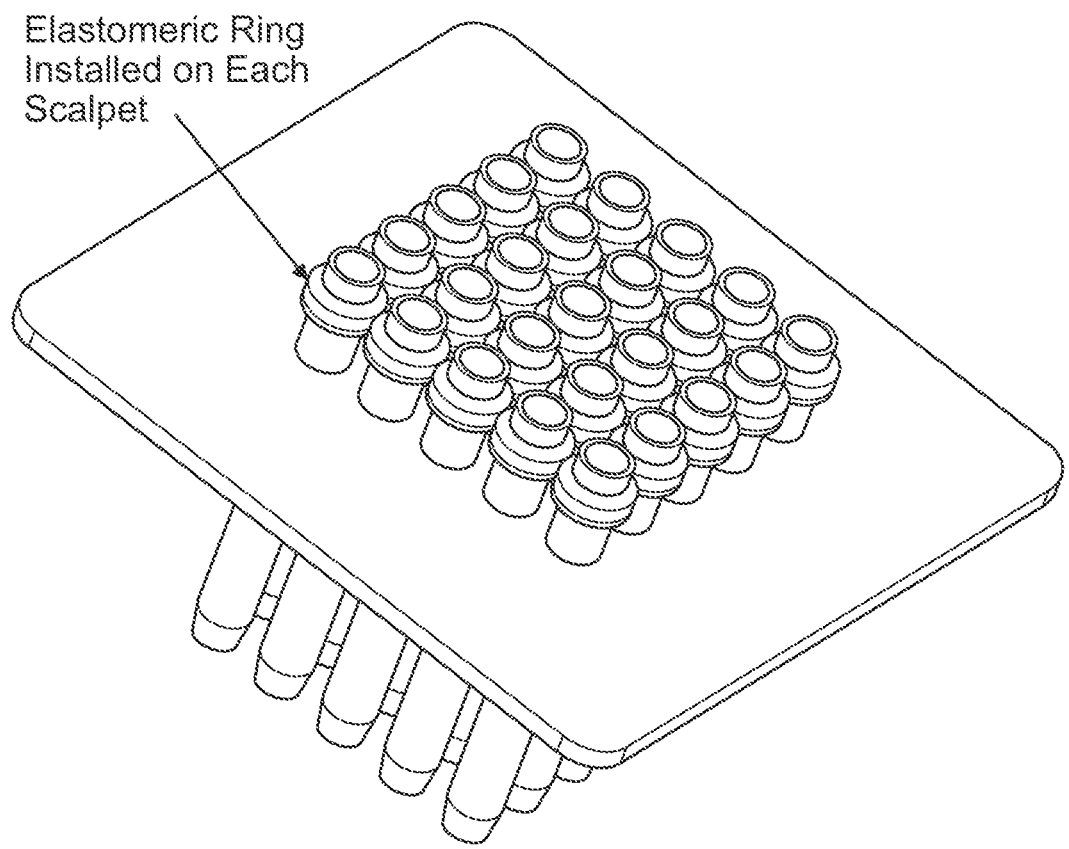
FIG. 48 shows an array including scalpets in a frictional drive configuration, under an embodiment.

In an alternative embodiment, a frictional drive is used to drive or rotate the scalpets of the arrays. FIG. 48 shows an array including scalpets in a frictional drive configuration, under an embodiment. The frictional drive configuration includes an elastomeric ring around each scalpet, similar to gear placement in the geared embodiment, and frictional forces between the rings of adjacent scalpets in compression results in rotation of the scalpets similar to the geared array.

Figure 49:
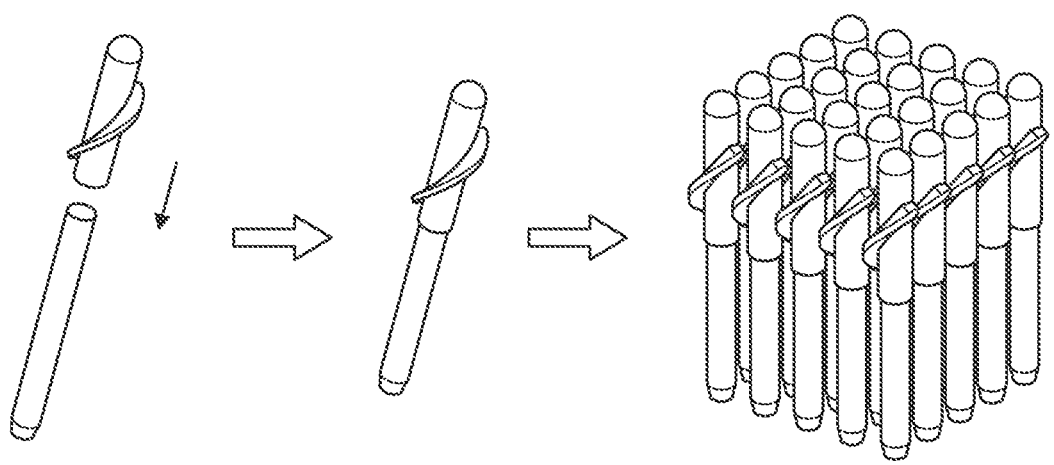
FIG. 49 shows a helical scalpet (external) and an array including helical scalpets (external), under an embodiment.
Figure 50:
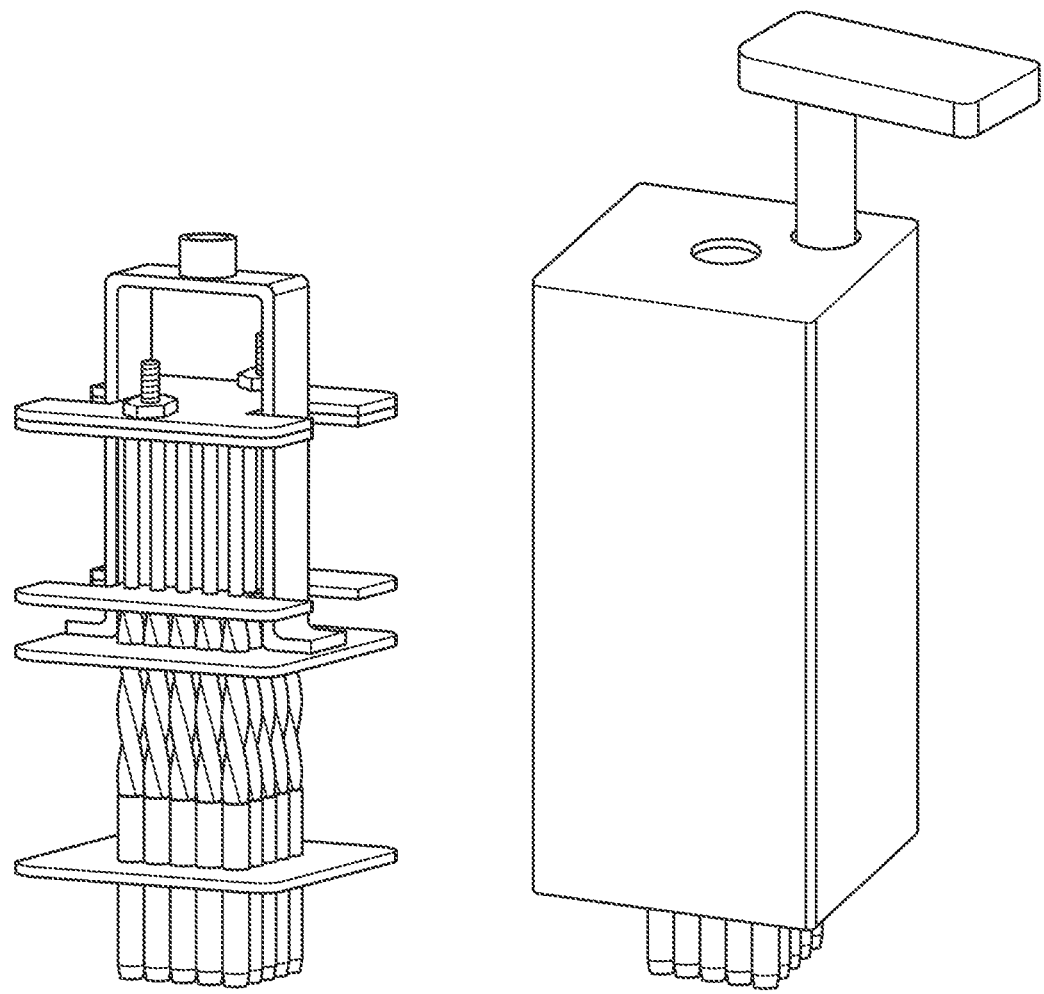
FIG. 50 shows side perspective views of a scalpet assembly including a helical scalpet array (left), and the resection device including the scalpet assembly with helical scalpet array (right) (housing shown), under an embodiment.
Figure 51:
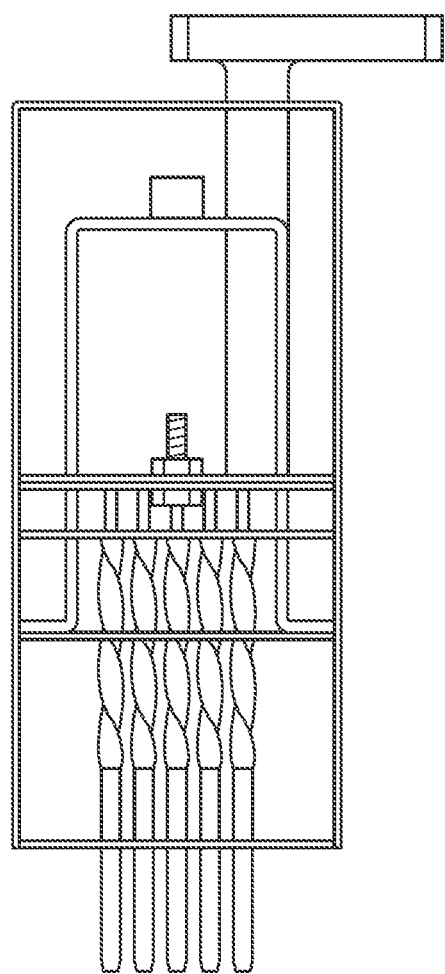
FIG. 51 is a side view of a resection device including the scalpet assembly with helical scalpet array assembly (housing depicted as transparent for clarity of details), under an embodiment.
Figure 52:
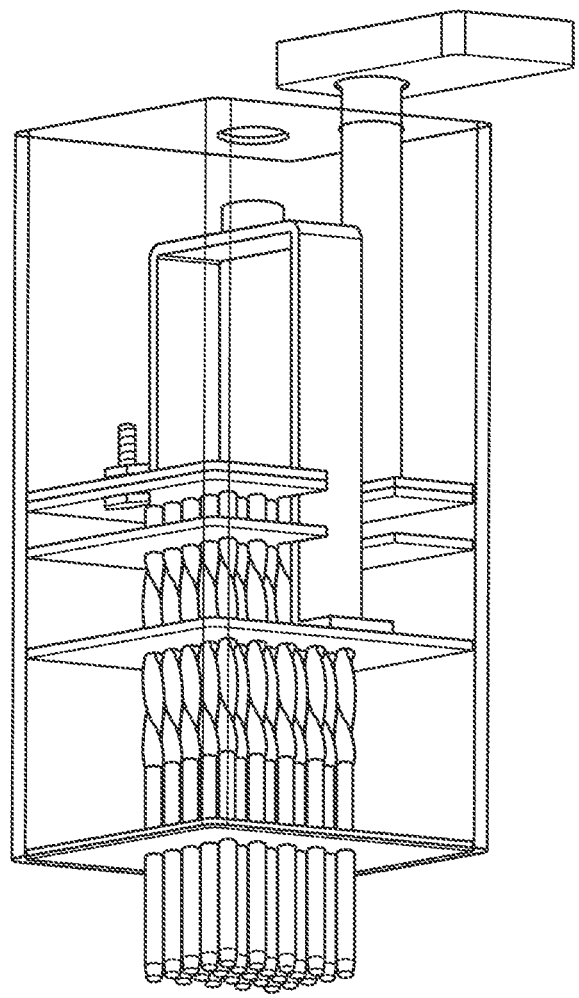
FIG. 52 is a bottom perspective view of a resection device including the scalpet assembly with helical scalpet array assembly (housing depicted as transparent for clarity of details), under an embodiment.
Figure 53:
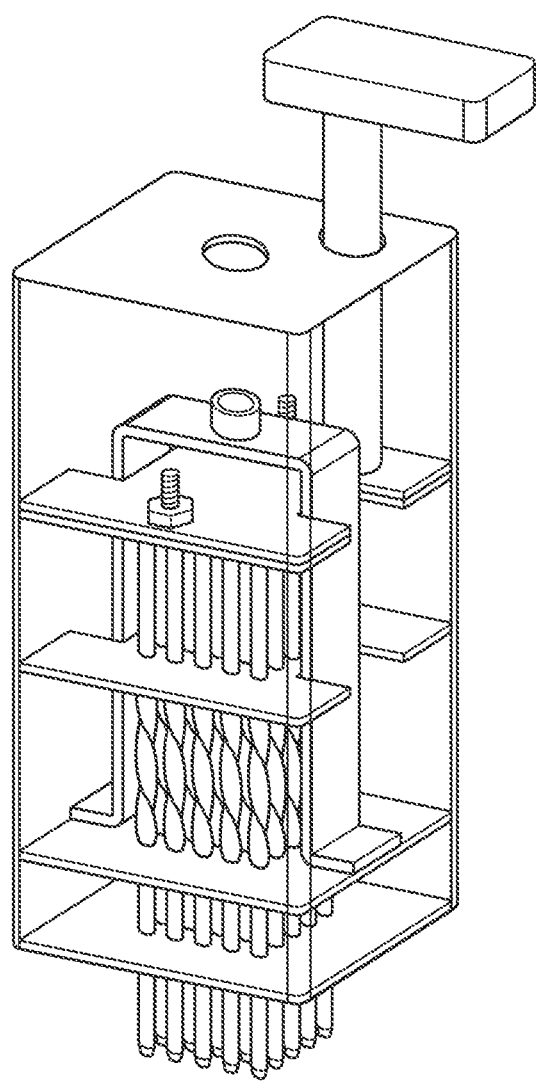
FIG. 53 is a top perspective view of a resection device including the scalpet assembly with helical scalpet array assembly (housing depicted as transparent for clarity of details), under an embodiment.

The resection devices comprise helical scalpet arrays, including but not limited to external and internal helical scalpet arrays. FIG. 49 shows a helical scalpet (external) and an array including helical scalpets (external), under an embodiment. FIG. 50 shows side perspective views of a scalpet assembly including a helical scalpet array (left), and the resection device including the scalpet assembly with helical scalpet array (right) (housing shown), under an embodiment. FIG. 51 is a side view of a resection device including the scalpet assembly with helical scalpet array assembly (housing depicted as transparent for clarity of details), under an embodiment. FIG. 52 is a bottom perspective view of a resection device including the scalpet assembly with helical scalpet array assembly (housing depicted as transparent for clarity of details), under an embodiment. FIG. 53 is a top perspective view of a resection device including the scalpet assembly with helical scalpet array assembly (housing depicted as transparent for clarity of details), under an embodiment.

The helical scalpet configuration comprises a sleeve configured to fit over an end region of the scalpet, and an external region of the sleeve includes one or more helical threads. Once each scalpet is fitted with a sleeve, the sleeved scalpets are configured as a unit or array so that each scalpet rotates in unison with the adjacent scalpets. Alternatively, the helical thread is formed on or as a component of each scalpet.

Figure 54:
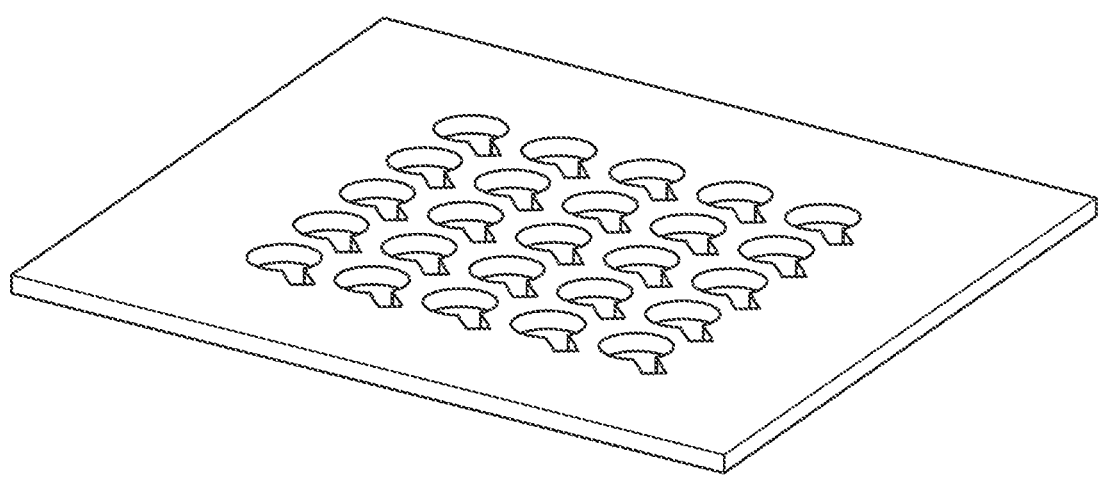
FIG. 54 is a push plate of the helical scalpet array, under an embodiment.
Figure 55:
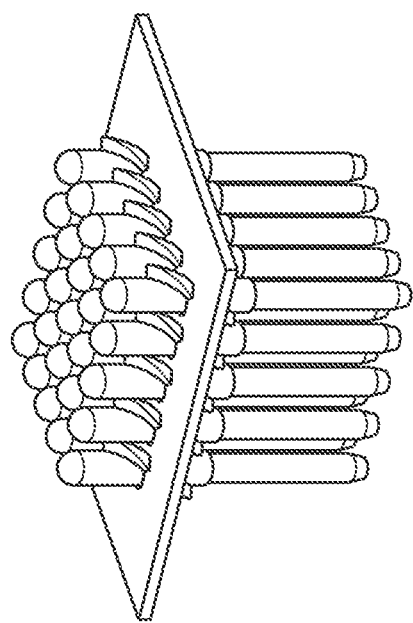
FIG. 55 shows the helical scalpet array with the push plate, under an embodiment.
Figure 55:
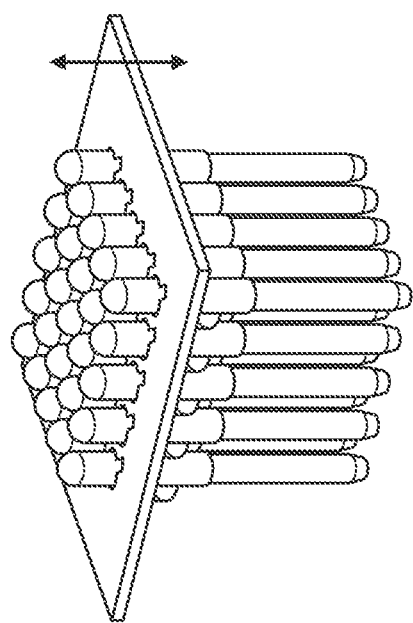

The helical scalpet array is configured to be driven by a push plate that oscillates up and down along a region of the central axis of the scalpet array. FIG. 54 is a push plate of the helical scalpet array, under an embodiment. The push plate includes a number of alignment holes corresponding to a number of scalpets in the array. Each alignment hole includes a notch configured to mate with the helical (external) thread on the scalpet sleeve. When the push plate is driven it causes rotation of each scalpet in the array. FIG. 55 shows the helical scalpet array with the push plate, under an embodiment.

Figure 56:
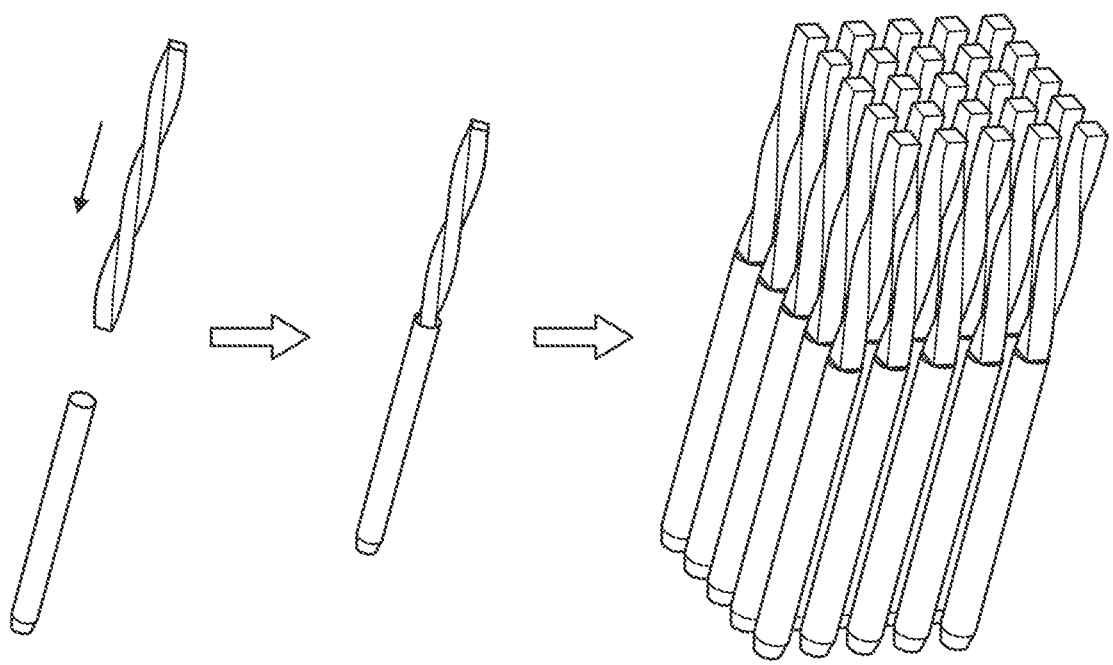
FIG. 56 shows an inner helical scalpet and an array including inner helical scalpets, under an embodiment.
Figure 57:
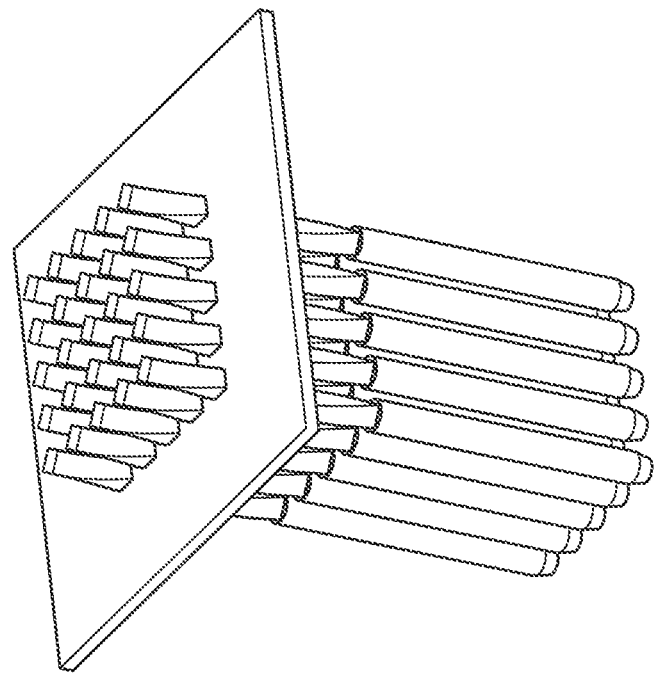
FIG. 57 shows the helical scalpet array with the drive plate, under an embodiment.
Figure 57:
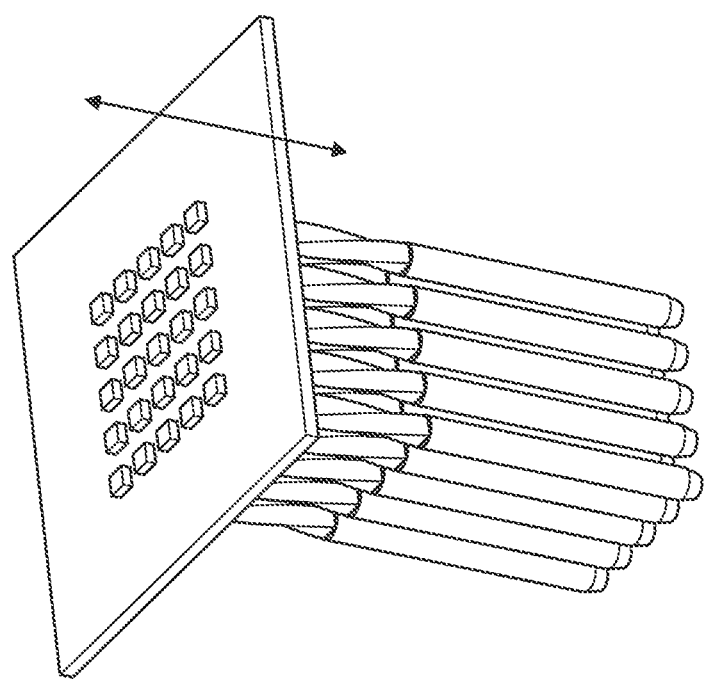

The resection devices further comprise internal helical scalpet arrays. The device comprises a housing configured to include the helical scalpet array assembly for the application of rotational torque for scalpet rotation. FIG. 56 shows an inner helical scalpet and an array including inner helical scalpets, under an embodiment. The inner helical scalpet includes a twisted square rod (e.g., solid, hollow, etc.) or insert that is fitted into an open end of the scalpet. Alternatively, the scalpet is configured to include a helical region. The twisted insert is held in place by bonding (e.g., crimping, bonding, brazing, welding, gluing, etc.) a portion of the scalpet around the insert. Alternative, the insert is held in place with an adhesive bond. Inner helical scalpets are then configured as a unit or array so that each scalpet is configured to rotate in unison with the adjacent scalpets. The helical scalpet array is configured to be driven by a drive plate that moves or oscillates up and down along the helical region of each scalpet of the scalpet array. The drive plate includes a number of square alignment holes corresponding to a number of scalpets in the array. When the drive plate is driven up and down it causes rotation of each scalpet in the array. FIG. 57 shows the helical scalpet array with the drive plate, under an embodiment.

Figure 58:
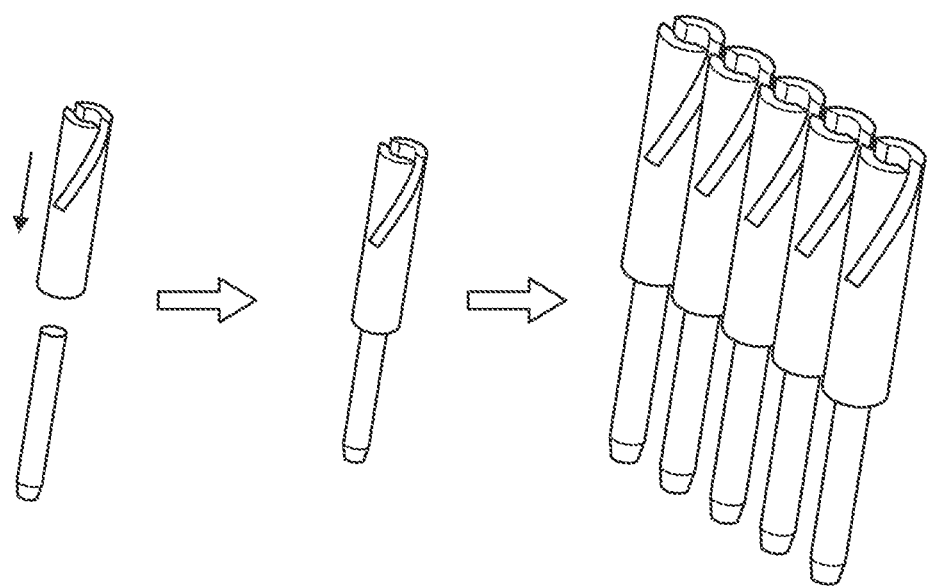
FIG. 58 shows a slotted scalpet and an array including slotted scalpets, under an embodiment.
Figure 59:
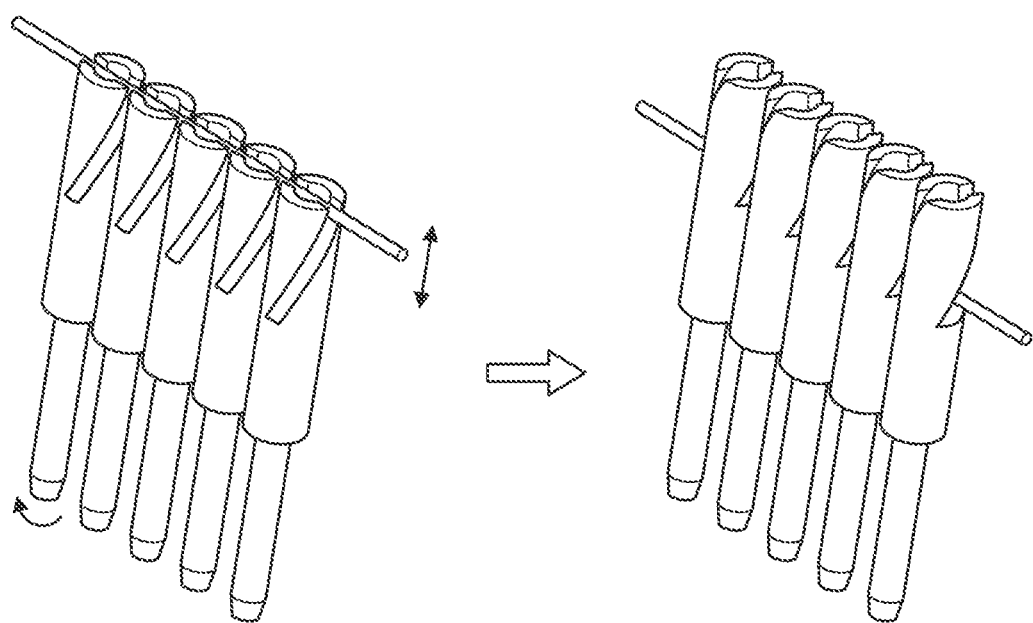
FIG. 59 shows a portion of a slotted scalpet array (e.g., four (4) scalpets) with the drive rod, under an embodiment.
Figure 60:
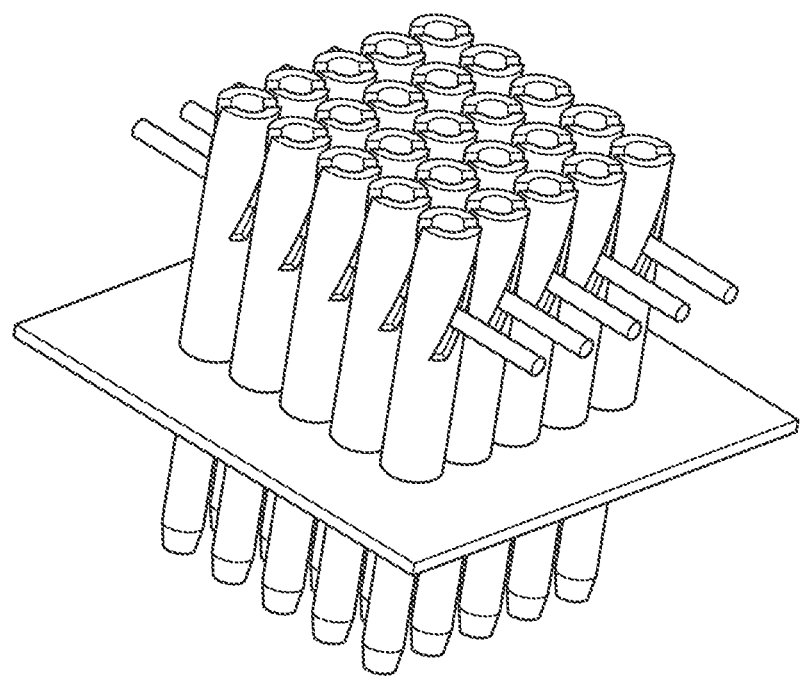
FIG. 60 shows an example slotted scalpet array (e.g., 25 scalpets) with the drive rod, under an embodiment.

FIG. 58 shows a slotted scalpet and an array including slotted scalpets, under an embodiment. The slotted scalpet configuration comprises a sleeve configured to fit over an end region of the scalpet, and the sleeve includes one or more spiral slots. Alternatively, each scalpet includes the spiral slot(s) without use of the sleeve. The sleeved scalpets are configured as a unit or array so that the top region of the slots of each scalpet are aligned adjacent one another. An external drive rod is aligned and fitted horizontally along the top of the slots. When the drive rod is driven downward, the result is a rotation of the scalpet array. FIG. 59 shows a portion of a slotted scalpet array (e.g., four (4) scalpets) with the drive rod, under an embodiment. FIG. 60 shows an example slotted scalpet array (e.g., 25 scalpets) with the drive rod, under an embodiment.

Figure 61:
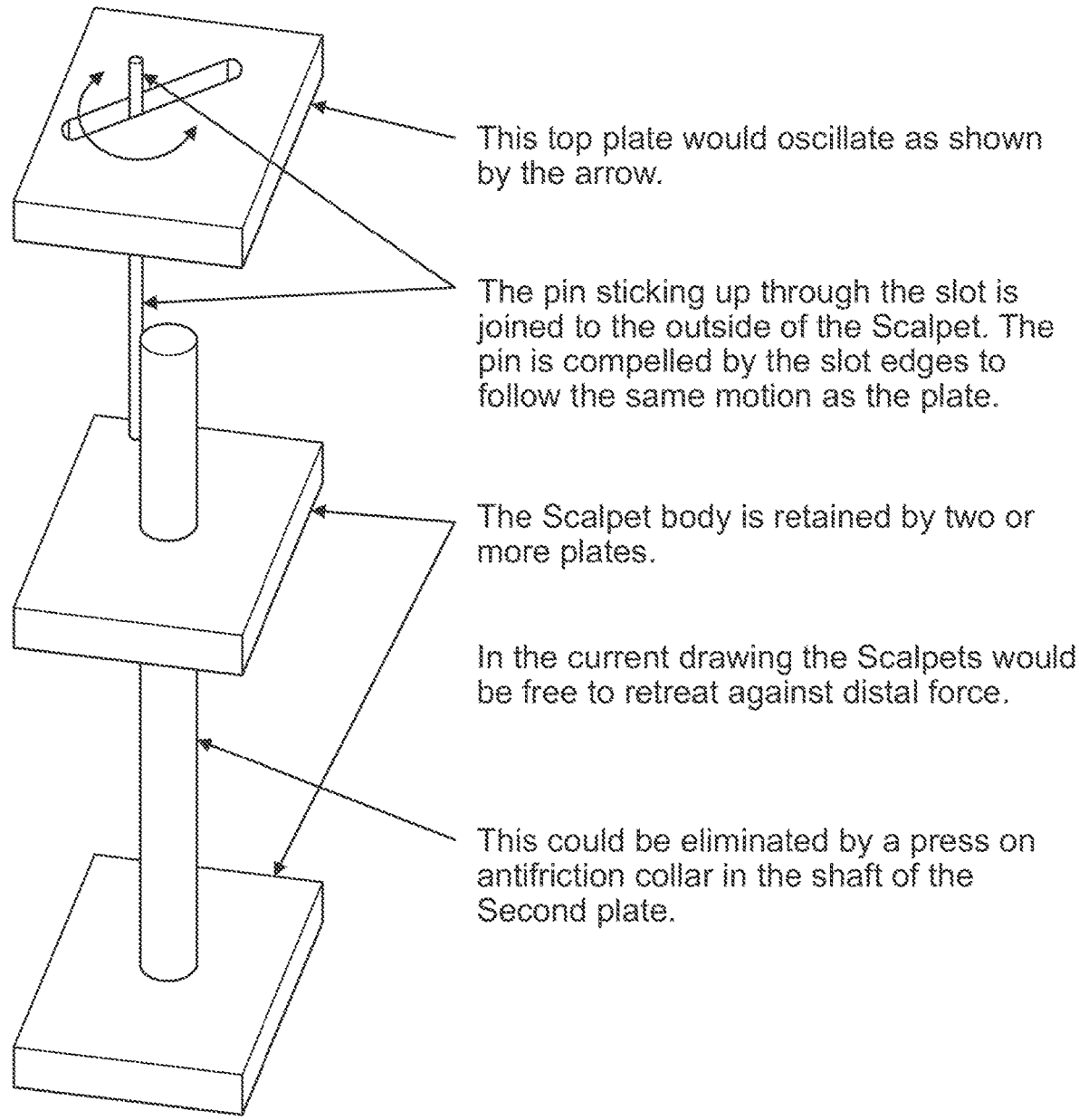
FIG. 61 shows an oscillating pin drive assembly with a scalpet, under an embodiment.

FIG. 61 shows an oscillating pin drive assembly with a scalpet, under an embodiment. The assembly includes a lower plate and a middle plate coupled or connected to the scalpet(s) and configured to retain the scalpet(s). A top plate, or drive plate, is positioned in an area above the scalpet and the middle plate, and includes a drive slot or slot. A pin is coupled or connected to a top portion of the scalpet, and a top region of the pin extends beyond a top of the scalpet. The slot is configured to receive and loosely retain the pin. The slot is positioned relative to the pin such that rotation or oscillation of the top plate causes the scalpet to rotate or oscillate via tracking of the pin in the slot.

One or more components of the scalpet device include an adjustment configured to control the amount (e.g., depth) of scalpet exposure during deployment of the scalpet array at the target site. For example, the adjustment of an embodiment is configured to collectively control a length of deployment of the scalpets of a scalpet array. The adjustment of an alternative embodiment is configured to collectively control a length of deployment of a portion or set of scalpets of a scalpet array. In another example embodiment, the adjustment is configured to separately control a length of deployment of each individual scalpet of a set of scalpets or scalpet array. The scalpet depth control includes numerous mechanisms configured for adjustable control of scalpet depth.

The depth control of an embodiment includes an adjustable collar or sleeve on each scalpet. The collar, which is configured for movement (e.g., slideable, etc.) along a length of the scalpet, is configured to prevent penetration of the scalpet into target tissue beyond a depth controlled by a position of the collar. The position of the collar is adjusted by a user of the scalpet device prior to use in a procedure, where the adjustment includes one or more of a manual adjustment, automatic adjustment, electronic adjustment, pneumatic adjustment, and adjustment under software control, for example.

The depth control of an alternative embodiment includes an adjustable plate configured for movement along a length of scalpets of the scalpet array. The plate is configured to prevent penetration of the scalpets of the scalpet array into target tissue beyond a depth controlled by a position of the plate. In this manner, the scalpet array is deployed into the target tissue to a depth equivalent to a length of the scalpets protruding beyond the plate. The position of the plate is adjusted by a user of the scalpet device prior to use in a procedure, where the adjustment includes one or more of a manual adjustment, automatic adjustment, electronic adjustment, pneumatic adjustment, and adjustment under software control, for example.

Figure 62:
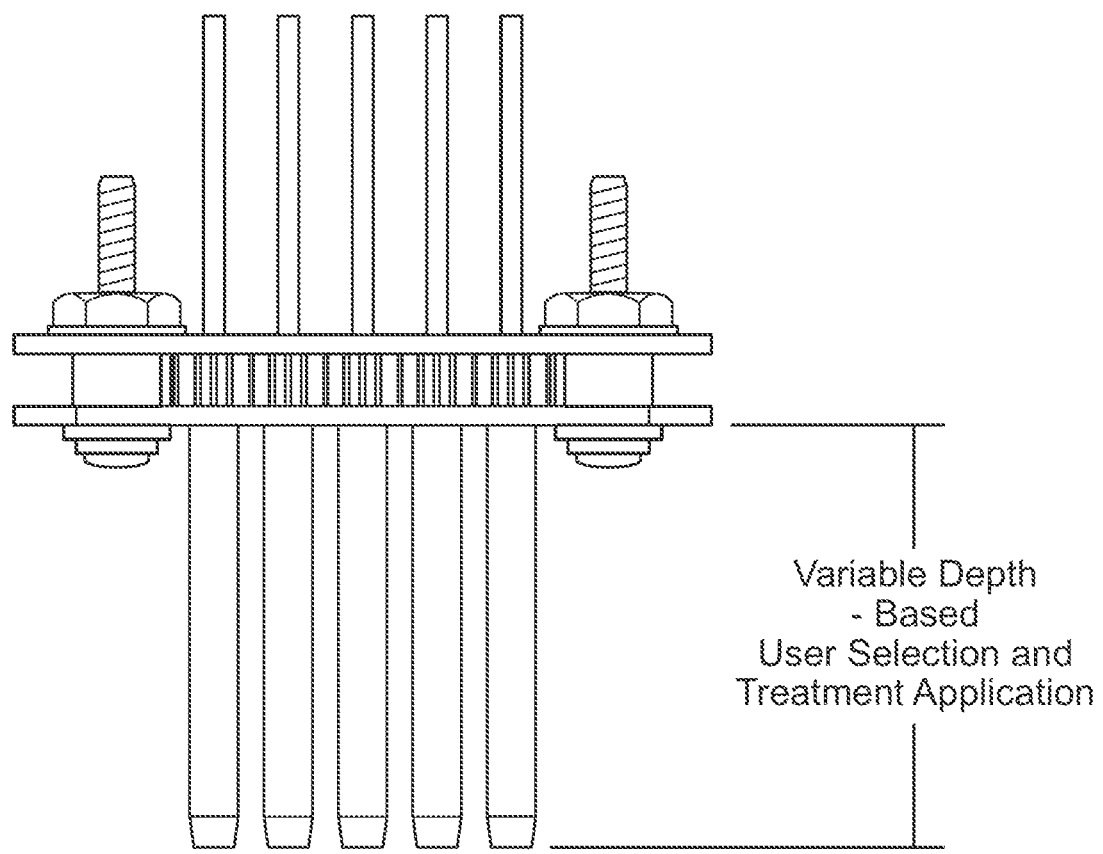
FIG. 62 shows variable scalpet exposure control with the scalpet guide plates, under an embodiment.

As an example of depth control adjustment using a plate, the variable length scalpet exposure is controlled through adjustments of the scalpet guide plates of the scalpet assembly, but is not so limited. FIG. 62 shows variable scalpet exposure control with the scalpet guide plates, under an embodiment. Alternative embodiments control scalpet exposure from within the scalpet array handpiece, and/or under one or more of software, hardware, and mechanical control.

Figure 63:
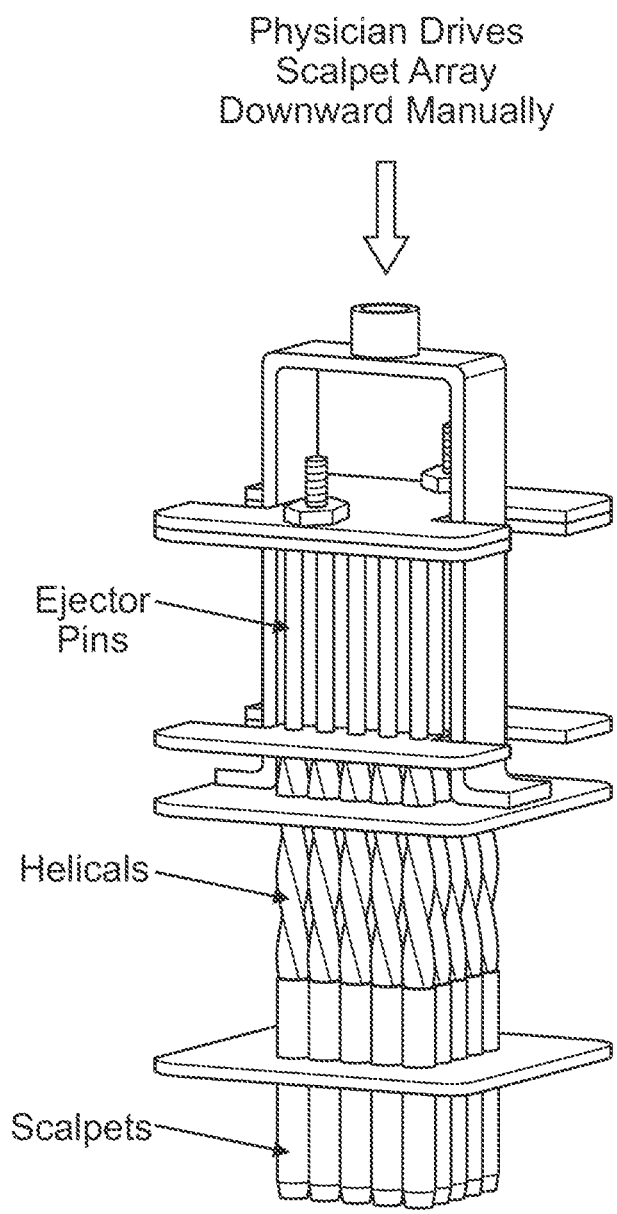
FIG. 63 shows a scalpet assembly including a scalpet array (e.g., helical) configured to be manually driven by an operator, under an embodiment.

Embodiments include a mechanical scalpet array in which axial force and rotational force are applied manually by the compressive force from the device operator. FIG. 63 shows a scalpet assembly including a scalpet array (e.g., helical) configured to be manually driven by an operator, under an embodiment.

Embodiments include and/or are coupled or connected to a source of rotation configured to provide optimal rotation (e.g., RPM) and rotational torque to incise skin in combination with axial force. Optimal rotation of the scalpets is configured according to the best balance between rotational velocity and increased cutting efficiency versus increased frictional losses. Optimal rotation for each scalpet array configuration is based on one or more of array size (number of scalpets), scalpet cutting surface geometry, material selection of scalpets and alignment plates, gear materials and the use of lubrication, and mechanical properties of the skin, to name a few.

Figure 64:
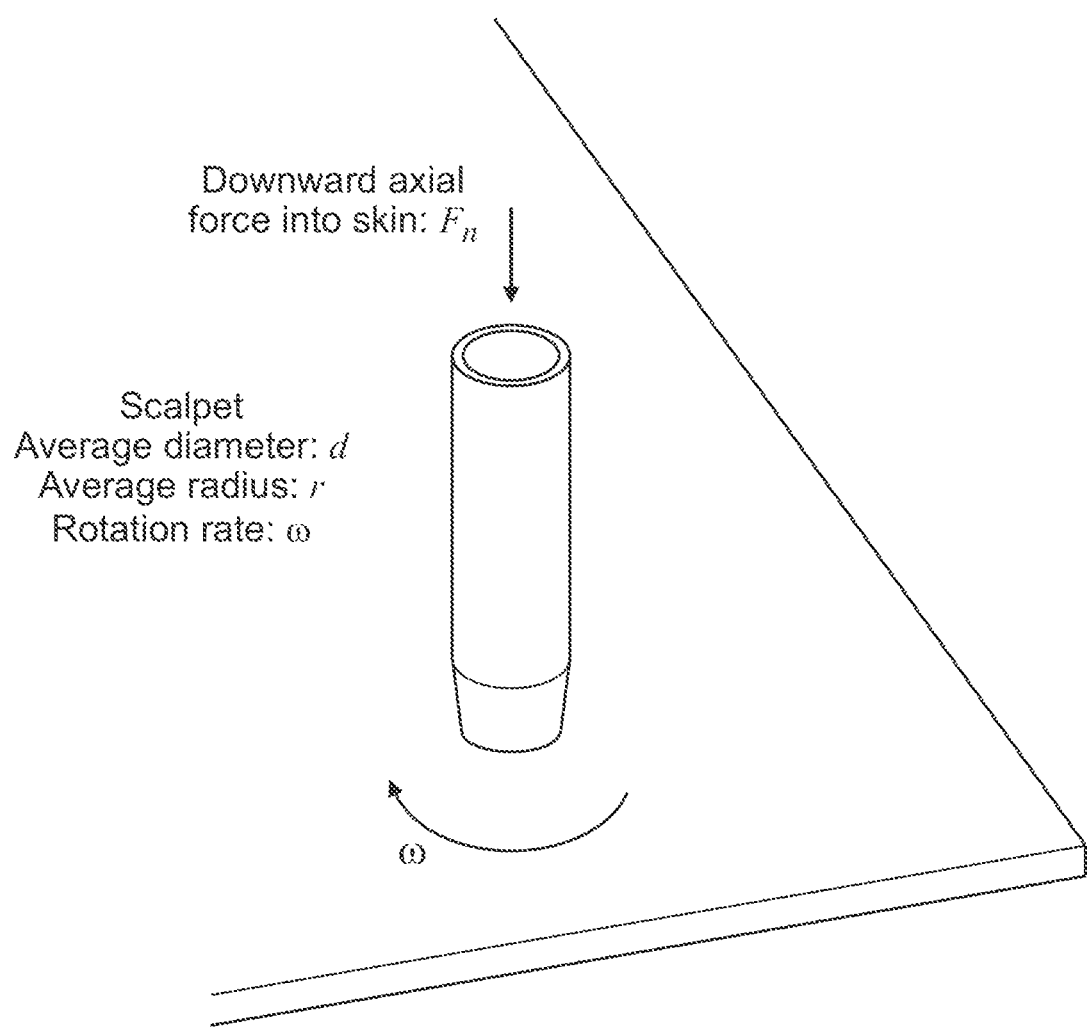
FIG. 64 shows forces exerted on a scalpet via application to the ski.

Regarding forces to be considered in configuration of the scalpets and scalpet arrays described herein, FIG. 64 shows forces exerted on a scalpet via application to the skin. The parameters considered in determining applicable forces under an embodiment include the following:

Average Scalpet Radius: r
Scalpet Rotation Rate: $\omega$
Scalpet Axial Force: $F_n$ (scalpet applied normal to skin)
Skin Friction Coefficient: $\mu$
Friction Force: $F_f$
Scalpet Torque: $\tau$
Motor Power: $P_{hp}$.

Upon initial application, the torque used to rotate the scalpet is a function of the axial force (applied normally to the surface of the skin) and the coefficient of friction between the scalpet and the skin. This friction force initially acts on the cutting surface of the scalpet. At initial application of scalpet to skin:

$F_f = \mu \cdot F_n$.
$\tau = F_f \cdot r$
$P_{hp} = \tau \cdot \omega / 63025$ The initial force for the scalpet to penetrate the skin, is a function of the scalpet sharpness, the axial force, the tensile strength of the skin, the coefficient of friction between the skin and the scalpet. Following penetration of the scalpet into the skin, the friction force increases as there are additional friction forces acting on the side walls of the scalpet.

Figure 65:
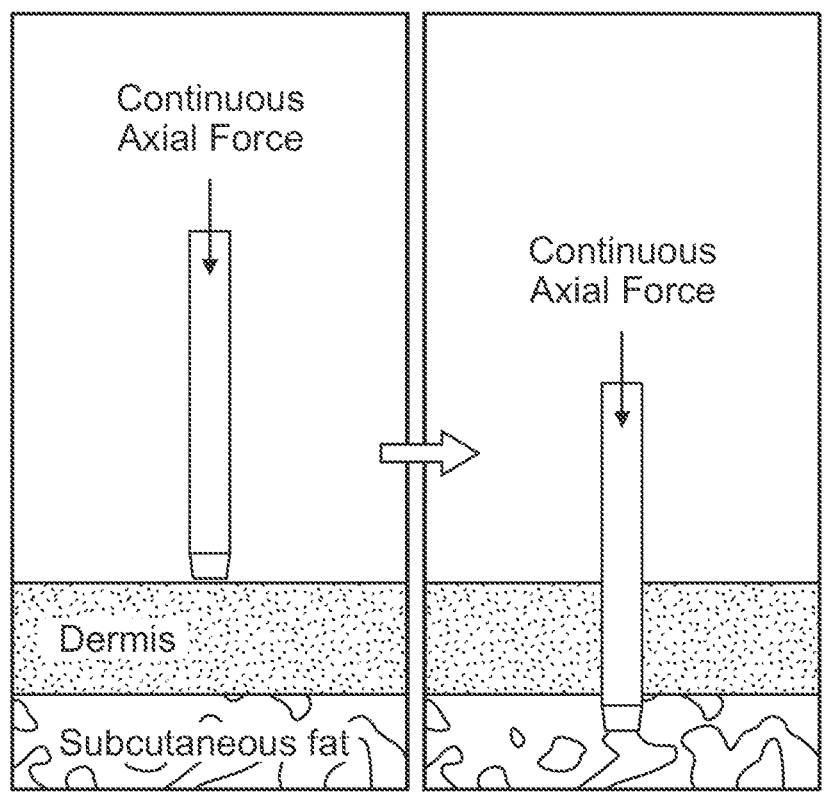
FIG. 65 depicts steady axial force compression using a scalpet, under an embodiment.

Resection devices of embodiments include kinetic impaction incision devices and methods for non-rotational piercing of the skin. Approaches for direct compression of the scalpet into the skin include, but are not limited to, axial force compression, single axial force compression plus kinetic impact force, and moving of the scalpet at a high velocity to impact and pierce the skin. FIG. 65 depicts steady axial force compression using a scalpet, under an embodiment. Steady axial force compression places the scalpet in direct contact with the skin. Once in place, a continuous and steady axial force is applied to the scalpet until it pierces the skin and proceeds through the dermis to the subcutaneous fat layer.

Figure 66:
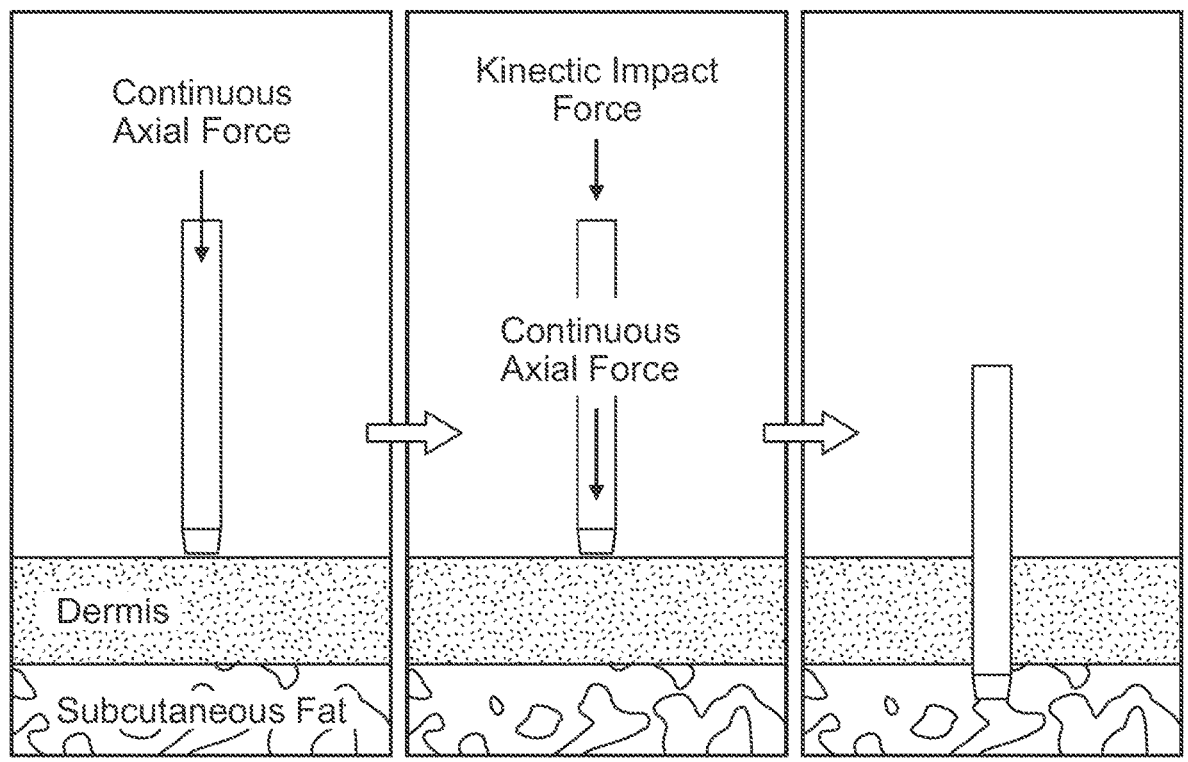
FIG. 66 depicts steady single axial force compression plus kinetic impact force using a scalpet, under an embodiment.

FIG. 66 depicts steady single axial force compression plus kinetic impact force using a scalpet, under an embodiment. Steady single axial force compression plus kinetic impact force places the scalpet in direct contact with the skin. An axial force is applied to maintain contact. The distal end of the scalpet is then struck by another object, imparting additional kinetic energy along the central axis. These forces cause the scalpet to pierce the skin and proceed through the dermis to the subcutaneous fat layer.

Figure 67:
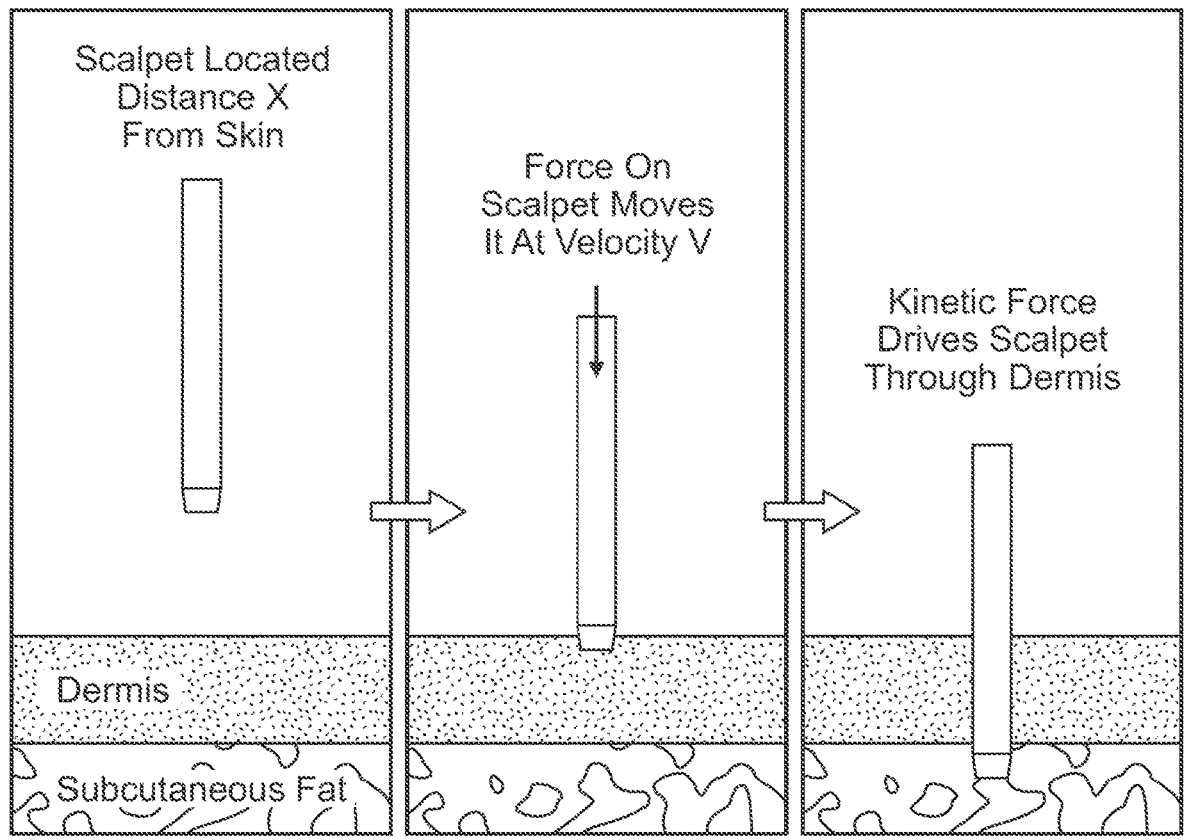
FIG. 67 depicts moving of the scalpet at a velocity to impact and pierce the skin, under an embodiment.

FIG. 67 depicts moving of the scalpet at a velocity to impact and pierce the skin, under an embodiment. The scalpet is positioned a short distance away from a target area of the skin. A kinetic force is applied to the scalpet to achieve a desired velocity for piercing the skin. The kinetic force causes the scalpet to pierce the skin and proceed through the dermis to the subcutaneous fat layer.

Figure 68:
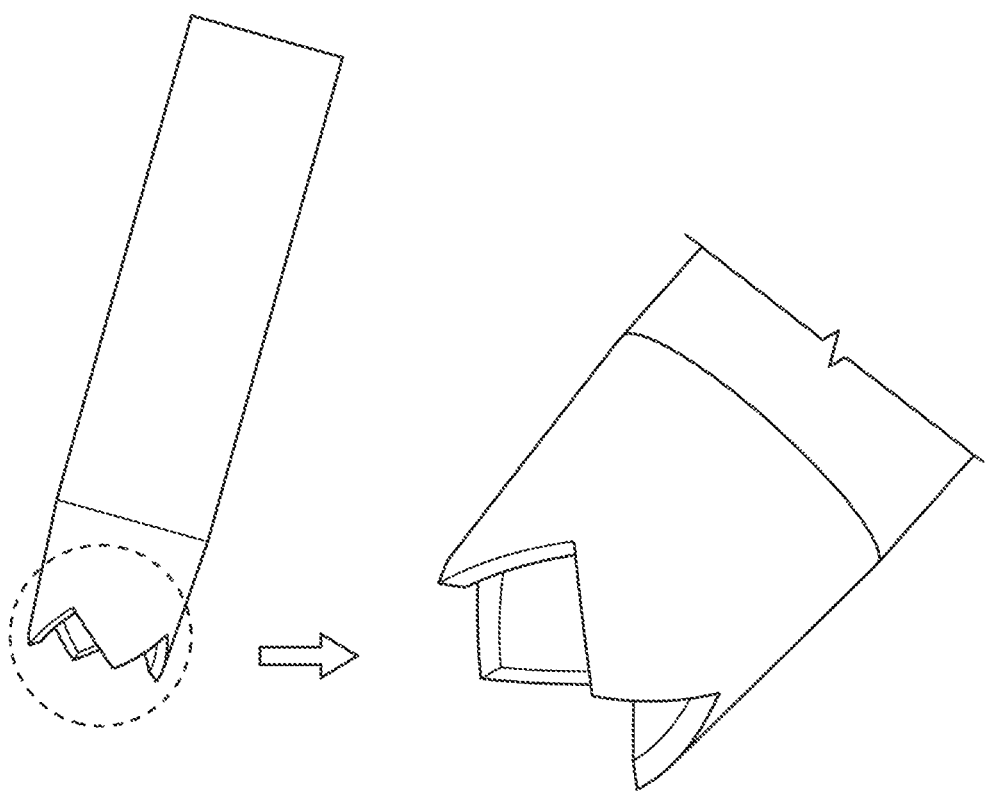
FIG. 68 depicts a multi-needle tip, under an embodiment.

Scalpets of an embodiment include numerous cutting surface or blade geometries as appropriate to an incision method of a procedure involving the scalpet. The scalpet blade geometries include, for example, straight edge (e.g., cylindrical), beveled, multiple-needle tip (e.g., sawtooth, etc.), and sinusoidal, but are not so limited. As but one example, FIG. 68 depicts a multi-needle tip, under an embodiment.

Figure 69:
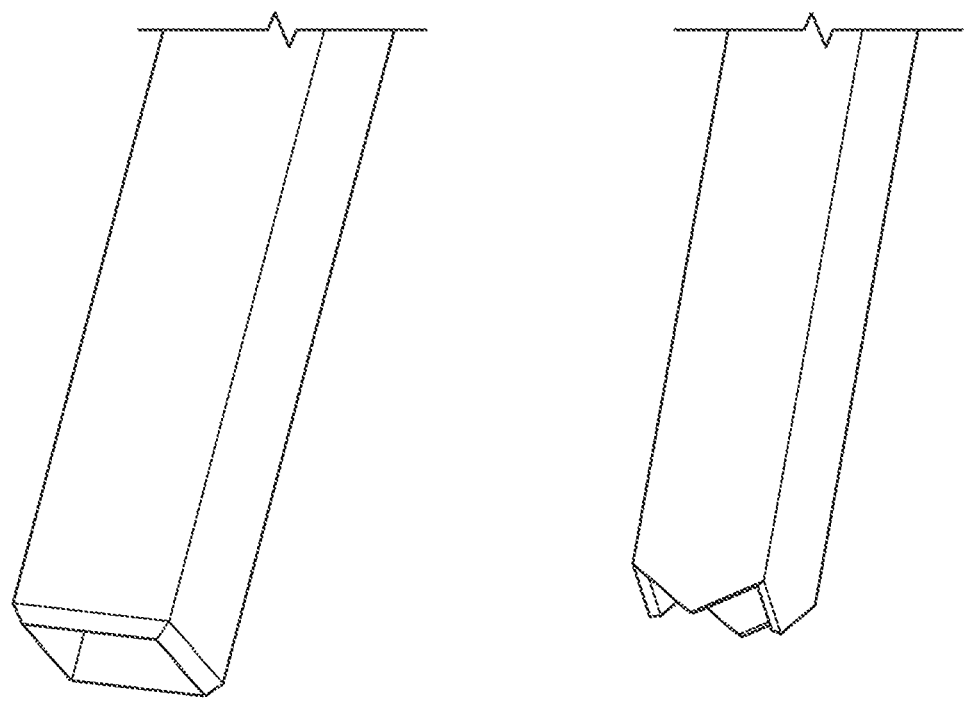
FIG. 69 shows a square scalpet without teeth (left), and a square scalpet with multiple teeth (right), under an embodiment.

The scalpets include one or more types of square scalpets, for example. The square scalpets include but are not limited to, square scalpets without multiple sharpened points, and square scalpets with multiple sharpened points or teeth. FIG. 69 shows a square scalpet without teeth (left), and a square scalpet with multiple teeth (right), under an embodiment.

The fractional resection devices of an embodiment involve the use of a square scalpet assembled onto a scalpet array that has multiple sharpened points to facilitate skin incising through direct non-rotational kinetic impacting. The square geometry of the harvested skin plug provides side-to-side and point-to-point approximation of the assembled skin plugs onto the adherent membrane. Closer approximation of the skin plugs provides a more uniform appearance of the skin graft at the recipient site. In addition, each harvested component skin plug will have additional surface area (e.g., 20-25%).

Figure 70:
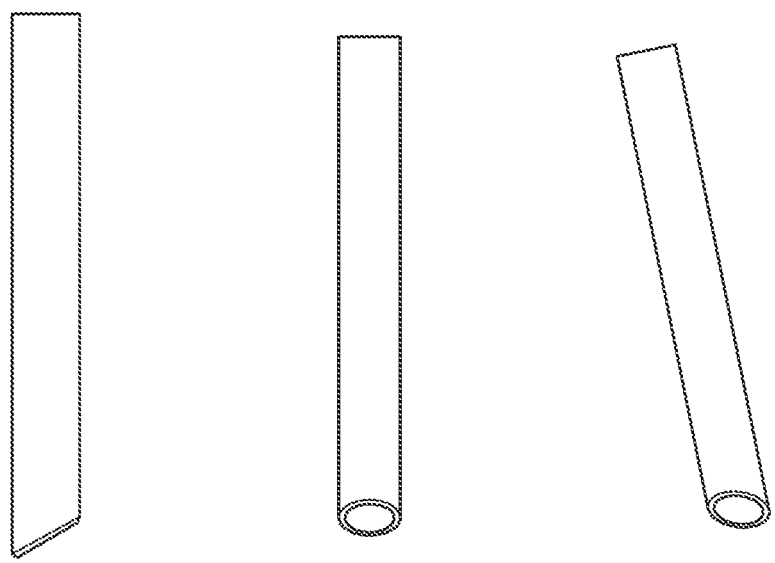
FIG. 70 shows multiple side, front (or back), and side perspective views of a round scalpet with an oblique tip, under an embodiment.
Figure 71:
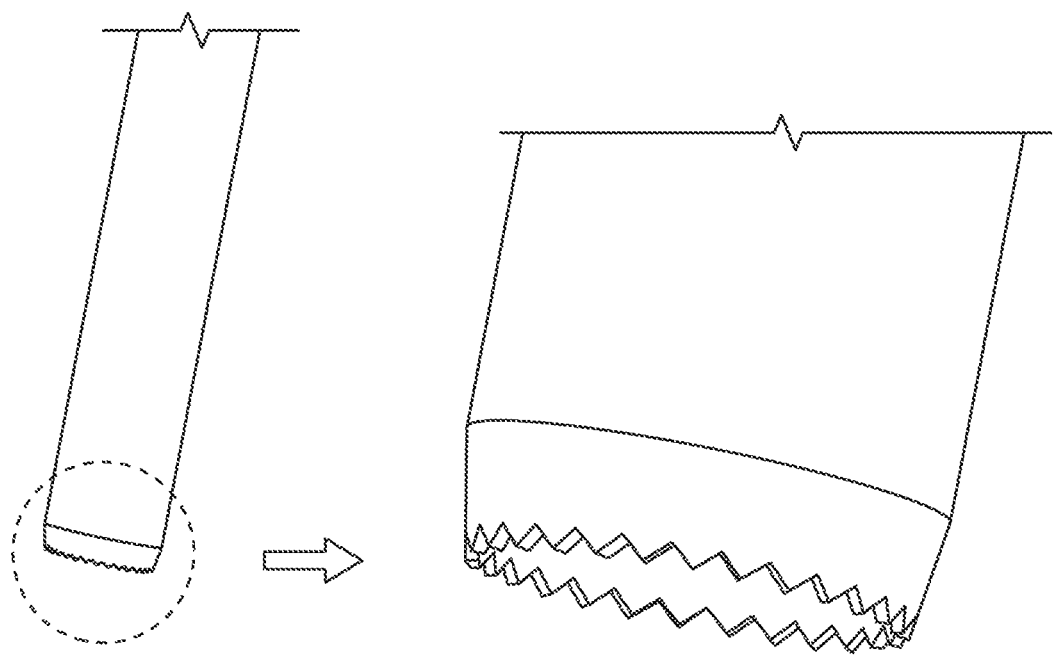
FIG. 71 shows a round scalpet with a serrated edge, under an embodiment.

Further, the scalpets include one or more types of elliptical or round scalpets. The round scalpets include but are not limited to, round scalpets with oblique tips, round scalpets without multiple sharpened points or teeth, and round scalpets with multiple sharpened points or teeth. FIG. 70 shows multiple side, front (or back), and side perspective views of a round scalpet with an oblique tip, under an embodiment. FIG. 71 shows a round scalpet with a serrated edge, under an embodiment.

Figure 72:
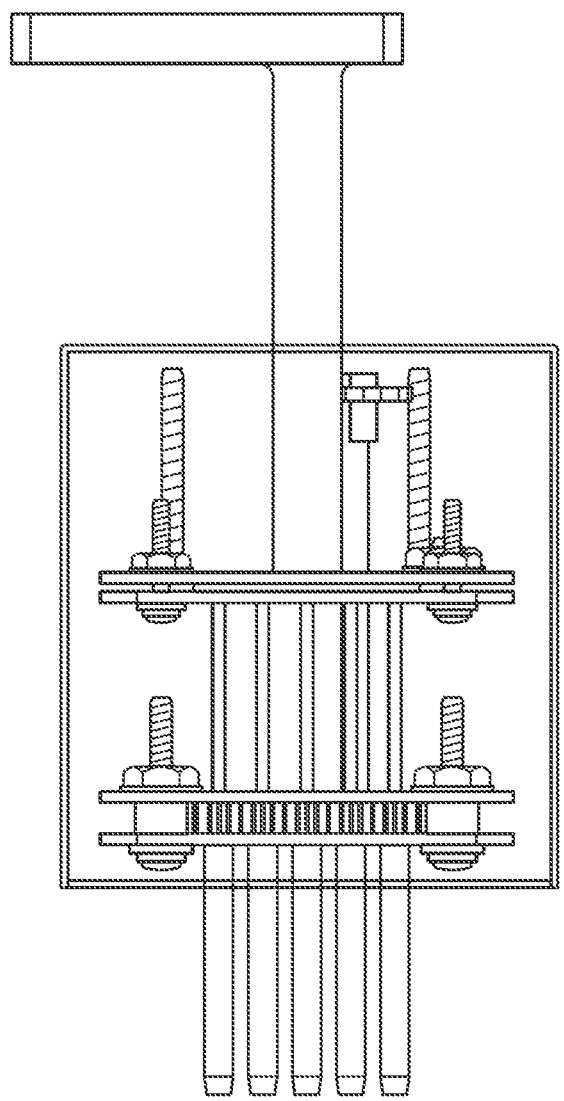
FIG. 72 shows a side view of the resection device including the scalpet assembly with scalpet array and extrusion pins (housing depicted as transparent for clarity of details), under an embodiment.
Figure 73:
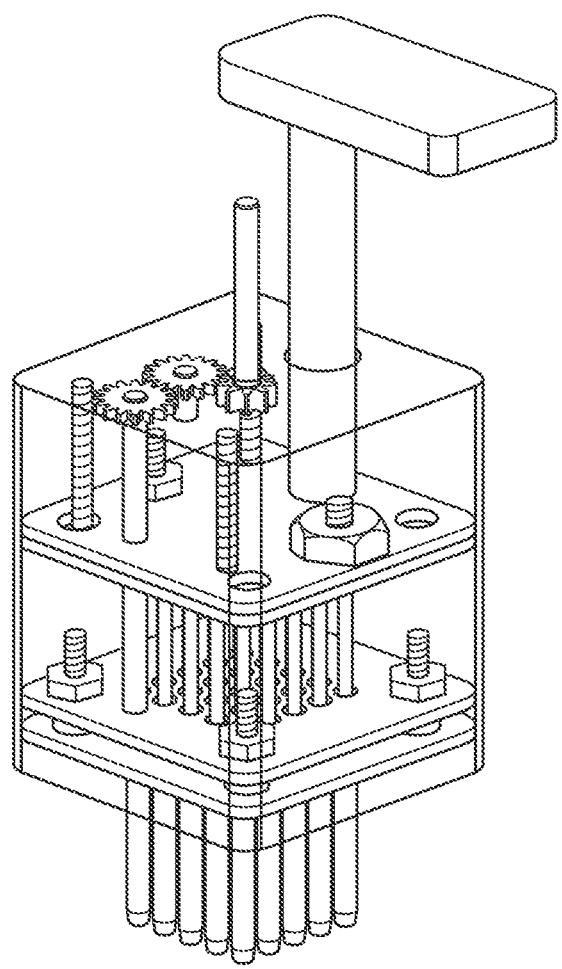
FIG. 73 shows a top perspective cutaway view of the resection device including the scalpet assembly with scalpet array and extrusion pins (housing depicted as transparent for clarity of details), under an embodiment.
Figure 74:
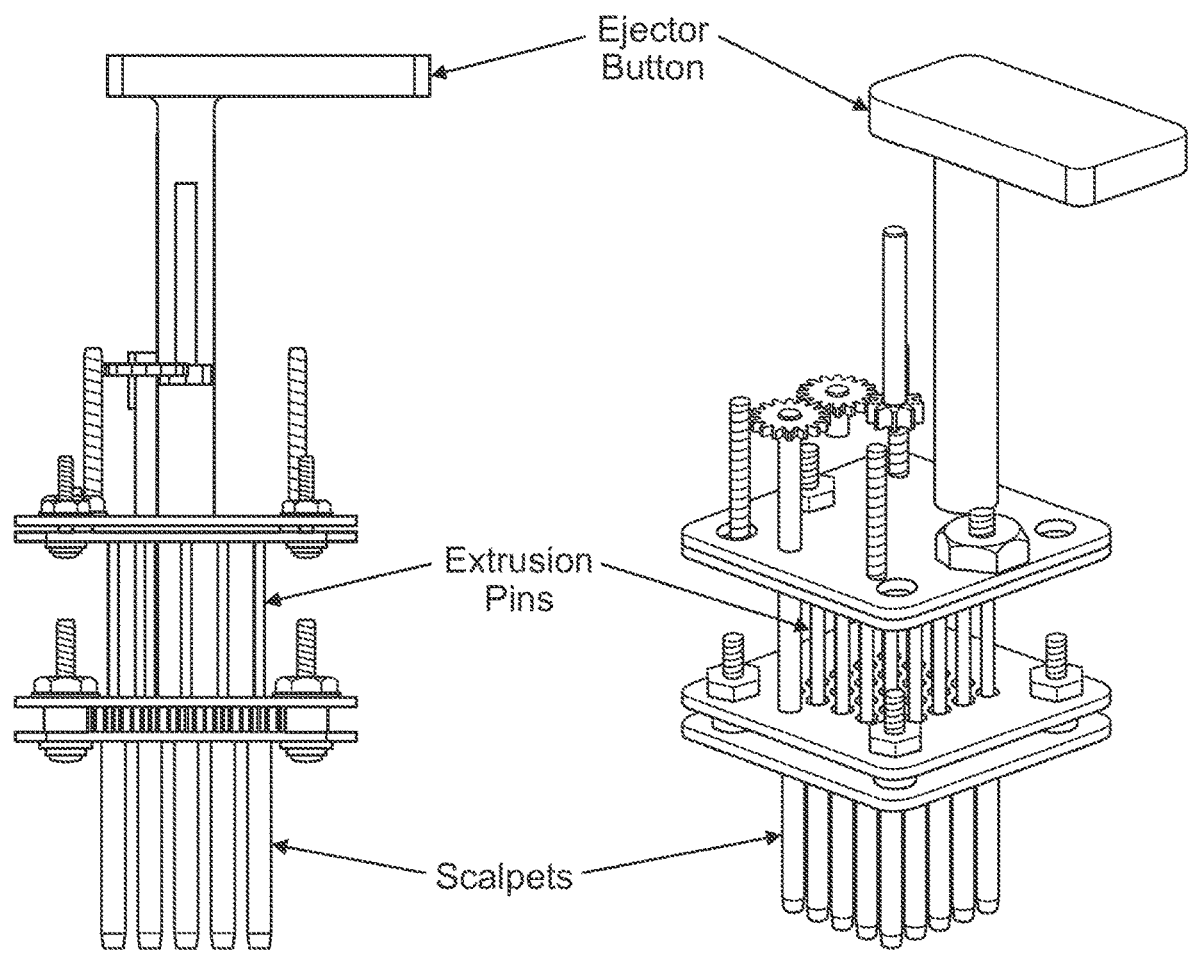
FIG. 74 shows side and top perspective views of the scalpet assembly including the scalpet array and extrusion pins, under an embodiment.

The resection device of an embodiment is configured to include extrusion pins corresponding to the scalpets. FIG. 72 shows a side view of the resection device including the scalpet assembly with scalpet array and extrusion pins (housing depicted as transparent for clarity of details), under an embodiment. FIG. 73 shows a top perspective cutaway view of the resection device including the scalpet assembly with scalpet array and extrusion pins (housing depicted as transparent for clarity of details), under an embodiment. FIG. 74 shows side and top perspective views of the scalpet assembly including the scalpet array and extrusion pins, under an embodiment.

The extrusion pins of an embodiment are configured to clear retained skin plugs, for example. The extrusion pins of an alternative embodiment are configured to inject into fractional defects at the recipient site. The extrusion pins of another alternative embodiment are configured to inject skin plugs into pixel canisters of a docking station for fractional skin grafting.

Figure 75:
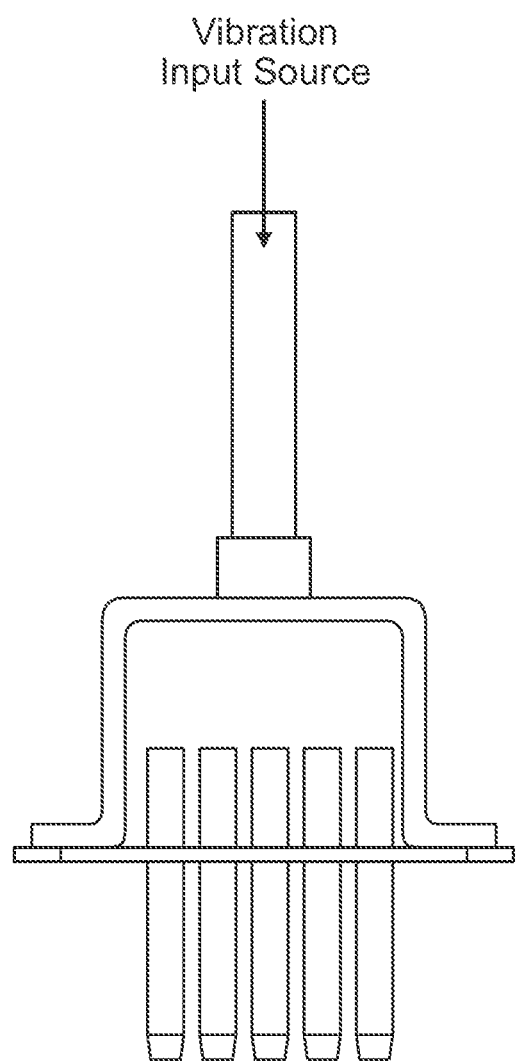
FIG. 75 is a side view of a resection device including the scalpet assembly with scalpet array assembly coupled to a vibration source, under an embodiment.

Embodiments herein include the use of a vibration component or system to facilitate skin incising with rotation torque/axial force and to use vibration to facilitate skin incising with direct impaction without rotation. FIG. 75 is a side view of a resection device including the scalpet assembly with scalpet array assembly coupled to a vibration source, under an embodiment.

Figure 76:
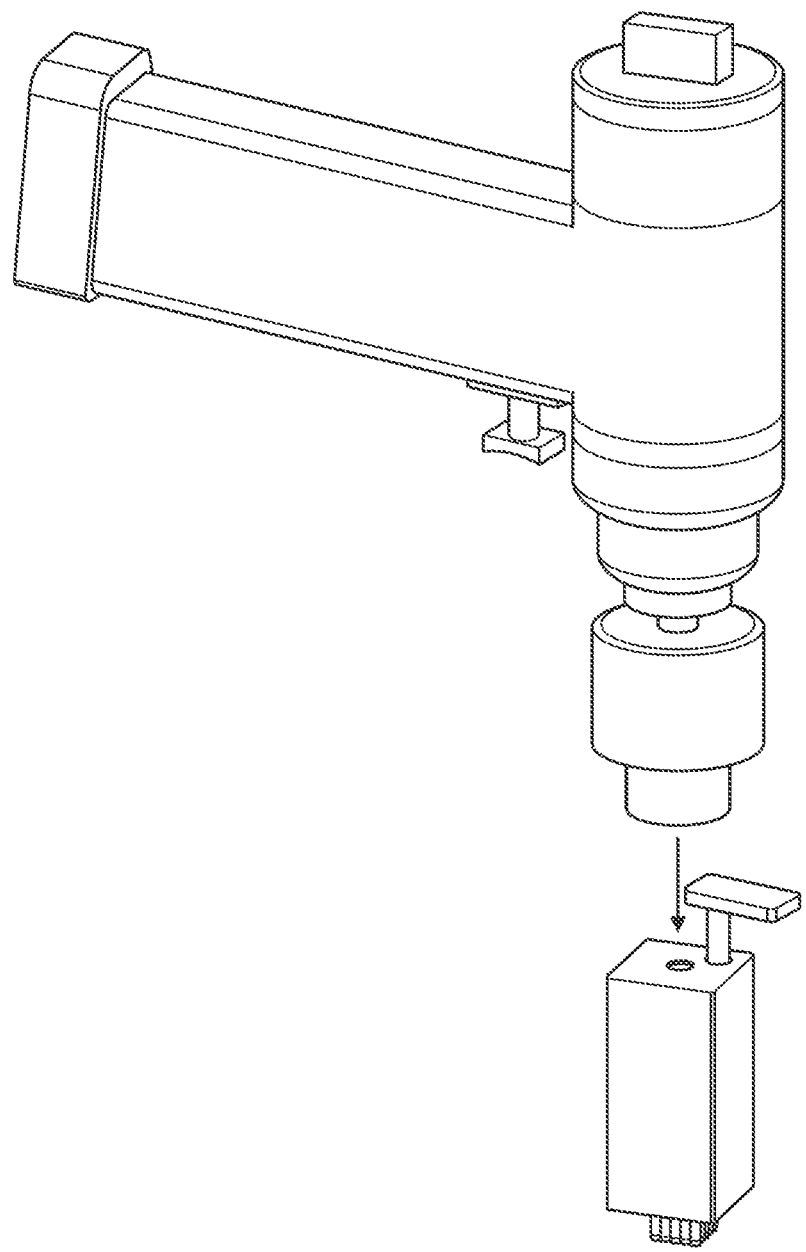
FIG. 76 shows a scalpet array driven by an electromechanical source or scalpet array generator, under an embodiment.

Embodiments herein include an electro-mechanical scalpet array generator. FIG. 76 shows a scalpet array driven by an electromechanical source or scalpet array generator, under an embodiment. The function of the generator is powered but is not electronically controlled, but embodiments are not so limited. The platform of an embodiment includes control software.

Embodiments include and/or are coupled or connected to a supplementary energy or force configured to reduce the axial force used to incise skin (or another tissue surface such as mucosa) by a scalpet in a scalpet array. Supplemental energies and forces include one or more of rotational torque, rotational kinetic energy of rotation (RPM), vibration, ultrasound, and electromagnetic energy (e.g., RF, etc.), but are not so limited.

Embodiments herein include a scalpet array generator comprising and/or coupled to an electromagnetic radiation source. The electromagnetic radiation source includes, for example, one or more of a Radio Frequency (RF) source, a laser source, and an ultrasound source. The electromagnetic radiation is provided to assist cutting with the scalpets.

Embodiments include a scalpet mechanism configured as a "sewing machine" scalpet or scalpet array in which the scalpets are repeatedly retracted and deployed under one or more of manual, electromechanical, and electronic control. This embodiment includes a moving scalpet or scalpet array to resect a site row-by-row. The resection can, for example take the form of a stamping approach where the scalpet or scalpet array moves, or the array could be rolled over the surface to be treated and the scalpet array resection at given distances traveled to achieve the desired resection density.

The fractional resection devices described herein are configured for fractional resection and grafting in which the harvesting of fractionally incised skin plugs is performed with a vacuum that deposits the plugs within the lumen of each scalpet shaft. The skin plugs are then inserted into a separate docking station described herein by a proximal pin array that extrudes the skin plug from within the shaft of the scalpet.

Figure 77:
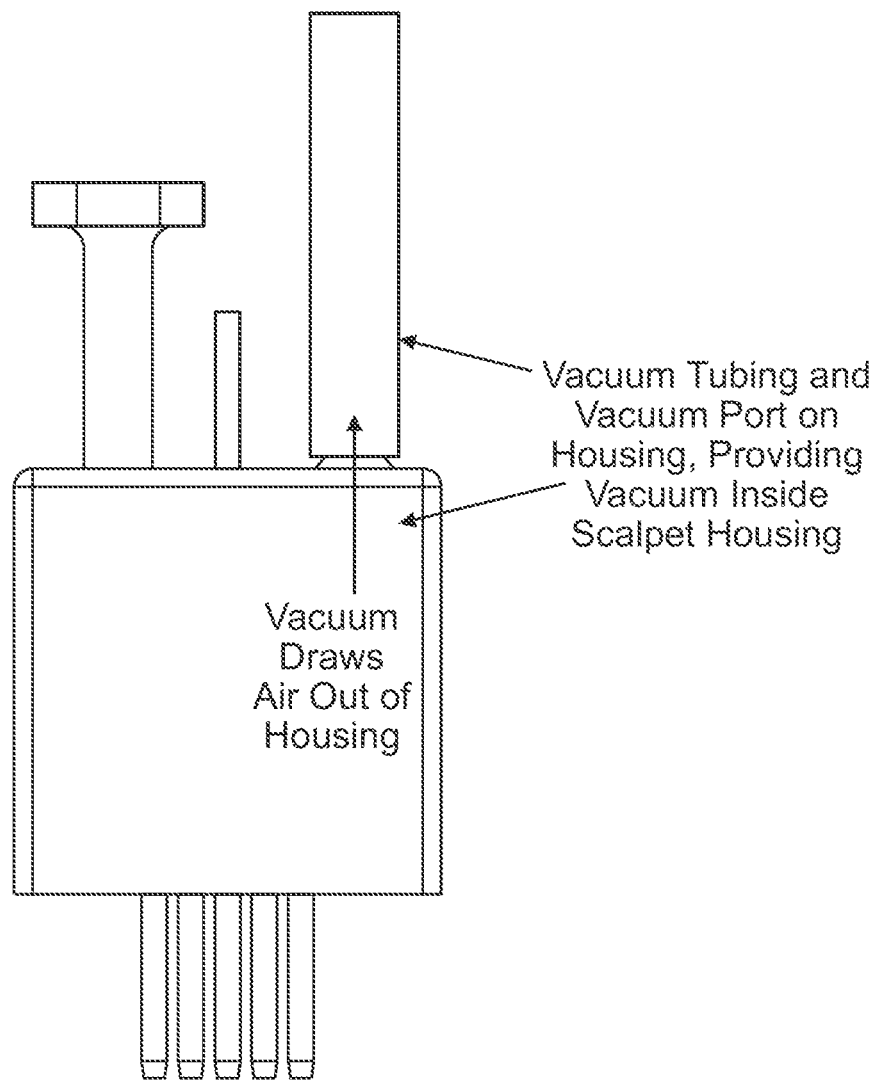
FIG. 77 is a diagram of the resection device including a vacuum system, under an embodiment.

FIG. 77 is a diagram of the resection device including a vacuum system, under an embodiment. The vacuum system comprises vacuum tubing and a vacuum port on/in the device housing, configured to generate a vacuum within the housing by drawing air out of the housing. The vacuum of an embodiment is configured to provide vacuum stenting/fixturing of the skin for scalpet incising, thereby providing improved depth control and cutting efficiency.

Figure 78:
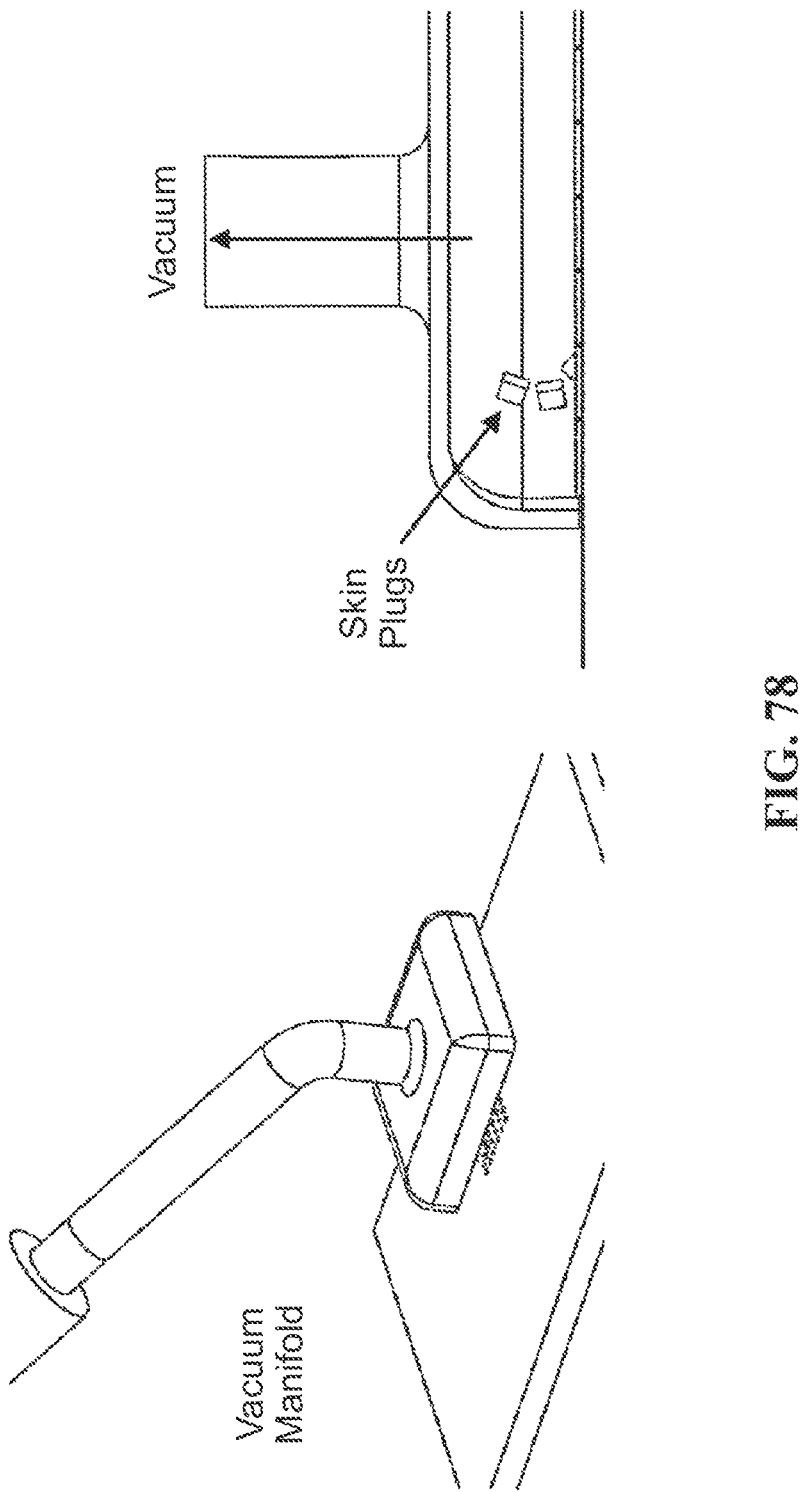
FIG. 78 shows a vacuum manifold applied to a target skin surface to evacuate/harvest excised skin/hair plugs, under an embodiment.
Figure 79:
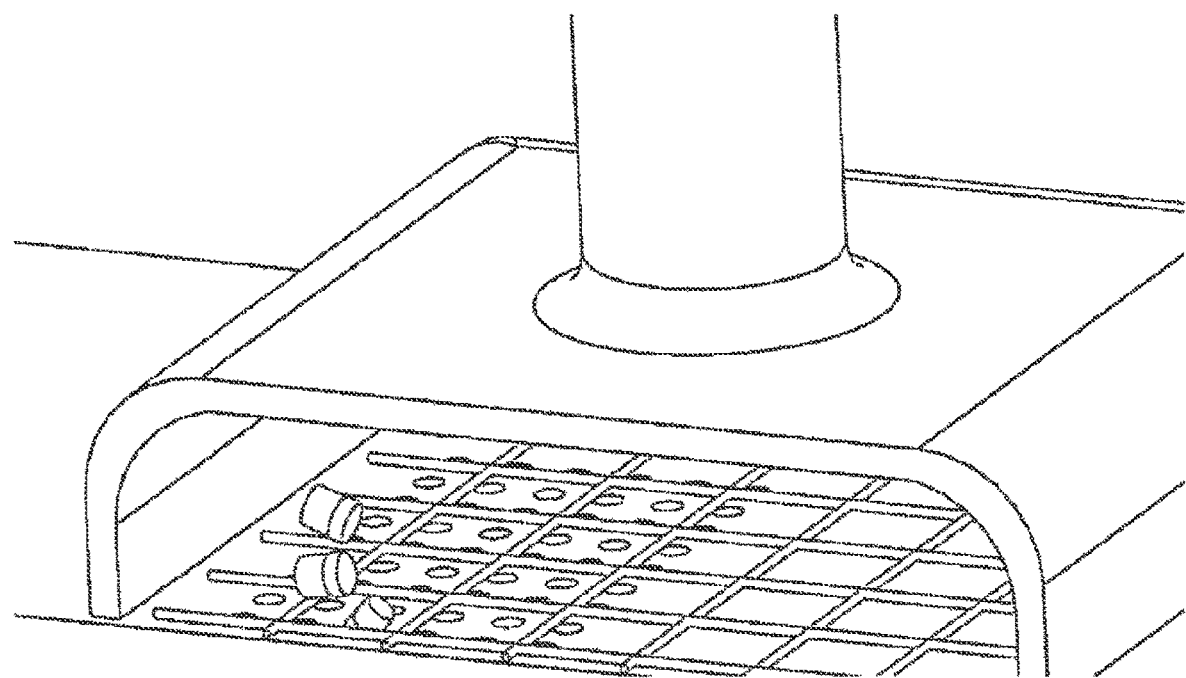
FIG. 79 shows a vacuum manifold with an integrated wire mesh applied to a target skin surface to evacuate/harvest excised skin/hair plugs, under an embodiment.

The vacuum of an alternative embodiment is configured for vacuum evacuation or harvesting of skin plugs and/or hair plugs through one or more of a scalpet lumen and an array manifold housing. FIG. 78 shows a vacuum manifold applied to a target skin surface to evacuate/harvest excised skin/hair plugs, under an embodiment. The vacuum manifold, which is configured for direct application onto a skin surface, is coupled or connected to a vacuum source. FIG. 79 shows a vacuum manifold with an integrated wire mesh applied to a target skin surface to evacuate/harvest excised skin/hair plugs, under an embodiment.

Figure 80:
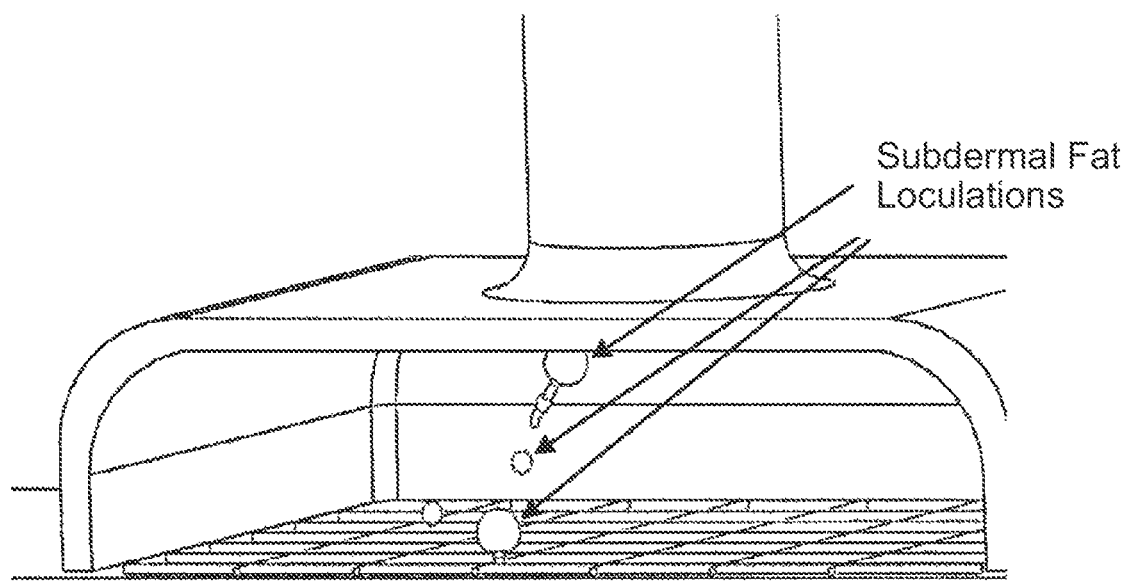
FIG. 80 shows a vacuum manifold with an integrated wire mesh configured to vacuum subdermal fat, under an embodiment.

Additionally, an external vacuum manifold is used with a suction-assisted lipectomy machine to percutaneously evacuate superficial sub-dermal fat through fractionally resection skin defects in a fractionally created field for the treatment of cellulite. FIG. 80 shows a vacuum manifold with an integrated wire mesh configured to vacuum subdermal fat, under an embodiment.

The external vacuum manifold can also be configured to include and be deployed with an incorporated docking station (described herein) to harvest skin plugs for grafting. The docking station can be one or more of static, expandable, and/or collapsible.

The fractional resection devices described herein comprise a separate docking station configured as a platform to assemble the fractionally harvested skin plugs into a more uniform sheet of skin for skin grafting. The docking station includes a perforated grid matrix comprising the same pattern and density of perforations as the scalpets on the scalpet array. A holding canister positioned subjacent to each perforation is configured to retain and maintain alignment of the harvested skin plug. In an embodiment, the epidermal surface is upward at the level of the perforation. In an alternative embodiment, the docking station is partially collapsible to bring docked skin plugs into closer approximation prior to capture onto an adherent membrane. The captured fractional skin graft on the adherent membrane is then defatted with either an incorporated or non-incorporated transection blade. In another alternative embodiment, the adherent membrane itself has an elastic recoil property that brings or positions the captured skin plugs into closed alignment. Regardless of embodiment, the contracted fractional skin graft/adherent membrane composite is then directly applied to the recipient site defect.

Figure 81:
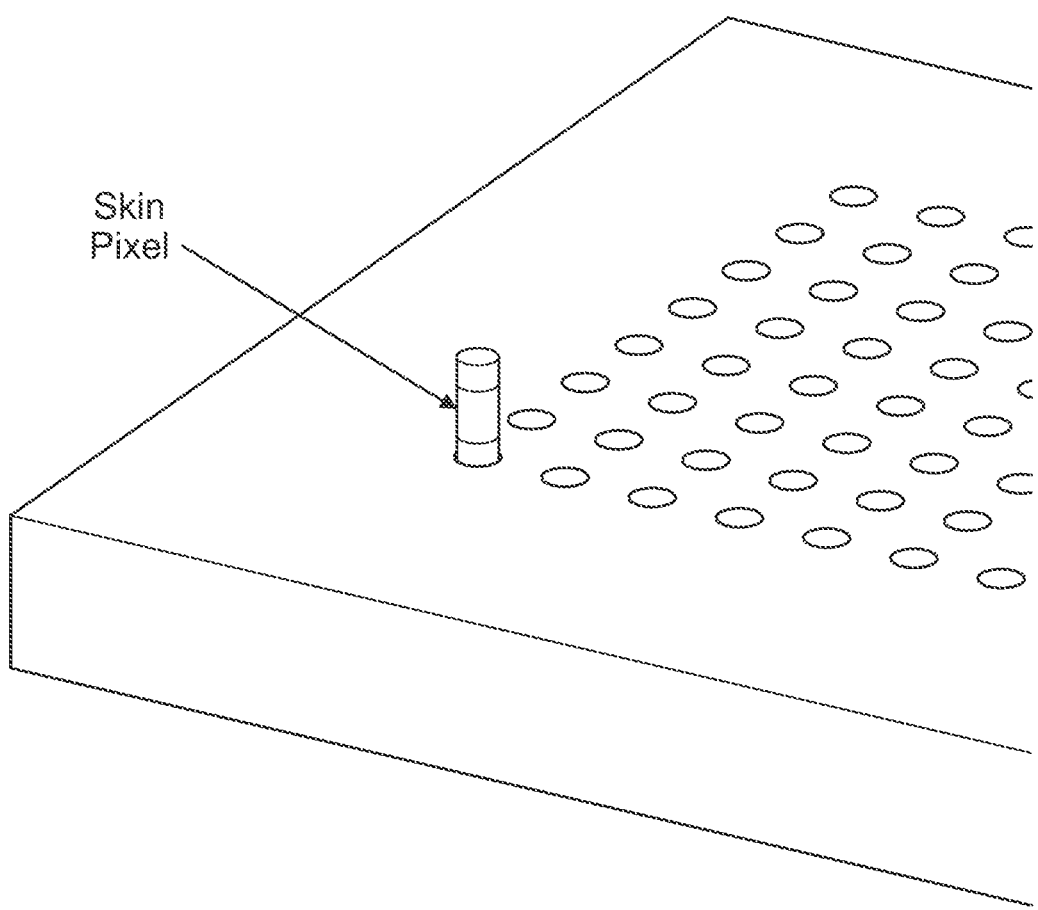
FIG. 81 depicts a collapsible docking station and an inserted skin pixel, under an embodiment. The docking station is formed from elastomeric material but is not so limited.
Figure 82:
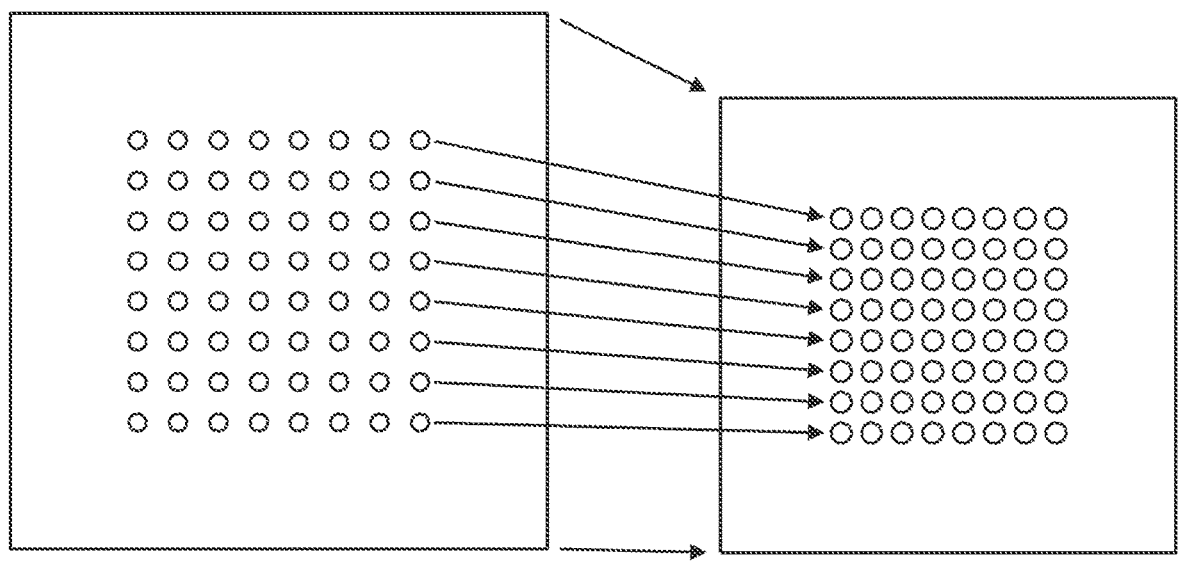
FIG. 82 is a top view of a docking station (e.g., elastomeric) in stretched (left) and un-stretched (right) configuration, under an embodiment, under an embodiment.

Embodiments include a collapsible docking station or tray configured to accept and maintain orientation of harvested skin and/or hair plugs once they have been removed or ejected from the scalpets via the extrusion pins. FIG. 81 depicts a collapsible docking station and an inserted skin pixel, under an embodiment. The docking station is formed from elastomeric material but is not so limited. The docking station is configured for stretching from a first shape to a second shape that aligns the pixel receptacles with the scalpet array on the handpiece. FIG. 82 is a top view of a docking station (e.g., elastomeric) in stretched (left) and un-stretched (right) configuration, under an embodiment, under an embodiment.

The pixels are ejected from the scalpet array into the docking station until it is full, and the docking station is then relaxed to its pre-stretched shape, which has the effect of bringing the pixels in closer proximity to each other. A flexible semi-permeable membrane with adhesive on one side is then stretched and placed over the docking station (adhesive side down). Once the pixels are adhered to the membrane, it is lifted away from the docking station. The membrane then returns to its normal un-stretched state, which also has the effect of pulling the pixels closer to each other. The membrane is then placed over the recipient defect.

Resection devices described herein include delivery of therapeutic agents through resectioned defects generated with the resection devices described herein. As such, the resection sites are configured for use as topically applied infusion sites for delivery or application of therapeutic agents for the reduction of fat cells (lipolysis) during or after a resectioning procedure.

Embodiments herein are configured for hair transplantation that includes vacuum harvesting of hair plugs into the scalpet at the donor site, and direct mass injection (without a separate collection reservoir) of harvested hair plugs into the fractionally resected defects of the recipient site. Under this embodiment, the donor scalpet array deployed at the occipital scalp comprises scalpets having a relatively larger diameter than the constituent scalpets of the scalpet array deployed to generate defects at the recipient site. Following harvesting of hair plugs at the donor site, the defects generated at the recipient site are plugged using the harvested hair plugs transferred in the scalpet array.

Due to the elastic retraction of the incised dermis, the elastically retracted diameter of the hair plug harvested at the occipital scalp will be similar to the elastically retracted diameter of the fractionally resected defect of the recipient site at the frontal-parietal-occipital scalp. In an embodiment, hair plugs harvested within the donor scalpet array are extruded directly with proximal pins in the lumen of the scalpet into a same pattern of fractionally defects created by the recipient site scalpet array. The scalpets (containing the donor hair plugs) of the scalpet array deployed at the donor site are aligned (e.g., visually) with the same pattern of fractionally resected field of defects at the recipient scalp site. Upon alignment, a proximal pin within the shaft of each scalpet is advanced down the shaft of the scalpet to extrude the hair plug into the fractionally resected defect of the recipient site, thereby effecting a simultaneous transplantation of multiple hair plugs to the recipient site. This mass transplantation of hair plugs into a fractionally resected recipient site (e.g., of a balding scalp) is more likely to maintain the hair shaft alignment with other mass transplanted hair plugs of that recipient scalp site. Directed closure of the donor site field is performed in the most clinically effective vector, but is not so limited.

The fractional resection devices described herein are configured for tattoo removal. Many patients later in life desire removal of pigmented tattoos for a variety of reasons. Generally, removal of a tattoo involves the removal of the impregnated pigment within the dermis. Conventional tattoo removal approaches have been described from thermal ablation of the pigment to direct surgical excision. Thermal ablation by lasers frequently results in depigmentation or area surface scarring. Surgical excision of a tattoo requires the requisite linear scarring of a surgical procedure. For many patients, the tradeoff between tattoo removal and the sequela of the procedure can be marginal.

The use of fractional resection to remove a tattoo allows for fractional removal of a significant proportion of the dermal pigment with minimal visible scarring. The fractional resection extends beyond the border of the tattoo to blend the resection into the non-resected and non-tattooed skin. Most apparently, de-delineation of the pattern of the tattoo will occur even if all residual pigment is not or cannot be removed. In an embodiment, initial fractional resections are performed with a scalpet array, and any subsequent fractional resections are performed by singular scalpet resections for residual dermal pigment. As with other applications described herein, directed closure is performed in the most clinically effective vector.

The fractional resection devices described herein are configured for treatment of cellulite. This aesthetic deformity has resisted effective treatment for several decades as the pathologic mechanism of action is multifactorial. Cellulite is a combination of age or weight loss skin laxity with growth and accentuation of the superficial fat loculations. The unsightly cobblestone appearance of the skin is commonly seen in the buttocks and lateral thighs. Effective treatment should address each contributing factor of the deformity.

The fractional resection devices described herein are configured for fractional resection of the skin in order to tighten the affected skin and to simultaneously reduce the prominent fat loculations that are contributing to the cobblestone surface morphology. Through the same fractionally resected defects created for skin tightening, topically applied vacuum is used to suction the superficial fat loculations percutaneously. In an embodiment, a clear manifold suction cannula is applied directly to the fractionally resected skin surface. The appropriate vacuum pressure used with the suction-assisted lipectomy (SAL) unit is determined by visually gauging that the appropriate amount of sub-dermal fat being suction resected. The appropriate time period of manifold application is also a monitored factor in the procedure. When combined with fractional skin tightening, only a relatively small amount of fat is suction resected to produce a smoother surface morphology. As with other applications described herein, the fractionally resected field will be closed with directed closure.

The fractional resection devices described herein are configured for revision of abdominal striae and scarring. Visually apparent scarring is a deformity that requires clear delineation of the scar from the adjacent normal skin. Delineation of the scar is produced by changes in texture, in pigment and in contour. To make a scar less visibly apparent, these three components of scarring must be addressed for a scar revision to significantly reduce the visual impact. Severe scars called contractures across a joint may also limit the range of motion. For the most part, scar revisions are performed surgically where the scar is elliptically excised and carefully closed by careful coaptation of excised margins of the non-scarred skin. However, any surgical revision reintroduces and replaces the pre-existing scar with an incumbent surgical scar that may be also be delineated or only partially de-delineated by a Z or W plasty.

Scarring is bifurcated diagnostically into hypertrophic and hypotrophic types. The hypertrophic scar typically has a raised contour, irregular texture and is more deeply pigmented. In contrast, the hypotrophic scar has a depressed contour below the level of the adjacent normal unscarred skin. In addition, the color is paler (depigmented) and the texture is smoother than the normal adjacent skin. Histologically, hypertrophic scars posses an abundance of disorganized dermal scar collagen with hyperactive melanocytes. Hypotrophic scars have a paucity of dermal collagen with little or no melanocytic activity.

The fractional resection devices described herein are configured for fractional scar revision of a scar that does not reintroduce additional surgical scarring but instead significantly de-delineates the visual impact of the deformity. Instead of a linear surgically induced scar, the fractional resection of the scar results in a net reduction of the pigmentary, textural and contour components. A fractional revision is performed along the linear dimension of the scar and also extends beyond the boundary of the scar into the normal skin. The fractional revision of a scar involves the direct fractional excision of scar tissue with micro-interlacing of the normal non-scarred skin with the residual scar. Essentially, a micro W-plasty is performed along the entire extent of the scar. As with other applications, the fractionally resected field is closed with directed closure. An example of the use of fractional revision includes revising a hypotrophic post-partum abdominal stria. The micro-interlacing of the depressed scar epithelium and dermis of the stria with the adjacent normal skin significantly reduces the depressed, linear and hypo-pigmented appearance of this deformity.

The fractional resection devices described herein are configured for vaginal repair for postpartum laxity and prolapse. The vaginal delivery of a full term fetus involves in part the massive stretching of the vaginal introitus and vaginal canal. During delivery, elongation of the longitudinal aspect of the vaginal canal occurs along with cross-sectional dilatation of the labia, vaginal introitus and vaginal vault. For many patients, the birth trauma results in a permanent stretching of the vaginal canal along the longitudinal and cross-sectional aspects. Vaginal repair for prolapse is typically performed as an anterior-posterior resection of vaginal mucosa with insertion of prosthetic mesh. For patients with severe prolapse, this procedure is required as addition support of the anterior and posterior vaginal wall is needed. However, many patients with post-partum vaginal laxity may be candidates for a less invasive procedure.

The fractional resection devices described herein are configured for fractional resection of the vaginal mucosa circumferentially to narrow the dilated vaginal canal at the labia and the introitus. The pattern for fractional resection can also be performed in a longitudinal dimension when the vaginal canal is elongated. Directed closure of the fractional field can be assisted with a vacuum tampon that will act as stent to shaped the fractionally resected vaginal canal into a pre-partum configuration.

The fractional resection devices described herein are configured for treatment of snoring and sleep apnea. There are few health implications of snoring but the disruptive auditory effect upon the relationship of sleeping partners can be severe. For the most part, snoring is due to the dysphonic vibration of intraoral and pharyngeal soft tissue structures within the oral, pharyngeal and nasal cavities during inspiration and expiration. More specifically, the vibration of the soft palate, nasal turbinates, lateral pharyngeal walls and base of the tongue are the key anatomic structures causing snoring. Many surgical procedures and medical devices have had limited success in ameliorating the condition. Surgical reductions of the soft palate are frequently complicated with a prolonged and painful recovery due to bacterial contamination of the incision site.

The fractional resection devices described herein are configured for fractional resection of the oropharyngeal mucosa in order to reduce the age related mucosal redundancy (and laxity) of intraoral and pharyngeal soft tissue structures and not be complicated with prolonged bacterial contamination of the fractional resection sites. The reduction in size and laxity of these structures reduces vibration caused by the passage of air. A perforated (to spray a topical local anesthetic onto the fractional resection field) intraoral dental retainer (that is secured to the teeth and wraps around the posterior aspect of the soft palate) is used to provide directed closure in the anterior-posterior dimension of the soft palate. A more severe condition called sleep apnea does have serious health implications due to the hypoxia caused by upper airway obstruction during sleep. Although CPAP has become a standard for the treatment of sleep apnea, selective fractional resection of the base of the tongue and the lateral pharyngeal walls can significantly reduce sleep related upper airway obstruction.

The fractional resection devices described herein are configured for fractional skin culturing/expansion, also referred to herein as "Culturespansion". The ability to grow skin organotypically would be a major accomplishment for patients with large skin defects such as burns and trauma and major congenital skin malformations such port-wine stains and large 'bathing trunk' nevi. Conventional capability is limited to providing prolonged viability of harvested skin, although some reports have indicated that wound healing has occurred with organotypic skin cultured specimens. It has been reported that enhanced cultured outcomes will occur with better substrates, cultured media and more effective filtration of metabolic byproducts. The use of gene expression proteinomics for growth hormone and wound healing stimulation is also promising. To date however, there is no report that skin has been grown organotypically.

The fractional harvesting of autologous donor skin for skin grafting under an embodiment provides an opportunity in the organotypic culture of skin that did not previously exist. The deposition of a fractionally harvested skin graft onto a collapsible docking station, as provided by the embodiments described herein, enables skin plugs to be brought into contact apposition with each other. The induction of a primary wound healing process can convert a fractional skin graft into a solid sheet by known or soon to be developed organotypic culture methodology. Further, the use of mechanical skin expansion can also greatly increase the surface area of the organotypically preserved/grown skin. Invitro substrate device iterations include without limitation, an expandable docking station comprising fractionally harvested skin plugs and a separate substrate (e.g., curved, flat, etc.) expander that is controllable to provide a gradual and continual expansion of the full thickness organotypically cultured skin. Additionally, the use of organotypic skin expansion may provide a continual and synergistic wound-healing stimulus for organotypic growth. A gradual and continual expansion is less likely to delaminate (the basement membrane) the epidermis from the dermis. Additionally, organotypic skin expansion helps avoid the surgical risk and pain associated in-vivo skin expansion.

The fractional resection devices described herein enable methods for the organotypic expansion of skin. The methods comprise an autologous fractional harvest of skin from a donor site of a patient. The use of a square scalpel array, for example, provides upon transfer side-to-side and tip-to-tip coaptation of fractionally harvested skin plugs. The method comprises transfer of the fractional skin plugs to a collapsible docking station that maintains orientation and provides apposition of skin plugs. The docked skin plugs are captured onto a porous adherent membrane that maintains orientation and apposition. The semi-elastic recoil property of the adherent membrane provides additional contact and apposition of skin plugs. The method includes transfer of the adherent membrane/fractional graft composite to a culture bay comprising a substrate and a culture media that retains viability and promotes organotypic wound healing and growth. Following healing of skin plug margins, the entire substrate is placed into a culture bath that has a mechanical expander substrate. Organotypic expansion is then initiated in a gradual and continuous fashion. The expanded full thickness skin is then autologously grafted to the patient's recipient site defect.

Organotypic skin expansion can be performed on non-fractional skin grafts or more generally, on any other tissue structure as organotypic expansion. The use of mechanical stimulation to evoke a wound healing response for organotypic culture can also be an effective adjunct.

The embodiments described herein are used with and/or as components of one or more of the devices and methods described in detail herein and in the Related Applications incorporated herein by reference. Additionally, the embodiments described herein can be used in devices and methods relating to fractional resection of skin and fat.

Embodiments include a novel minimally invasive surgical discipline with far-reaching advantages to conventional plastic surgery procedures. Fractional resection of skin is applied as new stand-alone procedures in anatomical areas that are off limits to conventional plastic surgery due to the poor tradeoff between the visibility of the incisional scar and amount of enhancement obtained. Fractional resection of skin is also applied as an adjunct to established plastic surgery procedures such as liposuction, and is employed to significantly reduce the length of incisions required for a particular application. The shortening of incisions has application in both the aesthetic and reconstructive realms of plastic surgery. Without limitation, both the procedural and apparatus development of fractional resection are described in detail herein.

Figure 83:
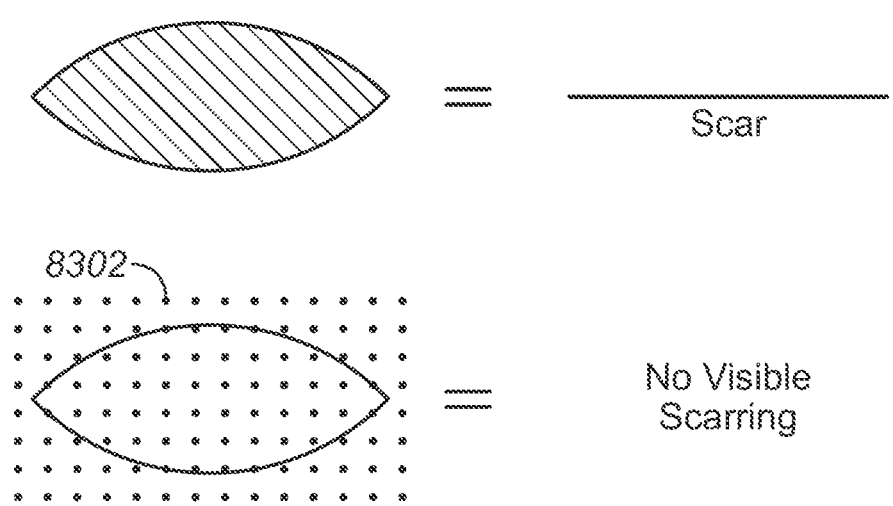
FIG. 83 depicts removal of lax excess skin without apparent scarring, under an embodiment.
Figure 84:
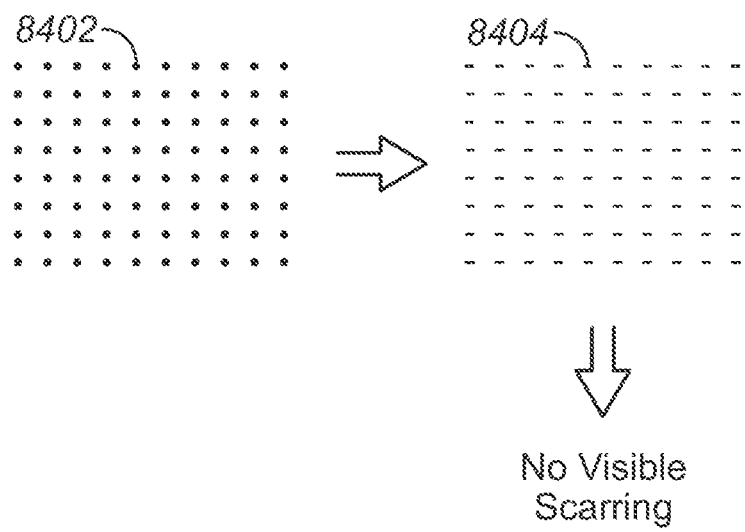
FIG. 84 depicts tightening of skin without apparent scarring, under an embodiment.
Figure 85:
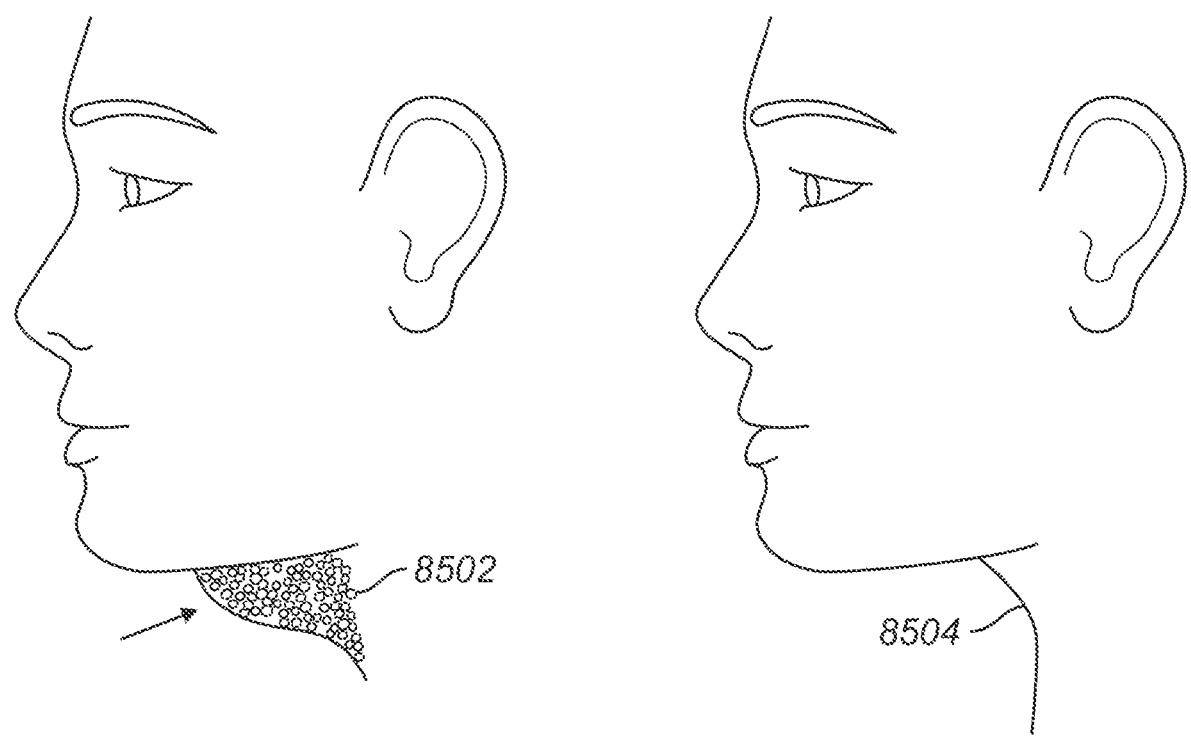
FIG. 85 depicts three-dimensional contouring of the skin envelop, under an embodiment.

Embodiments described herein are configured to remove multiple small sections of skin without scarring in lieu of the conventional linear resections of skin. The removal of multiple small sections of skin includes removal of lax excess skin without apparent scarring. As an example, FIG. 83 depicts removal of lax excess skin without apparent scarring, under an embodiment. The removal of multiple small sections of skin also includes tightening of skin without apparent scaring, for example, FIG. 84 depicts tightening of skin without apparent scaring, under an embodiment. The removal of multiple small sections of skin further includes fractional skin tightening in which the clinical endpoint results in three-dimensional contouring of the skin envelop. FIG. 85 depicts three-dimensional contouring of the skin envelop, under an embodiment.

The clinical effectiveness of any surgical manipulation requires a through understanding of the underlying processes that lead reliably to a clinical endpoint. For fractional skin tightening and contouring, a number of mechanisms of action are described herein. The principle mechanism of action identified is the conversion of two-dimensional fractional skin tightening into three-dimensional aesthetic contouring (e.g., see FIG. 3). Contributory to that principle clinical endpoint are secondary mechanisms of action that serve in concert with each other. The contributory mechanisms of action are described herein according to their capability to achieve the clinical endpoint, but are not so limited.

Figure 86:
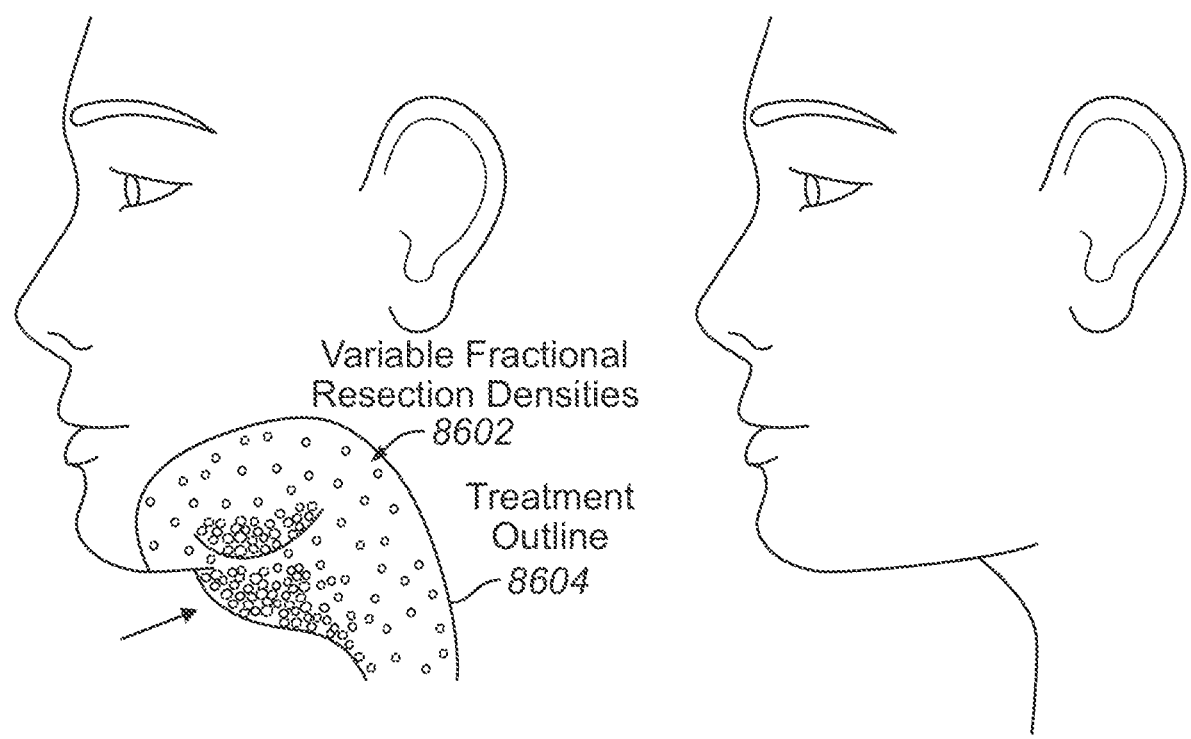
FIG. 86 depicts variable fractional resection densities in a treatment area, under an embodiment.

The density of fractional resection within an outlined fractional field is a primary determinate of two-dimensional skin tightening contributing to three-dimensional contouring. Generally, the density is the percentage of fractionally resected skin within the fractional field but is not so limited. FIG. 86 depicts variable fractional resection densities in a treatment area, under an embodiment. The density of fractional resection ("fractional density") can be varied to provide more selected skin tightening and contouring while providing smoother transitions into non-fractionally resected areas. Therefore, for example, transitions into non-fractionally resected areas include a reduction in the fractional density but are not so limited.

Figure 87:
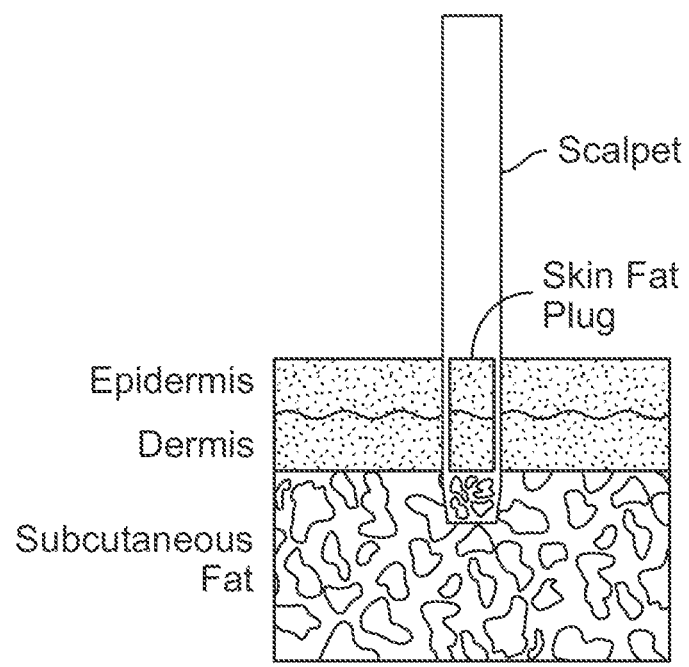
FIG. 87 depicts fractional resection of fat, under an embodiment.

Another mechanism of action associated with fractional skin resection is the fractional resection of fat. FIG. 87 depicts fractional resection of fat, under an embodiment. Immediately subjacent to the skin are the sub-dermal and subcutaneous fat layers where a variable amount of fat (based on depth and/or amount) can be fractionally resected in anatomical continuity with the resected skin plug. A variable amount of fat fractionally resected, and hence an amount of skin tightening and contouring, is controlled in an embodiment by controlling one or more of a depth of the resection at the target site and an amount of fat resected. Thus, the density of fractional resection ("fractional density") can be varied by controlling one or more of fractional density, resection depth, and amount of fact resected in order to provide more selected skin tightening and contouring while providing smoother transitions into non-fractionally resected areas. Therefore, for example, transitions into non-fractionally resected areas include a reduction in a combination of fractional density, resection depth, and amount of fact resected, but are not so limited.

Figure 88:
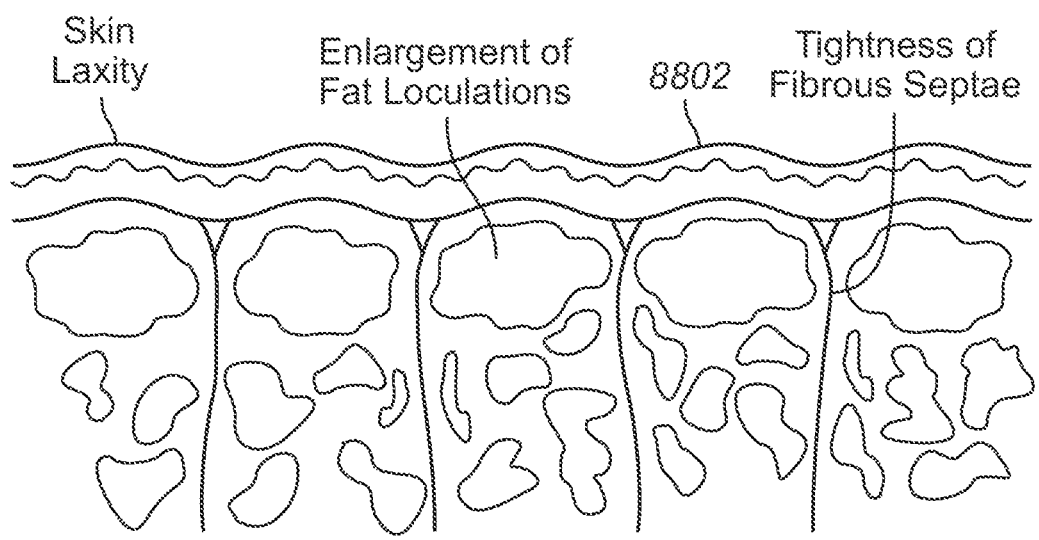
FIG. 88 depicts cobblestoning of the skin surface.

An additional modality for fractional fat resection is the percutaneous vacuum resection (PVR) of fat directly through the skin fractional defects. Numerous clinical applications of fractional fat resection are anticipated in the embodiments herein. The most significant aesthetic application of fractional fat resection is the reduction of cellulite. The combined in-continuity application of fractional skin and fat resection directly addresses the underlying pathology of this aesthetic deformity. The skin laxity and prominent loculations of fat producing visible surface cobblestoning of skin morphology are each resolved in concert with the application of this minimally invasive resection capability. FIG. 88 depicts cobblestoning of the skin surface.

Figure 89:
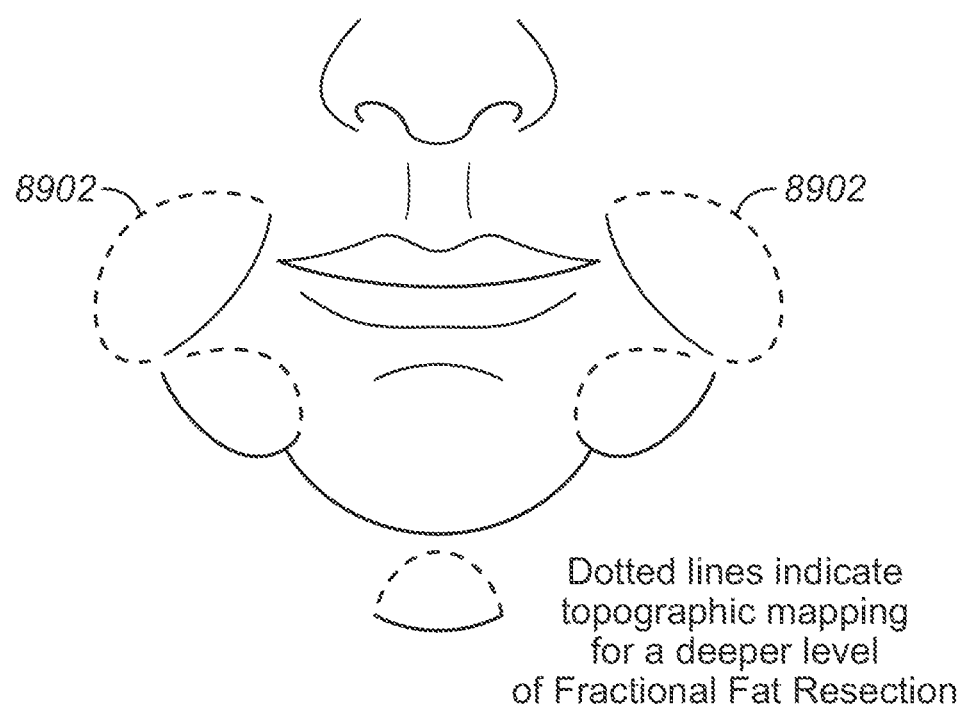
FIG. 89 depicts topographic mapping for a deeper level of fractional fat resection, under an embodiment.

Furthermore, another general application includes the ability to alter three-dimensional contour abnormalities with a combined in-continuity approach of fractional skin tightening and inward contouring from fractional fat resection. The pre-operative topographical contour mapping of the fractional field assists in providing a more predictable clinical outcome. Essentially, a topographical mapping of two-dimensional fractional skin resection is combined with a variable marking for fat resection. FIG. 89 depicts topographic mapping for a deeper level of fractional fat resection, under an embodiment. Mapping also includes the feathering or transition zones into non-resected areas where the fractional density is reduced. Depending upon the pre-operative topographical marking of the patient, a variable amount of fat is fractionally resected in continuity with fractional skin resection.

Areas to be corrected comprising convex contours undergo deeper fractional fat resections. Concave (or depressed) areas to be corrected are corrected using fractional skin resection. The net result within the mapped fractional field is overall smoothing of three-dimensional contours with two-dimensional tightening of the skin.

The use of combined fractional resection is most apparent with the reduction in the length required for conventional plastic surgery incisions and with the elimination of iatrogenic incisional skin redundancies ("Dog Ears"). Standard resection of skin lesions does not require the additional scarring of elliptical incisions but is significantly reduced in the linear dimension required for closure of an excised lesion (see FIG. 94).

Figure 90:
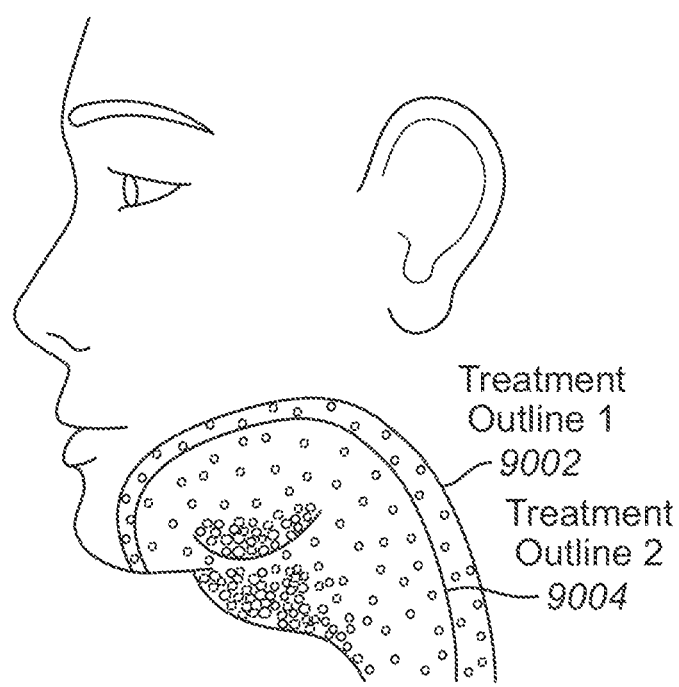
FIG. 90 depicts multiple treatment outlines, under an embodiment.

An additional mechanism of action associated with fractional skin resection is the size of the overall outlined pattern of the fractional resection field. The overall amount of fractionally resected skin also depends on the size of the fractionally resected field. The larger the field, the more skin tightening occurs with a specified density of fractional resection. FIG. 90 depicts multiple treatment outlines, under an embodiment.

Figure 91:
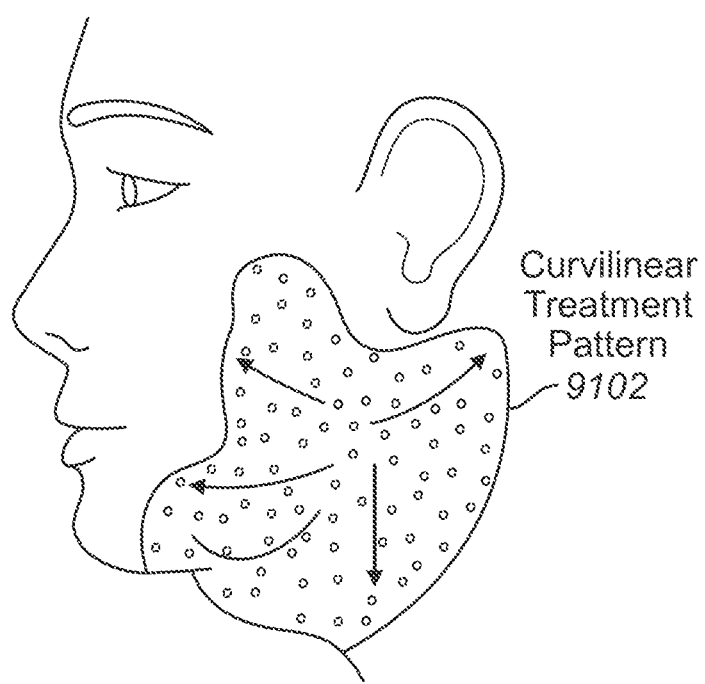
FIG. 91 depicts a curvilinear treatment pattern, under an embodiment.
Figure 92:
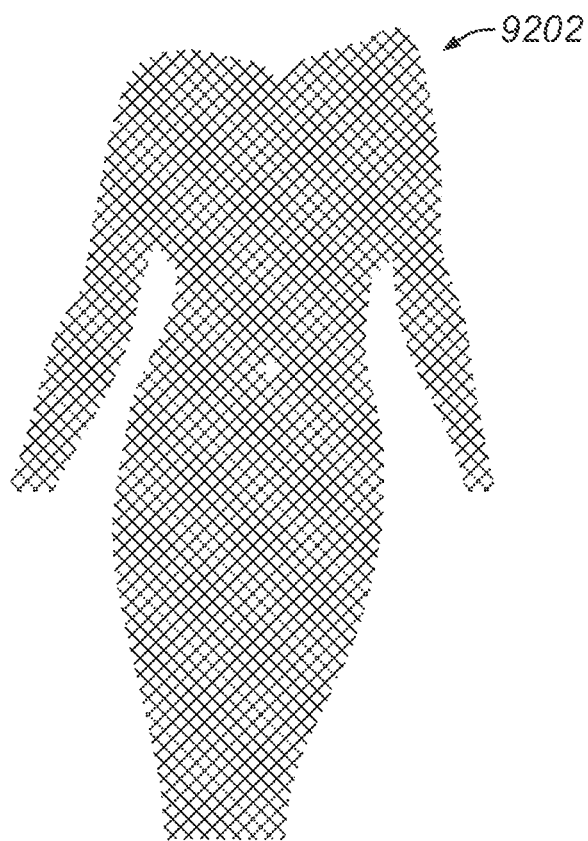
FIG. 92 depicts a digital image of a patient with rendered digital wire mesh program, under an embodiment.

The mechanism of action of a patterned outline includes the selective curvilinear patterning of each particular anatomical area for each particular patient. A topographical analysis with a digitally captured image of the patient involving a rendered (and re-rendered to an enhanced contour) digital wire mesh program assists in formatting the size and curvilinear outline for a selected anatomical region and patient. The pattern of standard aesthetic plastic surgery excisions for a particular anatomic region also assists in the formatting of the fractional resection pattern. FIG. 91 depicts a curvilinear treatment pattern, under an embodiment. FIG. 92 depicts a digital image of a patient with rendered digital wire mesh program, under an embodiment.

Figure 93:
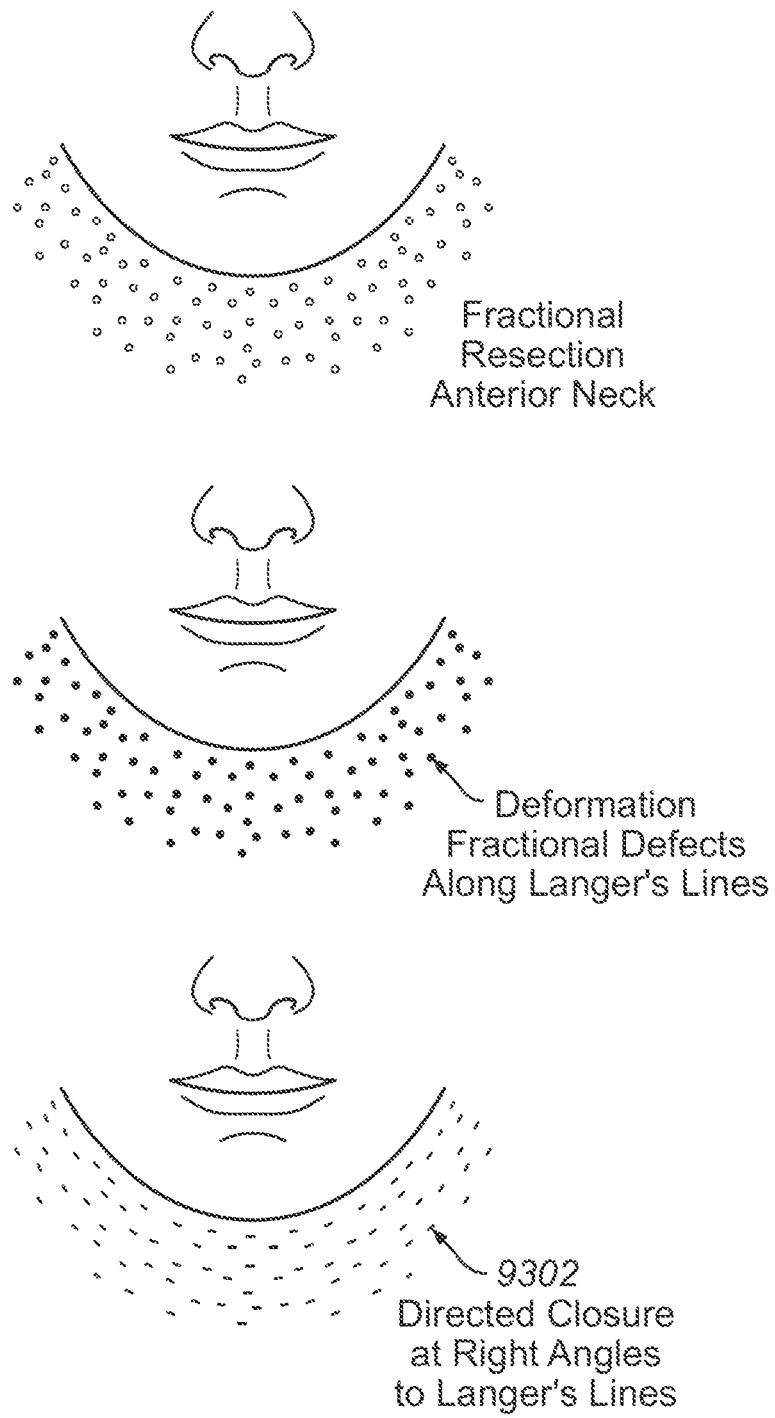
FIG. 93 depicts directed closure of a fractionally resected field, under an embodiment.

Directed closure of a fractionally resected field of an embodiment provides the capability of selectively tightening skin to achieve enhanced aesthetic contouring. For most applications, the closure occurs at right angles to Langer's lines but may also be done at a different direction that achieves maximal aesthetic contour such as closures that are based on resting skin tension lines. FIG. 93 depicts directed closure of a fractionally resected field, under an embodiment. The directed closure may also follow known vectors of closure used in conventional plastic surgery procedures (e.g., facelift for the facial/submental component of the facelift is upwards (corresponding to a horizontal directed closure of a fractional field) and the neck component below the cervical mandibular angle is more obliquely posterior (corresponding to a more vertical directed closure of the fractional field)). Multiple vectors of directed closure may also be used in more complicated topographical regions such as the face and neck.

Figure 94:
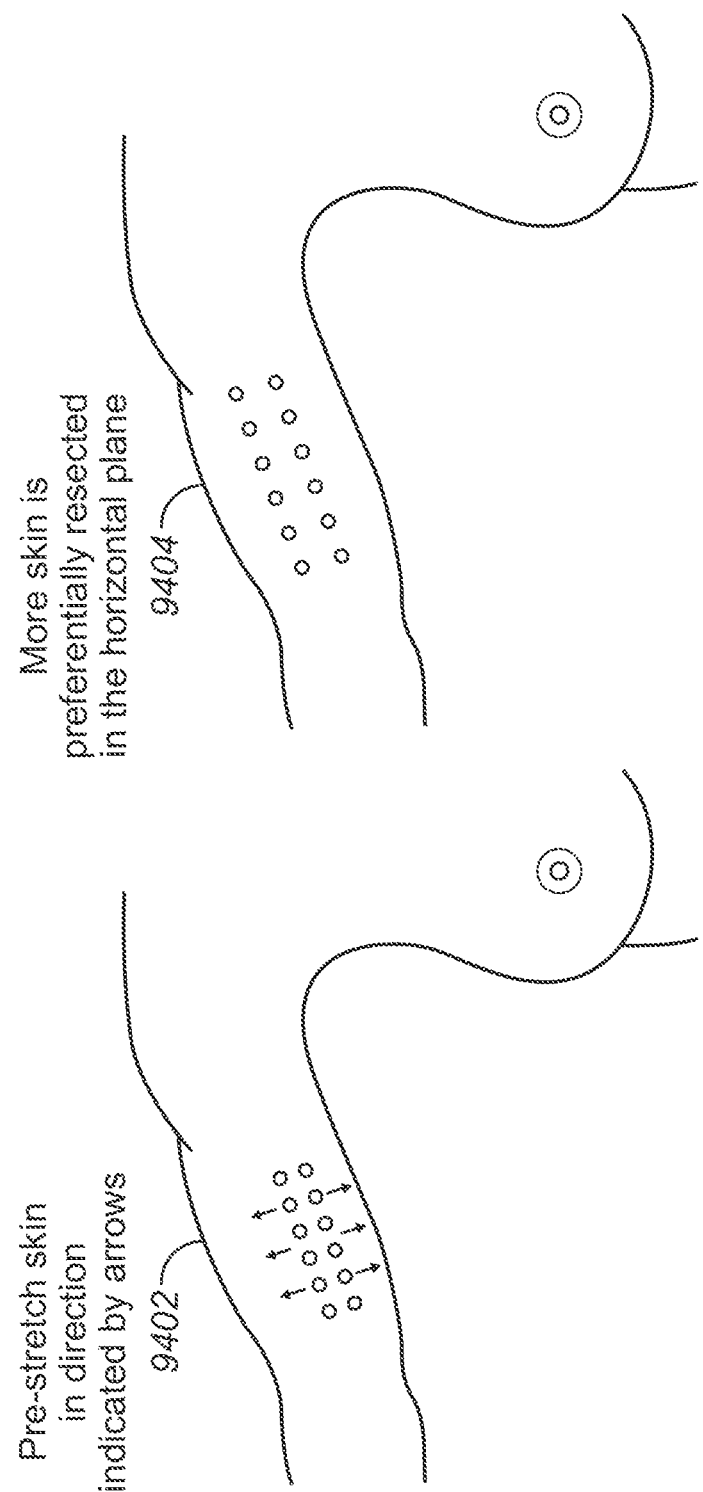
FIG. 94 depicts directed fractional resection of skin, under an embodiment.

Embodiments include directed fractional resection of skin, which enhances the effectiveness of the procedure. This process is performed by pre-stretching the skin at right angles to the preferred direction of maximal skin resection. FIG. 94 depicts directed fractional resection of skin, under an embodiment.

Embodiments include aesthetic contouring resulting from the mechanical pull (or vector) created from an adjacent fractional field adjacent to the targeted contour. This effect for a fractional field is based on plastic surgical procedures that are directed a distance from the targeted contour. Further, variable topographical transitioning of resection densities within the field and along the pattern outline are realized, which provide selective contouring and smoother transitioning into non-resected areas. Additionally, variable topographical transitioning of scalpet size resections within a patterned outline (and with different scalpet sizes within an array) provides selective two-dimensional skin tightening and three-dimensional contouring.

Embodiments described herein evoke a selective wound healing sequence with promotion of primary healing during the immediate post-operative period and delayed secondary contraction of skin during the collagen proliferative phase. Promotion of accurate coaptation of the skin margins is inherent to the multiple (fractional) resections of small segments of skin i.e., skin margins are more closely aligned prior to closure than larger linear resections of skin that are common with standard plastic surgery incisions. Subsequent evoking of wound contraction is also inherent to a fractionally resected field where elongation of the pattern of fractional resection provides a directed wound healing response along the longitudinal dimension of the fractionally resected pattern.

Clinical methods of fractional skin resection involve methods of directional closure. Depending upon the anatomical area, the directed closure of excisional skin defects within a fractional resection field is achieved by following Langer's lines, the resting skin lines, and/or in a direction that achieves the maximal of aesthetic contouring. The direction in which closure is most easily achieved can also be used as a guide for the most effective vector of directed closure. For many applications, the use of Langer's lines is used as a guide to provide maximal aesthetic tightening. Following the original work of Dr. Langer, the fractionally resected defects will elongate in the direction of a Langer line. The directed closure is performed at right angles to Langer's lines in an anatomical region where the skin margins of each fractional resection defect are in closest approximation.

Figure 95:
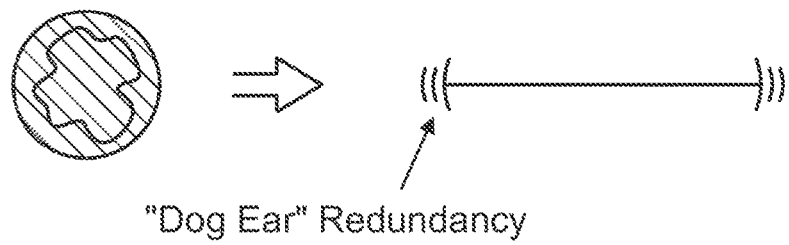
FIG. 95 depicts shortening of incisions through continuity fractional procedures, under an embodiment.
Figure 95:
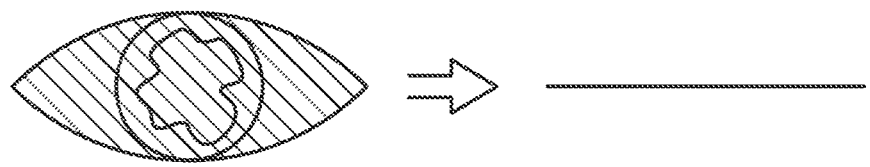
Figure 95:
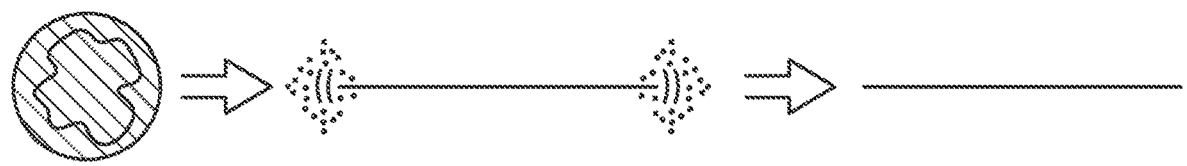

In continuity fractional procedures that are deployed adjacent or in continuity with plastic surgery incisions, the most significant capability provided by the embodiments herein includes the ability to shorten incisions. The need for elliptical excisions of skin tumors is reduced in both the application of this technique and in the length of the incision. Thus, the need to excise the lateral extension of a tumor resection is obviated by the fractional resection at that same lateral aspect. FIG. 95 depicts shortening of incisions through continuity fractional procedures, under an embodiment.

Figure 96:
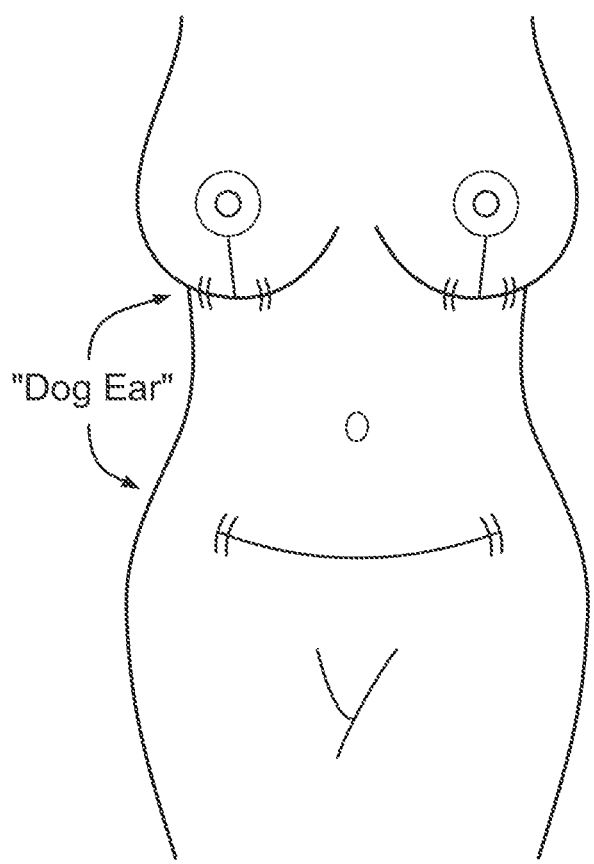

As the fractional field under an embodiment heals without visible scarring, the net result is significant reduction in the length of the excisional scar. Another application within this category is the shortening of conventional plastic surgery incisions used for breast reduction, Mastopexy and abdominoplasty. The lateral extent of these incisions can be shortened without the creation of "dog ear" skin redundancies that would otherwise occur with the same length incision. FIG. 96 is an example depiction of "dog ear" skin redundancies in breast reduction and abdominoplasty. For example, extensions of the incision beyond the lateral inframmary fold for breast reduction or beyond the Iliac crest for abdominoplasty would no longer be required. Fractional revisions of post-operative "dog ear" skin redundancies could also be performed without extension of the existing incision.

Embodiments include combined procedures that provide aesthetic enhancement at both the fractional resection harvest site and a recipient site. The most apparent application of this method is the use of fractional harvesting of the cervical beard for hair transplantation in the frontal and parietal scalp. A dual benefit is created by the procedure in which aesthetic contouring is created along the anterior neck and with restoration of the hair bearing scalp.

Embodiments include separate fractional procedures in anatomical areas that are not currently addressed by plastic surgery due to the poor tradeoff between the visibility of the surgical incision and the amount of aesthetic enhancement. Several examples exist in this category such as the suprapatellar knee, the upper arm, the elbow, bra skin redundancy of the back, and the medial and lateral thighs and the infragluteal folds.

Embodiments include adjunct fractional procedures that are deployed with conventional plastic surgery incisions in a non-contiguous fashion. This category includes suction-assisted lipectomy in which subcutaneous fat is removed by suction in areas of lipodystrophy such as the lateral hips and thighs. However, many patients have pre-existing skin laxity that is aggravated by suction lipectomy. The tightening of the skin envelope over these areas by fractional resection has several benefits to these patients. Many patients with skin laxity and lipodystrophy become candidates for liposuction who otherwise not qualify for the procedure. For patients without preexisting skin laxity but with more significant lipodystrophy, a larger contour reduction can be performed without iatrogenic skin laxity. The procedure can be deployed as a single combined procedure for smaller fractional resections or as a staged procedure.

Directed closure of the fractional field is performed without suturing and is achieved with the application of an adhesive stent membrane as described in detail herein. The fractional field is closed with an adhesive membrane using a number of methods. An example method includes anchoring the membrane outside the perimeter of the fractional field. Tension is then applied to the opposite end of the adhesive membrane. The body of the adhesive membrane is then applied to the fractional field row by row to the remaining skin within the field. The direction of application follows the selected vector of directed closure. This direction of application at times is at right angles to Langer's lines but is not so limited, and any direction of application can be chosen that provides maximal aesthetic contouring.

Another method includes use of the elastic property of the adherent stent dressing to selectively close a fractional field. With this method, the ends of the elastic stent dressing are stretched or preloaded, and the stent dressing is then applied to the fractional field. Upon release of the ends of the membrane, the elastic recoil of the stent dressing closes the fractional defects in a direction that is at right angles to the elastic recoil.

Embodiments described in detail herein include a skin Pixel Array Dermatome, also referred to herein as a "sPAD". The sPAD is a ganged multiple-scalpet array comprising a multiplicity of individual circular scalpels. The circular configuration enables rotational torque to be applied to the skin to facilitate incising. A coupling or linkage of the scalpets to an electromechanical power source is provided by series of gears between each scalpet and a drive shaft, as described herein. In addition, a vacuum is created within a housing and configured for stenting stabilization during incising. The same vacuum capability can also be applied as a pneumatic assist to apply additional axial (Z-axis) force during the incising duty cycle. Another vacuum application is the evacuation of incised skin plugs in the fractional field.

Figure 97:
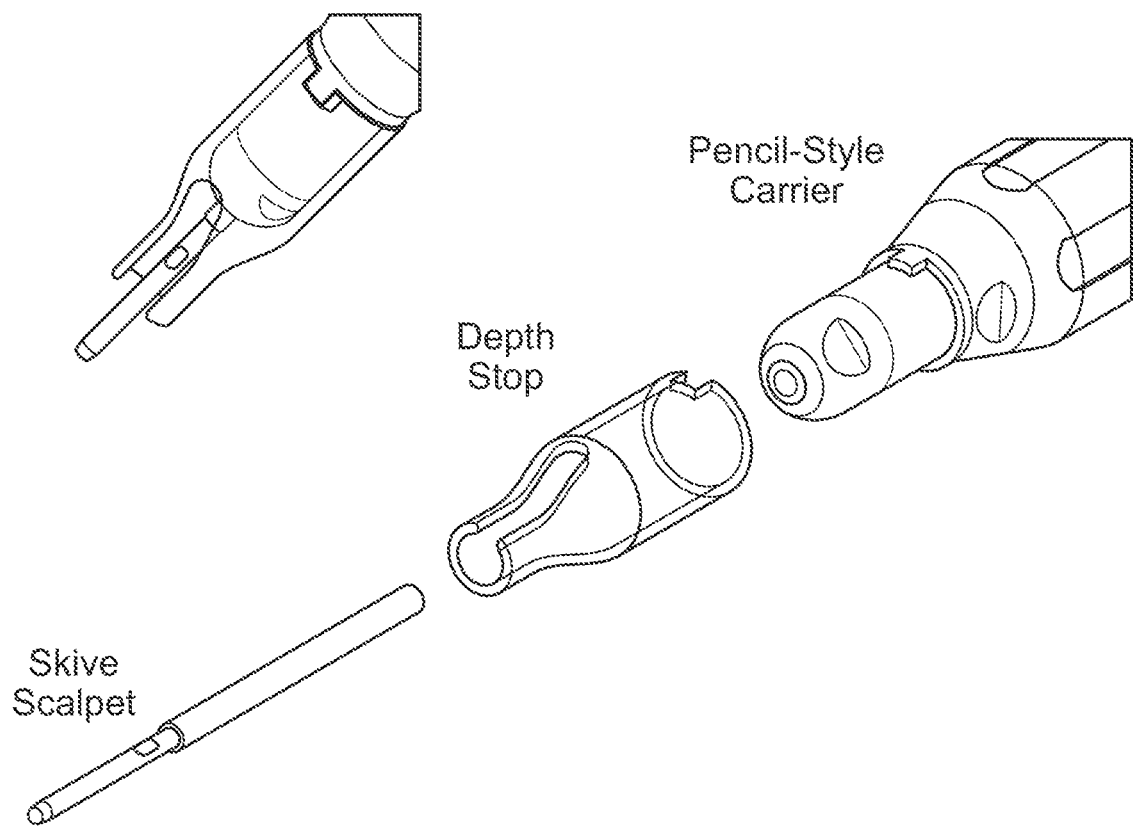
Figure 98:
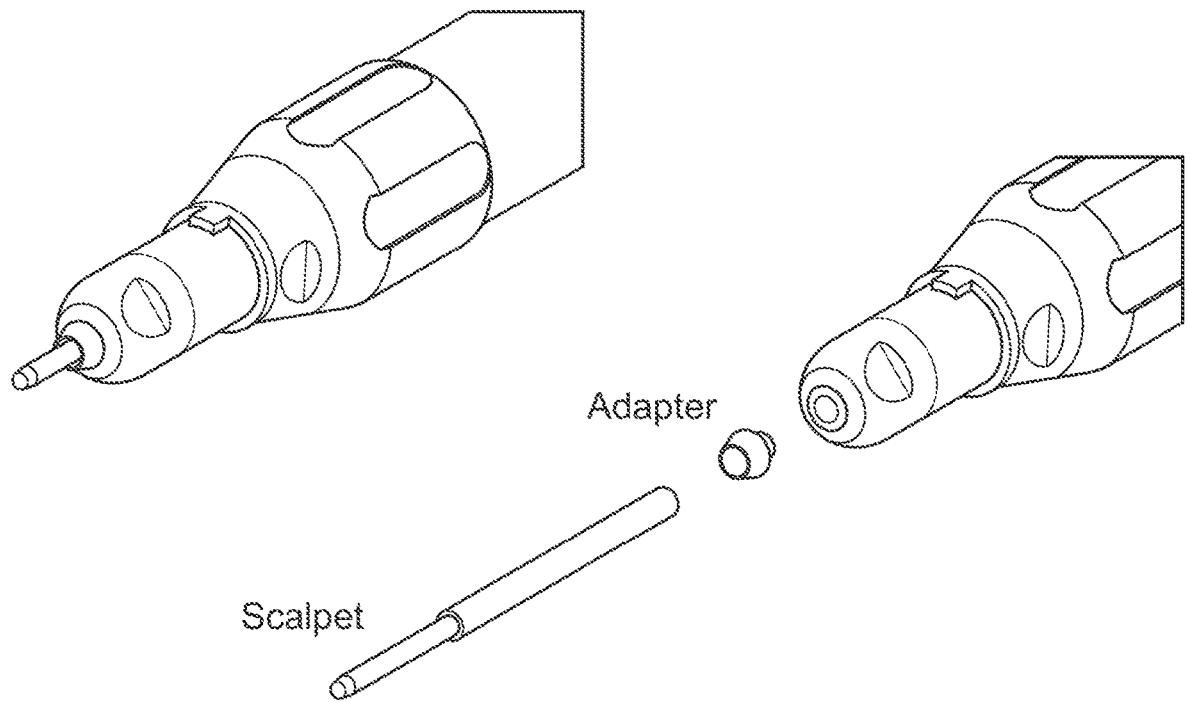
Figure 99:
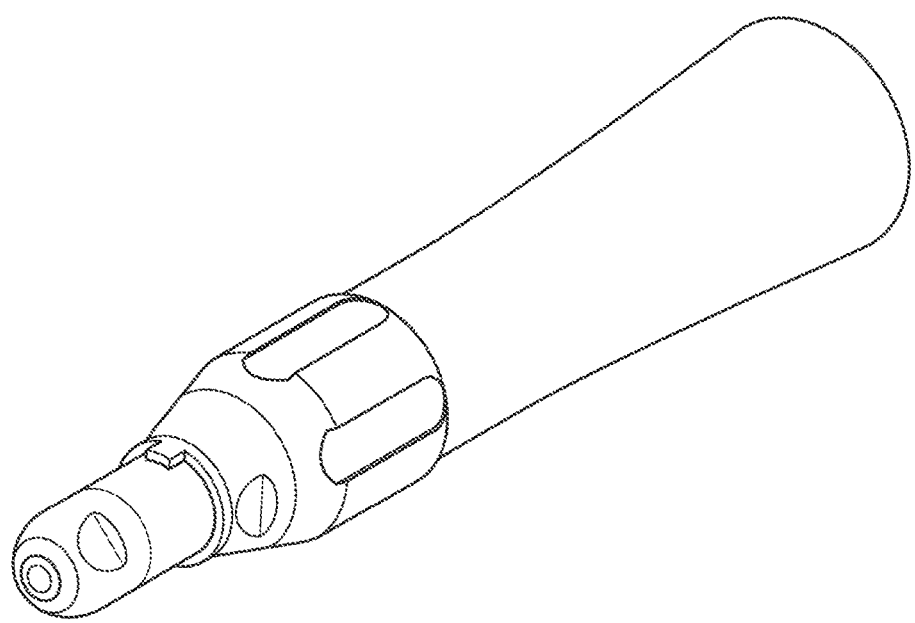
Figure 100:
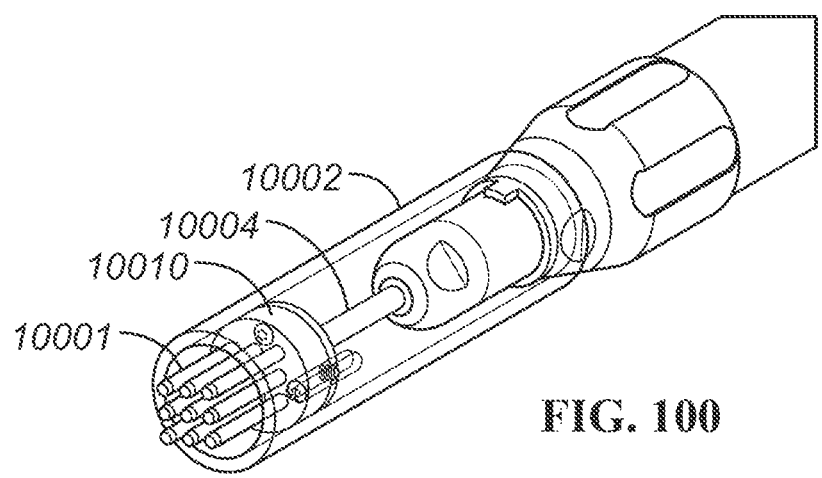

The sPAD includes numerous configurations as described in detail herein. FIG. 97 is a sPAD including a skived single scalpet with depth control, under an embodiment. FIG. 98 is a sPAD including a standard single scalpet, under an embodiment. FIG. 99 is a sPAD including a pencil-style gear reducing handpiece, under an embodiment. FIG. 100 is a sPAD including a 3×3 centerless array, under an embodiment.

Figure 101:
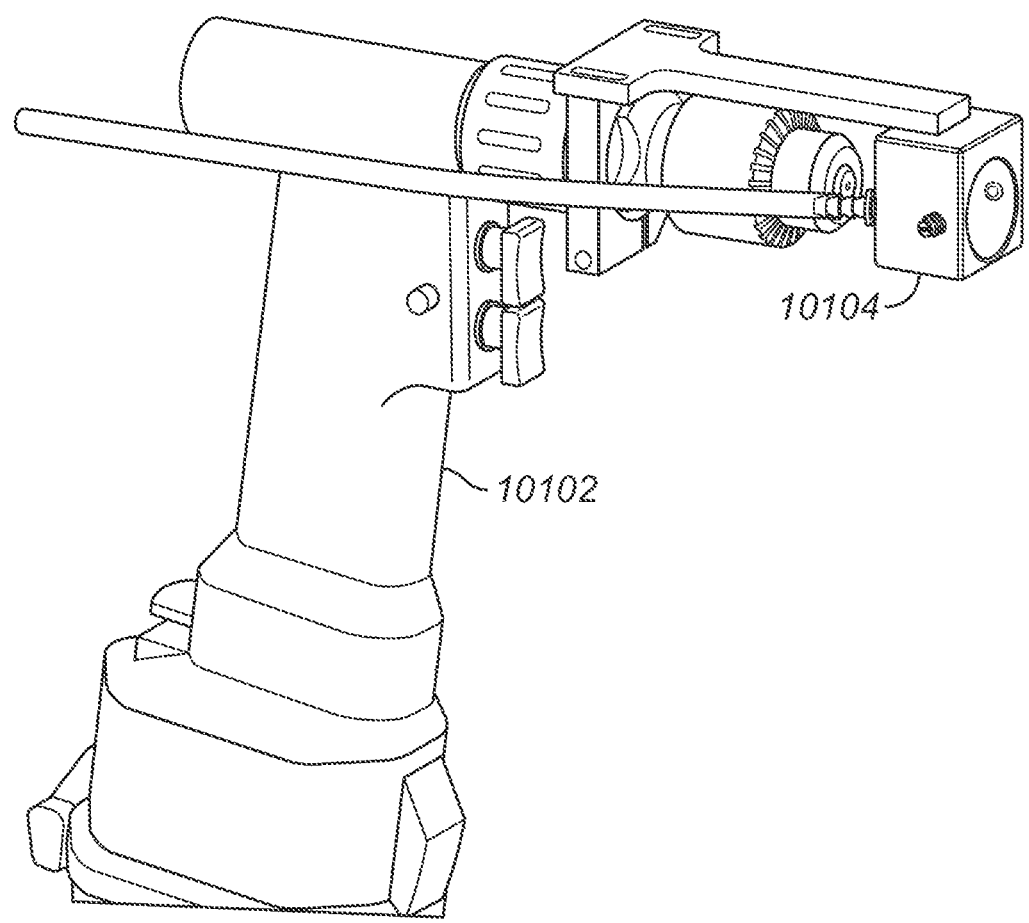
Figure 102:
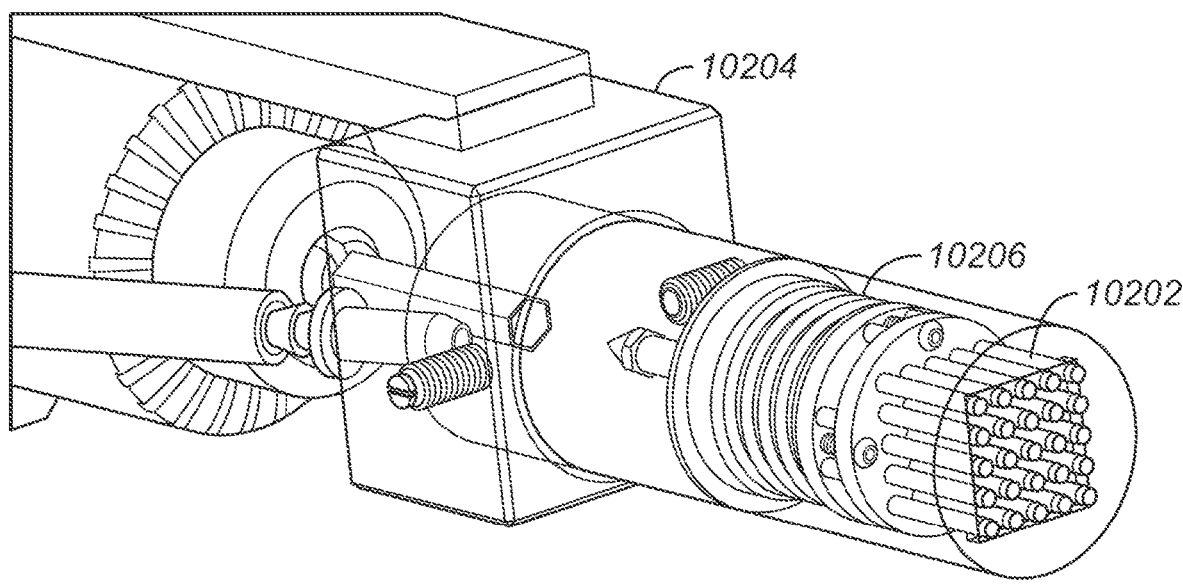

An instrument comprising a surgical drill is provided for use with the sPAD. FIG. 101 is a sPAD including a cordless surgical drill for large arrays, under an embodiment. FIG. 102 is a sPAD comprising a drill mounted 5×5 centerless array, under an embodiment.

Figure 103:
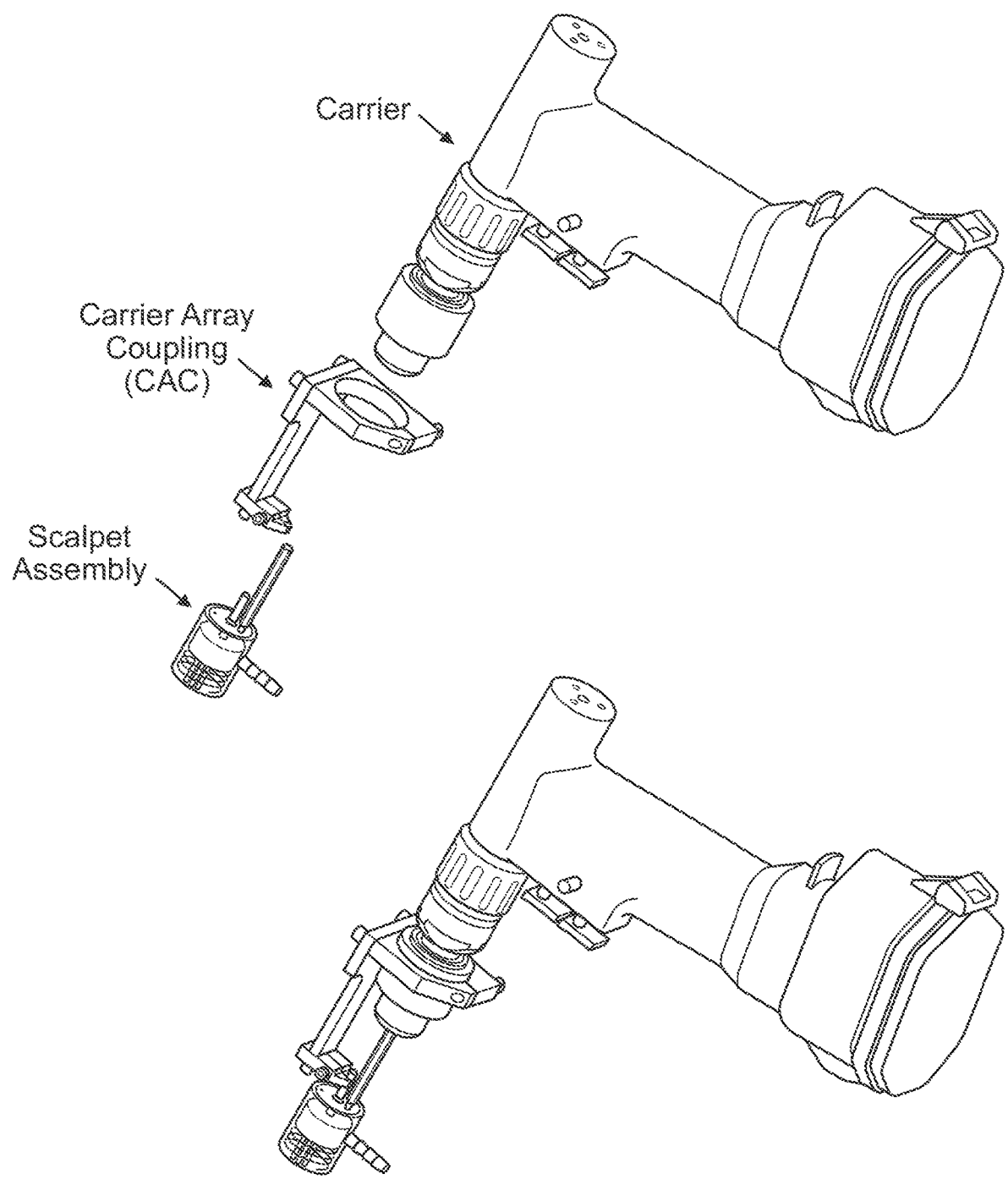
Figure 104:
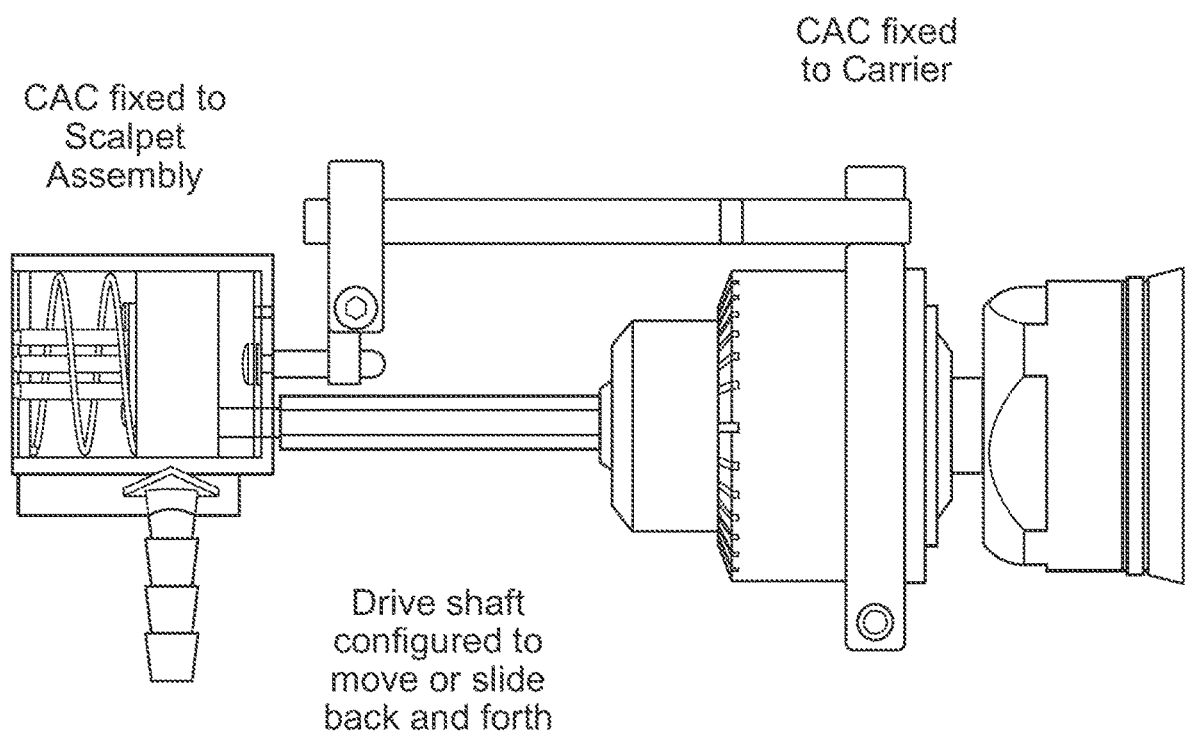

Embodiments include a Vacuum Assisted Pneumatic Resection (VAPR) Array sPAD, also referred to herein as a "VAPR sPAD". FIG. 103 is a sPAD including a vacuum assisted pneumatic resection sPAD, under an embodiment. The VAPR sPAD uses vacuum pressure configured to drive the scalpets from the sPAD into the treatment site. The VAPR sPAD is coupled or connected to a drill via a Drill Array Coupling (DAC). FIG. 104 is a VAPR sPAD coupled to a drill via a DAC, under an embodiment. The DAC fixes the housing of the VAPR sPAD to the drill, while the hexagonal tubing allows the VAPR sPAD drive shaft to slide up and down during the treatment. An externally supplied vacuum (not shown) is coupled or connected to the VAPR sPAD via the vacuum port.

Figure 105:
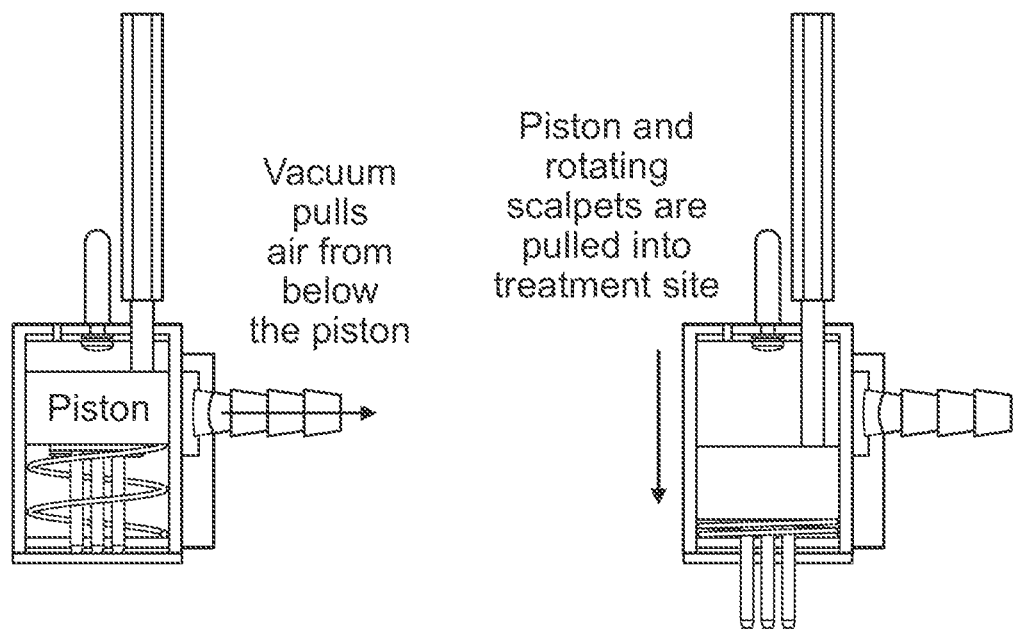

FIG. 105 depicts the VAPR sPAD in a ready state (left), and an extended treatment state (right), under an embodiment. With the vacuum and drill operating, a single treatment cycle comprises placing the VAPR sPAD against the treatment site, creating a seal between the housing and the treatment site. Once this seal is established, the vacuum pulls the piston with the rotating gears into the treatment site. After the desired depth of cutting has been achieved the SPAD is pulled away from the treatment site. This breaks the seal, and the spring inside the sPAD forces it back into its ready state. The cycle can now be repeated at a new treatment site.

Figure 106:
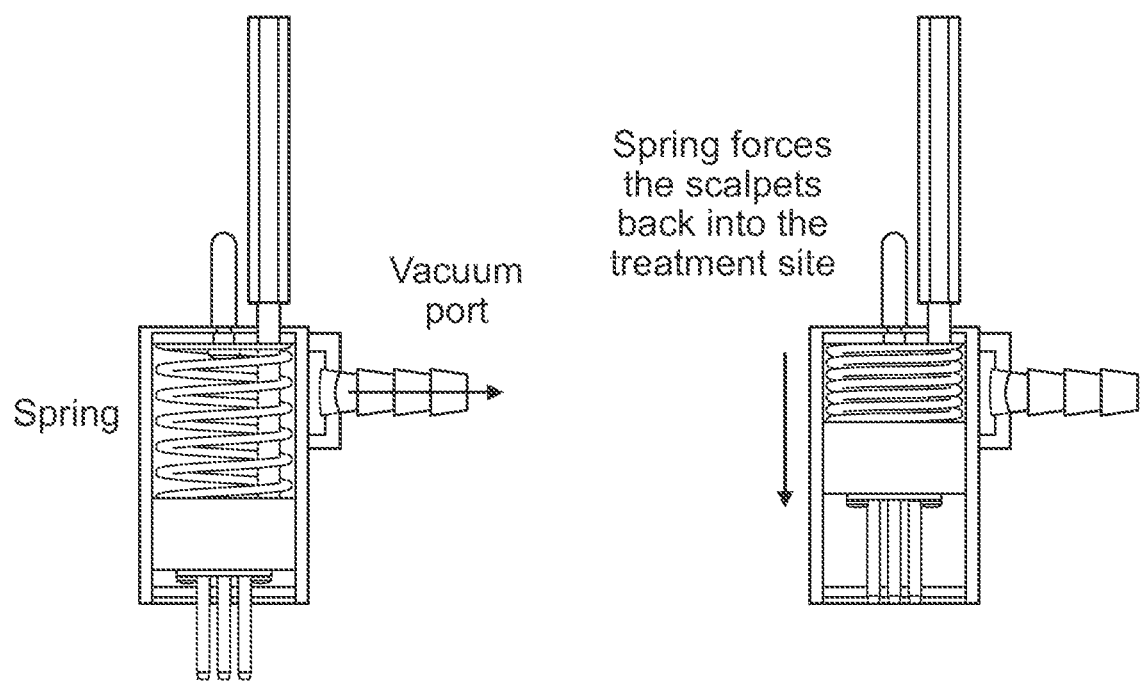

Embodiments include a Spring Assisted Vacuum Resection (SAVR) sPAD, which operates in a similar manner to the VAPR sPAD. FIG. 106 depicts the SAVR sPAD in a ready state (left), and a retracted state (right), under an embodiment. The SAVR sPAD is coupled or connected to the drill via the DAC. The vacuum port is attached to a separate vacuum supply. The drive shaft slides back and forth within the tube attached to the drill.

In the SAVR sPAD, the spring and vacuum locations have generally been reversed from the VAPR sPAD. The spring and vacuum port are both located on the proximal side of the piston but are not so limited. The vacuum assists in drawing the skin pixels out through the scalpets and hence away from the treatment site. The spring provides the axial force for the rotating scalpets to drive into the treatment site and resect the skin. The scalpets are extended outside the housing in array ready state.

The treatment cycle starts with the placement of the scalpets over the desired treatment location. The vacuum is turned on and the drill is applied downward, forcing the piston and scalpets back up into the housing (retracted state). The drill is turned, causing the scalpets to rotate. The spring force coupled with the scalpet rotation results in the resection. The vacuum draws the pixels generated by the resection up into and subsequently out of the housing. Once the desired cutting depth has been achieved, the SAVR sPAD is lifted off the treatment site and the cycle can be repeated.

Embodiments are described herein comprising instrumentation and procedures for aesthetic surgical skin tightening including, but not limited to, instruments or devices, and procedures that enable the repeated harvesting of skin grafts from the same donor site while eliminating donor site deformity. Embodiments herein include devices configured for fractional resection and corresponding methods or procedures, including single-scalpet and multi-scalpet array platforms using a vacuum manifold. Additional disclosure of corresponding devices configured for fractional resection and corresponding methods or procedures is found in the Related Applications, each of which is herein incorporated by reference in its entirety. Regarding the use of vacuum in a fractionally resected field, the vacuum manifold is configured to apply vacuum intraluminally within the scalpet (or within a multi-scalpet array). Alternatively, the vacuum manifold is configured to apply vacuum extraluminally as either a component of the scalpet assembly or as a separate manifold device that is directly applied to the skin of the fractional field.

Applications of the vacuum capacity of the scalpet assembly include the suction evacuation of fractionally incised skin plugs (e.g., FIGS. 108, 112, and 113). Furthermore, applications of the vacuum capacity of the scalpet assembly include the vacuum stabilization of the skin surface during fractional resection (e.g., FIGS. 109 and 114). Additional applications of the vacuum capacity of the scalpet assembly include fractional vacuum-assisted lipectomy of the subcutaneous and subdermal fat layer (e.g., FIG. 114).

FIG. 107A is a cross-sectional side view of a carrier 1071 including a vacuum manifold 1072, under an embodiment. FIG. 107B is an isometric cross-sectional side view of the carrier 1071 including the vacuum manifold 1072, under an embodiment. FIG. 107C is a side view of the carrier 1071 including the vacuum manifold 1072, under an embodiment. The vacuum manifold 1072 is configured to be coupled or attached to a distal region of the carrier 1071 and scalpet assembly/scalpet array 1073. The vacuum manifold 1072 of an embodiment comprises a "slip-on" or overlay encasement configured to be removeably coupled to the distal end of the carrier 1071. This embodiment includes a scalpet array 1073 with a single scalpet, but is not so limited.

The vacuum manifold 107-2 includes a vacuum port 1074 configured to couple to a vacuum source (not shown). The vacuum manifold 1072 of an embodiment also includes an aspirator (not shown) but is not so limited. The vacuum manifold 1072 is configured, for example, to couple to an aperture (e.g., distal, proximal, side, etc.) and/or lumen of the scalpet(s) 1073 to intraluminally direct vacuum force to the target site. Alternatively, the vacuum manifold 1072 is configured to direct the vacuum force to the target site extraluminally (not shown).

Vacuum delivery of the device of an embodiment is controlled by an aperture component configured for manipulation by a device operator. FIG. 108 is a solid side view of the carrier 107-1 with the vacuum manifold 1072 configured for manual control via an aperture 1075, under an embodiment. Alternatively, the vacuum component is controlled electronically. For example, the cycling on/off of the vacuum source is at least in part computer controlled (e.g., computer controlled duty cycle, etc.). The electronic controller can also be used to cycle a change in the rotary (RPM) component of the scalpet assembly. Scalpet length may also be one or more of manually and computer controlled.

The vacuum manifold 1072 of an embodiment is extended distally onto the scalpet to serve as a depth guide, such that a distal end of the vacuum manifold 1072 is configured to control a depth of penetration of the scalpet array 1073 into the tissue. Various depth guide-dependent vacuum manifolds address different clinical applications and variable dermal depths at different anatomical sites. In an embodiment, a plastic manifold is created as a single procedure disposable that has a separate vacuum port incorporated into the manifold, but embodiments are not so limited.

In an alternative embodiment, the vacuum capability is an "in-line" or "in-series" configuration of the carrier or handpiece through which the vacuum is applied internally and can extend down the length of the lumen and scalpet proximally or is diverted through a separate side aperture of the scalpet. FIG. 109A is an isometric view of a handpiece configured to include or incorporate vacuum, under an embodiment. FIG. 109B is an isometric cutaway view of the handpiece configured to include or incorporate vacuum, under an embodiment.

FIG. 110A is a cross-sectional side view of a vacuum manifold 1101 configured to be coupled or connected to an in-line vacuum component 1102, under an embodiment. FIG. 110B is an isometric cross-sectional view of a vacuum manifold configured to be coupled or attached to an in-line vacuum component, under an embodiment. FIG. 110C is a solid side view of a vacuum manifold configured to be coupled or attached to an in-line vacuum component, under an embodiment. This embodiment includes the vacuum manifol FIG. 111A is a cross-sectional side view of a scalpet array used with a vacuum aspirator, under an alternative embodiment. The device of this embodiment includes a scalpet assembly 1111 including a scalpet array 1112 with multiple scalpets, but is not so limited. FIG. 111B is an isometric cross-sectional view of a scalpet array used with a vacuum aspirator, under an embodiment. FIG. 111C is a side view of a scalpet array used with a vacuum aspirator, under an embodiment. The vacuum aspirator is coupled or connected to the scalpet assembly and is configured as one or more of a specifically adapted aspirator for fractional resection, and a device such as a conventional surgical aspirator or an aspirator used specifically for suction assisted lipectomy (SAL). In an embodiment, the intraluminal vacuum scalpet or scalpet array has a rotary component to enhance both a skin incisional and fat suction curettage capability, but is not so limited.

FIG. 112 is a cross-sectional side view of a single-scalpet device applied to a target tissue site, under an embodiment. This example operational embodiment shows tissue extracted with vacuum force from a fractional resection site via the lumen and side aperture of the scalpet. FIG. 113 is an isometric cross-sectional view of a single-scalpet device applied to a target tissue site, under an embodiment.

FIG. 114A is a cross-sectional side view of a multi-scalpet device applied to a target tissue site, under an embodiment. FIG. 114B is an isometric cross-sectional view of a multi-scalpet device applied to a target tissue site, under an embodiment. This example embodiment shows use of vacuum aspiration to remove fractionally resected tissue from the target site.

The scalpet devices of various embodiments include one or more scalpets. The scalpet types of an embodiment include one or more of a slotted scalpet and a slotted blunt micro-tip cannula. The scalpets or scalpet devices of an embodiment include one or more apertures or orifices positioned axially in the scalpet adjacent the scalpet interior lumen, but are not so limited. FIG. 115 is an example scalpet 1150 including apertures or slots 1151, under an embodiment. FIG. 116 is an example blunt micro-tip scalpet or cannula 1160 including apertures or slots 1161, under an embodiment.

The ability to fractionally suction subdermal/subcutaneous fat under embodiments herein has several applications depending upon the target anatomical region. These applications include without limitation, the flattening of a convex three-dimensional contour and the inward contouring of an anatomical region to restore an aesthetic feature such as the submentum and the cervical-mandibular angle, for example. For these applications, a side-slotted aperture scalpet and a blunt tip side-slotted aperture fractional cannula are described herein. The blunt tip cannula is configured for use in anatomical regions where key vascular or nerve structures are immediately subjacent to the fractional lipectomy field. Regardless of the type of scalpet/cannula, the combining of the rotary function of the system with a vacuum capability provides a means to more effectively suction curette the subdermal/subcutaneous fat layer.

Embodiments include, without limitation, fractional marking systems configured as guides to assure an adequate fractional resection density. The guides include, for example, a stencil and/or Adherent Semitransparent Perforated Plastic Membrane Guide (ASPPMP) configured for use as a guide for fractional resection. The stencil marking system includes a stencil (e.g., ink, etc.) comprising a grid pattern of either circles or dots that is temporarily applied preoperatively to a target site. The circles or dots include at least one of a positive and a negative stencil of the grid pattern, and the ink material is biocompatible and configured to not smear or degrade during prepping of the patient or during the conduct of the procedure. FIG. 117 is an example negative stencil marking system, under an embodiment. FIG. 118 is an example positive stencil marking system, under an embodiment.

The ASPPMP marking system includes an adherent semitransparent perforated plastic membrane. FIG. 119A shows a side view of the ASPPMP in use as a depth guide with the single-scalpet device, under an embodiment. FIG. 119B shows a top isometric view of the ASPPMP in use as a depth guide with the single-scalpet device, under an embodiment. The perforated plastic membrane is also configured to serve as a depth guide that assures that the prescribed depth of fractional resection is not exceeded.

Clinical applications of the single-scalpet and multi-scalpet array platform include aesthetic contouring, which is most effectively produced by a combination of skin tightening and inward contouring of an embodiment, but is not so limited. The ability to fractionally resect skin and fat during a procedure has produced a significant capability over previous electromagnetic devices and aesthetic plastic surgery procedures because the fractional resection includes the direct removal of skin (in an area of skin laxity) without visible scarring. The enhanced capability of an embodiment to fractionally resect skin is combined with fractional subdermal/subcutaneous lipectomy to restore more youthful aesthetic contours.

FIG. 120 shows fractional resection of skin and fractional subdermal/subcutaneous lipectomy, under an embodiment. An example of fractional resection of skin and fractional subdermal/subcutaneous lipectomy, without limitation, is the treatment of the submentum (under the chin). FIG. 121 shows a side view of the submentum as a target area for fractional resection of skin and fractional subdermal/subcutaneous lipectomy, under an embodiment. FIG. 122 shows an inferior view (looking upward) of the fractional resection field submentum as a target area for fractional resection of skin and fractional subdermal/subcutaneous lipectomy, under an embodiment. The presence of skin laxity and prominence of the submental fat pad are the main components of this aesthetic deformity. Each patient will have a variable amount of each soft tissue component requiring a selective correction tailored or configured for each particular patient. More specifically, the convex contour of the submentum is caused predominately by lipodystrophy of the submental fat pad and the loss of the cervical-mandibular angle is predominately due to skin laxity.

Patients typically present with a variable amount of submentum skin laxity and lipodystrophy, so embodiments use planning and marking of a patient for a specific procedure. The combined capability of the assembly of an embodiment correlates well with the need to modify the specific soft tissue components of the aesthetic deformity. For patients with more severe skin laxity, a larger horizontally aligned treatment area in the submentum and lateral neck is marked for fractional skin resection. FIG. 123 shows a horizontally aligned treatment area in the submentum and lateral neck for severe skin laxity, under an embodiment.

For patients will more severe lipodystrophy, a broader fractional lipectomy (through fractional resection skin defects) is marked within the treatment area. The depth of the fractional lipectomy may also be selectively altered to address the topographic features of this convex contour deformity. FIG. 124 shows broader fractional lipectomy in the submentum for severe lipodystrophy, under an embodiment.

Clinical applications of the single-scalpet and multi-scalpet array platform include directed closure specifications. To promote primary healing (healing per primum) that reduces scarring, an accurate closure of the incision is a key principle employed in plastic surgery procedures. However, the direction of the closure is also important for aesthetic contouring. The appropriate vector of skin tightening takes into account the anatomical structure to be aesthetically enhanced. For more complicated aesthetic contours such as the face and neck, multiple vectors of sign tightening are employed during a procedure.

FIG. 125 shows example face vector and neck vector directed closures, under an embodiment. In addition to the skin tightening vectors, various lines of closure also limit tension upon closure. Lines of closure include those described by Karl Langer, and FIG. 126 shows Langer's lines of closure. Closure of skin incisions as indicated by Langer's lines promotes primary healing because it reduces the tension of the closure. When there is conformity between the vector of skin tightening and Langer's lines, the resultant aesthetic contouring and primary healing will work in concert with each other to provide the optimal clinical outcome.

Embodiments herein include stepwise procedure algorithms configured to provide a more uniform reduction to practice that produces predictable clinical outcomes. Many of the procedural steps (and the sequences of steps) herein are unique developments for fractional resection procedures. Without limitation, a procedural algorithm is included for the fractional resection of the submentum.

According to the treatment procedures of an embodiment, initially, a patient is marked preoperatively in a sitting position. For patients with relatively more skin laxity, the area outlined for fractional resection is broader and extends onto the lateral neck. For patients with relatively little or no skin laxity, the outlined fractional resection area is limited to the area in which lipodystrophy of the submentum fat pad is producing a convex contour deformity. For patients with both skin laxity and lipodystrophy, both areas are individually outlined as components of a single combined treatment outline. FIG. 127 shows marked target areas for fractional resection of neck and submental lipectomy, under an embodiment.

To avoid a reduction in the fractional field density, a local anesthetic field block is administered to the demarcated area of the submentum/neck. A dot/circle stencil is then applied to assure adequacy of the fractional resectional density, as described in detail herein. FIG. 128 shows an example marking stencil, under an embodiment. These procedure steps can be reversed where stenciling is performed prior to injection of the local anesthetic. The distension of the stenciled skin can be compensated with a larger outlined treatment area. A fractional skin resection is then performed within the boundary of the entire demarcated treatment area.

Fractional lipectomy is limited to the topographically outlined area of lipodystrophy (e.g., FIG. 127) and is performed either during fractional skin resection or as a subsequent procedural step. Transitioning or freehand feathering beyond the demarcated outline is performed to de-delineate the boundary of the fractional resection. A directed closure of the fractional defects is performed with an absorbent adherent elastic bandage that is stretched (preloaded) in the preferred vector of closure/skin tightening.

The bandage (e.g., Flexzan, etc.) can be preloaded by first applying one end of the bandage at a lateral mooring point beyond the fractional field. Once secure, the load is then applied at the opposite end of the bandage. The load is maintained during application. An alternative loading technique is to first apply opposing loads at each lateral extend of the elastic bandage i.e., the bandage is first stretched along the longitudinal axis of the material prior to application. With the load being maintained, the elastic bandage is then fully applied to the fractional field. Release of the load results in an elastic recoil that closes the defects of the fractional field along the designated vector. In the submentum where skin laxity of the anterior neck is present, a bi-directional closure with two vectors is pursued, but embodiments are not so limited.

FIG. 129 shows example directed closure vectors of the submentum and anterior neck, under an embodiment. The vector for the anterior neck (below the submentum) is more transverse and is used to accentuate the cervical-mandibular angle. For the submentum, the vector of closure (as indicated by Langer's lines) is vertical. A sterile dressing is then applied to conclude the procedure. A compression garment is also applied to provide compression and vectored support during the post-operative phase.

Embodiments include fractional scar revision. The reduction of the visible impact of a pre-existing scar deformity has been a major focus of plastic surgery since the inception of this surgical specialty. Depending upon the type of scar deformity, different surgical techniques have been employed. A commonly employed technique is elliptical excision of the scar with a layered closure. Other techniques such as Z-plasty and W-plasty attempt to reduce the linearity of the scar. FIG. 130 depicts Z-plasty and W-plasty scar revision. However, these conventional techniques lengthen the scar deformity. Fractional scar revision is configured to reduce the visible impact of the scar without lengthening of the scar.

For linear scar deformities, embodiments include a fractional de-delineation technique in which an interdigitating fractional resection is performed along each margin of the scar. To maximize de-delineation, directed closure of the fractional field is performed at right angles to the linear scar. FIG. 131 shows an example of the fractional de-delineation technique of scar resection, under an embodiment.

Additional de-delineation is produced under an embodiment with freehand fractional resection beyond the margins of the scar. Embodiments include a fractional technique for broad hypotrophic scars that occur from shaved biopsy excisions of skin lesions. To reduce the width of the scar deformity, a fractional scar excision is performed within the margin of the scar. Directed closure is performed as described in detail herein. FIG. 132 shows an example of the fractional scar resection for broad hypotrophic scars, under an embodiment. Another alternative embodiment combines both fractional scar revision techniques where the combined revision is performed as a single procedure or as a planned sequence of procedures, but is not so limited.

Additional embodiments include application of fractional resection to shorten incisions required to excise lesions. This novel capability can also be applied to shorten longer plastic surgery incisions that are used to resect redundant skin. The elliptical extension of an incision (to avoid a "dog-ear" skin redundancy) is no longer required if the lateral aspect of each incision is fractionally resected using devices and methods described herein.

The fractional procedure can be performed concurrently or as a planned subsequent revision of the primary excisional procedure. Fractional resection of embodiments can also be used for pre-existing dog-ear redundancies post excision. An example is the shortening of the inframmary incision required for breast reduction and breast repositioning. FIG. 133 shows an example comprising shortening of the inframmary incision as applied to breast reduction and/or breast repositioning, under an embodiment. The incision becomes less visible as it no longer extends beyond the inframmary fold.

Embodiments described herein include fractional skin grafting. This includes the closure of full thickness skin defects, which has also been a primary focus of plastic surgeons. Large defects that cannot be closed by direct closure require a more complicated approach. The two conventional approaches developed by plastic surgery are flap closure and skin grafting. FIG. 134 shows an example flap closure. Local or distant flap closures require an intrinsic or pedicle blood supply that is harvested with the flap at the donor site. Flap closure of skin defects is also complicated by the formation of additional scarring at the donor site.

Skin grafting (either split thickness or full thickness) is the other approach used to close large full thickness skin defects. Using the skin grafting approach, skin graft donor sites are required and are associated with significant scarring and morbidity.

After the several decades in which these two plastic surgical approaches have been employed, a novel third approach is now described in the embodiments herein. Fractional skin grafting can avoid the side effects associated with sheet skin grafting because fractional skin grafting has the unique capability to avoid the donor site deformity associated with sheet skin grafting. Fractional skin grafting also provides the additional capability to harvest subsequent skin grafts from the same donor site. FIG. 135 shows an example comprising fractional skin graft harvesting to be applied to a donor site, under an embodiment.

Fractional skin grafting is especially important with patients having large surface area burns for which donor site availability is severely limited. This unique capability of serial harvest at the same donor site is also important in patients with skin defects of the lower extremity that are caused by reduced circulation. Patients such as these with venous stasis, ischemic and diabetic ulcers are especially at risk to sustain the loss of the extremity if skin coverage of the vascular compromised ulcer is not promptly obtained. Many of these patients must undergo a sequence of skin grafts before skin coverage is obtained. The morbidity associated with this prolonged skin grafting process involving multiple donor sites can be especially vexing in patients who also have other serious systemic conditions. With fractional skin grafting described herein, the absence of a single visible donor site deformity coupled with the capability of serial harvesting of skin grafts from the same donor site provides a uniquely capable treatment option for these patients. In comparison to split thickness skin graft donor sites, the directed closure of the fractional donor site provides more rapid healing that dramatically reduces donor site morbidity and scarring.

As the fractional skin graft of an embodiment is full thickness, the durability of the skin coverage is also enhanced over split thickness skin grafts. For wound healing in these compromised recipient sites, the application of the fractional skin graft can be performed without the forming of the fractional skin segments (pixels) onto a more uniform sheet. In this clinical setting, "side neovascularization" occurs between the individual fractional skin segments and the recipient bed. FIG. 136 shows an example comprising neovascularization of a fractional skin graft at a recipient site, under an embodiment. The recipient site functions as a biological docking station that organizes the fractional skin segments into a side orientation with the recipient bed.

For other non-compromised and more visible skin defects, embodiments include the option to first form the fractionally harvested skin segments into a more uniform graft at a mechanical docking station. FIG. 137 shows an example docking station comprising a docking tray and adjustable slides, under an embodiment. In this clinical setting, "bottom up neovascularization" occurs from the recipient bed into deep aspect of dermis (e.g., FIG. 136). With each clinical setting, a compressive stent dressing provides additional support and immobilization that promotes neovascularization or "take" of the skin graft.

Embodiments include a system comprising a carrier. The system includes a scalpet assembly configured to couple to the carrier, and comprising a scalpet array. The scalpet array includes at least one scalpet configured for at least one of fractional resection and fractional lipectomy of tissue at a target site of a subject. The carrier is configured to control application of a rotational force to the at least one scalpet during the fractional resection and fractional lipectomy. The system includes a vacuum component coupled to the scalpet assembly and configured to evacuate the tissue from the target site using vacuum force.

Embodiments include a system comprising: a carrier; a scalpet assembly configured to couple to the carrier, and comprising a scalpet array, wherein the scalpet array includes at least one scalpet configured for at least one of fractional resection and fractional lipectomy of tissue at a target site of a subject, wherein the carrier is configured to control application of a rotational force to the at least one scalpet during the fractional resection and fractional lipectomy; and a vacuum component coupled to the scalpet assembly and configured to evacuate the tissue from the target site using vacuum force.

The tissue includes skin plugs incised to form the fractional field during the fractional resection, and fat removed through the fractional field during the fractional lipectomy.

The at least one scalpet includes a lumen extending at least partially from a distal end towards a proximal end of the at least one scalpet.

The vacuum component includes a vacuum manifold configured to couple to a distal end of the carrier, wherein the vacuum manifold includes a vacuum port configured to couple to a vacuum source.

The vacuum manifold is configured to couple to the lumen and configured to direct the vacuum force to the target site intraluminally via the lumen.

The vacuum manifold is configured to direct the vacuum force to the target site extraluminally.

A distal end of the vacuum manifold is configured as a depth guide to control a depth of penetration of the scalpet array into the tissue.

A distal end of the vacuum manifold is configured for use with a depth guide.

The vacuum manifold comprises an overlay encasement.

The vacuum manifold is removeably coupled to the distal end of the carrier.

The vacuum component is configured for manual control of delivery of the vacuum force to the target site.

The system includes a controller configured to automatically control at least one of the rotational force to the at least one scalpet and delivery of the vacuum force to the target site.

The vacuum component includes a vacuum aspirator.

The vacuum force is configured for vacuum stabilization of the target site during the fractional resection.

The vacuum component is configured for placement in series with the carrier and the scalpet assembly.

The vacuum component includes a carrier lumen in an interior region of the carrier, wherein the carrier lumen is coupled to the lumen of the at least one scalpet, wherein the carrier lumen is configured to route the vacuum force to the target site via the lumen of the at least one scalpet.

The at least one scalpet comprises a cylindrical scalpet, wherein a distal region proximate to the distal end is configured to incise and receive tissue.

The distal region includes a cutting surface.

The cutting surface includes at least one of a sharpened edge, at least one sharpened point, and a serrated edge.

The cutting surface includes a blunt edge.

The lumen and the proximal end is configured to pass tissue from the target site.

The at least one scalpet includes at least one aperture positioned axially in the scalpet adjacent the lumen.

The at least one scalpet includes a plurality of apertures positioned axially in the scalpet adjacent the lumen.

The at least one aperture is configured to pass tissue from the target site.

The at least one aperture includes at least one cutting surface.

The at least one aperture is configured to divert received tissue at least one of radially outward from the lumen and radially inward toward the lumen.

The system includes a fractional marking system configured to indicate fractional resection density of a fractional field.

The fractional marking system comprises a stencil including a grid pattern of markers.

The stencil includes an ink stencil.

The stencil includes at least one of a positive stencil and a negative stencil.

The markers include at least one of circular markers and dot markers configured to mark the target site.

The markers include at least one notch to mark at least one corner of the fractional field.

The fractional marking system comprises a membrane including perforations.

The membrane is configured as a depth guide to control a depth of penetration of the scalpet array into the tissue.

The membrane comprises a material including at least one of plastic, polymer, and composite, wherein the membrane is semitransparent.

The membrane is configured to adhere to the target site.

The lumen of the scalpet is coupled to a reservoir configured to retain received tissue.

The reservoir comprises a canister.

The carrier is configured to be hand-held.

The system includes a motor coupled to the scalpet assembly and configured to drive the at least one scalpet.

The scalpet array includes a plurality of scalpets.

Each scalpet is configured to rotate around a central axis of the scalpet.

The scalpet assembly includes a drive assembly coupled to each scalpet, wherein the drive assembly is configured to impart a rotational force to a proximal region of each scalpet, wherein the rotational force rotates each scalpet around the central axis.

The drive assembly comprises at least one of a gear-drive system and a frictional drive system.

The system includes a depth guide to control a depth of penetration of the scalpet array into the tissue.

The system includes a housing including a distal region coupled to the vacuum component and configured to form a vacuum seal when in contact with proximate tissue adjacent the target site.

The scalpet assembly includes a spring device configured to control a position of the scalpet array relative to the target site.

The vacuum force is configured to control a position of the scalpet array relative to the target site.

The scalpet assembly includes a spring device configured to control a position of the scalpet array relative to the target site in concert with the vacuum force.

Embodiments include a device comprising a scalpet assembly configured to couple to a carrier. The scalpet assembly includes a scalpet array configured for at least one of fractional resection and fractional lipectomy of tissue at a target site of a subject. The carrier is configured to control application of rotational force to scalpets of the scalpet array during the fractional resection and fractional lipectomy. The device includes a manifold configured to removeably couple to the scalpet assembly. The manifold includes a depth control device configured to control a depth of penetration of scalpets of the scalpet array into the tissue. The manifold is configured to control a vacuum force applied to evacuate the tissue from the target site. The tissue includes skin plugs incised to form the fractional field during the fractional resection, and fat removed through the fractional field during the fractional lipectomy.

Embodiments include a device comprising: a scalpet assembly configured to couple to a carrier, wherein the scalpet assembly includes a scalpet array configured for at least one of fractional resection and fractional lipectomy of tissue at a target site of a subject, wherein the carrier is configured to control application of rotational force to scalpets of the scalpet array during the fractional resection and fractional lipectomy; and a manifold configured to removeably couple to the scalpet assembly, wherein the manifold includes a depth control device configured to control a depth of penetration of scalpets of the scalpet array into the tissue, wherein the manifold is configured to control a vacuum force applied to evacuate the tissue from the target site, wherein the tissue includes skin plugs incised to form the fractional field during the fractional resection, and fat removed through the fractional field during the fractional lipectomy.

Embodiments include a device comprising a carrier comprising a proximal region and a distal region. The proximal region is configured to be hand-held. The device includes a scalpet assembly configured to couple to the distal region. The scalpet assembly includes a scalpet array configured for at least one of fractional resection and fractional lipectomy of tissue at a target site of a subject. The scalpet array includes scalpets that each comprise a tube comprising a hollow region and a sharpened distal end configured to penetrate tissue at a target site of a subject. The device includes a manifold configured to couple to the distal region. The manifold is configured to control a vacuum force applied to evacuate the tissue from the target site. The tissue includes skin plugs incised to form the fractional field during the fractional resection, and fat removed through the fractional field during the fractional lipectomy.

Embodiments include a device comprising: a carrier comprising a proximal region and a distal region, wherein the proximal region is configured to be hand-held; a scalpet assembly configured to couple to the distal region, wherein the scalpet assembly includes a scalpet array configured for at least one of fractional resection and fractional lipectomy of tissue at a target site of a subject, wherein the scalpet array includes scalpets that each comprise a tube comprising a hollow region and a sharpened distal end configured to penetrate tissue at a target site of a subject; and a manifold configured to couple to the distal region, wherein the manifold is configured to control a vacuum force applied to evacuate the tissue from the target site, wherein the tissue includes skin plugs incised to form the fractional field during the fractional resection, and fat removed through the fractional field during the fractional lipectomy.

Embodiments include a method comprising configuring a carrier for at least one of fractional resection and fractional lipectomy of tissue at a target site of a subject by coupling the carrier to a scalpet assembly comprising a scalpet array. The method comprises configuring the carrier to control application of a rotational force to the scalpet array, and control application of a vacuum force by a vacuum component coupled to the scalpet assembly. The rotational force is configured to incise tissue at the target site. The vacuum force is configured to evacuate the tissue from the target site. The tissue includes at least one of skin plugs incised to form a fractional field during the fractional resection and fat removed through the fractional field during the fractional lipectomy.

Embodiments include a method comprising: configuring a carrier for at least one of fractional resection and fractional lipectomy of tissue at a target site of a subject by coupling the carrier to a scalpet assembly comprising a scalpet array; configuring the carrier to control application of a rotational force to the scalpet array, and control application of a vacuum force by a vacuum component coupled to the scalpet assembly, wherein the rotational force is configured to incise tissue at the target site, wherein the vacuum force is configured to evacuate the tissue from the target site, wherein the tissue includes at least one of skin plugs incised to form a fractional field during the fractional resection and fat removed through the fractional field during the fractional lipectomy.

The method includes marking the target site of the subject.

The marking comprises marking a perimeter of the target site of the subject.

The marking comprises use of a stencil including a grid pattern of markers.

The markers include at least one of circular markers and dot markers configured to mark the target site.

The stencil includes at least one notch to mark at least one corner of the fractional field.

The marking comprises marking at least one of a first region and a second region at the target site.

The first region presents skin laxity.

The second region presents lipodystrophy.

The second region presents lipodystrophy of the submentum fat pad.

The method includes marking a plurality of fractional resection sites within the at least one of the first region and the second region.

The marking of the plurality of fractional resection sites comprises applying a fractional marking system to the at least one of the first region and the second region.

The method includes performing the fractional resection in the at least one of the first region and the second region.

The method includes performing the fractional lipectomy in the second region.

The method includes performing the fractional lipectomy in the second region subsequent to the fractional resection.

The method includes performing the fractional resection in the second region subsequent to the fractional lipectomy.

The method includes performing the fractional lipectomy during the fractional resection.

The method includes de-delineating a boundary of the first region by feathering beyond the boundary.

The method includes closing the fractional field of the fractional resection, wherein the closing comprises directed closure.

The directed closure comprises at least one of closure substantially in a first direction, a plurality of directions, a substantially horizontal closure, and a substantially vertical closure.

The directed closure comprises use of Langer's lines.

The directed closure comprises use of resting skin tension lines.

The directed closure comprises use of closure vectors of surgical skin resection procedures.

The directed closure comprises at least one of a bandage and an adherent membrane instead of suturing.

The method includes applying a dressing at the target site.

The vacuum component includes a vacuum manifold configured to couple to a distal end of the carrier.

The vacuum manifold includes a vacuum port configured to couple to a vacuum source.

The vacuum manifold is coupled to a lumen of at least one scalpet of the scalpet array and configured to direct the vacuum force to the target site intraluminally via the lumen.

The vacuum manifold is configured to direct the vacuum force to the target site extraluminally.

The vacuum component includes a vacuum aspirator.

The vacuum force is configured for vacuum stabilization of the target site during the fractional resection.

The method includes a controller configured to automatically control at least one of the rotational force to the at least one scalpet and delivery of the vacuum force to the target site.

The scalpet array includes at least one scalpet comprising a cylindrical scalpet including a lumen extending at least partially from a distal end towards a proximal end of the at least one scalpet, wherein a distal region proximate to the distal end is configured to incise and receive tissue.

The distal region includes a cutting surface.

The cutting surface includes at least one of a sharpened edge, at least one sharpened point, a serrated edge, and a blunt edge.

The lumen and the proximal end is configured to pass tissue from the target site.

The at least one scalpet includes at least one aperture positioned axially adjacent the hollow region.

The at least one aperture is configured to divert received tissue at least one of radially outward from the lumen of the scalpet and radially inward toward the lumen of the scalpet.

The scalpet array includes a plurality of scalpets.

Each scalpet is configured to rotate around a central axis of the scalpet.

The scalpet array includes at least one scalpet, wherein the scalpet assembly includes a drive assembly coupled to each of the at least one scalpets, wherein the drive assembly is configured to impart a rotational force to a proximal region of each scalpet, wherein the rotational force rotates each scalpet around the central axis.

The configuring the carrier includes configuring the carrier for use with a depth guide, wherein the depth guide controls a depth of penetration of the scalpet array into the tissue.

Embodiments include a method comprising configuring a carrier for at least one of fractional resection and fractional lipectomy of tissue at a target site of a subject by coupling the carrier to a scalpet assembly comprising a scalpet array. The method comprises configuring the carrier to control application of a rotational force to the at least one scalpet, and control application of a vacuum force by a vacuum component coupled to the scalpet assembly. The vacuum force is configured to evacuate the tissue from the target site. The tissue includes at least one of skin plugs incised to form a fractional field during the fractional resection and fat removed through the fractional field during the fractional lipectomy.

Embodiments include a method comprising: configuring a carrier for at least one of fractional resection and fractional lipectomy of tissue at a target site of a subject by coupling the carrier to a scalpet assembly comprising a scalpet array; configuring the carrier to control application of a rotational force to the at least one scalpet, and control application of a vacuum force by a vacuum component coupled to the scalpet assembly, wherein the vacuum force is configured to evacuate the tissue from the target site, wherein the tissue includes at least one of skin plugs incised to form a fractional field during the fractional resection and fat removed through the fractional field during the fractional lipectomy.

Embodiments include a method comprising generating a protocol using patient data. The protocol includes at least one target site and a topographical map of fractional skin resections configured for application at the at least one target site. The method comprises positioning at the target site a carrier including a scalpet assembly comprising at least one scalpet and a depth control device. The at least one scalpet includes a lumen and a distal end configured to penetrate tissue at the at least one target site. The method comprises performing at least one of fractional resection and fractional lipectomy by circumferentially incising skin pixels at the at least one target site using the scalpet assembly, and controlling a depth of penetration of the incising using the depth control device. The method comprises removing at least one of the skin pixels and fat tissue underlying at least a portion of the at least one target site via an orifice in the at least one scalpet.

Embodiments include a method comprising: generating a protocol using patient data, wherein the protocol includes at least one target site and a topographical map of fractional skin resections configured for application at the at least one target site; positioning at the target site a carrier including a scalpet assembly comprising at least one scalpet and a depth control device, wherein the at least one scalpet includes a lumen and a distal end configured to penetrate tissue at the at least one target site; performing at least one of fractional resection and fractional lipectomy by circumferentially incising skin pixels at the at least one target site using the scalpet assembly, and controlling a depth of penetration of the incising using the depth control device; and removing at least one of the skin pixels and fat tissue underlying at least a portion of the at least one target site via an orifice in the at least one scalpet.

Embodiments include a method comprising configuring a carrier for aesthetic contouring comprising fractional resection and fractional lipectomy of tissue by coupling the carrier to a scalpet assembly comprising a scalpet array including at least one scalpet, and a vacuum component. The method comprises marking a target site of a subject. The method comprises generating a fractional field at the target site by fractionally resecting tissue according to the marking. The fractional resection includes circumferentially incising and removing at least one skin plug by application of the scalpet assembly. The method comprises removing fat tissue through the fractional field using the scalpet assembly, wherein the fat tissue is underlying at least a portion of the target site.

Embodiments include a method comprising: configuring a carrier for aesthetic contouring comprising fractional resection and fractional lipectomy of tissue by coupling the carrier to a scalpet assembly comprising a scalpet array including at least one scalpet, and a vacuum component; marking a target site of a subject; generating a fractional field at the target site by fractionally resecting tissue according to the marking, wherein the fractional resection includes circumferentially incising and removing at least one skin plug by application of the scalpet assembly; and removing fat tissue through the fractional field using the scalpet assembly, wherein the fat tissue is underlying at least a portion of the target site.

The marking comprises marking via application of the scalpet array.

The marking comprises marking a perimeter of the target site of the subject.

The marking comprises marking at least one of a first region and a second region at the target site.

The first region presents skin laxity.

The second region presents lipodystrophy.

The second region presents lipodystrophy of the submentum fat pad.

An area of the first region is larger than an area of the second region.

An area of the second region is determined based on a severity of the lipodystrophy.

The first region includes at least a portion of a submental space of the subject.

The first region includes at least a portion of a lateral neck area of the subject.

The marking comprises marking a plurality of fractional resection sites within the at least one of the first region and the second region.

The marking of the plurality of fractional resection sites comprises applying a fractional marking system to the at least one of the first region and the second region.

The method includes performing the fractional resection in the at least one of the first region and the second region.

The method includes performing the fractional lipectomy in the second region.

A depth of the fractional lipectomy is variable.

A depth of the fractional lipectomy is selectively controlled based on topographic features of a convex contour deformity of the second region.

The method includes performing the fractional lipectomy in the second region subsequent to the fractional resection.

The method includes performing the fractional resection in the second region subsequent to the fractional lipectomy.

The method includes performing the fractional lipectomy during the fractional resection.

The method includes de-delineating a boundary of the first region by feathering beyond the boundary.

The method includes closing the fractional field of the fractional resection, wherein the closing comprises directed closure.

The directed closure comprises at least one of closure substantially in a first direction, a horizontal direction, a vertical direction, and a plurality of directions.

The directed closure comprises closure substantially along a first vector and a second vector, wherein the first vector corresponds to a region of a face and the second vector corresponds to a region of a neck of the subject.

The directed closure comprises use of Langer's lines.

The directed closure comprises use of resting skin tension lines.

The directed closure comprises use of closure vectors of surgical skin resection procedures.

The directed closure comprises at least one of a bandage and an adherent membrane instead of suturing.

The method includes applying a dressing at the target site.

The configuring the carrier includes coupling a vacuum component to the scalpet assembly, wherein the vacuum component is configured to remove the tissue and the fat tissue using vacuum force.

The vacuum component includes a vacuum manifold configured to couple to a distal end of the carrier, wherein the vacuum manifold includes a vacuum port configured to couple to a vacuum source.

The vacuum manifold is coupled to a lumen of the at least one scalpet and configured to direct the vacuum force to the target site intraluminally via the lumen.

The vacuum manifold is configured to direct the vacuum force to the target site extraluminally.

The vacuum component includes a vacuum aspirator.

The vacuum force is configured for vacuum stabilization of the target site during the fractional resection.

The method includes a controller configured to automatically control at least one of the rotational force to the at least one scalpet and delivery of the vacuum force to the target site.

The at least one scalpet comprises a cylindrical scalpet including a lumen extending at least partially from a distal end towards a proximal end of the at least one scalpet, wherein a distal region proximate to the distal end is configured to incise and receive tissue.

The distal region includes a cutting surface.

The cutting surface includes at least one of a sharpened edge, at least one sharpened point, a serrated edge, and a blunt edge.

The lumen and the proximal end is configured to pass tissue from the target site.

The at least one scalpet includes at least one aperture positioned axially adjacent the hollow region.

The at least one aperture is configured to divert received tissue at least one of radially outward from an interior region of the scalpet and radially inward toward the interior region of the scalpet.

The scalpet array includes a plurality of scalpets.

Each scalpet is configured to rotate around a central axis of the scalpet.

The scalpet assembly includes a drive assembly coupled to each scalpet, wherein the drive assembly is configured to impart a rotational force to a proximal region of each scalpet, wherein the rotational force rotates each scalpet around the central axis.

The configuring the carrier includes configuring the carrier for use with a depth guide, wherein the depth guide controls a depth of penetration of the scalpet array into the tissue.

Embodiments include a method comprising configuring a carrier for aesthetic contouring comprising fractional resection and fractional lipectomy of tissue by coupling the carrier to a scalpet assembly comprising a scalpet array including at least one scalpet, and a vacuum component. The method comprises generating a fractional field at a target site by fractionally resecting tissue. The fractional resection includes circumferentially incising and removing at least one skin plug by application of the scalpet assembly. The method comprises removing fat tissue through at least a portion of the fractional field using the scalpet assembly. The fat tissue is underlying at least a portion of the target site.

Embodiments include a method comprising: configuring a carrier for aesthetic contouring comprising fractional resection and fractional lipectomy of tissue by coupling the carrier to a scalpet assembly comprising a scalpet array including at least one scalpet, and a vacuum component; generating a fractional field at a target site by fractionally resecting tissue, wherein the fractional resection includes circumferentially incising and removing at least one skin plug by application of the scalpet assembly; and removing fat tissue through at least a portion of the fractional field using the scalpet assembly, wherein the fat tissue is underlying at least a portion of the target site.

Embodiments include a method comprising configuring a carrier for fractional scar revision by coupling the carrier to a scalpet assembly comprising a scalpet array including at least one scalpet, and a vacuum component. The method comprises identifying at least one area adjacent a scar deformity as a target site of a subject. The method comprises generating a fractional field by fractionally resecting tissue proximate to the least one area adjacent the scar deformity. The fractional resection includes circumferentially incising and removing at least one skin plug by application of the scalpet assembly.

Embodiments include a method comprising: configuring a carrier for fractional scar revision by coupling the carrier to a scalpet assembly comprising a scalpet array including at least one scalpet, and a vacuum component; identifying at least one area adjacent a scar deformity as a target site of a subject; and generating a fractional field by fractionally resecting tissue proximate to the least one area adjacent the scar deformity, wherein the fractional resection includes circumferentially incising and removing at least one skin plug by application of the scalpet assembly.

The scar deformity includes a linear scar deformity.

The fractionally resecting tissue comprises fractionally resecting tissue along each margin of the scar deformity.

The method includes forming an interdigitating incised region on each margin of the scar deformity.

The method includes de-delineating a boundary of the incised region by fractionally resecting tissue beyond the respective margin.

The fractionally resecting tissue comprises fractionally resecting tissue at one or more ends of the scar deformity.

The scar deformity includes a broad scar deformity, wherein the fractionally resecting tissue comprises fractionally excising tissue within a margin of the scar deformity.

The fractionally resecting tissue comprises fractionally resecting tissue along each margin of the scar deformity, and fractionally excising tissue within a margin of the scar deformity.

The method includes forming an interdigitating incised region on each margin of the scar deformity.

The method includes de-delineating a boundary of the incised region by fractionally resecting tissue beyond the respective margin.

The method includes marking the target site, wherein the marking comprises marking a plurality of fractional resection sites in the at least one area adjacent the scar deformity.

The marking of the plurality of fractional resection sites comprises applying a fractional marking system to the at least one area adjacent the scar deformity.

The method includes closing the fractional field of the fractional resection, wherein the closing comprises directed closure.

The directed closure comprises directed closure approximately orthogonally to a direction of the scar deformity.

The directed closure comprises use of Langer's lines.

The directed closure comprises use of resting skin tension lines.

The directed closure comprises at least one of a bandage and an adherent membrane instead of suturing.

The method includes applying a dressing at the target site.

The configuring the carrier includes coupling a vacuum component to the scalpet assembly, wherein the vacuum component is configured to remove the tissue using vacuum force.

The vacuum component includes a vacuum manifold configured to couple to a distal end of the carrier, wherein the vacuum manifold includes a vacuum port configured to couple to a vacuum source.

The vacuum manifold is coupled to a lumen of the at least one scalpet and configured to direct the vacuum force to the target site intraluminally via the lumen.

The vacuum manifold is configured to direct the vacuum force to the target site extraluminally.

The vacuum component includes a vacuum aspirator.

The vacuum force is configured for vacuum stabilization of the target site during the fractional resection.

The method includes a controller configured to automatically control at least one of a rotational force to the at least one scalpet and delivery of the vacuum force to the target site.

The at least one scalpet comprises a cylindrical scalpet including a lumen extending at least partially from a distal end towards a proximal end of the at least one scalpet, wherein a distal region proximate to the distal end is configured to incise and receive tissue.

The distal region includes a cutting surface.

The cutting surface includes at least one of a sharpened edge, at least one sharpened point, a serrated edge, and a blunt edge.

The lumen and the proximal end is configured to pass tissue from the target site.

The at least one scalpet includes at least one aperture positioned axially adjacent the hollow region.

The at least one aperture is configured to divert received tissue at least one of radially outward from an interior region of the scalpet and radially inward toward the interior region of the scalpet.

The scalpet array includes a plurality of scalpets.

Each scalpet is configured to rotate around a central axis of the scalpet.

The scalpet assembly includes a drive assembly coupled to each scalpet, wherein the drive assembly is configured to impart a rotational force to a proximal region of each scalpet, wherein the rotational force rotates each scalpet around the central axis.

The configuring the carrier includes configuring the carrier for use with a depth guide, wherein the depth guide controls a depth of penetration of the scalpet array into the tissue.

Embodiments include a method comprising configuring a carrier for fractional skin grafting comprising fractional resection of tissue by coupling the carrier to a scalpet assembly comprising a scalpet array including at least one scalpet, and a vacuum component. The method comprises marking a target site of a subject. The target site includes a donor site. The method comprises generating a fractional field at the target site by fractionally resecting tissue according to the marking. The fractional resection includes circumferentially incising and removing a plurality of skin plugs by at least one application of the scalpet assembly. A skin graft comprises the plurality of skin plugs. The method comprises transferring and placing the skin graft at a recipient site.

Embodiments include a method comprising: configuring a carrier for fractional skin grafting comprising fractional resection of tissue by coupling the carrier to a scalpet assembly comprising a scalpet array including at least one scalpet, and a vacuum component; marking a target site of a subject, wherein the target site includes a donor site; generating a fractional field at the target site by fractionally resecting tissue according to the marking, wherein the fractional resection includes circumferentially incising and removing a plurality of skin plugs by at least one application of the scalpet assembly, wherein a skin graft comprises the plurality of skin plugs; and transferring and placing the skin graft at a recipient site.

The removing of the plurality of skin plugs includes directing the plurality of skin plugs into a collection canister.

The transferring of the skin graft comprises non-uniform transfer of the plurality of skin plugs.

The non-uniform transfer of the plurality of skin plugs includes free-form transfer.

The transferring of the skin graft comprises uniform transfer of the plurality of skin plugs.

The uniform transfer comprises transfer with a docking tray including a plurality of receptacles, wherein the docking tray receives the plurality of skin plugs removed from the donor site.

The docking tray maintains an orientation of the plurality of skin plugs removed from the donor site.

The docking tray comprises an elastomeric material.

The uniform transfer comprises transfer with an adherent substrate that captures the plurality of skin plugs from the docking tray.

The adherent substrate maintains relative positioning of the plurality of skin plugs during transfer to and application at the recipient site.

The adherent substrate applies the skin plugs to the recipient site.

The adherent substrate aligns the skin plugs at the recipient site.

The placing of the skin graft at the recipient site comprises spreading the plurality of skin plugs over the area of the recipient site.

The spreading includes placing the plurality of skin plugs in contact with the recipient site in a side orientation.

The plurality of skin plugs evokes side-neovascularization at the recipient site.

The spreading includes placing the plurality of skin plugs in contact with the recipient site in a horizontal orientation.

The plurality of skin plugs evoke a side to end neovascularization at the recipient site.

The plurality of skin plugs evoke a wound healing response at the recipient site.

The plurality of voids caused by removal of the plurality of skin plugs evoke a wound healing response at the donor site.

The marking comprises marking a plurality of fractional resection sites at the target site.

The marking of the plurality of fractional resection sites comprises applying a fractional marking system to the target site.

The applying of the fractional marking system to the target site includes application of the scalpet array at the target site.

Application of the scalpet array at the target site produces an adequate fractional density harvest at the target site.

The marking comprises marking a second plurality of fractional resection sites at the target site.

The method includes generating a second fractional field at the second plurality of fractional resection sites using a second fractional resection of tissue according to the marking.

The second fractional resection includes circumferentially incising and removing a second plurality of skin plugs by at least one application of the scalpet assembly, wherein a second skin graft comprises the second plurality of skin plugs.

The method includes transferring and placing the second skin graft at the recipient site.

The method includes identifying a second target site of the subject, wherein the second target site includes a second donor site.

The method includes generating a second fractional field at the second target site using a second fractional resection of tissue according to the second marking.

The second fractional resection includes circumferentially incising and removing a second plurality of skin plugs by at least one application of the scalpet assembly, wherein a second skin graft comprises the second plurality of skin plugs.

The method includes transferring and placing the second skin graft at the recipient site.

The vacuum component is configured to remove the tissue using vacuum force.

The vacuum component includes a vacuum manifold configured to couple to a distal end of the carrier, wherein the vacuum manifold includes a vacuum port configured to couple to a vacuum source.

The vacuum manifold is coupled to a lumen of the at least one scalpet and configured to direct the vacuum force to the target site intraluminally via the lumen.

The vacuum manifold is configured to direct the vacuum force to the target site extraluminally.

The vacuum component includes a vacuum aspirator.

The vacuum force is configured for vacuum stabilization of the target site during the fractional resection.

The method includes a controller configured to automatically control at least one of a rotational force to the at least one scalpet and delivery of the vacuum force to the target site.

The at least one scalpet comprises a cylindrical scalpet including a lumen extending at least partially from a distal end towards a proximal end of the at least one scalpet, wherein a distal region proximate to the distal end is configured to incise and receive tissue.

The distal region includes a cutting surface.

The cutting surface includes at least one of a sharpened edge, at least one sharpened point, a serrated edge, and a blunt edge.

The lumen and the proximal end is configured to pass tissue from the target site.

The at least one scalpet includes at least one aperture positioned axially adjacent the hollow region.

The at least one aperture is configured to divert received tissue at least one of radially outward from an interior region of the scalpet and radially inward toward the interior region of the scalpet.

The scalpet array includes a plurality of scalpets.

Each scalpet is configured to rotate around a central axis of the scalpet.

The scalpet assembly includes a drive assembly coupled to each scalpet, wherein the drive assembly is configured to impart a rotational force to a proximal region of each scalpet, wherein the rotational force rotates each scalpet around the central axis.

The configuring the carrier includes configuring the carrier for use with a depth guide, wherein the depth guide controls a depth of penetration of the scalpet array into the tissue.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import, when used in this application, refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments is not intended to be exhaustive or to limit the systems and methods to the precise forms disclosed. While specific embodiments of, and examples for, the medical devices and methods are described herein for illustrative purposes, various equivalent modifications are possible within the scope of the systems and methods, as those skilled in the relevant art will recognize. The teachings of the medical devices and methods provided herein can be applied to other systems and methods, not only for the systems and methods described above.

The elements and acts of the various embodiments described above can be combined to provide further embodiments. These and other changes can be made to the medical devices and methods in light of the above detailed description.

In general, in the following claims, the terms used should not be construed to limit the medical devices and methods and corresponding systems and methods to the specific embodiments disclosed in the specification and the claims, but should be construed to include all systems that operate under the claims. Accordingly, the medical devices and methods and corresponding systems and methods are not limited by the disclosure, but instead the scope is to be determined entirely by the claims.

While certain aspects of the medical devices and methods and corresponding systems and methods are presented below in certain claim forms, the inventors contemplate the various aspects of the medical devices and methods and corresponding systems and methods in any number of claim forms. Accordingly, the inventors reserve the right to add additional claims after filing the application to pursue such additional claim forms for other aspects of the medical devices and methods and corresponding systems and methods.

What is claimed is:

1. A system comprising:
a carrier;
a scalpet assembly configured to couple to the carrier, and comprising at least one scalpet configured for at least one of fractional resection and fractional lipectomy of tissue at a target site of a subject, wherein the carrier is configured to control application of a rotational force to the at least one scalpet, wherein the at least one scalpet includes a lumen coupled to a distal end and an aperture positioned axially in the scalpet, wherein the aperture includes at least one cutting surface and is configured to divert tissue received via the distal end; and
a vacuum component configured to evacuate the tissue from the target site via the aperture for harvesting, wherein the vacuum component includes a vacuum manifold configured to removably couple to a distal end of the carrier and a vacuum source.

2. The system of claim 1, wherein the tissue includes skin plugs incised to form the fractional field during the fractional resection, and fat removed through the fractional field during the fractional lipectomy.

3. The system of claim 1, wherein the lumen extends at least partially from the distal end towards a proximal end of the at least one scalpet.

4. The system of claim 3, wherein the vacuum manifold includes a vacuum port configured to couple to the vacuum source.

5. The system of claim 4, wherein the vacuum manifold is configured to couple to the lumen and configured to direct the vacuum force to the target site intraluminally via the lumen.

6. The system of claim 4, wherein the vacuum manifold is configured to couple to the lumen via an aperture in a distal region of the lumen, wherein the vacuum manifold directs the vacuum force to the lumen via the aperture.

7. The system of claim 4, wherein a distal end of the vacuum manifold is configured as a depth guide to control a depth of penetration of the at least one scalpet into the tissue.

8. The system of claim 4, wherein a distal end of the vacuum manifold is configured for use with a depth guide.

9. The system of claim 4, wherein the vacuum manifold comprises an overlay encasement.

10. The system of claim 4, wherein the vacuum manifold is removably coupled to the distal end of the carrier.

11. The system of claim 4, wherein the vacuum component is configured for manual control of delivery of the vacuum force to the target site.

12. The system of claim 4, comprising a controller configured to automatically control at least one of the rotational force to the at least one scalpet and delivery of the vacuum force to the target site.

13. The system of claim 4, wherein the vacuum force is configured for vacuum stabilization of the target site during the fractional resection.

14. The system of claim 3, wherein the vacuum component is configured for placement in series with the carrier and the scalpet assembly.

15. The system of claim 3, wherein the vacuum component includes a carrier lumen in an interior region of the carrier, wherein the carrier lumen is coupled to the lumen of the at least one scalpet, wherein the carrier lumen is configured to route the vacuum force to the target site via the lumen of the at least one scalpet.

16. The system of claim 3, wherein the at least one scalpet comprises a cylindrical scalpet, wherein a distal region proximate to the distal end is configured to incise and receive tissue.

17. The system of claim 16, wherein the distal region includes a cutting surface.

18. The system of claim 17, wherein the cutting surface includes at least one of a sharpened edge, at least one sharpened point, and a serrated edge.

19. The system of claim 16, wherein the aperture is configured to pass tissue from the target site.

20. The system of claim 3, comprising a fractional marking system configured to indicate fractional resection density of a fractional field.

21. The system of claim 20, wherein the fractional marking system comprises a stencil including a grid pattern of markers.

22. The system of claim 21, wherein the stencil includes an ink stencil.

23. The system of claim 21, wherein the stencil includes at least one of a positive stencil and a negative stencil.

24. The system of claim 21, wherein the markers include at least one of circular markers and dot markers configured to mark the target site.

25. The system of claim 21, wherein the markers include at least one notch to mark at least one corner of the fractional field.

26. The system of claim 20, wherein the fractional marking system comprises a membrane including perforations.

27. The system of claim 26, wherein the membrane is configured as a depth guide to control a depth of penetration of the at least one scalpet into the tissue.

28. The system of claim 26, wherein the membrane, comprises a material including at least one of plastic, polymer, and composite, wherein the membrane is semi-transparent.

29. The system of claim 26, wherein the membrane is configured to adhere to the target site.

30. The system of claim 3, wherein the carrier is configured to be hand-held.

31. The system of claim 3, comprising a depth guide to control a depth of penetration of the at least one scalpet into the tissue.

32. The system of claim 3, wherein the vacuum force is configured to control a position of the at least one scalpet relative to the target site.

* * * * *